(12) United States Patent
Zheng et al.

(10) Patent No.: US 10,239,947 B2
(45) Date of Patent: Mar. 26, 2019

(54) ANTI-CLL-1 ANTIBODIES AND IMMUNOCONJUGATES

(71) Applicant: Genentech, Inc., South San Francisco, CA (US)

(72) Inventors: Bing Zheng, Mountain View, CA (US); Andrew Polson, San Francisco, CA (US); Cecilia Chiu, San Carlos, CA (US); Wei-Ching Liang, Foster City, CA (US); Yan Wu, Foster City, CA (US)

(73) Assignee: Genentech, Inc., South San Francisco, CA (US)

( * ) Notice: Subject to any disclaimer, the term of this patent is extended or adjusted under 35 U.S.C. 154(b) by 52 days.

(21) Appl. No.: 15/657,471

(22) Filed: Jul. 24, 2017

(65) Prior Publication Data

US 2018/0044420 A1  Feb. 15, 2018

Related U.S. Application Data

(62) Division of application No. 14/852,369, filed on Sep. 11, 2015, now Pat. No. 9,751,946.

(60) Provisional application No. 62/049,876, filed on Sep. 12, 2014.

(51) Int. Cl.

| | | |
|---|---|---|
| *A61K 39/395* | (2006.01) | |
| *C07K 16/28* | (2006.01) | |
| *A61K 31/5517* | (2006.01) | |
| *A61K 31/706* | (2006.01) | |
| *A61K 51/10* | (2006.01) | |
| *C07K 16/30* | (2006.01) | |
| *G01N 33/574* | (2006.01) | |
| *A61K 47/68* | (2017.01) | |

(52) U.S. Cl.
CPC ...... *C07K 16/2851* (2013.01); *A61K 31/5517* (2013.01); *A61K 31/706* (2013.01); *A61K 47/68* (2017.08); *A61K 47/6817* (2017.08); *A61K 47/6867* (2017.08); *A61K 47/6889* (2017.08); *A61K 51/1069* (2013.01); *A61K 51/1093* (2013.01); *C07K 16/3061* (2013.01); *G01N 33/57426* (2013.01); *C07K 2317/14* (2013.01); *C07K 2317/24* (2013.01); *C07K 2317/33* (2013.01); *C07K 2317/34* (2013.01); *C07K 2317/52* (2013.01); *C07K 2317/76* (2013.01); *C07K 2317/77* (2013.01); *C07K 2317/92* (2013.01); *C07K 2317/94* (2013.01); *G01N 2333/7056* (2013.01)

(58) Field of Classification Search
None
See application file for complete search history.

(56) References Cited

U.S. PATENT DOCUMENTS

| | | |
|---|---|---|
| 9,000,130 B2 | 4/2015 | Bhakta et al. |
| 2006/0177451 A1 | 8/2006 | van den Oudenrijn et al. |
| 2010/0285037 A1 | 11/2010 | Arbo et al. |
| 2011/0256157 A1 | 10/2011 | Howard et al. |
| 2013/0028917 A1 | 1/2013 | Howard et al. |
| 2013/0266595 A1 | 10/2013 | Flygare et al. |
| 2014/0288280 A1 | 9/2014 | Bhakta et al. |
| 2014/0294868 A1 | 10/2014 | Howard |
| 2015/0165063 A1 | 6/2015 | Flygare et al. |
| 2016/0074527 A1 | 3/2016 | Flygare et al. |
| 2016/0075787 A1 | 3/2016 | Zheng et al. |

FOREIGN PATENT DOCUMENTS

| | | |
|---|---|---|
| WO | 2005/000894 A3 | 6/2005 |
| WO | 2011/061492 A2 | 5/2011 |
| WO | 2011/130598 A1 | 10/2011 |
| WO | 2011/156328 A1 | 12/2011 |
| WO | 2013/055987 A1 | 4/2013 |
| WO | 2013/165940 | 11/2013 |
| WO | 2013/169625 | 11/2013 |
| WO | 2014/051433 | 4/2014 |
| WO | 2014/159981 A2 | 10/2014 |
| WO | 2015/023355 A1 | 2/2015 |
| WO | 2015/095124 A1 | 6/2015 |
| WO | 2015/095212 A1 | 6/2015 |
| WO | 2015/181559 | 12/2015 |
| WO | 2016/040868 A1 | 3/2016 |
| WO | 2016/044560 A1 | 3/2016 |
| WO | 2016/090050 A1 | 6/2016 |

OTHER PUBLICATIONS

George et al. "Differential Effects of Anti-B2-Glycoprotein I Antibodies on Endothelial Cells on the Manifestations of Experimental Antiphospholipid Syndrome," Circulation. 1998; 97:900-906.

Lippincott-Schwartz (Current Protocols in Cell Biology, 16.0.1-16.0.2, 2002).

Anonymous, 'Human CICL/CLEC12A Antibody, Monoclonal Mouse IgG2B Clone #687317, Catalog No. MAB2946,' Dated Nov. 11, 2015, Retried from the internet: URL: https://resources.rndsystems.com/pdfs/datasheets/mab2946.pdf.

International Search Report and Written Opinion for International Application No. PCT/US2015/049794.

Lu et al., "Targeting human C-type lectin-like molecule-1 (CLL1) with a bispecific antibody for immunotherapy of acute myeloid leukemia" Angewandte Chemie International Edition 53(37):9841-9845 (Sep. 8, 2014).

International Search Report and Written Opinion for International Patent Application No. PCT/US2016/037381, pp. 1-13 (dated Jun. 16, 2015).

Brusa et al., "The PD-1/PD-L1 axis contributes to T-cell dysfunction in chronic lymphocytic leukemia" Haematologica, The Hematology Journal 98(6):953-963 (Jan. 8, 2013).

(Continued)

*Primary Examiner* — Sheela J. Huff

(74) *Attorney, Agent, or Firm* — McNeill Baur PLLC

(57) ABSTRACT

The invention provides anti-CLL-1 antibodies and immunoconjugates and methods of using the same.

80 Claims, 10 Drawing Sheets

Specification includes a Sequence Listing.

(56) References Cited

OTHER PUBLICATIONS

McClanahan et al., "PD-L1 checkpoint blockade prevents immune dysfunction and leukemia development in a mouse model of chronic lymphocytic leukemia" Blood 126(2):203-211 (Jul. 9, 2015).
Osada et al., "CEA/CD3-bispecific T cell-engaging (BiTE) antibody-mediated T lymphocyte cytotoxicity maximized by inhibition of both PD1 and PD-LI" Cancer Immunology and Immunology 64(6):677-688 (Jun. 1, 2015).

Light Chain Variable Region

| Kabat Number | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 27a | 27b | 27c | 27d | 28 | 29 | 30 | 31 | 32 | 33 | 34 | 35 | 36 | 37 | 38 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|
| m6E7  | D | I | V | L | T | Q | S | P | S | H | K | F | M | S | T | S | V | S | L | G | Q | R | A | T | I | S | C | R | A | S | Q | S | V | S | T | S | S | Y | M | H | W | F |
| m21C9 | D | I | Q | M | T | Q | S | P | A | I | M | S | A | S | P | G | E | K | V | T | M | T | C | S | A | S | Q |   |   |   |   |   | D | V | S | T | A | V | A | W | Y | Q |
| m20B1 | D | I | V | M | T | Q | S | P | S | S | L | S | A | S | V | G | D | R | V | T | I | T | C |   |   |   |   |   |   |   |   |   |   |   |   |   |   |   |   |   |   |   |
| m28H12| D | I | Q | M | T | Q | S | P | A | S | L | A | V | S | L | G | Q | R | A | T | I | S | C | R | A | S | Q | S | V | S | S | S | S | Y | S | Y | M | E | W | Y | Q | Q |

CDR L1 - Contact (24–34)
CDR L1 - Chothia (27–32)
CDR L1 - Kabat (24–34)

| Kabat Number | 39 | 40 | 41 | 42 | 43 | 44 | 45 | 46 | 47 | 48 | 49 | 50 | 51 | 52 | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 | 79 | 80 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|
| m6E7  | K | P | G | Q | P | P | K | L | L | I | Y | K | Y | A | S | N | L | E | S | G | V | P | A | R | F | S | G | S | G | S | G | T | D | F | T | L | N | I | H | P | V | E |
| m21C9 | K | P | G | Q | S | P | K | L | L | I | Y | S | P | S | Y | R | L | T | G | V | P | D | R | F | T | G | S | G | S | G | T | D | F | T | L | T | I | S | S | V | Q | A |
| m20B1 | K | P | G | T | S | P | K | L | L | I | L | W | I | Y | D | T | S | K | L | A | S | G | V | P | A | R | F | S | G | S | G | T | D | Y | S | L | T | I | S | S | M | E |
| m28H12| K | P | G | Q | P | P | K | L | L | I | Y | K | Y | A | S | N | L | E | S | G | V | P | A | R | F | S | G | S | G | T | D | F | T | L | N | I | H | P | V | E |

CDR L2 - Contact (50–56)
CDR L2 - Chothia (50–56)
CDR L2 - Kabat (50–56)

| Kabat Number | 81 | 82 | 83 | 84 | 85 | 86 | 87 | 88 | 89 | 90 | 91 | 92 | 93 | 94 | 95 | 96 | 97 | 98 | 99 | 100 | 101 | 102 | 103 | 104 | 105 | 106 | 107 |
|---|---|---|---|---|---|---|---|---|---|---|---|---|---|---|---|---|---|---|---|---|---|---|---|---|---|---|---|
| m6E7  | E | D | F | A | T | Y | Y | C | Q | H | S | W | E | I | P | Y | T | F | G | G | G | T | K | L | E | I | K |
| m21C9 | E | D | L | A | V | Y | Y | C | Q | Q | W | S | S | . | . | W | T | F | G | G | G | T | K | L | E | I | K |
| m20B1 | E | D | A | A | T | Y | Y | C | Q | Q | R | S | S | . | . | W | Y | F | F | G | G | G | T | K | L | E | I | K |
| m28H12| E | D | F | A | T | Y | Y | C | Q | H | S | W | E | I | P | Y | T | F | G | G | G | T | K | L | E | I | K |

CDR L3 - Contact (89–96)
CDR L3 - Chothia (89–97)
CDR L3 - Kabat (89–97)

FIG. 1A

Heavy Chain Variable Region

Light Chain Variable Region

| Kabat Number | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 | 36 | 37 | 38 | 39 | 40 | 41 | 42 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|
| K1H1 | D | I | Q | M | T | Q | S | P | S | S | L | S | A | S | V | G | D | R | V | T | I | T | C | R | A | S | Q | G | I | S | S | Y | L | A | W | Y | Q | Q | K | P | G | K |
| m21C9 | D | I | Q | M | T | Q | S | H | K | F | M | S | T | S | V | G | D | R | V | S | I | T | C | K | A | S | Q | D | V | S | T | A | V | A | W | F | Q | Q | K | P | G | Q |
| h21C9.L2H3 | D | I | Q | M | T | Q | S | P | S | S | L | S | A | S | V | G | D | R | V | T | I | T | C | K | A | S | Q | D | V | S | T | A | V | A | W | Y | Q | Q | K | P | G | K |

CDR L1 – Contact: 30–36
CDR L1 – Chothia: 24–34
CDR L1 – Kabat: 24–34

| Kabat Number | 43 | 44 | 45 | 46 | 47 | 48 | 49 | 50 | 51 | 52 | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 | 79 | 80 | 81 | 82 | 83 | 84 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|
| K1H1 | A | P | K | L | L | I | Y | A | A | S | S | L | Q | S | G | V | P | S | R | F | S | G | S | G | S | G | T | D | F | T | L | T | I | S | S | L | Q | P | E | D | F | A |
| m21C9 | S | P | K | L | L | I | Y | S | P | S | Y | R | Y | T | G | V | P | D | R | F | T | G | S | G | S | G | T | D | F | T | F | T | I | S | S | V | Q | A | E | D | L | A |
| h21C9.L2H3 | A | P | K | L | L | I | Y | S | P | S | Y | R | Y | T | G | V | P | S | R | F | S | G | S | G | S | G | T | D | F | T | L | T | I | S | S | L | Q | P | E | D | F | A |

CDR L2 – Contact: 46–55
CDR L2 – Chothia: 50–56
CDR L2 – Kabat: 50–56

| Kabat Number | 85 | 86 | 87 | 88 | 89 | 90 | 91 | 92 | 93 | 94 | 95 | 96 | 97 | 98 | 99 | 100 | 101 | 102 | 103 | 104 | 105 | 106 | 107 |
|---|---|---|---|---|---|---|---|---|---|---|---|---|---|---|---|---|---|---|---|---|---|---|---|
| K1H1 | T | Y | Y | C | Q | Q | Y | S | L | P | F | T | F | G | Q | G | T | K | V | E | I | K |  |
| m21C9 | V | Y | Y | C | Q | Q | Y | S | P | P | Y | T | F | G | G | G | T | K | L | E | I | K |  |
| h21C9.L2H3 | T | Y | Y | C | Q | Q | Y | S | P | P | Y | T | F | G | Q | G | T | K | V | E | I | K |  |

CDR L3 – Contact: 89–96
CDR L3 – Chothia: 89–97
CDR L3 – Kabat: 89–97

ANTI-CLL-1 ANTIBODIES AND IMMUNOCONJUGATES

CROSS REFERENCE TO RELATED APPLICATIONS

This patent application is a division of U.S. application Ser. No. 14/852,369, filed Sep. 11, 2015, which claims priority to U.S. Provisional Application Ser. No. 62/049,876, filed on Sep. 12, 2014, the contents of each of which is incorporated by reference in its entirety.

SEQUENCE LISTING

The instant application contains a Sequence Listing submitted via EFS-Web and hereby incorporated by reference in its entirety. Said ASCII copy, created on Sep. 2, 2015, is named P32314-1-NP_SL.txt.txt, and is 40,383 bytes in size.

FIELD OF THE INVENTION

The present invention relates to anti-CLL-1 antibodies and immunoconjugates and methods of using the same.

BACKGROUND

CLL-1 (also referred to as CLEC12A, MICL, and DCAL2), encodes a member of the C-type lectin/C-type lectin-like domain (CTL/CTLD) superfamily. Members of this family share a common protein fold and have diverse functions, such as cell adhesion, cell-cell signaling, glycoprotein turnover, and roles in inflammation and immune response. CLL-1 has been shown to type II transmembrane receptor comprising a single C-type lectin-like domain (which is not predicted to bind either calcium or sugar), a stalk region, a transmembrane domain and a short cytoplasmic tail containing an ITIM motif. Further, CLL-1 is present on monocytes and granulocytes in normal peripheral blood and bone marrow (BM), while absent in nonhematological tissues. CLL-1 is also expressed on acute myeloid leukemia (AML), myelodisplastic syndrome (MDS), and chronic myelogenous leukemia (CML) cells. In particular, CLL-1 is a leukemia stem cell (LSC)-associated surface antigen expressed on a fraction of CD34+CD38− AML cells in CD34 positive (CD34+) AML.

Monoclonal antibody (mAb)-based therapy has become an important treatment modality for cancer. Leukemia is well suited to this approach because of the accessibility of malignant cells in the blood, bone marrow, spleen, and lymph nodes and the well-defined immunophenotypes of the various lineages and stages of hematopoietic differentiation that permit identification of antigenic targets. Most studies for acute myeloid leukemia (AML) have focused on CD33. However, responses with the unconjugated anti-CD33 mAb lintuzumab have had modest single agent and activity against AML and failed to improve patient outcomes in two randomized trials when combined with conventional chemotherapy.

There is a need in the art for safe and effective agents that target AML including CLL-1 for the diagnosis and treatment of CLL-1-associated conditions, such as cancer. The invention fulfills that need and provides other benefits.

SUMMARY

The invention provides anti-CLL-1 antibodies and immunoconjugates and methods of using the same.

Provided herein are isolated monoclonal anti-CLL-1 antibodies, wherein the antibody binds an epitope and/or binds an overlapping epitope comprising amino acids of SEQ ID NO:49 and does not bind an epitope comprising SEQ ID NO:50 and/or SEQ ID NO:51. In some embodiments, the anti-CLL-1 antibody binds an epitope comprising amino acids of SEQ ID NO:49. In some embodiments, the anti-CLL-1 antibody binds an epitope consisting or consisting essentially of the amino acids of SEQ ID NO:49. In some embodiments, the epitope is determined by hydroxyl radical footprinting.

Further provided herein isolated antibody that binds to CLL-1, wherein the antibody comprises (a) HVR-H1 comprising the amino acid sequence of SEQ ID NO:8; (b) HVR-H2 comprising the amino acid sequence of SEQ ID NO:45; (c) HVR-H3 comprising the amino acid sequence of SEQ ID NO:10; (d) HVR-L1 comprising the amino acid sequence of SEQ ID NO:5; (e) HVR-L2 comprising the amino acid sequence of SEQ ID NO:6; and (f) HVR-L3 comprising the amino acid sequence of SEQ ID NO:7. In some embodiments, the antibody comprises HVR-H2 comprising the amino acid sequence of SEQ ID NO:9. In some embodiments, the antibody comprises HVR-H2 comprising the amino acid sequence of SEQ ID NO:47. In some embodiments, the antibody comprises HVR-H2 comprising the amino acid sequence of SEQ ID NO:11. In some embodiments, the antibody comprises HVR-H2 comprising the amino acid sequence of SEQ ID NO:43. In some embodiments, the antibody comprises HVR-H2 comprising the amino acid sequence of SEQ ID NO:44.

In some embodiments, the antibody comprises: (a) a heavy chain variable region comprising the sequence of SEQ ID NO: 33 and a light chain variable region comprising the sequence of SEQ ID NO: 32; (b) a heavy chain variable region comprising the sequence of SEQ ID NO: 34 and a light chain variable region comprising the sequence of SEQ ID NO: 32; (c) a heavy chain variable region comprising the sequence of SEQ ID NO: 46 and a light chain variable region comprising the sequence of SEQ ID NO: 32; or (d) a heavy chain variable region comprising the sequence of SEQ ID NO: 48 and a light chain variable region comprising the sequence of SEQ ID NO: 32. In some embodiments, the antibody comprises a heavy chain variable region comprising the sequence of SEQ ID NO: 48 and a light chain variable region comprising the sequence of SEQ ID NO: 32. In some embodiments, the antibody comprises a heavy chain variable region comprising the sequence of SEQ ID NO: 34 and a light chain variable region comprising the sequence of SEQ ID NO: 32.

Provided herein are also isolated antibodies that binds to CLL-1, wherein the antibody comprises (a) HVR-H1 comprising the amino acid sequence of SEQ ID NO:21; (b) HVR-H2 comprising the amino acid sequence of SEQ ID NO:22; (c) HVR-H3 comprising the amino acid sequence of SEQ ID NO:23; (d) HVR-L1 comprising the amino acid sequence of SEQ ID NO:18; (e) HVR-L2 comprising the amino acid sequence of SEQ ID NO:19; and (f) HVR-L3 comprising the amino acid sequence of SEQ ID NO:20. In some embodiments, the antibody comprises (a) a heavy chain variable region comprising the sequence of SEQ ID NO: 38 and (b) a light chain variable region comprising the sequence of SEQ ID NO: 37.

In some embodiments of any of the antibodies, the antibody binds to recombinant human CLL-1. In some embodiments of any of the antibodies, the antibody binds to recombinant cynomolgus monkey CLL-1. In some embodiments of any of the antibodies, the antibody binds to endogenous CLL-1 on the surface of human peripheral blood mononucleocytes (PBMCs). In some embodiments of any of the antibodies, the antibody binds to endogenous CLL-1 on the surface of cynomolgus monkey PBMCs. In some embodiments of any of the antibodies, the antibody binds to endogenous CLL-1 on the surface of a cancer cell. In some embodiments of any of the antibodies, the antibody binds to endogenous CLL-1 on the surface of an AML cancer cell. In some embodiments of any of the antibodies, the antibody binds to endogenous CLL-1 on the surface of HL-60 cells. In some embodiments of any of the antibodies, the antibody binds to endogenous CLL-1 on the surface of EOL-1 cells. In some embodiments of any of the antibodies, the antibody binds to CLL-1 comprising a K244Q mutation (SEQ ID NO:1 with K244Q). In some embodiments of any of the antibodies, the antibody binds an epitope and/or binds an overlapping epitope comprising amino acids of SEQ ID NO:49. In some embodiments of any of the antibodies, the antibody does not bind an epitope comprising SEQ ID NO:50 and/or SEQ ID NO:51. In some embodiments of any of the antibodies, the antibody competes for human CLL-1 binding with R&D System Clone 687317antibody. In some embodiments of any of the antibodies, the antibody binds to endogenous human CLL-1 with a Kd of less than 15 nM, less than 10 nM, less than 7 nM, less than 5 nM, or less than 3 nM. In some embodiments of any of the antibodies, the antibody binds to recombinant human CLL-1 with a Kd of less than 10 nM, less than 7 nM, less than 5 nM, or less than 3 nM. In some embodiments of any of the antibodies, the antibody binds to recombinant cynomolgus monkey CLL-1 with a Kd of less than 10 nM, less than 7 nM, less than 5 nM, or less than 3 nM, less than 2 nM, or less than 1 nM.

In some embodiments of any of the antibodies, the antibody comprises one or more engineered free cysteine amino acids residues. In some embodiments, the one or more engineered free cysteine amino acid residues is located in the light chain. In some embodiments, the one or more engineered free cysteine amino residues in the light chain comprises V205C according to Kabat numbering. In some embodiments, the one or more engineered free cysteine amino residues in the light chain comprises K149C according to Kabat numbering. In some embodiments, the one or more engineered free cysteine amino acid residues is located in the heavy chain. In some embodiments, the one or more engineered free cysteine amino residues in the heavy chain comprises A1118C according to EU numbering. In some embodiments, the one or more engineered free cysteine amino residues in the heavy chain comprises S400C according to EU numbering.

In some embodiments of any of the antibodies, the antibody is a monoclonal antibody. In some embodiments of any of the antibodies, the antibody is a human or chimeric antibody. In some embodiments of any of the antibodies, the antibody is an antibody fragment that binds CLL-1. In some embodiments of any of the antibodies, the antibody is an IgG1, IgG2a or IgG2b antibody.

Further provided herein are isolated nucleic acid encoding the antibodies described herein. Also provided herein are host cell comprising the nucleic acid encoding the antibodies described herein. Provided herein are also methods of producing an antibody comprising culturing the host cell comprising the nucleic acid encoding the antibodies described herein so that the antibody is produced.

Provided herein are immunoconjugates comprising the antibodies described herein and a cytotoxic agent. In particular, provided herein are immunoconjugates having the formula Ab-(L-D)p, wherein:

(a) Ab is the antibody described herein;

(b) L is a linker;

(c) D is a cytotoxic agent and the cytotoxic agent is a drug; and (d) p ranges from 1-8.

In some embodiments of any of the immunoconjugates, the cytotoxic agent is selected from a maytansinoid, a calicheamicin, a pyrrolobenzodiazepine, and a nemorubicin derivative. In some embodiments of any of the immunoconjugates, D is a pyrrolobenzodiazepine of Formula A:

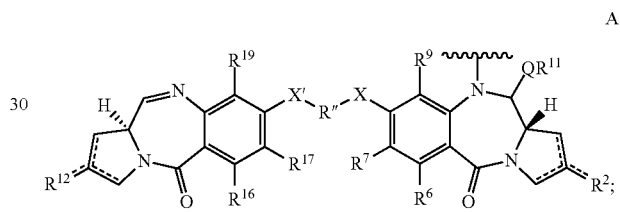

A wherein the dotted lines indicate the optional presence of a double bond between C1 and C2 or C2 and C3;

$R^2$ is independently selected from H, OH, =O, =CH$_2$, CN, R, OR, =CH—R$^D$, =C(R$^D$)$_2$, O—SO$_2$—R, CO$_2$R and COR, and optionally further selected from halo or dihalo, wherein R$^D$ is independently selected from R, CO$_2$R, COR, CHO, CO$_2$H, and halo;

$R^6$ and $R^9$ are independently selected from H, R, OH, OR, SH, SR, NH$_2$, NHR, NRR', NO$_2$, Me$_3$Sn and halo;

$R^7$ is independently selected from H, R, OH, OR, SH, SR, NH$_2$, NHR, NRR', NO$_2$, Me$_3$Sn and halo;

Q is independently selected from O, S and NH;

$R^{11}$ is either H, or R or, where Q is O, SO$_3$M, where M is a metal cation;

R and R' are each independently selected from optionally substituted C$_{1-8}$ alkyl, C$_{3-8}$ heterocyclyl and C$_{5-20}$ aryl groups, and optionally in relation to the group NRR', R and R' together with the nitrogen atom to which they are attached form an optionally substituted 4-, 5-, 6- or 7-membered heterocyclic ring;

$R^{12}$, $R^{16}$, $R^{19}$ and $R^{17}$ are as defined for $R^2$, $R^6$, $R^9$ and $R^7$ respectively;

R" is a C$_{3-12}$ alkylene group, which chain may be interrupted by one or more heteroatoms and/or aromatic rings that are optionally substituted; and X and X' are independently selected from O, S and N(H).

In some embodiments of any of the immunoconjugates, D has the structure:

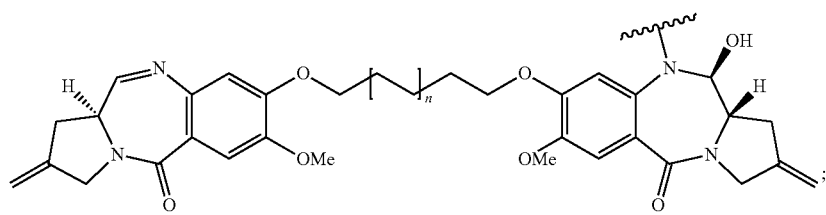

wherein n is 0 or 1.

In some embodiments of any of the immunoconjugates, D has a structure:

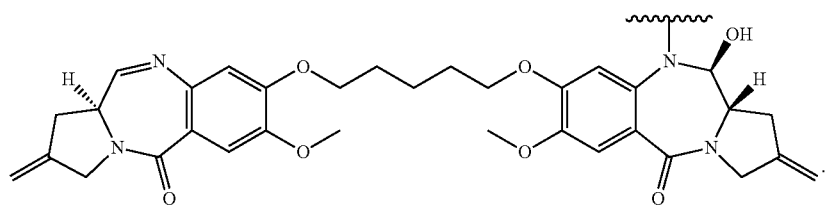

In some embodiments of any of the immunoconjugates, D is a nemorubicin derivative. In some embodiments of any of the immunoconjugates, D has a structure:

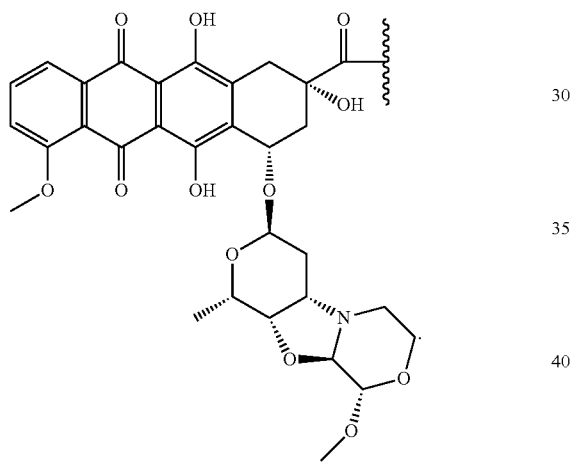

In some embodiments of any of the immunoconjugates, L is cleavable by a protease. In some embodiments of any of the immunoconjugates, L is acid-labile. In some embodiments of any of the immunoconjugates, L comprises hydrazone.

In some embodiments of any of the immunoconjugates, the immunoconjugate has a structure:

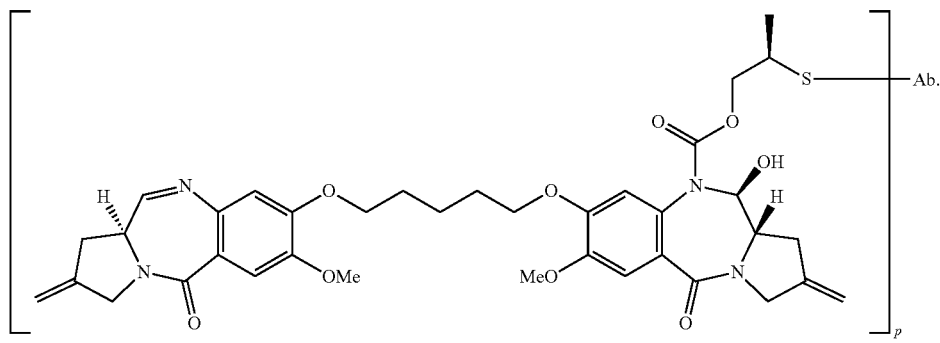

In some embodiments of any of the immunoconjugates, p ranges from 2-5.

In some embodiments, pharmaceutical formulations are provided. In some embodiments, a pharmaceutical formulation comprises an immunoconjugate described herein and a pharmaceutically acceptable carrier. In some embodiments, the pharmaceutical formulation comprises an additional therapeutic agent. In some embodiments, the additional therapeutic agent is an anthracycline. In some embodiments, the anthracycline is daunorubicin or idarubicin. In some embodiments, the additional therapeutic agent is cytarabine. In some embodiments, the additional therapeutic agent is cladribine. In some embodiments, the additional therapeutic agent is fludarabine or topotecan. In some embodiments, the additional therapeutic agent is 5-azacytidine or decitabine.

In some embodiments, methods of treatment are provided. In some embodiments, methods of treating CLL-1-positive cancers are provided. In some embodiments, a method of treatment comprises administering to an individual an effective amount of an immunoconjugate described herein or a pharmaceutical formulation described herein. In some embodiments, the cancer is a cancer. In some embodiments, the cancer is acute myeloid leukemia (AML), chronic myeloid leukemia (CML), and/or myelodysplastic syndrome (MDS). In some embodiments, the cancer is CLL-1 positive. In some embodiments, the CLL-1-positive cancer is AML. In some embodiments, the method comprises administering an additional therapeutic agent to the individual. In some embodiments, the additional therapeutic agent is an anthracycline. In some embodiments, the anthracycline is daunorubicin or idarubicin. In some embodiments, the additional therapeutic agent is cytarabine. In some embodiments, the additional therapeutic agent is cladribine. In some embodiments, the additional therapeutic agent is fludarabine or topotecan. In some embodiments, the additional therapeutic agent is 5-azacytidine or decitabine.

In some embodiments of any of the methods, the method further comprises administering to the subject a PD-1 axis binding antagonist or an additional therapeutic agent. In some embodiments, the PD-1 axis binding antagonist is a PD-1 binding antagonist. In some embodiments, the PD-1 axis binding antagonist is a PD-L1 binding antagonist. In some embodiments, the PD-1 axis binding antagonist is a PD-L2 binding antagonist.

In some embodiments, methods of inhibiting proliferation of a CLL-1-positive cell are provided. In some embodiments, the method comprises exposing the cell to an immunoconjugate described herein under conditions permissive for binding of the immunoconjugate to CLL-1 on the surface of the cell, thereby inhibiting proliferation of the cell. In some embodiments, the cell is an AML cancer cell.

In some embodiments, a method of detecting human CLL-1 in a biological sample is provided. In some embodiments, a method comprises contacting the biological sample with an anti-CLL-1 antibody under conditions permissive for binding of the anti-CLL-1 antibody to a naturally occurring human CLL-1, and detecting whether a complex is formed between the anti-CLL-1 antibody and a naturally occurring human CLL-1 in the biological sample. In some embodiments, an anti-CLL-1 antibody is an antibody described herein. In some embodiments, the biological sample is an AML cancer sample.

In some embodiments, a method for detecting a CLL-1-positive cancer is provided. In some such embodiments, a method comprises (i) administering a labeled anti-CLL-1 antibody to a subject having or suspected of having a CLL-1-positive cancer, and (ii) detecting the labeled anti-CLL-1 antibody in the subject, wherein detection of the labeled anti-CLL-1 antibody indicates a CLL-1-positive cancer in the subject. In some embodiments, an anti-CLL-1 antibody is an antibody described herein. In some such embodiments, the labeled anti-CLL-1 antibody comprises an anti-CLL-1 antibody conjugated to a positron emitter. In some embodiments, the positron emitter is $^{89}Zr$.

BRIEF DESCRIPTION OF THE FIGURES

FIGS. 1A-B shows alignment of the light chain variable region sequences (A) and heavy chain variable region sequences (B) of murine (m) 6E7 (SEQ ID NOS: 30 and 31, respectively), m21C9 (SEQ ID NOS: 37 and 38, respectively), m20B1 (SEQ ID NOS: 35 and 36, respectively), and m28H12 (SEQ ID NOS: 41 and 42, respectively).

FIGS. 2A-B shows alignment of the light chain variable region sequences (A) and heavy chain variable region sequences (B) of K1H1 (SEQ ID NOS: 72 and 73, respectively), m6E7 (SEQ ID NOS: 30 and 31, respectively), humanized (h) 6E7.L4H1e (SEQ ID NOS: 32 and 33, respectively), and h6E7.L4H1e.A54 (SEQ ID NOS: 32 and 34, respectively).

FIGS. 3A-B shows alignment of the light chain variable region sequences (A) and heavy chain variable region sequences (B) of K1H1 (SEQ ID NOS: 72 and 73, respectively), m21C9 (SEQ ID NOS: 37 and 38, respectively), and h21C9.L2H3 (SEQ ID NOS: 39 and 40, respectively).

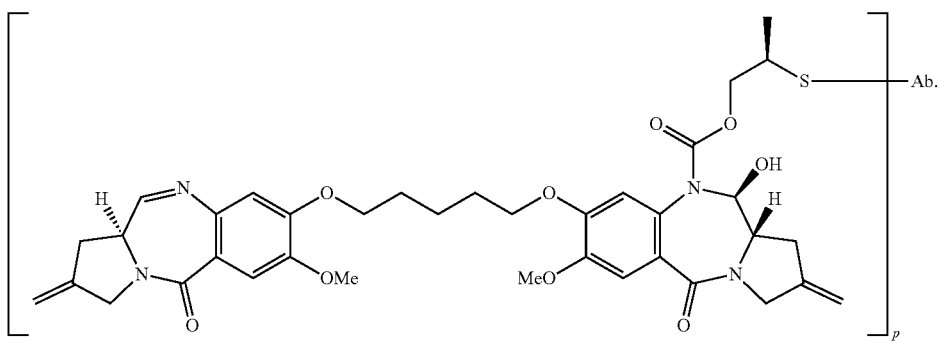

Figure 7:
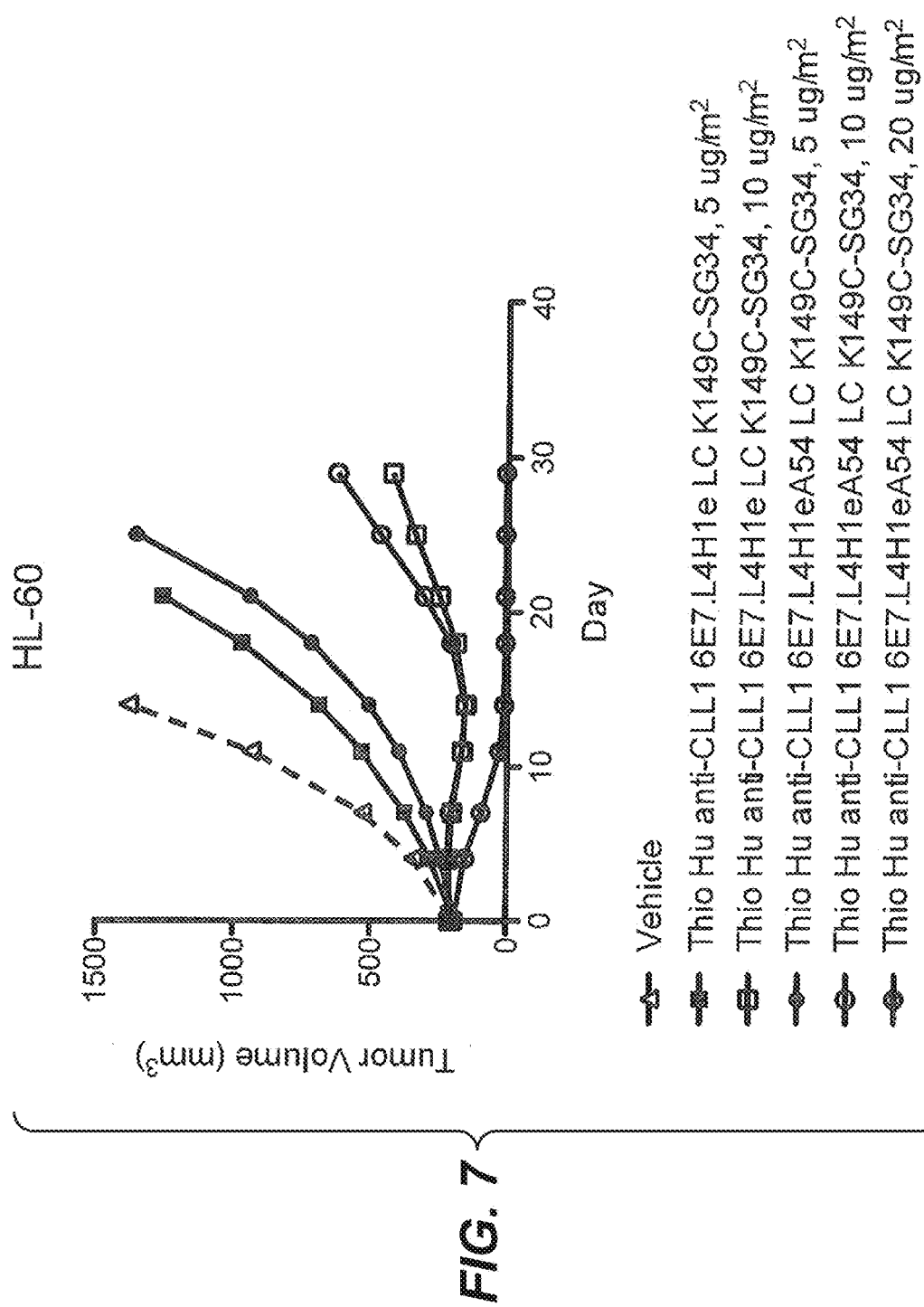

FIG. 7 shows change in tumor volume (mm³) over time upon treatment with the humanized antibody 6E7.L4H1e or 6E7.L4H1eN54A with a cysteine engineered light chain at amino acid residue number 149 according to Kabat numbering (K149C) conjugated to PBD (SG34) at 5 μg/m², 10 μg/m², or 20 μg/m² in HL-60 xenograft model.

DETAILED DESCRIPTION

I. Definitions

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Specific illustrative and exemplary embodiments for measuring binding affinity are described in the following.

An "affinity matured" antibody refers to an antibody with one or more alterations in one or more hypervariable regions (HVRs), compared to a parent antibody which does not possess such alterations, such alterations resulting in an improvement in the affinity of the antibody for antigen.

The terms "anti-CLL-1 antibody" and "an antibody that binds to CLL-1" refer to an antibody that is capable of binding CLL-1 with sufficient affinity such that the antibody is useful as a diagnostic and/or therapeutic agent in targeting CLL-1. In one embodiment, the extent of binding of an anti-CLL-1 antibody to an unrelated, non-CLL-1 protein is less than about 10% of the binding of the antibody to CLL-1 as measured, e.g., by a radioimmunoassay (RIA). In certain embodiments, an antibody that binds to CLL-1 has a dissociation constant (Kd) of ≤1 μM, ≤100 nM, ≤10 nM, ≤5 nm, ≤4 nM, ≤3 nM, ≤2 nM, ≤1 nM, ≤0.1 nM, ≤0.01 nM, or ≤0.001 nM (e.g., $10^{-8}$ M or less, e.g. from $10^{-8}$ M to $10^{-13}$ M, e.g., from $10^{-9}$M to $10^{-13}$ M). In certain embodiments, an anti-CLL-1 antibody binds to an epitope of CLL-1 that is conserved among CLL-1 from different species.

The term "antibody" is used herein in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

An "antibody fragment" refers to a molecule other than an intact antibody that comprises a portion of an intact antibody and that binds the antigen to which the intact antibody binds. Examples of antibody fragments include but are not limited to Fv, Fab, Fab', Fab'-SH, F(ab')₂; diabodies; linear antibodies; single-chain antibody molecules (e.g. scFv); and multispecific antibodies formed from antibody fragments.

The terms "cancer" and "cancerous" refer to or describe the physiological condition in mammals that is typically characterized by unregulated cell growth/proliferation. Examples of cancer include, but are not limited to, carcinoma, lymphoma (e.g., Hodgkin's and non-Hodgkin's lymphoma), blastoma, sarcoma, and leukemia. More particular examples of such cancers include acute myeloid leukemia (AML), myelodysplastic syndrome (MDS), chronic myelogenous leukemia (CML), chronic myelomonocytic leukemia, acute promyelocytic leukemia (APL), chronic myeloproliferative disorder, thrombocytic leukemia, precursor B-cell acute lymphoblastic leukemia (pre-B-ALL), precursor T-cell acute lymphoblastic leukemia (preT-ALL), multiple myeloma (MM), mast cell disease, mast cell leukemia, mast cell sarcoma, myeloid sarcomas, lymphoid leukemia, and undifferentiated leukemia. In some embodiments, the cancer is myeloid leukemia. In some embodiments, the cancer is acute myeloid leukemia (AML).

The term "chimeric" antibody refers to an antibody in which a portion of the heavy and/or light chain is derived from a particular source or species, while the remainder of the heavy and/or light chain is derived from a different source or species.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., IgG₁, IgG₂, IgG₃, IgG₄, IgA₁, and IgA₂. The heavy chain constant domains that correspond to the different classes of immunoglobulins are called α, δ, ε, γ, and μ, respectively.

The term "cytotoxic agent" as used herein refers to a substance that inhibits or prevents a cellular function and/or causes cell death or destruction. Cytotoxic agents include, but are not limited to, radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu); chemotherapeutic agents or drugs (e.g., methotrexate, adriamicin, *vinca* alkaloids (vincristine, vinblastine, etoposide), doxorubicin, melphalan, mitomycin C, chlorambucil, daunorubicin or other intercalating agents); growth inhibitory agents; enzymes and fragments thereof such as nucleolytic enzymes; antibiotics; toxins such as small molecule toxins or enzymatically active toxins of bacterial, fungal, plant or animal origin, including fragments and/or variants thereof; and the various antitumor or anticancer agents disclosed below.

"Effector functions" refer to those biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation.

An "effective amount" of an agent, e.g., a pharmaceutical formulation, refers to an amount effective, at dosages and for periods of time necessary, to achieve the desired therapeutic or prophylactic result.

The term "epitope" refers to the particular site on an antigen molecule to which an antibody binds. In some embodiments, the particular site on an antigen molecule to which an antibody binds is determined by hydroxyl radical footprinting.

The term "Fc region" herein is used to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., *Sequences of Proteins of Immunological Interest*, 5th Ed. Public Health Service, National Institutes of Health, Bethesda, Md., 1991.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3 (L3)-FR4.

The terms "full length antibody," "intact antibody," and "whole antibody" are used herein interchangeably to refer to an antibody having a structure substantially similar to a native antibody structure or having heavy chains that contain an Fc region as defined herein.

The term "glycosylated forms of CLL-1" refers to naturally occurring forms of CLL-1 that are post-translationally modified by the addition of carbohydrate residues.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., *Sequences of Proteins of Immunological Interest*, Fifth Edition, NIH Publication 91-3242, Bethesda Md. (1991), vols. 1-3. In one embodiment, for the VL, the subgroup is subgroup kappa I as in Kabat et al., supra. In one embodiment, for the VH, the subgroup is subgroup III as in Kabat et al., supra.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "hypervariable region" or "HVR," as used herein, refers to each of the regions of an antibody variable domain which are hypervariable in sequence and/or form structurally defined loops ("hypervariable loops"). Generally, native four-chain antibodies comprise six HVRs; three in the VH (H1, H2, H3), and three in the VL (L1, L2, L3). HVRs generally comprise amino acid residues from the hypervariable loops and/or from the "complementarity determining regions" (CDRs), the latter being of highest sequence variability and/or involved in antigen recognition. Exemplary hypervariable loops occur at amino acid residues 26-32 (L1), 50-52 (L2), 91-96 (L3), 26-32 (H1), 53-55 (H2), and 96-101 (H3). (Chothia and Lesk, *J. Mol. Biol.* 196:901-917 (1987).) Exemplary CDRs (CDR-L1, CDR-L2, CDR-L3, CDR-H1, CDR-H2, and CDR-H3) occur at amino acid residues 24-34 of L1, 50-56 of L2, 89-97 of L3, 31-35B of H1, 50-65 of H2, and 95-102 of H3. (Kabat et al., *Sequences of Proteins of Immunological Interest*, 5th Ed. Public Health Service, National Institutes of Health, Bethesda, Md. (1991).) With the exception of CDR1 in VH, CDRs generally comprise the amino acid residues that form the hypervariable loops. CDRs also comprise "specificity determining residues," or "SDRs," which are residues that contact antigen. SDRs are contained within regions of the CDRs called abbreviated-CDRs, or a-CDRs. Exemplary a-CDRs (a-CDR-L1, a-CDR-L2, a-CDR-L3, a-CDR-H1, a-CDR-H2, and a-CDR-H3) occur at amino acid residues 31-34 of L1, 50-55 of L2, 89-96 of L3, 31-35B of H1, 50-58 of H2, and 95-102 of H3. (See Almagro and Fransson, *Front. Biosci.* 13:1619-1633 (2008).) Unless otherwise indicated, HVR residues and other residues in the variable domain (e.g., FR residues) are numbered herein according to Kabat et al., supra.

An "immunoconjugate" is an antibody conjugated to one or more heterologous molecule(s), including but not limited to a cytotoxic agent.

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

An "isolated antibody" is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman et al., *J. Chromatogr. B* 848:79-87 (2007).

An "isolated nucleic acid" refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

"Isolated nucleic acid encoding an anti-CLL-1 antibody" refers to one or more nucleic acid molecules encoding antibody heavy and light chains (or fragments thereof), including such nucleic acid molecule(s) in a single vector or separate vectors, and such nucleic acid molecule(s) present at one or more locations in a host cell.

The term "CLL-1," as used herein, refers to any native, mature CLL-1 which results from processing of a CLL-1 precursor protein in a cell. The term includes CLL-1 from any vertebrate source, including mammals such as primates (e.g. humans and cynomolgus monkeys) and rodents (e.g., mice and rats), unless otherwise indicated. The term also includes naturally occurring variants of CLL-1, e.g., splice variants or allelic variants. The amino acid sequence of an exemplary human CLL-1 protein sequence is shown in SEQ ID NO:1. In some embodiments, the human CLL-1 protein sequence comprises the K244Q SNP (SEQ ID NO:1, wherein K244 is Q). The amino acid sequence of an exemplary extracellular domain is the amino acids of SEQ ID NO:2. The amino acid sequence of an exemplary C-type lectin like domain (CTLD) is the amino acids of SEQ ID NO:3. The amino acid sequence of an exemplary cynomolgus monkey CLL-1 protein is shown in SEQ ID NO:4.

The term "CLL-1-positive cancer" refers to a cancer comprising cells that express CLL-1 on their surface. In some embodiments, expression of CLL-1 on the cell surface is determined, for example, using antibodies to CLL-1 in a method such as immunohistochemistry, FACS, etc. Alternatively, CLL-1 mRNA expression is considered to correlate to CLL-1 expression on the cell surface and can be determined by a method selected from in situ hybridization and RT-PCR (including quantitative RT-PCR).

The term "CLL-1-positive cell" refers to a cell that expresses CLL-1 on its surface.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

A "naked antibody" refers to an antibody that is not conjugated to a heterologous moiety (e.g., a cytotoxic moiety) or radiolabel. The naked antibody may be present in a pharmaceutical formulation.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant domain.

The term "package insert" is used to refer to instructions customarily included in commercial packages of therapeutic products, that contain information about the indications, usage, dosage, administration, combination therapy, contraindications and/or warnings concerning the use of such therapeutic products.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S.

Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or to slow the progression of a disease.

A "chemotherapeutic agent" refers to a chemical compound useful in the treatment of cancer. Examples of chemotherapeutic agents include alkylating agents such as thiotepa and cyclosphosphamide (CYTOXAN®); alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlomaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omega1I (see, e.g., Nicolaou et al., Angew. Chem Intl. Ed. Engl., 33: 183-186 (1994)); CDP323, an oral alpha-4 integrin inhibitor; dynemicin, including dynemicin A; an esperamicin; as well as neocarzinostatin chromophore and related chromoprotein enediyne antibiotic chromophores), aclacinomysins, actinomycin, authramycin, azaserine, bleomycins, cactinomycin, carabicin, carminomycin, carzinophilin, chromomycins, dactinomycin, daunorubicin, detorubicin, 6-diazo-5-oxo-L-norleucine, doxorubicin (including ADRIAMYCIN®, morpholino-doxorubicin, cyanomorpholino-doxorubicin, 2-pyrrolino-doxorubicin, doxorubicin HCl liposome injection (DOXIL®), liposomal doxorubicin TLC D-99 (MYOCET®), peglylated liposomal doxorubicin (CAELYX®), and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate, gemcitabine (GEMZAR®), tegafur (UFTORAL®), capecitabine (XELODA®), an epothilone, and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfomithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2'-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); thiotepa; taxoid, e.g., paclitaxel (TAXOL®), albumin-engineered nanoparticle formulation of paclitaxel (ABRAXANE™), and docetaxel (TAXOTERE®); chloranbucil; 6-thioguanine; mercaptopurine; methotrexate; platinum agents such as cisplatin, oxaliplatin (e.g., ELOXATIN®), and carboplatin; vincas, which prevent tubulin polymerization from forming microtubules, including vinblastine (VELBAN®), vincristine (ONCOVIN®), vindesine (ELDISINE®, FILDESIN®), and vinorelbine (NAVELBINE®); etoposide (VP-16); ifosfamide; mitoxantrone; leucovorin; novantrone; edatrexate; daunomycin; aminopterin; ibandronate; topoisomerase inhibitor RFS 2000; difluoromethylornithine (DMFO); retinoids such as retinoic acid, including bexarotene (TARGRETIN®); bisphosphonates such as clodronate (for example, BONEFOS® or OSTAC®), etidronate (DIDROCAL®), NE-58095, zoledronic acid/zoledronate (ZOMETA®), alendronate (FOSAMAX®), pamidronate (AREDIA®), tiludronate (SKELID®), or risedronate (ACTONEL®); troxacitabine (a 1,3-dioxolane nucleoside cytosine analog); antisense oligonucleotides, particularly those that inhibit expression of genes in signaling pathways implicated in aberrant cell proliferation, such as, for example, PKC-alpha, Raf, H-Ras, and epidermal growth factor receptor (EGF-R); vaccines such as THERATOPE® vaccine and gene therapy vaccines, for example, ALLOVECTIN® vaccine, LEUVECTIN® vaccine, and VAXID® vaccine; topoisomerase 1 inhibitor (e.g., LURTOTECAN®); rmRH (e.g., ABARELIX®); BAY439006 (sorafenib; Bayer); SU-11248 (sunitinib, SUTENT®, Pfizer); perifosine, COX-2 inhibitor (e.g., celecoxib or etoricoxib), proteosome inhibitor (e.g., PS341); bortezomib (VELCADE®); CCI-779; tipifarnib (R11577); orafenib, ABT510; Bcl-2 inhibitor such as oblimersen sodium (GENASENSE®); pixantrone; EGFR inhibitors (see definition below); tyrosine kinase inhibitors; serine-threonine kinase inhibitors such as rapamycin (sirolimus, RAPAMUNE®); farnesyltransferase inhibitors such as lonafarnib (SCH 6636, SARASAR™); and pharmaceutically acceptable salts, acids or derivatives of any of the above; as well as combinations of two or more of the above such as CHOP, an abbreviation for a combined therapy of cyclophosphamide, doxorubicin, vincristine, and prednisolone; and FOLFOX, an abbreviation for a treatment regimen with oxaliplatin (ELOXATIN™) combined with 5-FU and leucovorin.

Chemotherapeutic agents as defined herein include "anti-hormonal agents" or "endocrine therapeutics" which act to regulate, reduce, block, or inhibit the effects of hormones that can promote the growth of cancer. They may be hormones themselves, including, but not limited to: anti-estrogens with mixed agonist/antagonist profile, including, tamoxifen (NOLVADEX®), 4-hydroxytamoxifen, toremifene (FARESTON®), idoxifene, droloxifene, raloxifene (EVISTA®), trioxifene, keoxifene, and selective estrogen receptor modulators (SERMs) such as SERM3; pure antiestrogens without agonist properties, such as fulvestrant (FASLODEX®), and EM800 (such agents may block estrogen receptor (ER) dimerization, inhibit DNA binding, increase ER turnover, and/or suppress ER levels); aromatase inhibitors, including steroidal aromatase inhibitors such as formestane and exemestane (AROMASIN®), and non-steroidal aromatase inhibitors such as anastrazole (ARIMIDEX®), letrozole (FEMARA®) and aminoglutethimide, and other aromatase inhibitors include vorozole (RIVISOR®), megestrol acetate (MEGASE®), fadrozole, and 4(5)-imidazoles; lutenizing hormone-releaseing hormone agonists, including leuprolide (LUPRON® and ELIGARD®), goserelin, buserelin, and tripterelin; sex steroids, including progestines such as megestrol acetate and medroxyprogesterone acetate, estrogens such as diethylstilbestrol and premarin, and androgens/retinoids such as fluoxymesterone, all transretionic acid and fenretinide; onapristone; anti-progesterones; estrogen receptor down-regulators (ERDs); anti-androgens such as flutamide, nilutamide and bicalutamide; and pharmaceutically acceptable salts, acids or derivatives of any of the above; as well as combinations of two or more of the above.

The term "immunosuppressive agent" as used herein for adjunct therapy refers to substances that act to suppress or mask the immune system of the mammal being treated herein. This would include substances that suppress cytokine production, down-regulate or suppress self-antigen expression, or mask the MHC antigens. Examples of such agents include 2-amino-6-aryl-5-substituted pyrimidines (see U.S. Pat. No. 4,665,077); non-steroidal anti-inflammatory drugs (NSAIDs); ganciclovir, tacrolimus, glucocorticoids such as cortisol or aldosterone, anti-inflammatory agents such as a cyclooxygenase inhibitor, a 5-lipoxygenase inhibitor, or a leukotriene receptor antagonist; purine antagonists such as azathioprine or mycophenolate mofetil (MMF); alkylating agents such as cyclophosphamide; bromocriptine; danazol; dapsone; glutaraldehyde (which masks the MHC antigens, as described in U.S. Pat. No. 4,120,649); anti-idiotypic antibodies for MHC antigens and MHC fragments; cyclosporin A; steroids such as corticosteroids or glucocorticosteroids or glucocorticoid analogs, e.g., prednisone, methylprednisolone, including SOLU-MEDROL® methylprednisolone sodium succinate, and dexamethasone; dihydrofolate reductase inhibitors such as methotrexate (oral or subcutaneous); anti-malarial agents such as chloroquine and hydroxychloroquine; sulfasalazine; leflunomide; cytokine or cytokine receptor antibodies including anti-interferon-alpha, -beta, or -gamma antibodies, antitumor necrosis factor(TNF)-alpha antibodies (infliximab (REMICADE®) or adalimumab), anti-TNF-alpha immunoadhesin (etanercept), anti-TNF-beta antibodies, anti-interleukin-2 (IL-2) antibodies and anti-IL-2 receptor antibodies, and anti-interleukin-6 (IL-6) receptor antibodies and antagonists (such as ACTEMRA™ (tocilizumab)); anti-LFA-1 antibodies, including anti-CD11a and anti-CD18 antibodies; anti-L3T4 antibodies; heterologous anti-lymphocyte globulin; pan-T antibodies, preferably anti-CD3 or anti-CD4/CD4a antibodies; soluble peptide containing a LFA-3 binding domain (WO 90/08187 published Jul. 26, 1990); streptokinase; transforming growth factor-beta (TGF-beta); streptodornase; RNA or DNA from the host; FK506; RS-61443; chlorambucil; deoxyspergualin; rapamycin; T-cell receptor (Cohen et al., U.S. Pat. No. 5,114,721); T-cell receptor fragments (Offner et al., *Science*, 251: 430-432 (1991); WO 90/11294; laneway, *Nature*, 341: 482 (1989); and WO 91/01133); BAFF antagonists such as BAFF antibodies and BR3 antibodies and zTNF4 antagonists (for review, see Mackay and Mackay, *Trends Immunol.*, 23:113-5 (2002) and see also definition below); biologic agents that interfere with T cell helper signals, such as anti-CD40 receptor or anti-CD40 ligand (CD154), including blocking antibodies to CD40-CD40 ligand (e.g., Durie et al., *Science*, 261: 1328-30 (1993); Mohan et al., *J. Immunol.*, 154: 1470-80 (1995)) and CTLA4-Ig (Finck et al., *Science*, 265: 1225-7 (1994)); and T-cell receptor antibodies (EP 340,109) such as T10B9. Some preferred immunosuppressive agents herein include cyclophosphamide, chlorambucil, azathioprine, leflunomide, MMF, or methotrexate.

The term "PD-1 axis binding antagonist" refers to a molecule that inhibits the interaction of a PD-1 axis binding partner with either one or more of its binding partner, so as to remove T-cell dysfunction resulting from signaling on the PD-1 signaling axis—with a result being to restore or enhance T-cell function (e.g., proliferation, cytokine production, target cell killing). As used herein, a PD-1 axis binding antagonist includes a PD-1 binding antagonist, a PD-L1 binding antagonist and a PD-L2 binding antagonist.

The term "PD-1 binding antagonist" refers to a molecule that decreases, blocks, inhibits, abrogates or interferes with signal transduction resulting from the interaction of PD-1 with one or more of its binding partners, such as PD-L1, PD-L2. In some embodiments, the PD-1 binding antagonist is a molecule that inhibits the binding of PD-1 to one or more of its binding partners. In a specific aspect, the PD-1 binding antagonist inhibits the binding of PD-1 to PD-L1 and/or PD-L2. For example, PD-1 binding antagonists include anti-PD-1 antibodies, antigen binding fragments thereof, immunoadhesins, fusion proteins, oligopeptides and other molecules that decrease, block, inhibit, abrogate or interfere with signal transduction resulting from the interaction of PD-1 with PD-L1 and/or PD-L2. In one embodiment, a PD-1 binding antagonist reduces the negative co-stimulatory signal mediated by or through cell surface proteins expressed on T lymphocytes mediated signaling through PD-1 so as render a dysfunctional T-cell less dysfunctional (e.g., enhancing effector responses to antigen recognition). In some embodiments, the PD-1 binding antagonist is an anti-PD-1 antibody. In a specific aspect, a PD-1 binding antagonist is MDX-1106 (nivolumab) described herein. In another specific aspect, a PD-1 binding antagonist is MK-3475 (lambrolizumab) described herein. In another specific aspect, a PD-1 binding antagonist is CT-011 (pidilizumab) described herein. In another specific aspect, a PD-1 binding antagonist is AMP-224 described herein.

The term "PD-L1 binding antagonist" refers to a molecule that decreases, blocks, inhibits, abrogates or interferes with signal transduction resulting from the interaction of PD-L1 with either one or more of its binding partners, such as PD-1, B7-1. In some embodiments, a PD-L1 binding antagonist is a molecule that inhibits the binding of PD-L1 to its binding partners. In a specific aspect, the PD-L1 binding antagonist inhibits binding of PD-L1 to PD-1 and/or B7-1. In some embodiments, the PD-L1 binding antagonists include anti-PD-L1 antibodies, antigen binding fragments thereof, immunoadhesins, fusion proteins, oligopeptides and other molecules that decrease, block, inhibit, abrogate or interfere with signal transduction resulting from the interaction of PD-L1 with one or more of its binding partners, such as PD-1, B7-1. In one embodiment, a PD-L1 binding antagonist reduces the negative co-stimulatory signal mediated by or through cell surface proteins expressed on T lymphocytes mediated signaling through PD-L1 so as to render a dysfunctional T-cell less dysfunctional (e.g., enhancing effector responses to antigen recognition). In some embodiments, a PD-L1 binding antagonist is an anti-PD-L1 antibody. In a specific aspect, an anti-PD-L1 antibody is YW243.55.S70 described herein. In another specific aspect, an anti-PD-L1 antibody is MDX-1105 described herein. In still another specific aspect, an anti-PD-L1 antibody is MPDL3280A described herein. In still another specific aspect, an anti-PD-L1 antibody is MEDI4736 described herein.

The term "PD-L2 binding antagonist" refers to a molecule that decreases, blocks, inhibits, abrogates or interferes with signal transduction resulting from the interaction of PD-L2 with either one or more of its binding partners, such as PD-1. In some embodiments, a PD-L2 binding antagonist is a molecule that inhibits the binding of PD-L2 to one or more of its binding partners. In a specific aspect, the PD-L2 binding antagonist inhibits binding of PD-L2 to PD-1. In some embodiments, the PD-L2 antagonists include anti-PD-L2 antibodies, antigen binding fragments thereof, immunoadhesins, fusion proteins, oligopeptides and other molecules that decrease, block, inhibit, abrogate or interfere with signal transduction resulting from the interaction of PD-L2 with either one or more of its binding partners, such as PD-1. In one embodiment, a PD-L2 binding antagonist reduces the negative co-stimulatory signal mediated by or through cell surface proteins expressed on T lymphocytes mediated signaling through PD-L2 so as render a dysfunctional T-cell less dysfunctional (e.g., enhancing effector responses to antigen recognition). In some embodiments, a PD-L2 binding antagonist is an immunoadhesin.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt et al. *Kuby Immunology*, 6$^{th}$ ed., W.H. Freeman and Co., page 91 (2007).) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., *J. Immunol.* 150:880-887 (1993); Clarkson et al., *Nature* 352:624-628 (1991).

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

"Alkyl" is $C_1$-$C_{18}$ hydrocarbon containing normal, secondary, tertiary or cyclic carbon atoms. Examples are methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$).

The term "$C_1$-$C_8$ alkyl," as used herein refers to a straight chain or branched, saturated or unsaturated hydrocarbon having from 1 to 8 carbon atoms. Representative "$C_1$-$C_8$ alkyl" groups include, but are not limited to, -methyl, -ethyl, -n-propyl, -n-butyl, -n-pentyl, -n-hexyl, -n-heptyl, -n-octyl, -n-nonyl and -n-decyl; while branched $C_1$-$C_8$ alkyls include, but are not limited to, -isopropyl, -sec-butyl, -isobutyl, -tert-butyl, -isopentyl, 2-methylbutyl, unsaturated $C_1$-$C_8$ alkyls include, but are not limited to, -vinyl, -allyl, -1-butenyl, -2-butenyl, -isobutylenyl, -1-pentenyl, -2-pentenyl, -3-methyl-1-butenyl, -2-methyl-2-butenyl, -2,3-dimethyl-2-butenyl, 1-hexyl, 2-hexyl, 3-hexyl, -acetylenyl, -propynyl, -1-butynyl, -2-butynyl, -1-pentynyl, -2-pentynyl, -3-methyl-1 butynyl. A $C_1$-$C_8$ alkyl group can be unsubstituted or substituted with one or more groups including, but not limited to, —$C_1$-$C_8$ alkyl, —O—($C_1$-$C_8$ alkyl), -aryl, —C(O)R', —OC(O)R', —C(O)OR', —C(O)NH$_2$, —C(O)NHR', —C(O)N(R')$_2$—NHC(O)R', —SO$_3$R', —S(O)$_2$R', —S(O)R', —OH, -halogen, —N$_3$, —NH$_2$, —NH(R'), —N(R')$_2$ and —CN; where each R' is independently selected from H, —$C_1$-$C_8$ alkyl and aryl.

The term "$C_1$-$C_{12}$ alkyl," as used herein refers to a straight chain or branched, saturated or unsaturated hydrocarbon having from 1 to 12 carbon atoms. A $C_1$-$C_{12}$ alkyl group can be unsubstituted or substituted with one or more groups including, but not limited to, —$C_1$-$C_8$ alkyl, —O—($C_1$-$C_8$ alkyl), -aryl, —C(O)R', —OC(O)R', —C(O)OR', —C(O)NH$_2$, —C(O)NHR', —C(O)N(R')$_2$—NHC(O)R', —SO$_3$R', —S(O)$_2$R', —S(O)R', —OH, -halogen, —N$_3$, —NH$_2$, —NH(R'), —N(R')$_2$ and —CN; where each R' is independently selected from H, —$C_1$-$C_8$ alkyl and aryl.

The term "$C_1$-$C_6$ alkyl," as used herein refers to a straight chain or branched, saturated or unsaturated hydrocarbon having from 1 to 6 carbon atoms. Representative "$C_1$-$C_6$ alkyl" groups include, but are not limited to, -methyl, -ethyl, -n-propyl, -n-butyl, -n-pentyl, -and n-hexyl; while branched $C_1$-$C_6$ alkyls include, but are not limited to, -isopropyl, -sec-butyl, -isobutyl, -tert-butyl, -isopentyl, and 2-methylbutyl; unsaturated $C_1$-$C_6$ alkyls include, but are not limited to, -vinyl, -allyl, -1-butenyl, -2-butenyl, and -isobutylenyl, -1-pentenyl, -2-pentenyl, -3-methyl-1-butenyl, -2-methyl-2-butenyl, -2,3-dimethyl-2-butenyl, 1-hexyl, 2-hexyl, and 3-hexyl. A $C_1$-$C_6$ alkyl group can be unsubstituted or substituted with one or more groups, as described above for $C_1$-$C_8$ alkyl group.

The term "$C_1$-$C_4$ alkyl," as used herein refers to a straight chain or branched, saturated or unsaturated hydrocarbon having from 1 to 4 carbon atoms. Representative "$C_1$-$C_4$ alkyl" groups include, but are not limited to, -methyl, -ethyl, -n-propyl, -n-butyl; while branched $C_1$-$C_4$ alkyls include, but are not limited to, -isopropyl, -sec-butyl, -isobutyl, -tert-butyl; unsaturated $C_1$-$C_4$ alkyls include, but are not limited to, -vinyl, -allyl, -1-butenyl, -2-butenyl, and -isobutylenyl. A $C_1$-$C_4$ alkyl group can be unsubstituted or substituted with one or more groups, as described above for $C_1$-$C_8$ alkyl group.

"Alkoxy" is an alkyl group singly bonded to an oxygen. Exemplary alkoxy groups include, but are not limited to, methoxy (—OCH$_3$) and ethoxy (—OCH$_2$CH$_3$). A "$C_1$-$C_5$ alkoxy" is an alkoxy group with 1 to 5 carbon atoms. Alkoxy groups may can be unsubstituted or substituted with one or more groups, as described above for alkyl groups.

"Alkenyl" is $C_2$-$C_{18}$ hydrocarbon containing normal, secondary, tertiary or cyclic carbon atoms with at least one site of unsaturation, i.e. a carbon-carbon, sp$^2$ double bond. Examples include, but are not limited to: ethylene or vinyl (—CH═CH$_2$), allyl (—CH$_2$CH═CH$_2$), cyclopentenyl (—C5H7), and 5-hexenyl (—CH$_2$ CH$_2$CH$_2$CH$_2$CH═CH$_2$). A "$C_2$-$C_8$ alkenyl" is a hydrocarbon containing 2 to 8 normal, secondary, tertiary or cyclic carbon atoms with at least one site of unsaturation, i.e. a carbon-carbon, sp$^2$ double bond.

"Alkynyl" is $C_2$-$C_{18}$ hydrocarbon containing normal, secondary, tertiary or cyclic carbon atoms with at least one site of unsaturation, i.e. a carbon-carbon, sp triple bond. Examples include, but are not limited to: acetylenic (—C≡CH) and propargyl (—CH$_2$C≡CH). A "$C_2$-$C_8$ alkynyl" is a hydrocarbon containing 2 to 8 normal, secondary, tertiary or cyclic carbon atoms with at least one site of unsaturation, i.e. a carbon-carbon, sp triple bond.

"Alkylene" refers to a saturated, branched or straight chain or cyclic hydrocarbon radical of 1-18 carbon atoms, and having two monovalent radical centers derived by the removal of two hydrogen atoms from the same or two different carbon atoms of a parent alkane. Typical alkylene radicals include, but are not limited to: methylene (—CH$_2$—) 1,2-ethyl (—CH$_2$CH$_2$—), 1,3-propyl (—CH$_2$CH$_2$CH$_2$—), 1,4-butyl (—CH$_2$CH$_2$CH$_2$CH$_2$—), and the like.

A "$C_1$-$C_{10}$ alkylene" is a straight chain, saturated hydrocarbon group of the formula —(CH$_2$)$_{1-10}$-. Examples of a C1-$C_{10}$ alkylene include methylene, ethylene, propylene, butylene, pentylene, hexylene, heptylene, ocytylene, nonylene and decalene.

"Alkenylene" refers to an unsaturated, branched or straight chain or cyclic hydrocarbon radical of 2-18 carbon atoms, and having two monovalent radical centers derived by the removal of two hydrogen atoms from the same or two different carbon atoms of a parent alkene. Typical alkenylene radicals include, but are not limited to: 1,2-ethylene (—CH═CH—).

"Alkynylene" refers to an unsaturated, branched or straight chain or cyclic hydrocarbon radical of 2-18 carbon atoms, and having two monovalent radical centers derived by the removal of two hydrogen atoms from the same or two different carbon atoms of a parent alkyne. Typical alkynylene radicals include, but are not limited to: acetylene (—C≡C—), propargyl (—CH$_2$C≡C—), and 4-pentynyl (—CH$_2$CH$_2$CH$_2$C≡C—).

"Aryl" refers to a carbocyclic aromatic group. Examples of aryl groups include, but are not limited to, phenyl, naphthyl and anthracenyl. A carbocyclic aromatic group or a heterocyclic aromatic group can be unsubstituted or substituted with one or more groups including, but not limited to, —$C_1$-$C_8$ alkyl, —O—($C_1$-$C_8$ alkyl), -aryl, —C(O)R', —OC(O)R', —C(O)OR', —C(O)NH$_2$, —C(O)NHR', —C(O)N(R')$_2$—NHC(O)R', —S(O)$_2$R', —S(O)R', —OH, -halogen, —N$_3$, —NH$_2$, —NH(R'), —N(R')$_2$ and —CN; wherein each R' is independently selected from H, —$C_1$-$C_8$ alkyl and aryl.

A "$C_5$-$C_{20}$ aryl" is an aryl group with 5 to 20 carbon atoms in the carbocyclic aromatic rings. Examples of $C_5$-$C_{20}$ aryl groups include, but are not limited to, phenyl, naphthyl and anthracenyl. A C5-$C_{20}$ aryl group can be substituted or unsubstituted as described above for aryl groups. A "$C_5$-$C_{14}$ aryl" is an aryl group with 5 to 14 carbon atoms in the carbocyclic aromatic rings. Examples of $C_5$-$C_{14}$ aryl groups include, but are not limited to, phenyl, naphthyl and anthracenyl. A $C_5$-$C_{14}$ aryl group can be substituted or unsubstituted as described above for aryl groups.

An "arylene" is an aryl group which has two covalent bonds and can be in the ortho, meta, or para configurations as shown in the following structures:

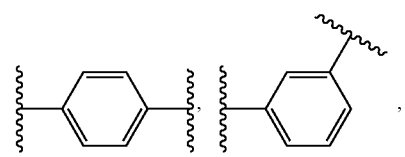

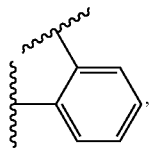

in which the phenyl group can be unsubstituted or substituted with up to four groups including, but not limited to, —$C_1$-$C_8$ alkyl, —O—($C_1$-$C_8$ alkyl), -aryl, —C(O)R', —OC(O)R', —C(O)OR', —C(O)$NH_2$, —C(O)NHR', —C(O)N(R')$_2$—NHC(O)R', —S(O)$_2$R', —S(O)R', —OH, -halogen, —$N_3$, —$NH_2$, —NH(R'), —N(R')$_2$ and —CN; wherein each R' is independently selected from H, —$C_1$-$C_8$ alkyl and aryl.

"Arylalkyl" refers to an acyclic alkyl radical in which one of the hydrogen atoms bonded to a carbon atom, typically a terminal or $sp^3$ carbon atom, is replaced with an aryl radical. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. The arylalkyl group comprises 6 to 20 carbon atoms, e.g. the alkyl moiety, including alkanyl, alkenyl or alkynyl groups, of the arylalkyl group is 1 to 6 carbon atoms and the aryl moiety is 5 to 14 carbon atoms.

"Heteroarylalkyl" refers to an acyclic alkyl radical in which one of the hydrogen atoms bonded to a carbon atom, typically a terminal or $sp^3$ carbon atom, is replaced with a heteroaryl radical. Typical heteroarylalkyl groups include, but are not limited to, 2-benzimidazolylmethyl, 2-furylethyl, and the like. The heteroarylalkyl group comprises 6 to 20 carbon atoms, e.g. the alkyl moiety, including alkanyl, alkenyl or alkynyl groups, of the heteroarylalkyl group is 1 to 6 carbon atoms and the heteroaryl moiety is 5 to 14 carbon atoms and 1 to 3 heteroatoms selected from N, O, P, and S. The heteroaryl moiety of the heteroarylalkyl group may be a monocycle having 3 to 7 ring members (2 to 6 carbon atoms or a bicycle having 7 to 10 ring members (4 to 9 carbon atoms and 1 to 3 heteroatoms selected from N, O, P, and S), for example: a bicyclo [4,5], [5,5], [5,6], or [6,6] system.

"Substituted alkyl," "substituted aryl," and "substituted arylalkyl" mean alkyl, aryl, and arylalkyl respectively, in which one or more hydrogen atoms are each independently replaced with a substituent. Typical substituents include, but are not limited to, —X, —R, —O⁻, —OR, —SR, —S⁻, —$NR_2$, —$NR_3$, =NR, —$CX_3$, —CN, —OCN, —SCN, —N=C=O, —NCS, —NO, —$NO_2$, =$N_2$, —$N_3$, NC(=O)R, —C(=O)R, —C(=O)$NR_2$, —$SO_3^-$, —$SO_3H$, —S(=O)$_2$R, —OS(=O)$_2$OR, —S(=O)$_2$NR, —S(=O)R, —OP(=O)(OR)$_2$, —P(=O)(OR)$_2$, —$PO^-_3$, —$PO_3H_2$, —C(=O)R, —C(=O)X, —C(=S)R, —$CO_2$R, —$CO_2^-$, —C(=S)OR, —C(=O)SR, —C(=S)SR, —C(=O)$NR_2$, —C(=S)$NR_2$, —C(=NR)$NR_2$, where each X is independently a halogen: F, Cl, Br, or I; and each R is independently —H, $C_2$-$C_{18}$ alkyl, $C_6$-$C_{20}$ aryl, $C_3$-$C_{14}$ heterocycle, protecting group or prodrug moiety. Alkylene, alkenylene, and alkynylene groups as described above may also be similarly substituted.

"Heteroaryl" and "heterocycle" refer to a ring system in which one or more ring atoms is a heteroatom, e.g. nitrogen, oxygen, and sulfur. The heterocycle radical comprises 3 to 20 carbon atoms and 1 to 3 heteroatoms selected from N, O, P, and S. A heterocycle may be a monocycle having 3 to 7 ring members (2 to 6 carbon atoms and 1 to 3 heteroatoms selected from N, O, P, and S) or a bicycle having 7 to 10 ring members (4 to 9 carbon atoms and 1 to 3 heteroatoms selected from N, O, P, and S), for example: a bicyclo [4,5], [5,5], [5,6], or [6,6] system.

Exemplary heterocycles are described, e.g., in Paquette, Leo A., "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and *J. Am. Chem. Soc.* (1960) 82:5566.

Examples of heterocycles include by way of example and not limitation pyridyl, dihydroypyridyl, tetrahydropyridyl (piperidyl), thiazolyl, tetrahydrothiophenyl, sulfur oxidized tetrahydrothiophenyl, pyrimidinyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, bis-tetrahydrofuranyl, tetrahydropyranyl, bis-tetrahydropyranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thienyl, thianthrenyl, pyranyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazolyl, purinyl, 4H-quinolizinyl, phthalazinyl, naphthyridinyl, quinoxalinyl, quinazolinyl, cinnolinyl, pteridinyl, 4aH-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, and isatinoyl.

By way of example and not limitation, carbon bonded heterocycles are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Still more typically, carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl.

By way of example and not limitation, nitrogen bonded heterocycles are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline. Still more typically, nitrogen bonded heterocycles include 1-aziridyl, 1-azetedyl, 1-pyrrolyl, 1-imidazolyl, 1-pyrazolyl, and 1-piperidinyl.

A "$C_3$-$C_8$ heterocycle" refers to an aromatic or non-aromatic $C_3$-$C_8$ carbocycle in which one to four of the ring carbon atoms are independently replaced with a heteroatom from the group consisting of O, S and N. Representative examples of a $C_3$-$C_8$ heterocycle include, but are not limited to, benzofuranyl, benzothiophene, indolyl, benzopyrazolyl, coumarinyl, isoquinolinyl, pyrrolyl, thiophenyl, furanyl, thiazolyl, imidazolyl, pyrazolyl, triazolyl, quinolinyl, pyrimidinyl, pyridinyl, pyridonyl, pyrazinyl, pyridazinyl, isothiazolyl, isoxazolyl and tetrazolyl. A $C_3$-$C_8$ heterocycle can be unsubstituted or substituted with up to seven groups including, but not limited to, —$C_1$-$C_8$ alkyl, —O—($C_1$-$C_8$ alkyl), -aryl, —C(O)R', —OC(O)R', —C(O)OR', —C(O)NH$_2$, —C(O)NHR', —C(O)N(R')$_2$—NHC(O)R', —S(O)$_2$R', —S(O)R', —OH, -halogen, —N$_3$, —NH$_2$, —NH(R'), —N(R')$_2$ and —CN; wherein each R' is independently selected from H, —$C_1$-$C_8$ alkyl and aryl.

"$C_3$-$C_8$ heterocyclo" refers to a $C_3$-$C_8$ heterocycle group defined above wherein one of the heterocycle group's hydrogen atoms is replaced with a bond. A $C_3$-$C_8$ heterocyclo can be unsubstituted or substituted with up to six groups including, but not limited to, —$C_1$-$C_8$ alkyl, —O—($C_1$-$C_8$ alkyl), -aryl, —C(O)R', —OC(O)R', —C(O)OR', —C(O)NH$_2$, —C(O)NHR', —C(O)N(R')$_2$—NHC(O)R', —S(O)$_2$R', —S(O)R', —OH, -halogen, —N$_3$, —NH$_2$, —NH(R'), —N(R')$_2$ and —CN; wherein each R' is independently selected from H, —$C_1$-$C_8$ alkyl and aryl.

A "$C_3$-$C_{20}$ heterocycle" refers to an aromatic or non-aromatic $C_3$-$C_8$ carbocycle in which one to four of the ring carbon atoms are independently replaced with a heteroatom from the group consisting of O, S and N. A $C_3$-$C_{20}$ heterocycle can be unsubstituted or substituted with up to seven groups including, but not limited to, —$C_1$-$C_8$ alkyl, —O— ($C_1$-$C_8$ alkyl), -aryl, —C(O)R', —OC(O)R', —C(O)OR', —C(O)NH$_2$, —C(O)NHR', —C(O)N(R')$_2$—NHC(O)R', —S(O)$_2$R', —S(O)R', —OH, -halogen, —N$_3$, —NH$_2$, —NH(R'), —N(R')$_2$ and —CN; wherein each R' is independently selected from H, —$C_1$-$C_8$ alkyl and aryl.

"$C_3$-$C_{20}$ heterocyclo" refers to a $C_3$-$C_{20}$ heterocycle group defined above wherein one of the heterocycle group's hydrogen atoms is replaced with a bond.

"Carbocycle" means a saturated or unsaturated ring having 3 to 7 carbon atoms as a monocycle or 7 to 12 carbon atoms as a bicycle. Monocyclic carbocycles have 3 to 6 ring atoms, still more typically 5 or 6 ring atoms. Bicyclic carbocycles have 7 to 12 ring atoms, e.g. arranged as a bicyclo [4,5], [5,5], [5,6] or [6,6] system, or 9 or 10 ring atoms arranged as a bicyclo [5,6] or [6,6] system. Examples of monocyclic carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cycloheptyl, and cyclooctyl.

A "$C_3$-$C_8$ carbocycle" is a 3-, 4-, 5-, 6-, 7- or 8-membered saturated or unsaturated non-aromatic carbocyclic ring. Representative $C_3$-$C_8$ carbocycles include, but are not limited to, -cyclopropyl, -cyclobutyl, -cyclopentyl, -cyclopentadienyl, -cyclohexyl, -cyclohexenyl, -1,3-cyclohexadienyl, -1,4-cyclohexadienyl, -cycloheptyl, -1,3-cycloheptadienyl, -1,3,5-cycloheptatrienyl, -cyclooctyl, and -cyclooctadienyl. A $C_3$-$C_8$ carbocycle group can be unsubstituted or substituted with one or more groups including, but not limited to, —$C_1$-$C_8$ alkyl, —O—($C_1$-$C_8$ alkyl), -aryl, —C(O)R', —OC(O)R', —C(O)OR', —C(O)NH$_2$, —C(O)NHR', —C(O)N (R')$_2$—NHC(O)R', —S(O)$_2$R', —S(O)R', —OH, -halogen, —N$_3$, —NH$_2$, —NH(R'), —N(R')$_2$ and —CN; where each R' is independently selected from H, —$C_1$-$C_8$ alkyl and aryl.

A "$C_3$-$C_8$ carbocyclo" refers to a $C_3$-$C_8$ carbocycle group defined above wherein one of the carbocycle groups' hydrogen atoms is replaced with a bond.

"Linker" refers to a chemical moiety comprising a covalent bond or a chain of atoms that covalently attaches an antibody to a drug moiety. In various embodiments, linkers include a divalent radical such as an alkyldiyl, an aryldiyl, a heteroaryldiyl, moieties such as: —(CR$_2$)$_n$O(CR$_2$)$_n$—, repeating units of alkyloxy (e.g. polyethylenoxy, PEG, polymethyleneoxy) and alkylamino (e.g. polyethyleneamino, Jeffamine™); and diacid ester and amides including succinate, succinamide, diglycolate, malonate, and caproamide. In various embodiments, linkers can comprise one or more amino acid residues, such as valine, phenylalanine, lysine, and homolysine.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., *Stereochemistry of Organic Compounds* (1994) John Wiley & Sons, Inc., New York. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

"Leaving group" refers to a functional group that can be substituted by another functional group. Certain leaving groups are well known in the art, and examples include, but are not limited to, a halide (e.g., chloride, bromide, iodide), methanesulfonyl (mesyl), p-toluenesulfonyl (tosyl), trifluoromethylsulfonyl (triflate), and trifluoromethylsulfonate.

The term "protecting group" refers to a substituent that is commonly employed to block or protect a particular functionality while reacting other functional groups on the compound. For example, an "amino-protecting group" is a substituent attached to an amino group that blocks or protects the amino functionality in the compound. Suitable amino-protecting groups include, but are not limited to, acetyl, trifluoroacetyl, t-butoxycarbonyl (BOC), benzyloxycarbonyl (CBZ) and 9-fluorenylmethylenoxycarbonyl (Fmoc). For a general description of protecting groups and their use, see T. W. Greene, Protective Groups in Organic Synthesis, John Wiley & Sons, New York, 1991, or a later edition.

II. Compositions and Methods

In one aspect, the invention is based, in part, on antibodies that bind to CLL-1 and immunoconjugates comprising such antibodies. Antibodies and immunoconjugates of the invention are useful, e.g., for the diagnosis or treatment of CLL-1-positive cancers.

The invention provides anti-CLL-1 antibodies and immunoconjugates and methods of using the same.

Provided herein are isolated monoclonal anti-CLL-1 antibodies, wherein the antibody binds an epitope and/or binds an overlapping epitope comprising amino acids of SEQ ID NO:49 and does not bind an epitope comprising SEQ ID NO:50 and/or SEQ ID NO:51. In some embodiments, the anti-CLL-1 antibody binds an epitope comprising amino acids of SEQ ID NO:49. In some embodiments, the anti-CLL-1 antibody binds an epitope consisting or consisting essentially of the amino acids of SEQ ID NO:49. In some embodiments, the epitope is determined by hydroxyl radical footprinting. In some embodiments, the epitiope as determined by hydroxyl radical footprinting has a ratio of [rate constant of the antigen]/[rate constant of the antigen and antibody complex] greater than about any of 1.8, 1.9, 2.0, 2.1, 2.2, 2.3, 2.4, 2.5, 2.6, 2.7, 2.8, 2.9, or 3.0. In some embodiments, the epitope as determined by hydroxyl radical footprinting has a ratio of [rate constant of the antigen]/[rate constant of the antigen and antibody complex] greater than about 2.0.

Hydroxyl radical footprinting may be performed as described in the Examples. For example, samples are exposed to hydroxyl radicals for intervals of 0, 10, 15, and 20 milliseconds (ms) using the X28c Beam line at the Brookhaven National Laboratory. The labeled samples may be subjected to deglycosylation using PNGase F. The samples may be precipitated using Trichloroacetic acid in acetone, and subjected to LC-MS analysis. The samples may be then subjected to reduction and alkylation, digestion using Trypsin, followed by liquid chromatography coupled with high-resolution mass spectrometry (LC-MS). The MS data may be analyzed using ProtMapMS, resulting in dose response plots for each peptide. Results from the free antigen may be compared against each of the complex forms. A homology-based model of the antigen may be generated using Swiss-Model software, and the solvent protected regions may be mapped for each of the three complexes. The selected ion chromatograms (SIC) may be extracted and integrated for the unoxidized and all oxidized forms of peptide ion (with particular m/z). These peak area values may be used to characterize reaction kinetics in the form of dose response (DR) plots, which measure the loss of intact peptide as a function of the hydroxyl radical exposure. The solvent protected regions in the complex experience gradual oxidation reaction as opposed to the free antigen, and the differences in the rate of oxidation (called rate constant, RC) may serve to highlight the location of the epitope.

In some embodiments of any of the antibodies, the antibody binds to recombinant human CLL-1. In some embodiments of any of the antibodies, the antibody binds to recombinant cynomolgus monkey CLL-1. In some embodiments of any of the antibodies, the antibody binds to endogenous CLL-1 on the surface of human peripheral blood mononucleocytes (PBMCs). In some embodiments of any of the antibodies, the antibody binds to endogenous CLL-1 on the surface of cynomolgus monkey PBMCs. In some embodiments of any of the antibodies, the antibody binds to endogenous CLL-1 on the surface of a cancer cell. In some embodiments of any of the antibodies, the antibody binds to endogenous CLL-1 on the surface of an AML cancer cell. In some embodiments of any of the antibodies, the antibody binds to endogenous CLL-1 on the surface of HL-60 cells. In some embodiments of any of the antibodies, the antibody binds to endogenous CLL-1 on the surface of EOL-1 cells. In some embodiments of any of the antibodies, the antibody binds to CLL-1 comprising a K244Q mutation (SEQ ID NO:1 with K244Q). In some embodiments of any of the antibodies, the antibody binds an epitope and/or binds an overlapping epitope comprising amino acids of SEQ ID NO:49. In some embodiments of any of the antibodies, the antibody does not bind an epitope comprising SEQ ID NO:50 and/or SEQ ID NO:51. In some embodiments of any of the antibodies, the antibody competes for human CLL-1 binding with R&D System Clone 687317antibody. In some embodiments of any of the antibodies, the antibody binds to endogenous human CLL-1 with a Kd of less than 15 nM, less than 10 nM, less than 7 nM, less than 5 nM, or less than 3 nM. In some embodiments of any of the antibodies, the antibody binds to recombinant human CLL-1 with a Kd of less than 10 nM, less than 7 nM, less than 5 nM, or less than 3 nM. In some embodiments of any of the antibodies, the antibody binds to recombinant cynomolgus monkey CLL-1 with a Kd of less than 10 nM, less than 7 nM, less than 5 nM, or less than 3 nM, less than 2 nM, or less than 1 nM.

In some embodiments, the characteristics of the antibody are determined as described herein in the Examples below.

Antibody 6E7 and Other Embodiments

In some embodiments, the invention provides an anti-CLL-1 antibody comprising at least one, two, three, four, five, or six HVRs selected from (a) HVR-H1 comprising the amino acid sequence of SEQ ID NO:8; (b) HVR-H2 comprising the amino acid sequence of SEQ ID NO:45; (c) HVR-H3 comprising the amino acid sequence of SEQ ID NO:10; (d) HVR-L1 comprising the amino acid sequence of SEQ ID NO:5; (e) HVR-L2 comprising the amino acid sequence of SEQ ID NO:6; and (f) HVR-L3 comprising the amino acid sequence of SEQ ID NO:7. In some embodiments, HVR-H2 comprises the amino acid sequences of SEQ ID NO:9. In some embodiments, HVR-H2 comprises the amino acid sequences of SEQ ID NO:47. In some embodiments, HVR-H2 comprises the amino acid sequences of SEQ ID NO:11. In some embodiments, HVR-H2 comprises the amino acid sequences of SEQ ID NO:43. In some embodiments, HVR-H2 comprises the amino acid sequences of SEQ ID NO:44.

In one aspect, the invention provides an antibody comprising at least one, at least two, or all three VH HVR sequences selected from (a) HVR-H1 comprising the amino acid sequence of SEQ ID NO:8; (b) HVR-H2 comprising the amino acid sequence of SEQ ID NO:45; and (c) HVR-H3 comprising the amino acid sequence of SEQ ID NO:10. In one embodiment, the antibody comprises HVR-H3 comprising the amino acid sequence of SEQ ID NO:10. In another embodiment, the antibody comprises HVR-H3 comprising the amino acid sequence of SEQ ID NO:10 and HVR-L3 comprising the amino acid sequence of SEQ ID NO:7. In a further embodiment, the antibody comprises HVR-H3 comprising the amino acid sequence of SEQ ID NO:10, HVR-L3 comprising the amino acid sequence of SEQ ID NO:7, and HVR-H2 comprising the amino acid sequence of SEQ ID NO:45. In a further embodiment, the antibody comprises (a) HVR-H1 comprising the amino acid sequence of SEQ ID NO:8; (b) HVR-H2 comprising the amino acid sequence of SEQ ID NO:45; and (c) HVR-H3 comprising the amino acid sequence of SEQ ID NO:10. In some embodiments, HVR-H2 comprises the amino acid sequences of SEQ ID NO:9. In some embodiments, HVR-H2 comprises the amino acid sequences of SEQ ID NO:47. In some embodiments, HVR-H2 comprises the amino acid sequences of SEQ ID NO:11. In some embodiments, HVR-H2 comprises the amino acid sequences of SEQ ID NO:43. In some embodiments, HVR-H2 comprises the amino acid sequences of SEQ ID NO:44.

In another aspect, the invention provides an antibody comprising at least one, at least two, or all three VL HVR sequences selected from (a) HVR-L1 comprising the amino acid sequence of SEQ ID NO:5; (b) HVR-L2 comprising the amino acid sequence of SEQ ID NO:6; and (c) HVR-L3 comprising the amino acid sequence of SEQ ID NO:7. In one embodiment, the antibody comprises (a) HVR-L1 comprising the amino acid sequence of SEQ ID NO:5; (b) HVR-L2 comprising the amino acid sequence of SEQ ID NO:6; and (c) HVR-L3 comprising the amino acid sequence of SEQ ID NO:7.

In another aspect, an antibody of the invention comprises (a) a VH domain comprising at least one, at least two, or all three VH HVR sequences selected from (i) HVR-H1 comprising the amino acid sequence of SEQ ID NO:8, (ii) HVR-H2 comprising the amino acid sequence of SEQ ID NO:45, and (iii) HVR-H3 comprising an amino acid sequence selected from SEQ ID NO:10; and (b) a VL domain comprising at least one, at least two, or all three VL HVR sequences selected from (i) HVR-L1 comprising the amino acid sequence of SEQ ID NO:5, (ii) HVR-L2 comprising the amino acid sequence of SEQ ID NO:6, and (c) HVR-L3 comprising the amino acid sequence of SEQ ID NO:7.

In another aspect, the invention provides an antibody comprising (a) HVR-H1 comprising the amino acid sequence of SEQ ID NO:8; (b) HVR-H2 comprising the amino acid sequence of SEQ ID NO:45; (c) HVR-H3 comprising the amino acid sequence of SEQ ID NO:10; (d) HVR-L1 comprising the amino acid sequence of SEQ ID NO:5; (e) HVR-L2 comprising the amino acid sequence of SEQ ID NO:6; and (f) HVR-L3 comprising the amino acid sequence of SEQ ID NO:7. In some embodiments, the antibody comprises (a) HVR-H1 comprising the amino acid sequence of SEQ ID NO:8; (b) HVR-H2 comprising the amino acid sequence of SEQ ID NO:9; (c) HVR-H3 comprising the amino acid sequence of SEQ ID NO:10; (d) HVR-L1 comprising the amino acid sequence of SEQ ID NO:5; (e) HVR-L2 comprising the amino acid sequence of SEQ ID NO:6; and (f) HVR-L3 comprising the amino acid sequence of SEQ ID NO:7. In some embodiments, the antibody comprises (a) HVR-H1 comprising the amino acid sequence of SEQ ID NO:8; (b) HVR-H2 comprising the amino acid sequence of SEQ ID NO:47; (c) HVR-H3 comprising the amino acid sequence of SEQ ID NO:10; (d) HVR-L1 comprising the amino acid sequence of SEQ ID NO:5; (e) HVR-L2 comprising the amino acid sequence of SEQ ID NO:6; and (f) HVR-L3 comprising the amino acid sequence of SEQ ID NO:7. In some embodiments, the antibody comprises (a) HVR-H1 comprising the amino acid sequence of SEQ ID NO:8; (b) HVR-H2 comprising the amino acid sequence of SEQ ID NO:11; (c) HVR-H3 comprising the amino acid sequence of SEQ ID NO:10; (d) HVR-L1 comprising the amino acid sequence of SEQ ID NO:5; (e) HVR-L2 comprising the amino acid sequence of SEQ ID NO:6; and (f) HVR-L3 comprising the amino acid sequence of SEQ ID NO:7. In some embodiments, the antibody comprises (a) HVR-H1 comprising the amino acid sequence of SEQ ID NO:8; (b) HVR-H2 comprising the amino acid sequence of SEQ ID NO:43; (c) HVR-H3 comprising the amino acid sequence of SEQ ID NO:10; (d) HVR-L1 comprising the amino acid sequence of SEQ ID NO:5; (e) HVR-L2 comprising the amino acid sequence of SEQ ID NO:6; and (f) HVR-L3 comprising the amino acid sequence of SEQ ID NO:7. In some embodiments, the antibody comprises (a) HVR-H1 comprising the amino acid sequence of SEQ ID NO:8; (b) HVR-H2 comprising the amino acid sequence of SEQ ID NO:11; (c) HVR-H3 comprising the amino acid sequence of SEQ ID NO:10; (d) HVR-L1 comprising the amino acid sequence of SEQ ID NO:5; (e) HVR-L2 comprising the amino acid sequence of SEQ ID NO:6; and (f) HVR-L3 comprising the amino acid sequence of SEQ ID NO:7.

In any of the above embodiments, an anti-CLL-1 antibody is humanized. In one embodiment, an anti-CLL-1 antibody comprises HVRs as in any of the above embodiments, and further comprises a human acceptor framework, e.g. a human immunoglobulin framework or a human consensus framework. In certain embodiments, the human acceptor framework is the human VL kappa I consensus ($VL_{KI}$) framework and/or the VH framework $VH_1$. In certain embodiments, the human acceptor framework is the human VL kappa I consensus ($VL_{KI}$) framework and/or the VH framework $VH_1$ comprising any one of the following mutations.

In another aspect, an anti-CLL-1 antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO:31, SEQ ID NO:33, SEQ ID NO:34, SEQ ID NO:46 and/or SEQ ID NO:48. In certain embodiments, a VH sequence having at least 90%, 91%, 92%, 93%, 94%, 95%, 96%, 97%, 98%, or 99% identity to the amino acid sequence of SEQ ID NO:31, SEQ ID NO:33, SEQ ID NO:34, SEQ ID NO:46 and/or SEQ ID NO:48 contains substitutions (e.g., conservative substitutions), insertions, or deletions relative to the reference sequence, but an anti-CLL-1 antibody comprising that sequence retains the ability to bind to CLL-1. In certain embodiments, a total of 1 to 10 amino acids have been substituted, inserted and/or deleted in SEQ ID NO:31, SEQ ID NO:33, SEQ ID NO:34, SEQ ID NO:46 and/or SEQ ID NO:48. In certain embodiments, a total of 1 to 5 amino acids have been substituted, inserted and/or deleted in SEQ ID NO:31, SEQ ID NO:33, SEQ ID NO:34, SEQ ID NO:46 and/or SEQ ID NO:48. In certain embodiments, substitutions, insertions, or deletions occur in regions outside the HVRs (i.e., in the FRs). Optionally, the anti-CLL-1 antibody comprises the VH sequence of SEQ ID NO:31, SEQ ID NO:33, and/or SEQ ID NO:34, including post-translational modifications of that sequence. In a particular embodiment, the VH comprises one, two or three HVRs selected from: (a) HVR-H1 comprising the amino acid sequence of SEQ ID NO:8, (b) HVR-H2 comprising the amino acid sequence of SEQ ID NO:45, and (c) HVR-H3 comprising the amino acid sequence of SEQ ID NO:10. In some embodiments, HVR-H2 comprises the amino acid sequences of SEQ ID NO:9. In some embodiments, HVR-H2 comprises the amino acid sequences of SEQ ID NO:47. In some embodiments, HVR-H2 comprises the amino acid sequences of SEQ ID NO:11. In some embodiments, HVR-H2 comprises the amino acid sequences of SEQ ID NO:43. In some embodiments, HVR-H2 comprises the amino acid sequences of SEQ ID NO:44.

In another aspect, an anti-CLL-1 antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO:30 and/or SEQ ID NO:32. In certain embodiments, a VL sequence having at least 90%, 91%, 92%, 93%, 94%, 95%, 96%, 97%, 98%, or 99% identity to the amino acid sequence of SEQ ID NO:30 and/or SEQ ID NO:32 contains substitutions (e.g., conservative substitutions), insertions, or deletions relative to the reference sequence, but an anti-CLL-1 antibody comprising that sequence retains the ability to bind to CLL-1. In certain embodiments, a total of 1 to 10 amino acids have been substituted, inserted and/or deleted in SEQ ID NO:30 and/or SEQ ID NO:32. In certain embodiments, a total of 1 to 5 amino acids have been substituted, inserted and/or deleted in SEQ ID NO:30 and/or SEQ ID NO:32. In certain embodiments, the substitutions, insertions, or deletions occur in regions outside the HVRs (i.e., in the FRs). Optionally, the anti-CLL-1 antibody comprises the VL sequence of SEQ ID NO:30 and/or SEQ ID NO:32, including post-translational modifications of that sequence. In a particular embodiment, the VL comprises one, two or three HVRs selected from (a) HVR-L1 comprising the amino acid sequence of SEQ ID NO:5; (b) HVR-L2 comprising the amino acid sequence of SEQ ID NO:6; and (c) HVR-L3 comprising the amino acid sequence of SEQ ID NO:7.

In another aspect, an anti-CLL-1 antibody is provided, wherein the antibody comprises a VH as in any of the embodiments provided above, and a VL as in any of the embodiments provided above.

In one embodiment, the antibody comprises the VH and VL sequences in SEQ ID NO:31 and SEQ ID NO:30, respectively, including post-translational modifications of those sequences. In one embodiment, the antibody comprises the VH and VL sequences in SEQ ID NO:33 and SEQ ID NO:32, respectively, including post-translational modifications of those sequences. In one embodiment, the antibody comprises the VH and VL sequences in SEQ ID NO:34 and SEQ ID NO:33, respectively, including post-translational modifications of those sequences. In one embodiment, the antibody comprises the VH and VL sequences in SEQ ID NO:46 and SEQ ID NO:33, respectively, including post-translational modifications of those sequences. In one embodiment, the antibody comprises the VH and VL sequences in SEQ ID NO:48 and SEQ ID NO:33, respectively, including post-translational modifications of those sequences.

In a further aspect, provided are herein are antibodies that bind to the same epitope as an anti-CLL-1 antibody provided herein. For example, in certain embodiments, an antibody is provided that binds to the same epitope as an anti-CLL-1 antibody comprising a VH sequence of SEQ ID NO:31, SEQ ID NO:33, SEQ ID NO:34, SEQ ID NO:46 and/or SEQ ID NO:48 and a VL sequence of SEQ ID NO:30 and/or SEQ ID NO:32, respectively.

Figure 2A:
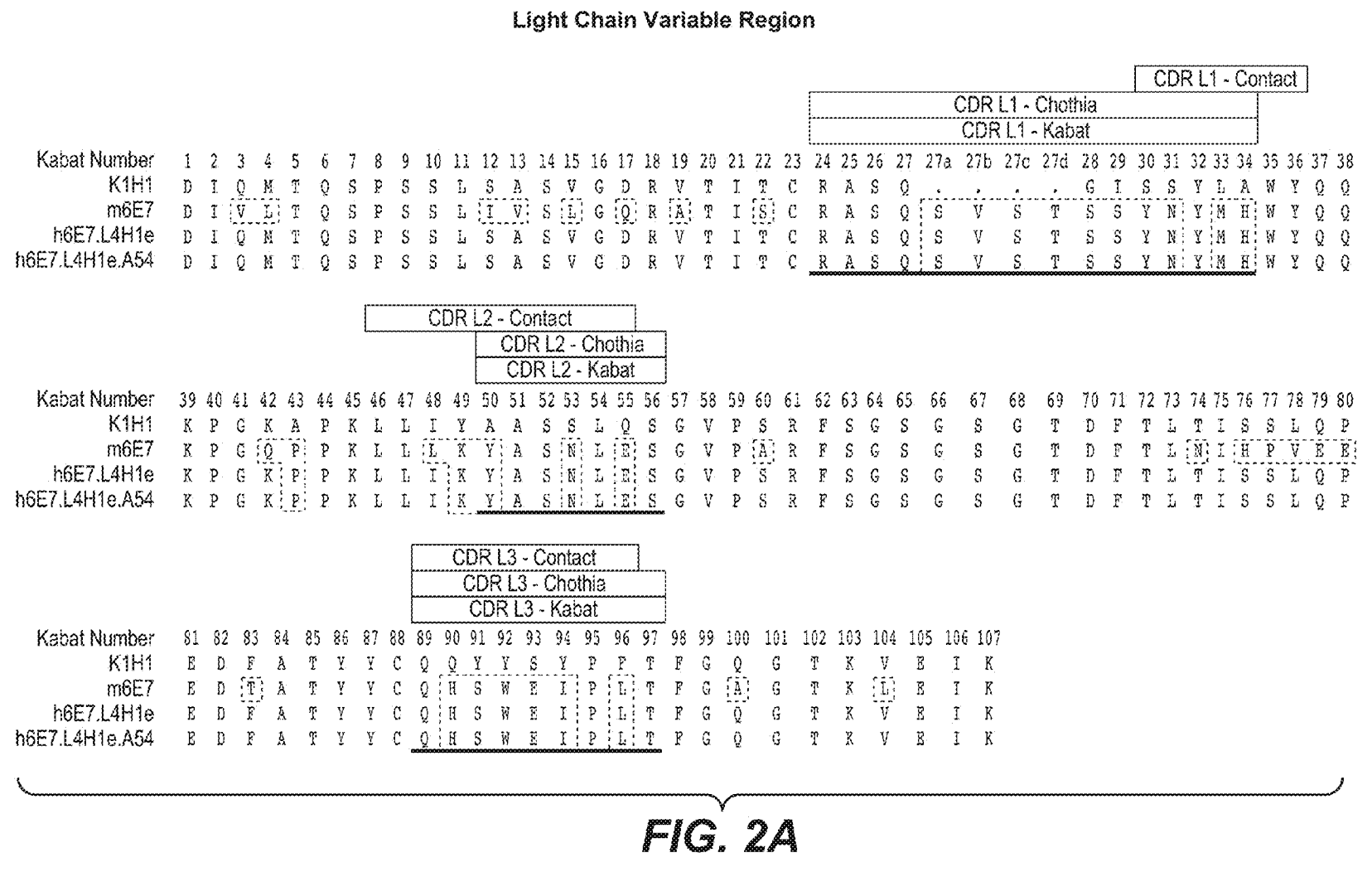
Figure 2B:
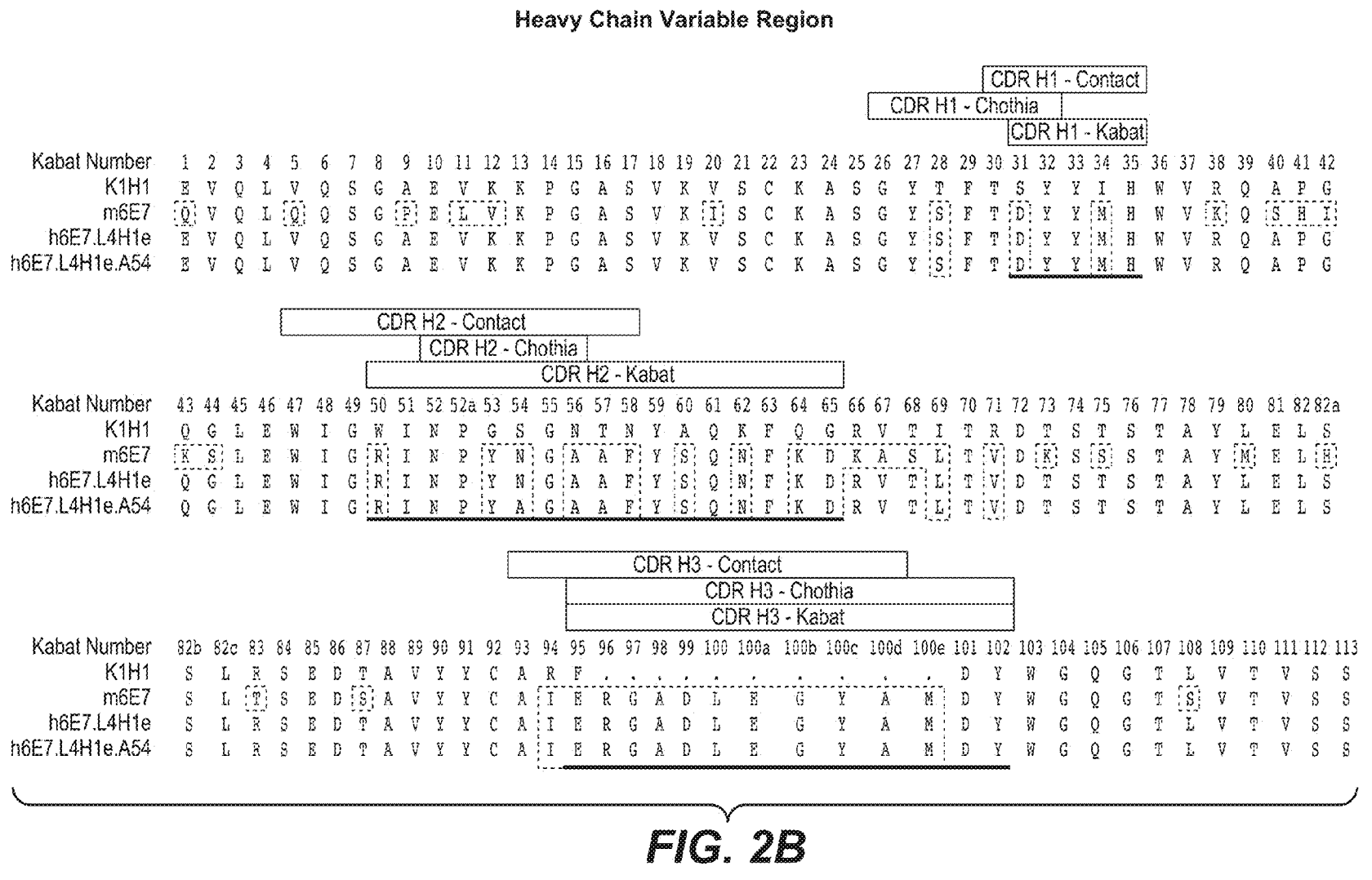

Provided herein are antibodies comprising a light chain variable domain comprising the HVR1-LC, HVR2-LC and HVR3-LC sequence according to Kabat numbering as depicted in FIG. 2A and a heavy chain variable domain comprising the HVR1-HC, HVR2-HC and HVR3-HC sequence according to Kabat numbering as depicted in FIG. 2B. In some embodiments, the antibody comprises a light chain variable domain comprising the HVR1-LC, HVR2-LC and/or HVR3-LC sequence, and the FR1-LC, FR2-LC, FR3-LC and/or FR4-LC sequence as depicted in FIG. 2A. In some embodiments, the antibody comprises a heavy chain variable domain comprising the HVR1-HC, HVR2-HC and/ or HVR3-HC sequence, and the FR1-HC, FR2-HC, FR3-HC and/or FR4-HC sequence as depicted in FIG. 2B.

In a further aspect of the invention, an anti-CLL-1 antibody according to any of the above embodiments is a monoclonal antibody, including a human antibody. In one embodiment, an anti-CLL-1 antibody is an antibody fragment, e.g., a Fv, Fab, Fab', scFv, diabody, or F(ab')$_2$ fragment. In another embodiment, the antibody is a substantially full length antibody, e.g., an IgG1 antibody, IgG2a antibody or other antibody class or isotype as defined herein.

Antibody 20B1 and Other Embodiments

In some embodiments, the invention provides an anti-CLL-1 antibody comprising at least one, two, three, four, five, or six HVRs selected from (a) HVR-H1 comprising the amino acid sequence of SEQ ID NO:15; (b) HVR-H2 comprising the amino acid sequence of SEQ ID NO:16; (c) HVR-H3 comprising the amino acid sequence of SEQ ID NO:17; (d) HVR-L1 comprising the amino acid sequence of SEQ ID NO:12; (e) HVR-L2 comprising the amino acid sequence of SEQ ID NO:13; and (f) HVR-L3 comprising the amino acid sequence of SEQ ID NO:14.

In one aspect, the invention provides an antibody comprising at least one, at least two, or all three VH HVR sequences selected from (a) HVR-H1 comprising the amino acid sequence of SEQ ID NO: 15; (b) HVR-H2 comprising the amino acid sequence of SEQ ID NO:16; and (c) HVR-H3 comprising the amino acid sequence of SEQ ID NO:17. In one embodiment, the antibody comprises HVR-H3 comprising the amino acid sequence of SEQ ID NO:17. In another embodiment, the antibody comprises HVR-H3 comprising the amino acid sequence of SEQ ID NO:17 and HVR-L3 comprising the amino acid sequence of SEQ ID NO:14. In a further embodiment, the antibody comprises HVR-H3 comprising the amino acid sequence of SEQ ID NO:17, HVR-L3 comprising the amino acid sequence of SEQ ID NO:14, and HVR-H2 comprising the amino acid sequence of SEQ ID NO:16. In a further embodiment, the antibody comprises (a) HVR-H1 comprising the amino acid sequence of SEQ ID NO: 15; (b) HVR-H2 comprising the amino acid sequence of SEQ ID NO:16; and (c) HVR-H3 comprising the amino acid sequence of SEQ ID NO:17.

In another aspect, the invention provides an antibody comprising at least one, at least two, or all three VL HVR sequences selected from (a) HVR-L1 comprising the amino acid sequence of SEQ ID NO: 12; (b) HVR-L2 comprising the amino acid sequence of SEQ ID NO:13; and (c) HVR-L3 comprising the amino acid sequence of SEQ ID NO:14. In one embodiment, the antibody comprises (a) HVR-L1 comprising the amino acid sequence of SEQ ID NO:12; (b) HVR-L2 comprising the amino acid sequence of SEQ ID NO:13; and (c) HVR-L3 comprising the amino acid sequence of SEQ ID NO:14.

In another aspect, an antibody of the invention comprises (a) a VH domain comprising at least one, at least two, or all three VH HVR sequences selected from (i) HVR-H1 comprising the amino acid sequence of SEQ ID NO:15, (ii) HVR-H2 comprising the amino acid sequence of SEQ ID NO:16, and (iii) HVR-H3 comprising an amino acid sequence selected from SEQ ID NO:17; and (b) a VL domain comprising at least one, at least two, or all three VL HVR sequences selected from (i) HVR-L1 comprising the amino acid sequence of SEQ ID NO:12, (ii) HVR-L2 comprising the amino acid sequence of SEQ ID NO:13, and (c) HVR-L3 comprising the amino acid sequence of SEQ ID NO:14.

In another aspect, the invention provides an antibody comprising (a) HVR-H1 comprising the amino acid sequence of SEQ ID NO:15; (b) HVR-H2 comprising the amino acid sequence of SEQ ID NO: 16; (c) HVR-H3 comprising the amino acid sequence of SEQ ID NO:17; (d) HVR-L1 comprising the amino acid sequence of SEQ ID NO:12; (e) HVR-L2 comprising the amino acid sequence of SEQ ID NO:13; and (f) HVR-L3 comprising the amino acid sequence of SEQ ID NO:14. In some embodiments, the antibody comprises (a) HVR-H1 comprising the amino acid sequence of SEQ ID NO: 15; (b) HVR-H2 comprising the amino acid sequence of SEQ ID NO:16; (c) HVR-H3 comprising the amino acid sequence of SEQ ID NO:17; (d) HVR-L1 comprising the amino acid sequence of SEQ ID NO: 12; (e) HVR-L2 comprising the amino acid sequence of SEQ ID NO:13; and (f) HVR-L3 comprising the amino acid sequence of SEQ ID NO:14.

In any of the above embodiments, an anti-CLL-1 antibody is humanized. In one embodiment, an anti-CLL-1 antibody comprises HVRs as in any of the above embodiments, and further comprises a human acceptor framework, e.g. a human immunoglobulin framework or a human consensus framework. In certain embodiments, the human acceptor framework is the human VL kappa I consensus ($VL_{KI}$) framework and/or the VH framework $VH_1$. In certain embodiments, the human acceptor framework is the human VL kappa I consensus ($VL_{KI}$) framework and/or the VH framework $VH_1$ comprising any one of the following mutations.

In another aspect, an anti-CLL-1 antibody is provided, wherein the antibody comprises a VH as in any of the embodiments provided above, and a VL as in any of the embodiments provided above.

In one embodiment, the antibody comprises the VH and VL sequences in SEQ ID NO:36 and SEQ ID NO:35, respectively, including post-translational modifications of those sequences.

In a further aspect, provided are herein are antibodies that bind to the same epitope as an anti-CLL-1 antibody provided herein. For example, in certain embodiments, an antibody is provided that binds to the same epitope as an anti-CLL-1 antibody comprising a VH sequence of SEQ ID NO:36 and a VL sequence of SEQ ID NO:35, respectively.

Figure 1B:
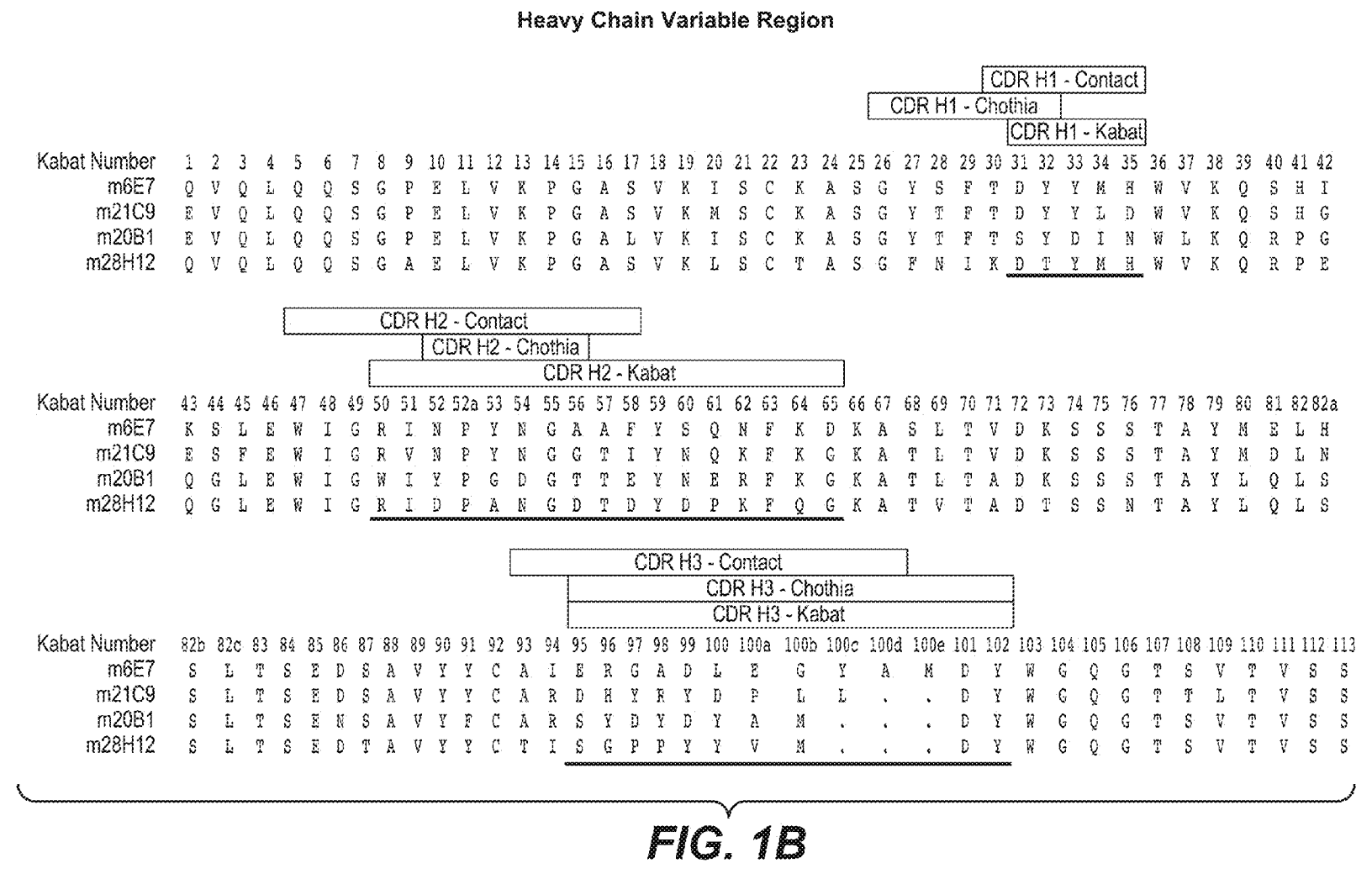

Provided herein are antibodies comprising a light chain variable domain comprising the HVR1-LC, HVR2-LC and HVR3-LC sequence according to Kabat numbering as depicted in FIG. 1A and a heavy chain variable domain comprising the HVR1-HC, HVR2-HC and HVR3-HC sequence according to Kabat numbering as depicted in FIG. 1B.

In a further aspect of the invention, an anti-CLL-1 antibody according to any of the above embodiments is a monoclonal antibody, including a human antibody. In one embodiment, an anti-CLL-1 antibody is an antibody fragment, e.g., a Fv, Fab, Fab', scFv, diabody, or F(ab')$_2$ fragment. In another embodiment, the antibody is a substantially full length antibody, e.g., an IgG1 antibody, IgG2a antibody or other antibody class or isotype as defined herein.

Antibody 21C9 and Other Embodiments

In some embodiments, the invention provides an anti-CLL-1 antibody comprising at least one, two, three, four, five, or six HVRs selected from (a) HVR-H1 comprising the amino acid sequence of SEQ ID NO:21; (b) HVR-H2 comprising the amino acid sequence of SEQ ID NO:22; (c) HVR-H3 comprising the amino acid sequence of SEQ ID NO:23; (d) HVR-L1 comprising the amino acid sequence of SEQ ID NO:18; (e) HVR-L2 comprising the amino acid sequence of SEQ ID NO:19; and (f) HVR-L3 comprising the amino acid sequence of SEQ ID NO:20.

In one aspect, the invention provides an antibody comprising at least one, at least two, or all three VH HVR sequences selected from (a) HVR-H1 comprising the amino acid sequence of SEQ ID NO:21; (b) HVR-H2 comprising the amino acid sequence of SEQ ID NO:22; and (c) HVR-H3 comprising the amino acid sequence of SEQ ID NO:23. In one embodiment, the antibody comprises HVR-H3 comprising the amino acid sequence of SEQ ID NO:23. In another embodiment, the antibody comprises HVR-H3 comprising the amino acid sequence of SEQ ID NO:23 and HVR-L3 comprising the amino acid sequence of SEQ ID NO:20. In a further embodiment, the antibody comprises HVR-H3 comprising the amino acid sequence of SEQ ID NO:23, HVR-L3 comprising the amino acid sequence of SEQ ID NO:20, and HVR-H2 comprising the amino acid sequence of SEQ ID NO:22. In a further embodiment, the antibody comprises (a) HVR-H1 comprising the amino acid sequence of SEQ ID NO:21; (b) HVR-H2 comprising the amino acid sequence of SEQ ID NO:22; and (c) HVR-H3 comprising the amino acid sequence of SEQ ID NO:23.

In another aspect, the invention provides an antibody comprising at least one, at least two, or all three VL HVR sequences selected from (a) HVR-L1 comprising the amino acid sequence of SEQ ID NO: 18; (b) HVR-L2 comprising the amino acid sequence of SEQ ID NO:19; and (c) HVR-L3 comprising the amino acid sequence of SEQ ID NO:20. In one embodiment, the antibody comprises (a) HVR-L1 comprising the amino acid sequence of SEQ ID NO:18; (b) HVR-L2 comprising the amino acid sequence of SEQ ID NO:19; and (c) HVR-L3 comprising the amino acid sequence of SEQ ID NO:20.

In another aspect, an antibody of the invention comprises (a) a VH domain comprising at least one, at least two, or all three VH HVR sequences selected from (i) HVR-H1 comprising the amino acid sequence of SEQ ID NO:21, (ii) HVR-H2 comprising the amino acid sequence of SEQ ID NO:22, and (iii) HVR-H3 comprising an amino acid sequence selected from SEQ ID NO:23; and (b) a VL domain comprising at least one, at least two, or all three VL HVR sequences selected from (i) HVR-L1 comprising the amino acid sequence of SEQ ID NO:18, (ii) HVR-L2 comprising the amino acid sequence of SEQ ID NO:19, and (c) HVR-L3 comprising the amino acid sequence of SEQ ID NO:20.

In another aspect, the invention provides an antibody comprising (a) HVR-H1 comprising the amino acid sequence of SEQ ID NO:21; (b) HVR-H2 comprising the amino acid sequence of SEQ ID NO:22; (c) HVR-H3 comprising the amino acid sequence of SEQ ID NO:23; (d) HVR-L1 comprising the amino acid sequence of SEQ ID NO:18; (e) HVR-L2 comprising the amino acid sequence of SEQ ID NO:19; and (f) HVR-L3 comprising the amino acid sequence of SEQ ID NO:20. In some embodiments, the antibody comprises (a) HVR-H1 comprising the amino acid sequence of SEQ ID NO:21; (b) HVR-H2 comprising the amino acid sequence of SEQ ID NO:22; (c) HVR-H3 comprising the amino acid sequence of SEQ ID NO:23; (d) HVR-L1 comprising the amino acid sequence of SEQ ID NO: 18; (e) HVR-L2 comprising the amino acid sequence of SEQ ID NO:19; and (f) HVR-L3 comprising the amino acid sequence of SEQ ID NO:20.

In any of the above embodiments, an anti-CLL-1 antibody is humanized. In one embodiment, an anti-CLL-1 antibody comprises HVRs as in any of the above embodiments, and further comprises a human acceptor framework, e.g. a human immunoglobulin framework or a human consensus framework. In certain embodiments, the human acceptor framework is the human VL kappa I consensus (VL$_{KI}$) framework and/or the VH framework VH$_1$. In certain embodiments, the human acceptor framework is the human VL kappa I consensus (VL$_{KI}$) framework and/or the VH framework VH$_1$ comprising any one of the following mutations.

In another aspect, an anti-CLL-1 antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO:38 and/or SEQ ID NO:40. In certain embodiments, a VH sequence having at least 90%, 91%, 92%, 93%, 94%, 95%, 96%, 97%, 98%, or 99% identity to the amino acid sequence of SEQ ID NO:38 and/or SEQ ID NO:40 contains substitutions (e.g., conservative substitutions), insertions, or deletions relative to the reference sequence, but an anti-CLL-1 antibody comprising that sequence retains the ability to bind to CLL-1. In certain embodiments, a total of 1 to 10 amino acids have been substituted, inserted and/or deleted in SEQ ID NO:38 and/or SEQ ID NO:40. In certain embodiments, a total of 1 to 5 amino acids have been substituted, inserted and/or deleted in SEQ ID NO:38 and/or SEQ ID NO:40. In certain embodiments, substitutions, insertions, or deletions occur in regions outside the HVRs (i.e., in the FRs). Optionally, the anti-CLL-1 antibody comprises the VH sequence of SEQ ID NO:38 and/or SEQ ID NO:40, including post-translational modifications of that sequence. In a particular embodiment, the VH comprises one, two or three HVRs selected from: (a) HVR-H1 comprising the amino acid sequence of SEQ ID NO:21, (b) HVR-H2 comprising the amino acid sequence of SEQ ID NO:22, and (c) HVR-H3 comprising the amino acid sequence of SEQ ID NO:23.

In another aspect, an anti-CLL-1 antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO:37 and/or SEQ ID NO:39. In certain embodiments, a VL sequence having at least 90%, 91%, 92%, 93%, 94%, 95%, 96%, 97%, 98%, or 99% identity to the amino acid sequence of SEQ ID NO:37 and/or SEQ ID NO:39 contains substitutions (e.g., conservative substitutions), insertions, or deletions relative to the reference sequence, but an anti-CLL-1 antibody comprising that sequence retains the ability to bind to CLL-1. In certain embodiments, a total of 1 to 10 amino acids have been substituted, inserted and/or deleted in SEQ ID NO:37 and/or SEQ ID NO:39. In certain embodiments, a total of 1 to 5 amino acids have been substituted, inserted and/or deleted in SEQ ID NO:37 and/or SEQ ID NO:39. In certain embodiments, the substitutions, insertions, or deletions occur in regions outside the HVRs (i.e., in the FRs). Optionally, the anti-CLL-1 antibody comprises the VL sequence of SEQ ID NO:37 and/or SEQ ID NO:39, including post-translational modifications of that sequence. In a particular embodiment, the VL comprises one, two or three HVRs selected from (a) HVR-L1 comprising the amino acid sequence of SEQ ID NO:18; (b) HVR-L2 comprising the amino acid sequence of SEQ ID NO:19; and (c) HVR-L3 comprising the amino acid sequence of SEQ ID NO:20.

In another aspect, an anti-CLL-1 antibody is provided, wherein the antibody comprises a VH as in any of the embodiments provided above, and a VL as in any of the embodiments provided above.

In one embodiment, the antibody comprises the VH and VL sequences in SEQ ID NO:38 and SEQ ID NO:37, respectively, including post-translational modifications of those sequences. In one embodiment, the antibody comprises the VH and VL sequences in SEQ ID NO:40 and SEQ ID NO:39, respectively, including post-translational modifications of those sequences.

In a further aspect, provided are herein are antibodies that bind to the same epitope as an anti-CLL-1 antibody provided herein. For example, in certain embodiments, an antibody is provided that binds to the same epitope as an anti-CLL-1 antibody comprising a VH sequence of SEQ ID NO:38 and/or SEQ ID NO:40 and a VL sequence of SEQ ID NO:37 and/or SEQ ID NO:39, respectively.

Figure 3B:
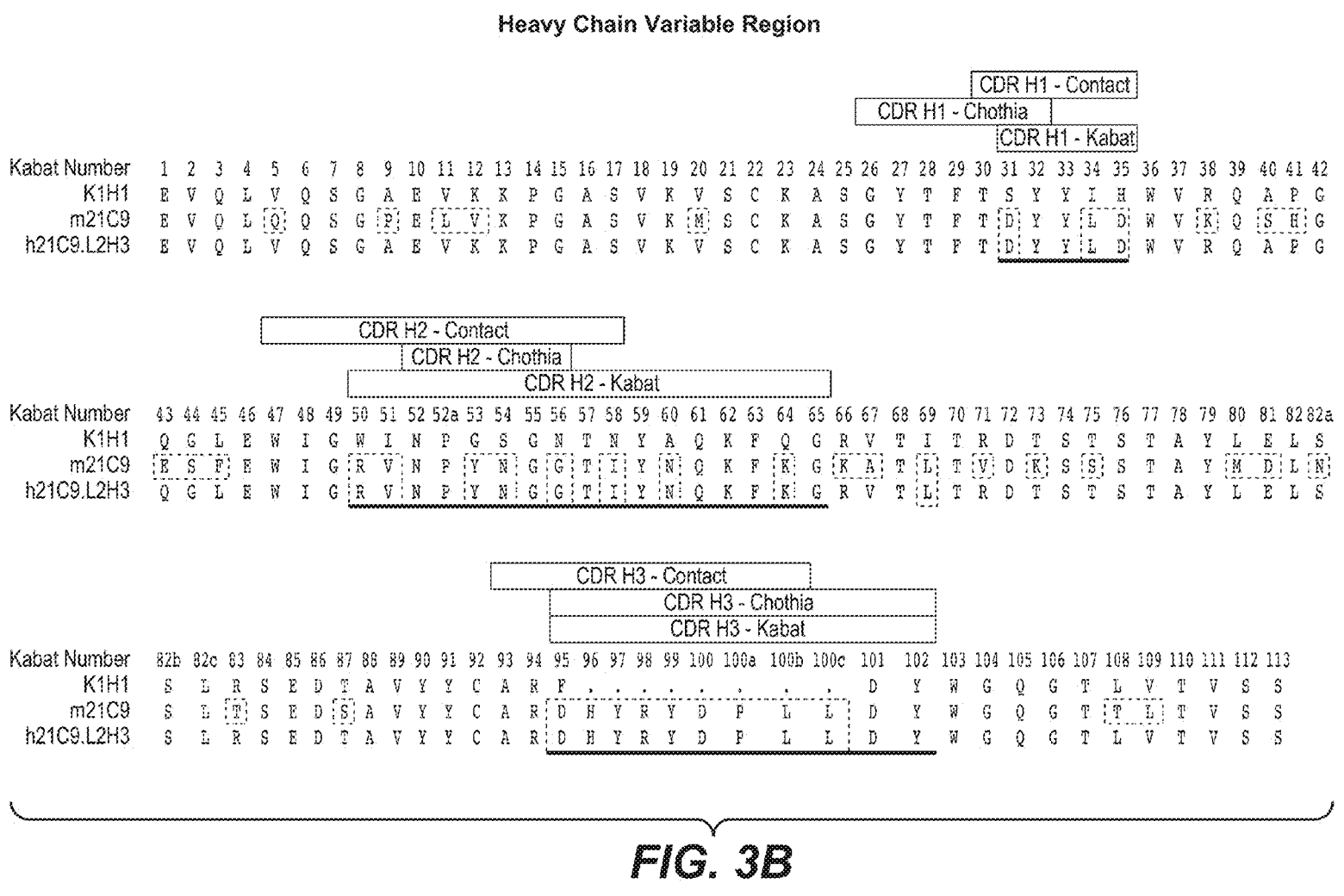

Provided herein are antibodies comprising a light chain variable domain comprising the HVR1-LC, HVR2-LC and HVR3-LC sequence according to Kabat numbering as depicted in FIG. 3A and a heavy chain variable domain comprising the HVR1-HC, HVR2-HC and HVR3-HC sequence according to Kabat numbering as depicted in FIG. 3B. In some embodiments, the antibody comprises a light chain variable domain comprising the HVR1-LC, HVR2-LC and/or HVR3-LC sequence, and the FR1-LC, FR2-LC, FR3-LC and/or FR4-LC sequence as depicted in FIG. 3A. In some embodiments, the antibody comprises a heavy chain variable domain comprising the HVR1-HC, HVR2-HC and/or HVR3-HC sequence, and the FR1-HC, FR2-HC, FR3-HC and/or FR4-HC sequence as depicted in FIG. 3B.

In a further aspect of the invention, an anti-CLL-1 antibody according to any of the above embodiments is a monoclonal antibody, including a human antibody. In one embodiment, an anti-CLL-1 antibody is an antibody fragment, e.g., a Fv, Fab, Fab', scFv, diabody, or F(ab')$_2$ fragment. In another embodiment, the antibody is a substantially full length antibody, e.g., an IgG1 antibody, IgG2a antibody or other antibody class or isotype as defined herein.

Antibody 28H12 and Other Embodiments

In some embodiments, the invention provides an anti-CLL-1 antibody comprising at least one, two, three, four, five, or six HVRs selected from (a) HVR-H1 comprising the amino acid sequence of SEQ ID NO:27; (b) HVR-H2 comprising the amino acid sequence of SEQ ID NO:28; (c) HVR-H3 comprising the amino acid sequence of SEQ ID NO:29; (d) HVR-L1 comprising the amino acid sequence of SEQ ID NO:24; (e) HVR-L2 comprising the amino acid sequence of SEQ ID NO:25; and (f) HVR-L3 comprising the amino acid sequence of SEQ ID NO:26.

In one aspect, the invention provides an antibody comprising at least one, at least two, or all three VH HVR sequences selected from (a) HVR-H1 comprising the amino acid sequence of SEQ ID NO:27; (b) HVR-H2 comprising the amino acid sequence of SEQ ID NO:28; and (c) HVR-H3 comprising the amino acid sequence of SEQ ID NO:29. In one embodiment, the antibody comprises HVR-H3 comprising the amino acid sequence of SEQ ID NO:29. In another embodiment, the antibody comprises HVR-H3 comprising the amino acid sequence of SEQ ID NO:29 and HVR-L3 comprising the amino acid sequence of SEQ ID NO:26. In a further embodiment, the antibody comprises HVR-H3 comprising the amino acid sequence of SEQ ID NO:29, HVR-L3 comprising the amino acid sequence of SEQ ID NO:26, and HVR-H2 comprising the amino acid sequence of SEQ ID NO:28. In a further embodiment, the antibody comprises (a) HVR-H1 comprising the amino acid sequence of SEQ ID NO:27; (b) HVR-H2 comprising the amino acid sequence of SEQ ID NO:28; and (c) HVR-H3 comprising the amino acid sequence of SEQ ID NO:29.

In another aspect, the invention provides an antibody comprising at least one, at least two, or all three VL HVR sequences selected from (a) HVR-L1 comprising the amino acid sequence of SEQ ID NO:24; (b) HVR-L2 comprising the amino acid sequence of SEQ ID NO:25; and (c) HVR-L3 comprising the amino acid sequence of SEQ ID NO:26. In one embodiment, the antibody comprises (a) HVR-L1 comprising the amino acid sequence of SEQ ID NO:24; (b) HVR-L2 comprising the amino acid sequence of SEQ ID NO:25; and (c) HVR-L3 comprising the amino acid sequence of SEQ ID NO:26.

In another aspect, an antibody of the invention comprises (a) a VH domain comprising at least one, at least two, or all three VH HVR sequences selected from (i) HVR-H1 comprising the amino acid sequence of SEQ ID NO:27, (ii) HVR-H2 comprising the amino acid sequence of SEQ ID NO:28, and (iii) HVR-H3 comprising an amino acid sequence selected from SEQ ID NO:29; and (b) a VL domain comprising at least one, at least two, or all three VL HVR sequences selected from (i) HVR-L1 comprising the amino acid sequence of SEQ ID NO:24, (ii) HVR-L2 comprising the amino acid sequence of SEQ ID NO:25, and (c) HVR-L3 comprising the amino acid sequence of SEQ ID NO:26.

In another aspect, the invention provides an antibody comprising (a) HVR-H1 comprising the amino acid sequence of SEQ ID NO:27; (b) HVR-H2 comprising the amino acid sequence of SEQ ID NO:28; (c) HVR-H3 comprising the amino acid sequence of SEQ ID NO:29; (d) HVR-L1 comprising the amino acid sequence of SEQ ID NO:24; (e) HVR-L2 comprising the amino acid sequence of SEQ ID NO:25; and (f) HVR-L3 comprising the amino acid sequence of SEQ ID NO:26. In some embodiments, the antibody comprises (a) HVR-H1 comprising the amino acid sequence of SEQ ID NO:27; (b) HVR-H2 comprising the amino acid sequence of SEQ ID NO:28; (c) HVR-H3 comprising the amino acid sequence of SEQ ID NO:29; (d) HVR-L1 comprising the amino acid sequence of SEQ ID NO:24; (e) HVR-L2 comprising the amino acid sequence of SEQ ID NO:25; and (f) HVR-L3 comprising the amino acid sequence of SEQ ID NO:26.

In any of the above embodiments, an anti-CLL-1 antibody is humanized. In one embodiment, an anti-CLL-1 antibody comprises HVRs as in any of the above embodiments, and further comprises a human acceptor framework, e.g. a human immunoglobulin framework or a human consensus framework. In certain embodiments, the human acceptor framework is the human VL kappa I consensus ($VL_{KI}$) framework and/or the VH framework $VH_1$. In certain embodiments, the human acceptor framework is the human VL kappa I consensus ($VL_{KI}$) framework and/or the VH framework $VH_1$ comprising any one of the following mutations.

In another aspect, an anti-CLL-1 antibody is provided, wherein the antibody comprises a VH as in any of the embodiments provided above, and a VL as in any of the embodiments provided above.

In one embodiment, the antibody comprises the VH and VL sequences in SEQ ID NO:42 and SEQ ID NO:41, respectively, including post-translational modifications of those sequences.

In a further aspect, provided are herein are antibodies that bind to the same epitope as an anti-CLL-1 antibody provided herein. For example, in certain embodiments, an antibody is provided that binds to the same epitope as an anti-CLL-1 antibody comprising a VH sequence of SEQ ID NO:42 and a VL sequence of SEQ ID NO:41, respectively.

Provided herein are antibodies comprising a light chain variable domain comprising the HVR1-LC, HVR2-LC and HVR3-LC sequence according to Kabat numbering as depicted in FIG. 1A and a heavy chain variable domain comprising the HVR1-HC, HVR2-HC and HVR3-HC sequence according to Kabat numbering as depicted in FIG. 1B.

In a further aspect of the invention, an anti-CLL-1 antibody according to any of the above embodiments is a monoclonal antibody, including a human antibody. In one embodiment, an anti-CLL-1 antibody is an antibody fragment, e.g., a Fv, Fab, Fab', scFv, diabody, or F(ab')$_2$ fragment. In another embodiment, the antibody is a substantially full length antibody, e.g., an IgG1 antibody, IgG2a antibody or other antibody class or isotype as defined herein.

In a further aspect, an anti-CLL-1 antibody according to any of the above embodiments may incorporate any of the features, singly or in combination, as described below.

1. Antibody Affinity

In certain embodiments, an antibody provided herein has a dissociation constant (Kd) of ≤1 µM, ≤100 nM, ≤50 nM, ≤10 nM, ≤5 nM, ≤1 nM, ≤0.1 nM, ≤0.01 nM, or ≤0.001 nM, and optionally is ≥$10^{-13}$ M. (e.g. $10^{-8}$M or less, e.g. from $10^{-8}$ M to $10^{-13}$ M, e.g., from $10^{-9}$M to $10^{-13}$ M).

In one embodiment, Kd is measured by a radiolabeled antigen binding assay (RIA) performed with the Fab version of an antibody of interest and its antigen as described by the following assay. Solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen et al., *J. Mol. Biol.* 293:865-881(1999)). To establish conditions for the assay, MICROTITER® multi-well plates (Thermo Scientific) are coated overnight with 5 µg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 pM or 26 pM [$^{125}$I]-antigen are mixed with serial dilutions of a Fab of interest (e.g., consistent with assessment of the anti-VEGF antibody, Fab-12, in Presta et al., *Cancer Res.* 57:4593-4599 (1997)). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN-20®) in PBS. When the plates have dried, 150 µl/well of scintillant (MICROSCINT-20 ™; Packard) is added, and the plates are counted on a TOP-COUNT™ gamma counter (Packard) for ten minutes. Concentrations of each Fab that give less than or equal to 20% of maximal binding are chosen for use in competitive binding assays.

According to another embodiment, Kd is measured using surface plasmon resonance assays using a BIACORE®-2000, BAICORE®-T200 or a BIACORE®-3000 (BIAcore, Inc., Piscataway, N.J.) at 25° C. with immobilized antigen CM5 chips at ~10 response units (RU). Briefly, carboxymethylated dextran biosensor chips (CM5, BIACORE®, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 µg/ml (~0.2 µM) and/or HBS-P (0.01 M Hepes pH7.4, 0.15M NaCl, 0.005% Surfactant P20) before injection at a flow rate of 5 µl/minute and/or 30 µl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20™) surfactant (PBST) at 25° C. at a flow rate of approximately 25 µl/min. Association rates ($k_{on}$) and dissociation rates ($k_{off}$) are calculated using a simple one-to-one Langmuir binding model (BIACORE® Evaluation Software version 3.2) by simultaneously fitting the association and dissociation sensorgrams. The equilibrium dissociation constant (Kd) is calculated as the ratio $k_{off}/k_{on}$. See, e.g., Chen et al., *J. Mol. Biol.* 293:865-881 (1999). If the on-rate exceeds $10^6$ $M^{-1}$ $s^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophometer (Aviv Instruments) or a 8000-series SLM-AMINCO™ spectrophotometer (ThermoSpectronic) with a stirred cuvette.

2. Antibody Fragments

In certain embodiments, an antibody provided herein is an antibody fragment. Antibody fragments include, but are not limited to, Fab, Fab', Fab'-SH, F(ab')₂, Fv, and scFv fragments, and other fragments described below. For a review of certain antibody fragments, see Hudson et al. *Nat. Med.* 9:129-134 (2003). For a review of scFv fragments, see, e.g., Pluckthün, in *The Pharmacology of Monoclonal Antibodies*, vol. 113, Rosenburg and Moore eds., (Springer-Verlag, New York), pp. 269-315 (1994); see also WO 93/16185; and U.S. Pat. Nos. 5,571,894 and 5,587,458. For discussion of Fab and F(ab')₂ fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP 404,097; WO 1993/01161; Hudson et al., *Nat. Med.* 9:129-134 (2003); and Hollinger et al., *Proc. Natl. Acad. Sci. USA* 90: 6444-6448 (1993). Triabodies and tetrabodies are also described in Hudson et al., *Nat. Med.* 9:129-134 (2003).

Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, Mass.; see, e.g., U.S. Pat. No. 6,248,516 B1).

Antibody fragments can be made by various techniques, including but not limited to proteolytic digestion of an intact antibody as well as production by recombinant host cells (e.g. *E. coli* or phage), as described herein.

3. Chimeric and Humanized Antibodies

In certain embodiments, an antibody provided herein is a chimeric antibody. Certain chimeric antibodies are described, e.g., in U.S. Pat. No. 4,816,567; and Morrison et al., *Proc. Natl. Acad. Sci. USA*, 81:6851-6855 (1984)). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro and Fransson, *Front. Biosci.* 13:1619-1633 (2008), and are further described, e.g., in Riechmann et al., *Nature* 332:323-329 (1988); Queen et al., *Proc. Nat'l Acad. Sci. USA* 86:10029-10033 (1989); U.S. Pat. Nos. 5,821,337, 7,527,791, 6,982,321, and 7,087,409; Kashmiri et al., *Methods* 36:25-34 (2005) (describing SDR (a-CDR) grafting); Padlan, *Mol. Immunol.* 28:489-498 (1991) (describing "resurfacing"); Dall'Acqua et al., *Methods* 36:43-60 (2005) (describing "FR shuffling"); and Osbourn et al., *Methods* 36:61-68 (2005) and Klimka et al., *Br. J. Cancer,* 83:252-260 (2000) (describing the "guided selection" approach to FR shuffling).

Human framework regions that may be used for humanization include but are not limited to: framework regions selected using the "best-fit" method (see, e.g., Sims et al. *J. Immunol.* 151:2296 (1993)); framework regions derived from the consensus sequence of human antibodies of a particular subgroup of light or heavy chain variable regions (see, e.g., Carter et al. *Proc. Natl. Acad. Sci. USA,* 89:4285 (1992); and Presta et al. *J. Immunol.,* 151:2623 (1993)); human mature (somatically mutated) framework regions or human germline framework regions (see, e.g., Almagro and Fransson, *Front. Biosci.* 13:1619-1633 (2008)); and framework regions derived from screening FR libraries (see, e.g., Baca et al., *J. Biol. Chem.* 272:10678-10684 (1997) and Rosok et al., *J. Biol. Chem.* 271:22611-22618 (1996)).

4. Human Antibodies

In certain embodiments, an antibody provided herein is a human antibody. Human antibodies can be produced using various techniques known in the art. Human antibodies are described generally in van Dijk and van de Winkel, *Curr. Opin. Pharmacol.* 5: 368-74 (2001) and Lonberg, *Curr. Opin. Immunol.* 20:450-459 (2008).

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, *Nat. Biotech.* 23:1117-1125 (2005). See also, e.g., U.S. Pat. Nos. 6,075,181 and 6,150,584 describing XENO-MOUSE™ technology; U.S. Pat. No. 5,770,429 describing HuMAb® technology; U.S. Pat. No. 7,041,870 describing K-M MOUSE® technology, and U.S. Patent Application Publication No. US 2007/0061900, describing VELOCI-MOUSE® technology). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor *J. Immunol.*, 133: 3001 (1984); Brodeur et al., *Monoclonal Antibody Production Techniques and Applications*, pp. 51-63 (Marcel Dekker, Inc., New York, 1987); and Boerner et al., *J. Immunol.*, 147: 86 (1991).) Human antibodies generated via human B-cell hybridoma technology are also described in Li et al., *Proc. Natl. Acad. Sci. USA,* 103:3557-3562 (2006). Additional methods include those described, for example, in U.S. Pat. No. 7,189,826 (describing production of monoclonal human IgM antibodies from hybridoma cell lines) and Ni, *Xiandai Mianyixue,* 26(4):265-268 (2006) (describing human-human hybridomas). Human hybridoma technology (Trioma technology) is also described in Vollmers and Brandlein, *Histology and Histopathology,* 20(3):927-937 (2005) and Vollmers and Brandlein, *Methods and Findings in Experimental and Clinical Pharmacology,* 27(3): 185-91 (2005).

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

5. Library-Derived Antibodies

Antibodies of the invention may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom et al. in *Methods in Molecular Biology* 178: 1-37 (O'Brien et al., ed., Human Press, Totowa, N.J., 2001) and further described, e.g., in the McCafferty et al., *Nature* 348:552-554; Clackson et al., *Nature* 352: 624-628 (1991); Marks et al., *J. Mol. Biol.* 222: 581-597 (1992); Marks and Bradbury, in *Methods in Molecular Biology* 248:161-175 (Lo, ed., Human Press, Totowa, N.J., 2003); Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci. USA* 101(34): 12467-12472 (2004); and Lee et al., *J. Immunol. Methods* 284(1-2): 119-132(2004).

In certain phage display methods, repertoires of VH and VL genes are separately cloned by polymerase chain reaction (PCR) and recombined randomly in phage libraries, which can then be screened for antigen-binding phage as described in Winter et al., *Ann. Rev. Immunol.,* 12: 433-455 (1994). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self antigens without any immunization as described by Griffiths et al., *EMBO J,* 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, *J. Mol. Biol.,* 227: 381-388 (1992). Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

Antibodies or antibody fragments isolated from human antibody libraries are considered human antibodies or human antibody fragments herein.

6. Multispecific Antibodies

In certain embodiments, an antibody provided herein is a multispecific antibody, e.g. a bispecific antibody. Multispecific antibodies are monoclonal antibodies that have binding specificities for at least two different sites. In certain embodiments, one of the binding specificities is for CLL-1 and the other is for any other antigen. In certain embodiments, one of the binding specificities is for CLL-1 and the other is for CD3. See, e.g., U.S. Pat. No. 5,821,337. In certain embodiments, bispecific antibodies may bind to two different epitopes of CLL-1. Bispecific antibodies may also be used to localize cytotoxic agents to cells which express CLL-1. Bispecific antibodies can be prepared as full length antibodies or antibody fragments. In some embodiments, multispecific antibodies are monoclonal antibodies that have binding specificities for at least two different sites.

In some embodiments, multispecific antibodies are monoclonal antibodies that have binding specificities for at least two different antigen binding sites (such as a bispecific antibody). In some embodiments, the first antigen-binding domain and the second antigen-binding domain of the multispecific antibody may bind the two epitopes within one and the same molecule (intramolecular binding). For example, the first antigen-binding domain and the second antigen-binding domain of the multispecific antibody may bind to two different epitopes on the same CLL-1 molecule. In certain embodiments, the two different epitopes that a multispecific antibody binds are epitopes that are not normally bound at the same time by one monospecific antibody, such as e.g. a conventional antibody or one immunoglobulin single variable domain. In some embodiments, the first antigen-binding domain and the second antigen-binding domain of the multispecific antibody may bind epitopes located within two distinct molecules (intermolecular binding). For example, the first antigen-binding domain of the multispecific antibody may bind to one epitope on one CLL-1 molecule, whereas the second antigen-binding domain of the multispecific antibody may bind to another epitope on a different CLL-1 molecule, thereby cross-linking the two molecules.

In some embodiments, the antigen-binding domain of a multispecific antibody (such as a bispecific antibody) comprises two VH/VL units, wherein a first VH/VL unit binds to a first epitope and a second VH/VL unit binds to a second epitope, wherein each VH/VL unit comprises a heavy chain variable domain (VH) and a light chain variable domain (VL). Such multispecific antibodies include, but are not limited to, full length antibodies, antibodies having two or more VL and VH domains, and antibody fragments (such as Fab, Fv, dsFv, scFv, diabodies, bispecific diabodies and triabodies, antibody fragments that have been linked covalently or non-covalently). A VH/VL unit that further comprises at least a portion of a heavy chain variable region and/or at least a portion of a light chain variable region may also be referred to as an "arm" or "hemimer" or "half antibody." In some embodiments, a hemimer comprises a sufficient portion of a heavy chain variable region to allow intramolecular disulfide bonds to be formed with a second hemimer. In some embodiments, a hemimer comprises a knob mutation or a hole mutation, for example, to allow heterodimerization with a second hemimer or half antibody that comprises a complementary hole mutation or knob mutation. Knob mutations and hole mutations are discussed further below.

In certain embodiments, a multispecific antibody provided herein may be a bispecific antibody. The term "bispecific antibody" is as used herein refers to a multispecific antibody comprising an antigen-binding domain that is capable of binding to two different epitopes on one molecule or is capable of binding to epitopes on two different molecules. A bispecific antibody may also be referred to herein as having "dual specificity" or as being "dual specific." Exemplary bispecific antibodies may bind both CLL-1 and any other antigen. In certain embodiments, one of the binding specificities is for CLL-1 and the other is for CD3. See, e.g., U.S. Pat. No. 5,821,337. In certain embodiments, bispecific antibodies may bind to two different epitopes of the same CLL-1 molecule. In certain embodiments, bispecific antibodies may bind to two different epitopes on two different CLL-1 molecules. Bispecific antibodies may also be used to localize cytotoxic agents to cells which express CLL-1. Bispecific antibodies can be prepared as full length antibodies or antibody fragments.

Techniques for making multispecific antibodies include, but are not limited to, recombinant co-expression of two immunoglobulin heavy chain-light chain pairs having different specificities (see Milstein and Cuello, *Nature* 305: 537 (1983)), WO 93/08829, and Traunecker et al., *EMBO J.* 10: 3655 (1991)), and "knob-in-hole" engineering (see, e.g., U.S. Pat. No. 5,731,168), WO2009/089004, US2009/0182127, US2011/0287009, Marvin and Zhu, Acta Pharmacol. Sin. (2005) 26(6):649-658, and Kontermann (2005) Acta Pharmacol. Sin., 26:1-9). The term "knob-into-hole" or "KnH" technology as used herein refers to the technology directing the pairing of two polypeptides together in vitro or in vivo by introducing a protuberance (knob) into one polypeptide and a cavity (hole) into the other polypeptide at an interface in which they interact. For example, KnHs have been introduced in the Fc:Fc binding interfaces, CL:CH1 interfaces or VH/VL interfaces of antibodies (see, e.g., US 2011/0287009, US2007/0178552, WO 96/027011, WO 98/050431, and Zhu et al., 1997, *Protein Science* 6:781-788). In some embodiments, KnHs drive the pairing of two different heavy chains together during the manufacture of multispecific antibodies. For example, multispecific antibodies having KnH in their Fc regions can further comprise single variable domains linked to each Fc region, or further comprise different heavy chain variable domains that pair with similar or different light chain variable domains. KnH technology can be also be used to pair two different receptor extracellular domains together or any other polypeptide sequences that comprises different target recognition sequences (e.g., including affibodies, peptibodies and other Fc fusions).

The term "knob mutation" as used herein refers to a mutation that introduces a protuberance (knob) into a polypeptide at an interface in which the polypeptide interacts with another polypeptide. In some embodiments, the other polypeptide has a hole mutation.

The term "hole mutation" as used herein refers to a mutation that introduces a cavity (hole) into a polypeptide at an interface in which the polypeptide interacts with another polypeptide. In some embodiments, the other polypeptide has a knob mutation.

A brief nonlimiting discussion is provided below.

A "protuberance" refers to at least one amino acid side chain which projects from the interface of a first polypeptide and is therefore positionable in a compensatory cavity in the adjacent interface (i.e. the interface of a second polypeptide) so as to stabilize the heteromultimer, and thereby favor heteromultimer formation over homomultimer formation, for example. The protuberance may exist in the original interface or may be introduced synthetically (e.g., by altering nucleic acid encoding the interface). In some embodiments, nucleic acid encoding the interface of the first polypeptide is altered to encode the protuberance. To achieve this, the nucleic acid encoding at least one "original" amino acid residue in the interface of the first polypeptide is replaced with nucleic acid encoding at least one "import" amino acid residue which has a larger side chain volume than the original amino acid residue. It will be appreciated that there can be more than one original and corresponding import residue. The side chain volumes of the various amino residues are shown, for example, in Table 1 of US2011/0287009. A mutation to introduce a "protuberance" may be referred to as a "knob mutation."

In some embodiments, import residues for the formation of a protuberance are naturally occurring amino acid residues selected from arginine (R), phenylalanine (F), tyrosine (Y) and tryptophan (W). In some embodiments, an import residue is tryptophan or tyrosine. In some embodiment, the original residue for the formation of the protuberance has a small side chain volume, such as alanine, asparagine, aspartic acid, glycine, serine, threonine or valine.

A "cavity" refers to at least one amino acid side chain which is recessed from the interface of a second polypeptide and therefore accommodates a corresponding protuberance on the adjacent interface of a first polypeptide. The cavity may exist in the original interface or may be introduced synthetically (e.g. by altering nucleic acid encoding the interface). In some embodiments, nucleic acid encoding the interface of the second polypeptide is altered to encode the cavity. To achieve this, the nucleic acid encoding at least one "original" amino acid residue in the interface of the second polypeptide is replaced with DNA encoding at least one "import" amino acid residue which has a smaller side chain volume than the original amino acid residue. It will be appreciated that there can be more than one original and corresponding import residue. In some embodiments, import residues for the formation of a cavity are naturally occurring amino acid residues selected from alanine (A), serine (S), threonine (T) and valine (V). In some embodiments, an import residue is serine, alanine or threonine. In some embodiments, the original residue for the formation of the cavity has a large side chain volume, such as tyrosine, arginine, phenylalanine or tryptophan. A mutation to introduce a "cavity" may be referred to as a "hole mutation."

The protuberance is "positionable" in the cavity which means that the spatial location of the protuberance and cavity on the interface of a first polypeptide and second polypeptide respectively and the sizes of the protuberance and cavity are such that the protuberance can be located in the cavity without significantly perturbing the normal association of the first and second polypeptides at the interface. Since protuberances such as Tyr, Phe and Trp do not typically extend perpendicularly from the axis of the interface and have preferred conformations, the alignment of a protuberance with a corresponding cavity may, in some instances, rely on modeling the protuberance/cavity pair based upon a three-dimensional structure such as that obtained by X-ray crystallography or nuclear magnetic resonance (NMR). This can be achieved using widely accepted techniques in the art.

In some embodiments, a knob mutation in an IgG1 constant region is T366W (EU numbering). In some embodiments, a hole mutation in an IgG1 constant region comprises one or more mutations selected from T366S, L368A and Y407V (EU numbering). In some embodiments, a hole mutation in an IgG1 constant region comprises T366S, L368A and Y407V (EU numbering).

In some embodiments, a knob mutation in an IgG4 constant region is T366W (EU numbering). In some embodiments, a hole mutation in an IgG4 constant region comprises one or more mutations selected from T366S, L368A, and Y407V (EU numbering). In some embodiments, a hole mutation in an IgG4 constant region comprises T366S, L368A, and Y407V (EU numbering).

Multi-specific antibodies may also be made by engineering electrostatic steering effects for making antibody Fc-heterodimeric molecules (WO 2009/089004A1); cross-linking two or more antibodies or fragments (see, e.g., U.S. Pat. No. 4,676,980, and Brennan et al., *Science*, 229: 81 (1985)); using leucine zippers to produce bi-specific antibodies (see, e.g., Kostelny et al., *J. Immunol.*, 148(5):1547-1553 (1992)); using "diabody" technology for making bispecific antibody fragments (see, e.g., Hollinger et al., *Proc. Natl. Acad. Sci. USA*, 90:6444-6448 (1993)); and using single-chain Fv (sFv) dimers (see, e.g. Gruber et al., *J. Immunol.*, 152:5368 (1994)); and preparing trispecific antibodies as described, e.g., in Tutt et al. *J. Immunol.* 147: 60 (1991).

Engineered antibodies with three or more functional antigen binding sites, including "Octopus antibodies" or "dual-variable domain immunoglobulins" (DVDs) are also included herein (see, e.g., US 2006/0025576A1, and Wu et al. *Nature Biotechnology* (2007)).). The antibody or fragment herein also includes a "Dual Acting FAb" or "DAF" comprising an antigen binding site that binds to CLL-1 as well as another, different antigen (see, US 2008/0069820, for example).

7. Antibody Variants

In certain embodiments, amino acid sequence variants of the antibodies provided herein are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

a) Substitution, Insertion, and Deletion Variants

In certain embodiments, antibody variants having one or more amino acid substitutions are provided. Sites of interest for substitutional mutagenesis include the HVRs and FRs. Conservative substitutions are shown in Table 1 under the heading of "preferred substitutions." More substantial changes are provided in Table 1 under the heading of "exemplary substitutions," and as further described below in reference to amino acid side chain classes. Amino acid substitutions may be introduced into an antibody of interest and the products screened for a desired activity, e.g., retained/improved antigen binding, decreased immunogenicity, or improved ADCC or CDC.

TABLE 1

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:
(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

One type of substitutional variant involves substituting one or more hypervariable region residues of a parent antibody (e.g. a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g. binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, *Methods Mol. Biol.* 207:179-196 (2008)), and/or SDRs (a-CDRs), with the resulting variant VH or VL being tested for binding affinity. Affinity maturation by constructing and reselecting from secondary libraries has been described, e.g., in Hoogenboom et al. in *Methods in Molecular Biology* 178:1-37 (O'Brien et al., ed., Human Press, Totowa, N.J., (2001).) In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may be outside of HVR "hotspots" or SDRs. In certain embodiments of the variant VH and VL sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham and Wells (1989) *Science,* 244:1081-1085. In this method, a residue or group of target residues (e.g., charged residues such as arg, asp, his, lys, and glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex is used to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g. for ADEPT) or a polypeptide which increases the serum half-life of the antibody.

b) Glycosylation Variants

In certain embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the $CH_2$ domain of the Fc region. See, e.g., Wright et al. *TIBTECH* 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties.

In one embodiment, antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e. g. complex, hybrid and high mannose structures) as measured by MALDI-TOF mass spectrometry, as described in WO 2008/077546, for example. Asn297 refers to the asparagine residue located at about position 297 in the Fc region (Eu numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. *J. Mol. Biol.* 336:1239-1249 (2004); Yamane-Ohnuki et al. *Biotech. Bioeng.* 87: 614 (2004). Examples of cell lines capable of producing defucosylated antibodies include Lec13 CHO cells deficient in protein fucosylation (Ripka et al. *Arch. Biochem. Biophys.* 249:533-545 (1986); US Pat Appl No US 2003/0157108 A1, Presta, L; and WO 2004/056312 A1, Adams et al., especially at Example 11), and knockout cell lines, such as alpha-1,6-fucosyltransferase gene, FUT8, knockout CHO cells (see, e.g., Yamane-Ohnuki et al. *Biotech. Bioeng.* 87: 614 (2004); Kanda, Y. et al., *Biotechnol. Bioeng.,* 94(4):680-688 (2006); and WO2003/085107).

Antibodies variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878 (Jean-Mairet et al.); U.S. Pat. No. 6,602,684 (Umana et al.); and US 2005/0123546 (Umana et al.). Antibody variants with at least one galactose residue in the oligosaccharide attached to the Fc region are also provided. Such antibody variants may have improved CDC function. Such antibody variants are described, e.g., in WO 1997/30087 (Patel et al.); WO 1998/58964 (Raju, S.); and WO 1999/22764 (Raju, S.).

c) Fc Region Variants

In certain embodiments, one or more amino acid modifications may be introduced into the Fc region of an antibody provided herein, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

In certain embodiments, the invention contemplates an antibody variant that possesses some but not all effector functions, which make it a desirable candidate for applications in which the half life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express Fc(RIII only, whereas monocytes express Fc(RI, Fc(RII and Fc(RIII. FcR expression on hematopoietic cells is summarized in Table 3 on page 464 of Ravetch and Kinet, *Annu. Rev. Immunol.* 9:457-492 (1991). Non-limiting examples of in vitro assays to assess ADCC activity of a molecule of interest is described in U.S. Pat. No. 5,500,362 (see, e.g. Hellstrom, I. et al. *Proc. Nat'l Acad. Sci. USA* 83:7059-7063 (1986)) and Hellstrom, I et al., *Proc. Nat'l Acad. Sci. USA* 82:1499-1502 (1985); U.S. Pat. No. 5,821,337 (see Bruggemann, M. et al., *J. Exp. Med.* 166:1351-1361 (1987)). Alternatively, non-radioactive assays methods may be employed (see, for example, ACTI™ non-radioactive cytotoxicity assay for flow cytometry (CellTechnology, Inc. Mountain View, Calif.; and CytoTox 96® non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. *Proc. Nat'l Acad. Sci. USA* 95:652-656 (1998). C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al., *J. Immunol. Methods* 202:163 (1996); Cragg, M. S. et al., *Blood* 101:1045-1052 (2003); and Cragg, M. S. and M. J. Glennie, *Blood* 103:2738-2743 (2004)). FcRn binding and in vivo clearance/half life determinations can also be performed using methods known in the art (see, e.g., Petkova, S. B. et al., *Int'l. Immunol.* 18(12):1759-1769 (2006)).

In some embodiments, one or more amino acid modifications may be introduced into the Fc portion of the antibody provided herein in order to increase IgG binding to the neonatal Fc receptor. In certain embodiments, the antibody comprises the following three mutations according to EU numbering: M252Y, S254T, and T256E (the "YTE mutation") (U.S. Pat. No. 8,697,650; see also Dall'Acqua et al., Journal of Biological Chemistry 281(33):23514-23524 (2006). In certain embodiments, the YTE mutation does not affect the ability of the antibody to bind to its cognate antigen. In certain embodiments, the YTE mutation increases the antibody's serum half-life compared to the native (i.e., non-YTE mutant) antibody. In some embodiments, the YTE mutation increases the serum half-life of the antibody by 3-fold compared to the native (i.e., non-YTE mutant) antibody. In some embodiments, the YTE mutation increases the serum half-life of the antibody by 2-fold compared to the native (i.e., non-YTE mutant) antibody. In some embodiments, the YTE mutation increases the serum half-life of the antibody by 4-fold compared to the native (i.e., non-YTE mutant) antibody. In some embodiments, the YTE mutation increases the serum half-life of the antibody by at least 5-fold compared to the native (i.e., non-YTE mutant) antibody. In some embodiments, the YTE mutation increases the serum half-life of the antibody by at least 10-fold compared to the native (i.e., non-YTE mutant) antibody. See, e.g., U.S. Pat. No. 8,697,650; see also Dall'Acqua et al., Journal of Biological Chemistry 281(33): 23514-23524 (2006).

In certain embodiments, the YTE mutant provides a means to modulate antibody-dependent cell-mediated cytotoxicity (ADCC) activity of the antibody. In certain embodiments, the YTEO mutant provides a means to modulate ADCC activity of a humanized IgG antibody directed against a human antigen. See, e.g., U.S. Pat. No. 8,697,650; see also Dall'Acqua et al., Journal of Biological Chemistry 281(33):23514-23524 (2006).

In certain embodiments, the YTE mutant allows the simultaneous modulation of serum half-life, tissue distribution, and antibody activity (e.g., the ADCC activity of an IgG antibody). See, e.g., U.S. Pat. No. 8,697,650; see also Dall'Acqua et al., Journal of Biological Chemistry 281(33): 23514-23524 (2006).

Antibodies with reduced effector function include those with substitution of one or more of Fc region residues 238, 265, 269, 270, 297, 327 and 329 according to EU numbering (U.S. Pat. No. 6,737,056). Such Fc mutants include Fc mutants with substitutions at two or more of amino acid positions 265, 269, 270, 297 and 327 according to EU numbering, including the so-called "DANA" Fc mutant with substitution of residues 265 and 297 to alanine according to EU numbering (i.e., D265A and N297A according to EU numbering) (U.S. Pat. No. 7,332,581). In certain embodiments the Fc mutant comprises the following two amino acid substitutions: D265A and N297A. In certain embodiments the Fc mutant consists of the following two amino acid substitutions: D265A and N297A.

In certain embodiments, the proline at position 329 (EU numbering) (P329) of a wild-type human Fc region is substituted with glycine or arginine or an amino acid residue large enough to destroy the proline sandwich within the Fc/Fcγ receptor interface, that is formed between the P329 of the Fc and tryptophane residues W87 and W110 of FcgRIII (Sondermann et al.: Nature 406, 267-273 (20 Jul. 2000)). In a further embodiment, at least one further amino acid substitution in the Fc variant is S228P, E233P, L234A, L235A, L235E, N297A, $N_{297}D$, or P331S and still in another embodiment said at least one further amino acid substitution is L234A and L235A of the human IgG1 Fc region or S228P and L235E of the human IgG4 Fc region, all according to EU numbering (U.S. Pat. No. 8,969,526 which is incorporated by reference in its entirety).

In certain embodiments, a polypeptide comprises the Fc variant of a wild-type human IgG Fc region wherein the polypeptide has P329 of the human IgG Fc region substituted with glycine and wherein the Fc variant comprises at least two further amino acid substitutions at L234A and L235A of the human IgG1 Fc region or S228P and L235E of the human IgG4 Fc region, and wherein the residues are numbered according to the EU numbering (U.S. Pat. No. 8,969,526 which is incorporated by reference in its entirety). In certain embodiments, the polypeptide comprising the P329G, L234A and L235A (EU numbering) substitutions exhibit a reduced affinity to the human FcγRIIIA and FcγRIIA, for down-modulation of ADCC to at least 20% of the ADCC induced by the polypeptide comprising the wild-type human IgG Fc region, and/or for down-modulation of ADCP (U.S. Pat. No. 8,969,526 which is incorporated by reference in its entirety).

In a specific embodiment the polypeptide comprising an Fc variant of a wildtype human Fc polypeptide comprises a triple mutation: an amino acid substitution at position Pro329, a L234A and a L235A mutation according to EU numbering (P329/LALA) (U.S. Pat. No. 8,969,526 which is incorporated by reference in its entirety). In specific embodiments, the polypeptide comprises the following amino acid substitutions: P329G, L234A, and L235A according to EU numbering.

Certain antibody variants with improved or diminished binding to FcRs are described. (See, e.g., U.S. Pat. No. 6,737,056; WO 2004/056312, and Shields et al., *J. Biol. Chem.* 9(2): 6591-6604 (2001).)

In certain embodiments, an antibody variant comprises an Fc region with one or more amino acid substitutions which improve ADCC, e.g., substitutions at positions 298, 333, and/or 334 of the Fc region (EU numbering).

In some embodiments, alterations are made in the Fc region that result in altered (i. e., either improved or diminished) C1q binding and/or Complement Dependent Cytotoxicity (CDC), e.g., as described in U.S. Pat. No. 6,194,551, WO 99/51642, and Idusogie et al. *J Immunol.* 164: 4178-4184 (2000).

Antibodies with increased half lives and improved binding to the neonatal Fc receptor (FcRn), which is responsible for the transfer of maternal IgGs to the fetus (Guyer et al., *J. Immunol.* 117:587 (1976) and Kim et al., *J. Immunol.* 24:249 (1994)), are described in US2005/0014934A1 (Hinton et al.). Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826) according to EU numbering. See also Duncan & Winter, *Nature* 322:738-40 (1988); U.S. Pat. No. 5,648,260; U.S. Pat. No. 5,624,821; and WO 94/29351 concerning other examples of Fc region variants.

d) Cysteine Engineered Antibody Variants

In certain embodiments, it may be desirable to create cysteine engineered antibodies, e.g., "THIOMAB™ antibody," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug intermediates, to create an immunoconjugate, as described further herein. In certain embodiments, any one or more of the following residues may be substituted with cysteine: V205 (Kabat numbering) of the light chain; A140 (EU numbering) of the heavy chain; L174 (EU numbering) of the heavy chain; Y373 (EU numbering) of the heavy chain; K149 (Kabat numbering) of the light chain; A118 (EU numbering) of the heavy chain; and S400 (EU numbering) of the heavy chain Fc region. In specific embodiments, the antibodies described herein comprise the HC-A140C (EU numbering) cysteine substitution. In specific embodiments, the antibodies described herein comprise the LC-K149C (Kabat numbering) cysteine substitution. In specific embodiments, the antibodies described herein comprise the HC-A118C (EU numbering) cysteine substitution. Cysteine engineered antibodies may be generated as described, e.g., in U.S. Pat. No. 7,521,541.

In certain embodiments, the antibody comprises one of the following heavy chain cysteine substitutions:

| Chain (HC/LC) | Residue | EU Mutation Site # | Kabat Mutation Site # |
|---|---|---|---|
| HC | T | 114 | 110 |
| HC | A | 140 | 136 |
| HC | L | 174 | 170 |
| HC | L | 179 | 175 |
| HC | T | 187 | 183 |
| HC | T | 209 | 205 |
| HC | V | 262 | 258 |
| HC | G | 371 | 367 |
| HC | Y | 373 | 369 |
| HC | E | 382 | 378 |
| HC | S | 424 | 420 |
| HC | N | 434 | 430 |
| HC | Q | 438 | 434 |

In certain embodiments, the antibody comprises one of the following light chain cysteine substitutions:

| Chain (HC/LC) | Residue | EU Mutation Site # | Kabat Mutation Site # |
|---|---|---|---|
| LC | I | 106 | 106 |
| LC | R | 108 | 108 |
| LC | R | 142 | 142 |
| LC | K | 149 | 149 | e) Antibody Derivatives

In certain embodiments, an antibody provided herein may be further modified to contain additional nonproteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1, 3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and nonproteinaceous moiety that may be selectively heated by exposure to radiation are provided. In one embodiment, the nonproteinaceous moiety is a carbon nanotube (Kam et al., *Proc. Natl. Acad. Sci. USA* 102: 11600-11605 (2005)). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

B. Recombinant Methods and Compositions

Antibodies may be produced using recombinant methods and compositions, e.g., as described in U.S. Pat. No. 4,816, 567. In one embodiment, isolated nucleic acid encoding an anti-CLL-1 antibody described herein is provided. Such nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, e.g. a Chinese Hamster Ovary (CHO) cell or lymphoid cell (e.g., Y0, NS0, Sp20 cell). In one embodiment, a method of making an anti-CLL-1 antibody is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an anti-CLL-1 antibody, nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, *Methods in Molecular Biology*, Vol. 248 (B. K. C. Lo, ed., Humana Press, Totowa, N.J., 2003), pp. 245-254, describing expression of antibody fragments in *E. coli*.) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, *Nat. Biotech.* 22:1409-1414 (2004), and Li et al., *Nat. Biotech.* 24:210-215 (2006).

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., *J. Gen Virol.* 36:59 (1977)); baby hamster kidney cells (BHK); mouse sertoli cells (TM4 cells as described, e.g., in Mather, *Biol. Reprod.* 23:243-251 (1980)); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al., *Annals N. Y. Acad. Sci.* 383:44-68 (1982); MRC 5 cells; and FS4 cells. Other useful mammalian host cell lines include Chinese hamster ovary (CHO) cells, including DHFR⁻ CHO cells (Urlaub et al., *Proc. Natl. Acad. Sci. USA* 77:4216 (1980)); and myeloma cell lines such as Y0, NS0 and Sp2/0. For a review of certain mammalian host cell lines suitable for antibody production, see, e.g., Yazaki and Wu, *Methods in Molecular Biology*, Vol. 248 (B. K. C. Lo, ed., Humana Press, Totowa, N.J.), pp. 255-268 (2003).

C. Assays

Anti-CLL-1 antibodies provided herein may be identified, screened for, or characterized for their physical/chemical properties and/or biological activities by various assays known in the art.

In one aspect, an antibody of the invention is tested for its antigen binding activity, e.g., by known methods such as ELISA, BIACore®, FACS, or Western blot.

In another aspect, competition assays may be used to identify an antibody that competes with any of the antibodies described herein for binding to CLL-1. In certain embodiments, such a competing antibody binds to the same epitope (e.g., a linear or a conformational epitope) that is bound by an antibody described herein. Detailed exemplary methods for mapping an epitope to which an antibody binds are provided in Morris (1996) "Epitope Mapping Protocols," in *Methods in Molecular Biology* vol. 66 (Humana Press, Totowa, N.J.).

In an exemplary competition assay, immobilized CLL-1 is incubated in a solution comprising a first labeled antibody that binds to CLL-1 (e.g., any of the antibodies described herein) and a second unlabeled antibody that is being tested for its ability to compete with the first antibody for binding to CLL-1. The second antibody may be present in a hybridoma supernatant. As a control, immobilized CLL-1 is incubated in a solution comprising the first labeled antibody but not the second unlabeled antibody. After incubation under conditions permissive for binding of the first antibody to CLL-1, excess unbound antibody is removed, and the amount of label associated with immobilized CLL-1 is measured. If the amount of label associated with immobilized CLL-1 is substantially reduced in the test sample relative to the control sample, then that indicates that the second antibody is competing with the first antibody for binding to CLL-1. See Harlow and Lane (1988)*Antibodies: A Laboratory Manual* ch. 14 (Cold Spring Harbor Laboratory, Cold Spring Harbor, N.Y.).

D. Immunoconjugates

The invention also provides immunoconjugates comprising an anti-CLL-1 antibody herein conjugated to one or more cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes (i.e., a radioconjugate).

Immunoconjugates allow for the targeted delivery of a drug moiety to a tumor, and, in some embodiments intracellular accumulation therein, where systemic administration of unconjugated drugs may result in unacceptable levels of toxicity to normal cells (Polakis P. (2005) *Current Opinion in Pharmacology* 5:382-387).

Antibody-drug conjugates (ADC) are targeted chemotherapeutic molecules which combine properties of both antibodies and cytotoxic drugs by targeting potent cytotoxic drugs to antigen-expressing tumor cells (Teicher, B. A. (2009) *Current Cancer Drug Targets* 9:982-1004), thereby enhancing the therapeutic index by maximizing efficacy and minimizing off-target toxicity (Carter, P. J. and Senter P. D. (2008) *The Cancer Jour.* 14(3):154-169; Chari, R. V. (2008) *Ace. Chem. Res.* 41:98-107

The ADC compounds of the invention include those with anticancer activity. In some embodiments, the ADC compounds include an antibody conjugated, i.e. covalently attached, to the drug moiety. In some embodiments, the antibody is covalently attached to the drug moiety through a linker. The antibody-drug conjugates (ADC) of the invention selectively deliver an effective dose of a drug to tumor tissue whereby greater selectivity, i.e. a lower efficacious dose, may be achieved while increasing the therapeutic index ("therapeutic window").

The drug moiety (D) of the antibody-drug conjugates (ADC) may include any compound, moiety or group that has a cytotoxic or cytostatic effect. Drug moieties may impart their cytotoxic and cytostatic effects by mechanisms including but not limited to tubulin binding, DNA binding or intercalation, and inhibition of RNA polymerase, protein synthesis, and/or topoisomerase. Exemplary drug moieties include, but are not limited to, a maytansinoid, dolastatin, auristatin, calicheamicin, pyrrolobenzodiazepine (PBD), nemorubicin and its derivatives, PNU-159682, anthracycline, duocarmycin, *vinca* alkaloid, taxane, trichothecene, CC1065, camptothecin, elinafide, and stereoisomers, isosteres, analogs, and derivatives thereof that have cytotoxic activity. Nonlimiting examples of such immunoconjugates are discussed in further detail below.

1. Exemplary Antibody-Drug Conjugates

An exemplary embodiment of an antibody-drug conjugate (ADC) compound comprises an antibody (Ab) which targets a tumor cell, a drug moiety (D), and a linker moiety (L) that attaches Ab to D. In some embodiments, the antibody is attached to the linker moiety (L) through one or more amino acid residues, such as lysine and/or cysteine.

An exemplary ADC has Formula I:

Ab-(L-D)$_p$    I where p is 1 to about 20. In some embodiments, the number of drug moieties that can be conjugated to an antibody is limited by the number of free cysteine residues. In some embodiments, free cysteine residues are introduced into the antibody amino acid sequence by the methods described herein. Exemplary ADC of Formula I include, but are not limited to, antibodies that have 1, 2, 3, or 4 engineered cysteine amino acids (Lyon, R. et al (2012) *Methods in Enzym.* 502:123-138). In some embodiments, one or more free cysteine residues are already present in an antibody, without the use of engineering, in which case the existing free cysteine residues may be used to conjugate the antibody to a drug. In some embodiments, an antibody is exposed to reducing conditions prior to conjugation of the antibody in order to generate one or more free cysteine residues.

a) Exemplary Linkers

A "Linker" (L) is a bifunctional or multifunctional moiety that can be used to link one or more drug moieties (D) to an antibody (Ab) to form an antibody-drug conjugate (ADC) of Formula I. In some embodiments, antibody-drug conjugates (ADC) can be prepared using a Linker having reactive functionalities for covalently attaching to the drug and to the antibody. For example, in some embodiments, a cysteine thiol of an antibody (Ab) can form a bond with a reactive functional group of a linker or a drug-linker intermediate to make an ADC.

In one aspect, a linker has a functionality that is capable of reacting with a free cysteine present on an antibody to form a covalent bond. Nonlimiting exemplary such reactive functionalities include maleimide, haloacetamides, α-haloacetyl, activated esters such as succinimide esters, 4-nitrophenyl esters, pentafluorophenyl esters, tetrafluorophenyl esters, anhydrides, acid chlorides, sulfonyl chlorides, isocyanates, and isothiocyanates. See, e.g., the conjugation method at page 766 of Klussman, et al (2004), *Bioconjugate Chemistry* 15(4):765-773, and the Examples herein.

In some embodiments, a linker has a functionality that is capable of reacting with an electrophilic group present on an antibody. Exemplary such electrophilic groups include, but are not limited to, aldehyde and ketone carbonyl groups. In some embodiments, a heteroatom of the reactive functionality of the linker can react with an electrophilic group on an antibody and form a covalent bond to an antibody unit. Nonlimiting exemplary such reactive functionalities include, but are not limited to, hydrazide, oxime, amino, hydrazine, thiosemicarbazone, hydrazine carboxylate, and arylhydrazide.

A linker may comprise one or more linker components. Exemplary linker components include 6-maleimidocaproyl ("MC"), maleimidopropanoyl ("MP"), valine-citrulline ("val-cit" or "vc"), alanine-phenylalanine ("ala-phe"), p-aminobenzyloxycarbonyl (a "PAB"), N-Succinimidyl 4-(2-pyridylthio) pentanoate ("SPP"), and 4-(N-maleimidomethyl) cyclohexane-1 carboxylate ("MCC"). Various linker components are known in the art, some of which are described below.

A linker may be a "cleavable linker," facilitating release of a drug. Nonlimiting exemplary cleavable linkers include acid-labile linkers (e.g., comprising hydrazone), protease-sensitive (e.g., peptidase-sensitive) linkers, photolabile linkers, or disulfide-containing linkers (Chari et al., Cancer Research 52:127-131 (1992); U.S. Pat. No. 5,208,020).

In certain embodiments, a linker has the following Formula II:

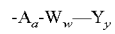

-A$_a$-W$_w$—Y$_y$    II wherein A is a "stretcher unit", and a is an integer from 0 to 1; W is an "amino acid unit", and w is an integer from 0 to 12; Y is a "spacer unit", and y is 0, 1, or 2; and Ab, D, and p are defined as above for Formula I. Exemplary embodiments of such linkers are described in U.S. Pat. No. 7,498,298, which is expressly incorporated herein by reference.

In some embodiments, a linker component comprises a "stretcher unit" that links an antibody to another linker component or to a drug moiety. Nonlimiting exemplary stretcher units are shown below (wherein the wavy line indicates sites of covalent attachment to an antibody, drug, or additional linker components):

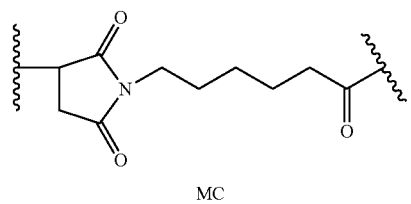

MC

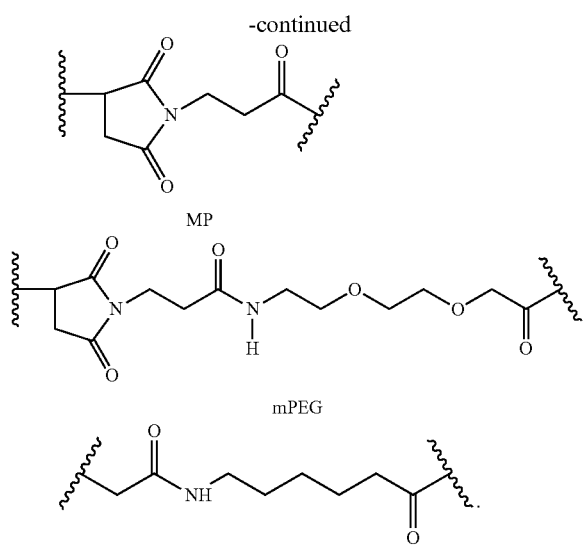

MP mPEG

In some embodiments, the linker may be a peptidomimetic linker such as those described in WO2015/095227, WO2015/095124 or WO2015/095223, which documents are hereby incorporated by reference in their entirety.

In some embodiments, a linker component comprises an "amino acid unit". In some such embodiments, the amino acid unit allows for cleavage of the linker by a protease, thereby facilitating release of the drug from the immunoconjugate upon exposure to intracellular proteases, such as lysosomal enzymes (Doronina et al. (2003) Nat. Biotechnol. 21:778-784). Exemplary amino acid units include, but are not limited to, dipeptides, tripeptides, tetrapeptides, and pentapeptides. Exemplary dipeptides include, but are not limited to, valine-citrulline (vc or val-cit), alanine-phenylalanine (af or ala-phe); phenylalanine-lysine (fk or phe-lys); phenylalanine-homolysine (phe-homolys); and N-methylvaline-citrulline (Me-val-cit). Exemplary tripeptides include, but are not limited to, glycine-valine-citrulline (gly-val-cit) and glycine-glycine-glycine (gly-gly-gly). An amino acid unit may comprise amino acid residues that occur naturally and/or minor amino acids and/or non-naturally occurring amino acid analogs, such as citrulline. Amino acid units can be designed and optimized for enzymatic cleavage by a particular enzyme, for example, a tumor-associated protease, cathepsin B, C and D, or a plasmin protease.

In some embodiments, a linker component comprises a "spacer" unit that links the antibody to a drug moiety, either directly or through a stretcher unit and/or an amino acid unit. A spacer unit may be "self-immolative" or a "non-self-immolative." A "non-self-immolative" spacer unit is one in which part or all of the spacer unit remains bound to the drug moiety upon cleavage of the ADC. Examples of non-self-immolative spacer units include, but are not limited to, a glycine spacer unit and a glycine-glycine spacer unit. In some embodiments, enzymatic cleavage of an ADC containing a glycine-glycine spacer unit by a tumor-cell associated protease results in release of a glycine-glycine-drug moiety from the remainder of the ADC. In some such embodiments, the glycine-glycine-drug moiety is subjected to a hydrolysis step in the tumor cell, thus cleaving the glycine-glycine spacer unit from the drug moiety.

A "self-immolative" spacer unit allows for release of the drug moiety. In certain embodiments, a spacer unit of a linker comprises a p-aminobenzyl unit. In some such embodiments, a p-aminobenzyl alcohol is attached to an amino acid unit via an amide bond, and a carbamate, methylcarbamate, or carbonate is made between the benzyl alcohol and the drug (Hamann et al. (2005) Expert Opin. Ther. Patents (2005) 15:1087-1103). In some embodiments, the spacer unit is p-aminobenzyloxycarbonyl (PAB). In some embodiments, an ADC comprising a self-immolative linker has the structure:

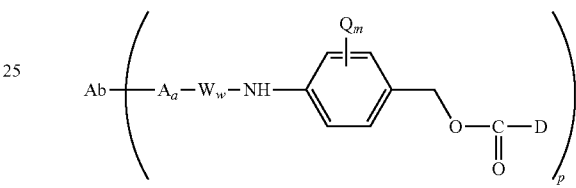

wherein Q is $-C_1-C_8$ alkyl, $-O-(C_1-C_8$ alkyl), -halogen, -nitro, or -cyno; m is an integer ranging from 0 to 4; and p ranges from 1 to about 20. In some embodiments, p ranges from 1 to 10, 1 to 7, 1 to 5, or 1 to 4.

Other examples of self-immolative spacers include, but are not limited to, aromatic compounds that are electronically similar to the PAB group, such as 2-aminoimidazol-5-methanol derivatives (U.S. Pat. No. 7,375,078; Hay et al. (1999) Bioorg. Med. Chem. Lett. 9:2237) and ortho- or para-aminobenzylacetals. In some embodiments, spacers can be used that undergo cyclization upon amide bond hydrolysis, such as substituted and unsubstituted 4-aminobutyric acid amides (Rodrigues et al (1995) Chemistry Biology 2:223), appropriately substituted bicyclo[2.2.1] and bicyclo[2.2.2] ring systems (Storm et al (1972) J. Amer. Chem. Soc. 94:5815) and 2-aminophenylpropionic acid amides (Amsberry, et al (1990) J. Org. Chem. 55:5867). Linkage of a drug to the α-carbon of a glycine residue is another example of a self-immolative spacer that may be useful in ADC (Kingsbury et al (1984) J. Med. Chem. 27:1447).

In some embodiments, linker L may be a dendritic type linker for covalent attachment of more than one drug moiety to an antibody through a branching, multifunctional linker moiety (Sun et al (2002) Bioorganic & Medicinal Chemistry Letters 12:2213-2215; Sun et al (2003) Bioorganic & Medicinal Chemistry 11:1761-1768). Dendritic linkers can increase the molar ratio of drug to antibody, i.e. loading, which is related to the potency of the ADC. Thus, where an antibody bears only one reactive cysteine thiol group, a multitude of drug moieties may be attached through a dendritic linker.

Nonlimiting exemplary linkers are shown below in the context of an ADC of Formula I:

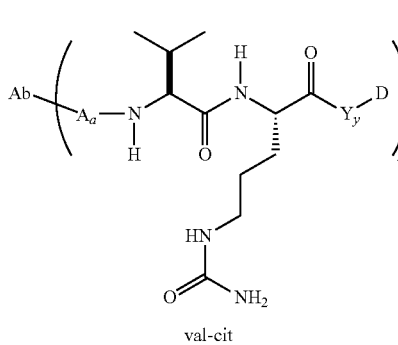

val-cit

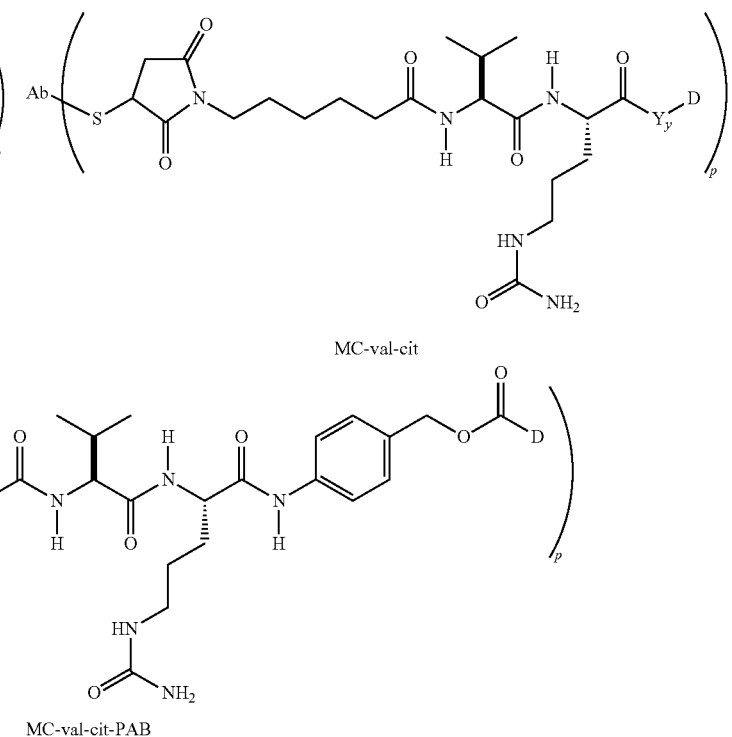

MC-val-cit

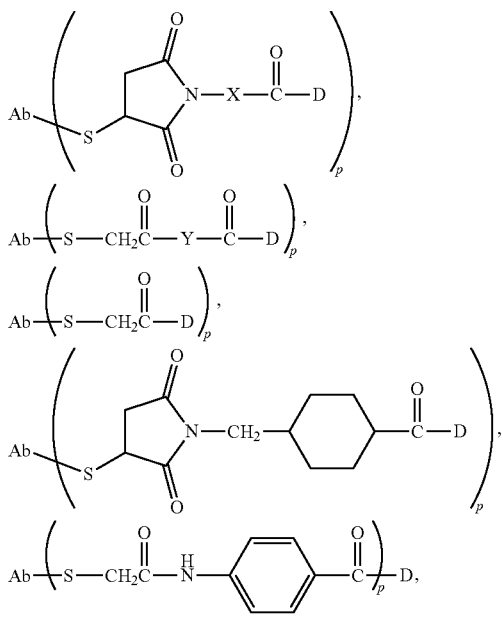

MC-val-cit-PAB

Further nonlimiting exemplary ADCs include the structures:

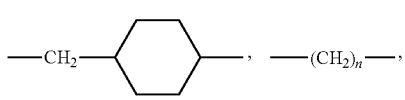

where X is:

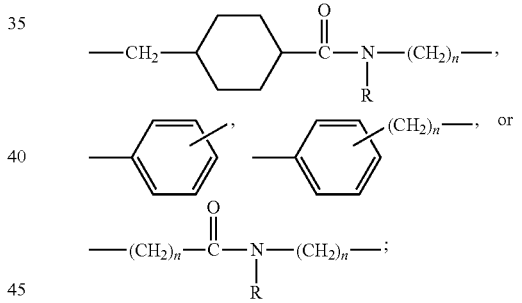

Y is:

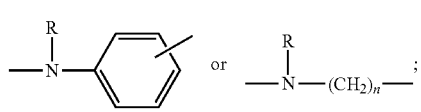

each R is independently H or $C_1$-$C_6$ alkyl; and n is 1 to 12.

Typically, peptide-type linkers can be prepared by forming a peptide bond between two or more amino acids and/or peptide fragments. Such peptide bonds can be prepared, for example, according to a liquid phase synthesis method (e.g., E. Schröder and K. Lübke (1965) "The Peptides", volume 1, pp 76-136, Academic Press).

In some embodiments, a linker is substituted with groups that modulate solubility and/or reactivity. As a nonlimiting example, a charged substituent such as sulfonate ($—SO_3^-$) or ammonium may increase water solubility of the linker reagent and facilitate the coupling reaction of the linker reagent with the antibody and/or the drug moiety, or facilitate the coupling reaction of Ab-L (antibody-linker intermediate) with D, or D-L (drug-linker intermediate) with Ab, depending on the synthetic route employed to prepare the ADC. In some embodiments, a portion of the linker is coupled to the antibody and a portion of the linker is coupled to the drug, and then the Ab-(linker portion)$^a$ is coupled to drug-(linker portion)$^b$ to form the ADC of Formula I. In some such embodiments, the antibody comprises more than one (linker portion)$^a$ substituents, such that more than one drug is coupled to the antibody in the ADC of Formula I.

The compounds of the invention expressly contemplate, but are not limited to, ADC prepared with the following linker reagents: bis-maleimido-trioxyethylene glycol (BMPEO), N-(β-maleimidopropyloxy)-N-hydroxy succinimide ester (BMPS), N-(ε-maleimidocaproyloxy) succinimide ester (EMCS), N-[γ-maleimidobutyryloxy]succinimide ester (GMBS), 1,6-hexane-bis-vinylsulfone (HBVS), succinimidyl 4-(N-maleimidomethyl)cyclohexane-1-carboxy-(6-amidocaproate) (LC-SMCC), m-maleimidobenzoyl-N-hydroxysuccinimide ester (MBS), 4-(4-N-Maleimidophenyl)butyric acid hydrazide (MPBH), succinimidyl 3-(bromoacetamido)propionate (SBAP), succinimidyl iodoacetate (SIA), succinimidyl (4-iodoacetyl) aminobenzoate (SIAB), N-succinimidyl-3-(2-pyridyldithio)propionate (SPDP), N-succinimidyl-4-(2-pyridylthio)pentanoate (SPP), succinimidyl 4-(N-maleimidomethyl)cyclohexane-1-carboxylate (SMCC), succinimidyl 4-(p-maleimidophenyl)butyrate (SMPB), succinimidyl 6-[(beta-maleimidopropionamido)hexanoate] (SMPH), iminothiolane (IT), sulfo-EMCS, sulfo-GMBS, sulfo-KMUS, sulfo-MBS, sulfo-SIAB, sulfo-SMCC, and sulfo-SMPB, and succinimidyl-(4-vinylsulfone)benzoate (SVSB), and including bis-maleimide reagents: dithiobismaleimidoethane (DTME), 1,4-Bismaleimidobutane (BMB), 1,4 Bismaleimidyl-2,3-dihydroxybutane (BMDB), bismaleimidohexane (BMH), bismaleimidoethane (BMOE), BM(PEG)$_2$ (shown below), and BM(PEG)$_3$ (shown below); bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). In some embodiments, bis-maleimide reagents allow the attachment of the thiol group of a cysteine in the antibody to a thiol-containing drug moiety, linker, or linker-drug intermediate. Other functional groups that are reactive with thiol groups include, but are not limited to, iodoacetamide, bromoacetamide, vinyl pyridine, disulfide, pyridyl disulfide, isocyanate, and isothiocyanate.

Certain useful linker reagents can be obtained from various commercial sources, such as Pierce Biotechnology, Inc. (Rockford, Ill.), Molecular Biosciences Inc. (Boulder, Colo.), or synthesized in accordance with procedures described in the art; for example, in Toki et al (2002) *J. Org. Chem.* 67:1866-1872; Dubowchik, et al. (1997) *Tetrahedron Letters*, 38:5257-60; Walker, M. A. (1995) *J. Org. Chem.* 60:5352-5355; Frisch et al (1996) *Bioconjugate Chem.* 7:180-186; U.S. Pat. No. 6,214,345; WO 02/088172; US 2003130189; US2003096743; WO 03/026577; WO 03/043583; and WO 04/032828.

Carbon-14-labeled 1-isothiocyanatobenzyl-3-methyldiethylene triaminepentaacetic acid (MX-DTPA) is an exemplary chelating agent for conjugation of radionucleotide to the antibody. See, e.g., WO94/11026.

b) Exemplary Drug Moieties
(1) Maytansine and Maytansinoids

In some embodiments, an immunoconjugate comprises an antibody conjugated to one or more maytansinoid molecules. Maytansinoids are derivatives of maytansine, and are mitototic inhibitors which act by inhibiting tubulin polymerization. Maytansine was first isolated from the east African shrub *Maytenus serrata* (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinoids are disclosed, for example, in U.S. Pat. Nos. 4,137,230; 4,248,870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,364,866; 4,424,219; 4,450,254; 4,362,663; and 4,371,533.

Maytansinoid drug moieties are attractive drug moieties in antibody-drug conjugates because they are: (i) relatively accessible to prepare by fermentation or chemical modification or derivatization of fermentation products, (ii) amenable to derivatization with functional groups suitable for conjugation through non-disulfide linkers to antibodies, (iii) stable in plasma, and (iv) effective against a variety of tumor cell lines.

Certain maytansinoids suitable for use as maytansinoid drug moieties are known in the art and can be isolated from natural sources according to known methods or produced using genetic engineering techniques (see, e.g., Yu et al (2002) PNAS 99:7968-7973). Maytansinoids may also be prepared synthetically according to known methods.

Exemplary maytansinoid drug moieties include, but are not limited to, those having a modified aromatic ring, such as: C-19-dechloro (U.S. Pat. No. 4,256,746) (prepared, for example, by lithium aluminum hydride reduction of ansamytocin P2); C-20-hydroxy (or C-20-demethyl)+/−C-19-dechloro (U.S. Pat. Nos. 4,361,650 and 4,307,016) (prepared, for example, by demethylation using *Streptomyces* or *Actinomyces* or dechlorination using LAH); and C-20-demethoxy, C-20-acyloxy (—OCOR), +/−dechloro (U.S. Pat. No. 4,294,757) (prepared, for example, by acylation using acyl chlorides), and those having modifications at other positions of the aromatic ring.

Exemplary maytansinoid drug moieties also include those having modifications such as: C-9-SH (U.S. Pat. No. 4,424,219) (prepared, for example, by the reaction of maytansinol with H2S or P2S5); C-14-alkoxymethyl(demethoxy/CH$_2$OR)(U.S. Pat. No. 4,331,598); C-14-hydroxymethyl or acyloxymethyl (CH$_2$OH or CH$_2$OAc) (U.S. Pat. No. 4,450,254) (prepared, for example, from *Nocardia*); C-15-hydroxy/acyloxy (U.S. Pat. No. 4,364,866) (prepared, for example, by the conversion of maytansinol by *Streptomyces*); C-15-methoxy (U.S. Pat. Nos. 4,313,946 and 4,315,929) (for example, isolated from *Trewia nudlflora*); C-18-N-demethyl (U.S. Pat. Nos. 4,362,663 and 4,322,348) (prepared, for example, by the demethylation of maytansinol by *Strepto-*

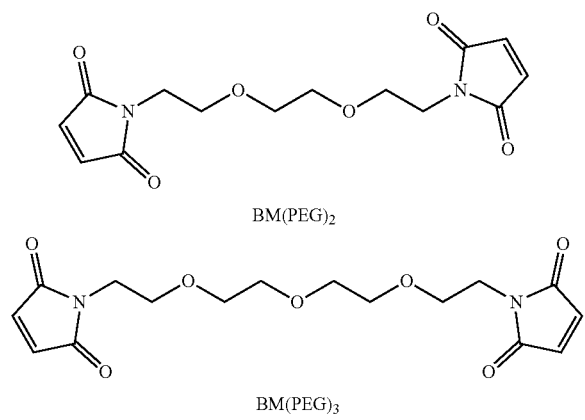

BM(PEG)$_2$

BM(PEG)$_3$

*myces*); and 4,5-deoxy (U.S. Pat. No. 4,371,533) (prepared, for example, by the titanium trichloride/LAH reduction of maytansinol).

Many positions on maytansinoid compounds are useful as the linkage position. For example, an ester linkage may be formed by reaction with a hydroxyl group using conventional coupling techniques. In some embodiments, the reaction may occur at the C-3 position having a hydroxyl group, the C-14 position modified with hydroxymethyl, the C-15 position modified with a hydroxyl group, and the C-20 position having a hydroxyl group. In some embodiments, the linkage is formed at the C-3 position of maytansinol or a maytansinol analogue.

Maytansinoid drug moieties include those having the structure:

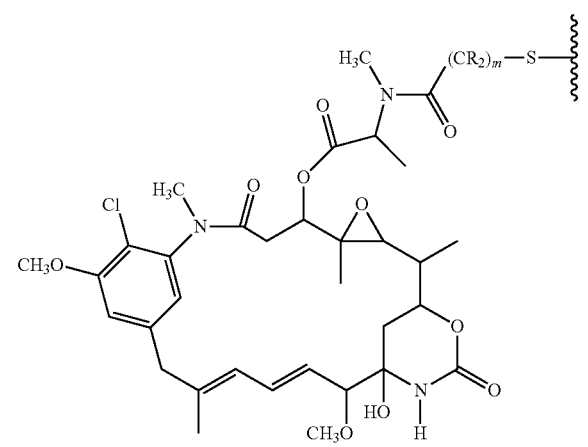

where the wavy line indicates the covalent attachment of the sulfur atom of the maytansinoid drug moiety to a linker of an ADC. Each R may independently be H or a $C_1$-$C_6$ alkyl. The alkylene chain attaching the amide group to the sulfur atom may be methanyl, ethanyl, or propyl, i.e., m is 1, 2, or 3 (US 633410; U.S. Pat. No. 5,208,020; Chari et al (1992) *Cancer Res.* 52:127-131; Liu et al (1996) *Proc. Natl. Acad. Sci USA* 93:8618-8623).

All stereoisomers of the maytansinoid drug moiety are contemplated for the ADC of the invention, i.e. any combination of R and S configurations at the chiral carbons (U.S. Pat. Nos. 7,276,497; 6,913,748; 6,441,163; US 633,410 (RE39151); U.S. Pat. No. 5,208,020; Widdison et al (2006) *J. Med. Chem.* 49:4392-4408, which are incorporated by reference in their entirety). In some embodiments, the maytansinoid drug moiety has the following stereochemistry:

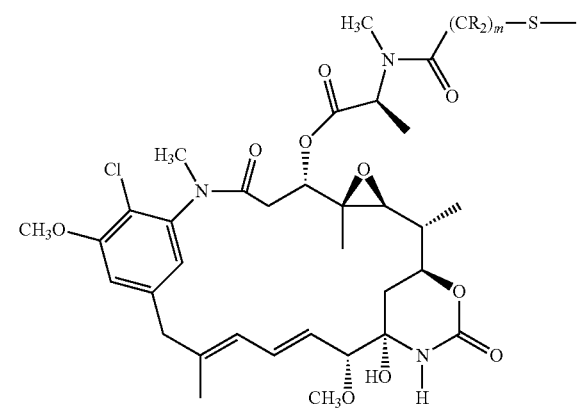

Exemplary embodiments of maytansinoid drug moieties include, but are not limited to, DM1; DM3; and DM4, having the structures:

DM1

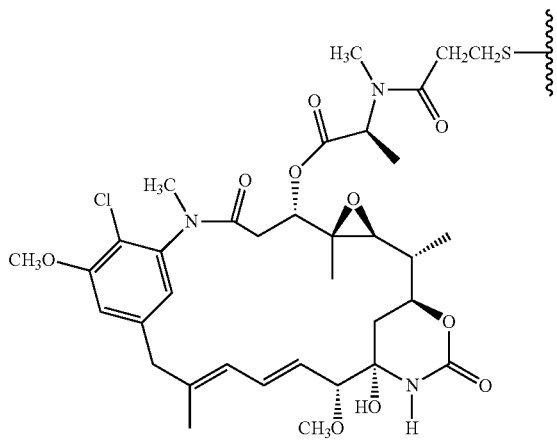

DM3

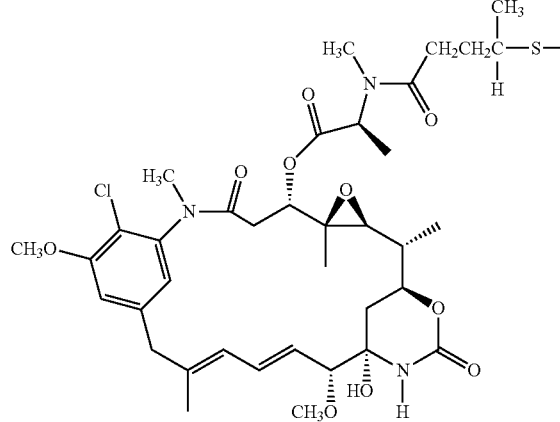

DM4

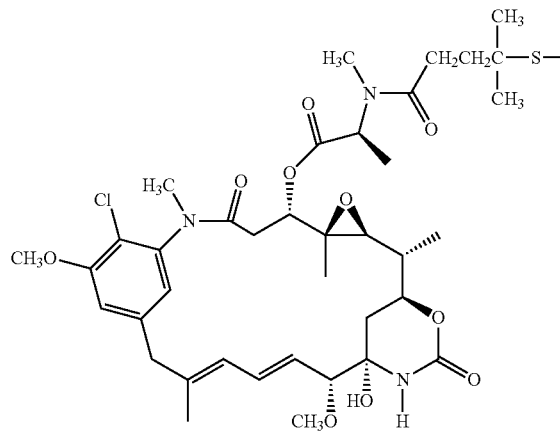

wherein the wavy line indicates the covalent attachment of the sulfur atom of the drug to a linker (L) of an antibody-drug conjugate.

Other exemplary maytansinoid antibody-drug conjugates have the following structures and abbreviations (wherein Ab is antibody and p is 1 to about 20. In some embodiments, p is 1 to 10, p is 1 to 7, p is 1 to 5, or p is 1 to 4):

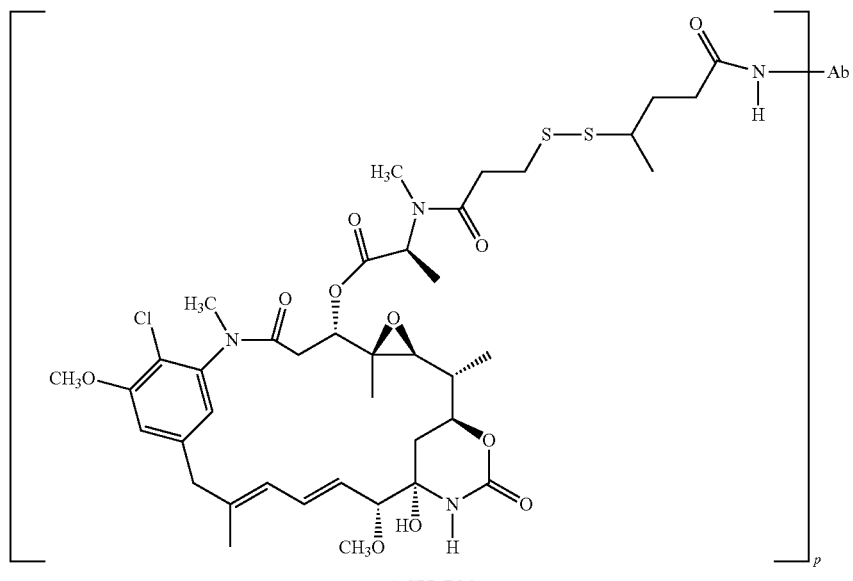
Ab-SPP-DM1
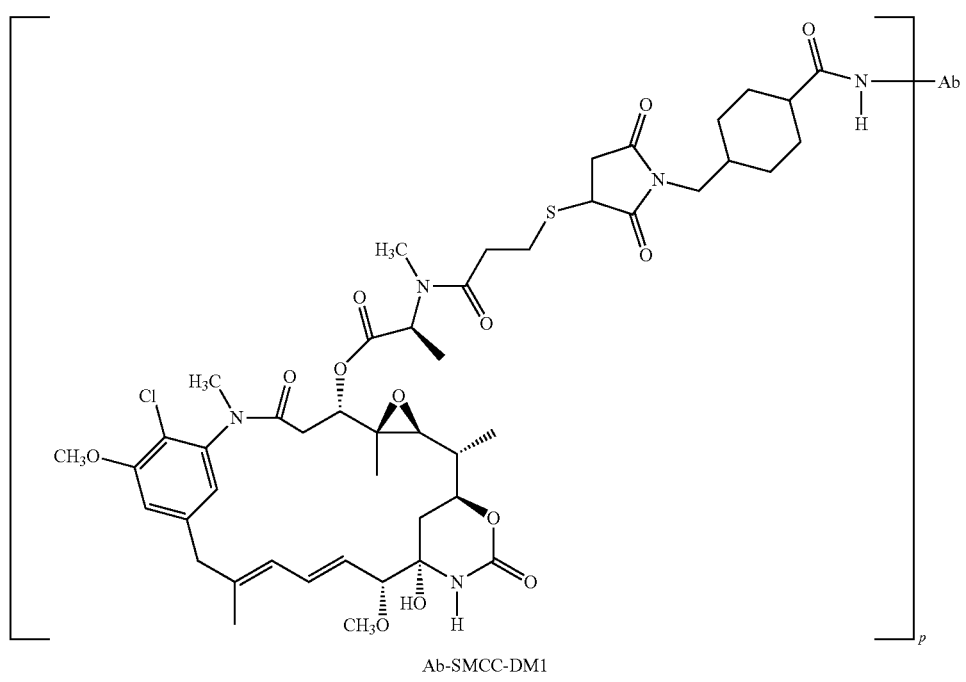
Ab-SMCC-DM1

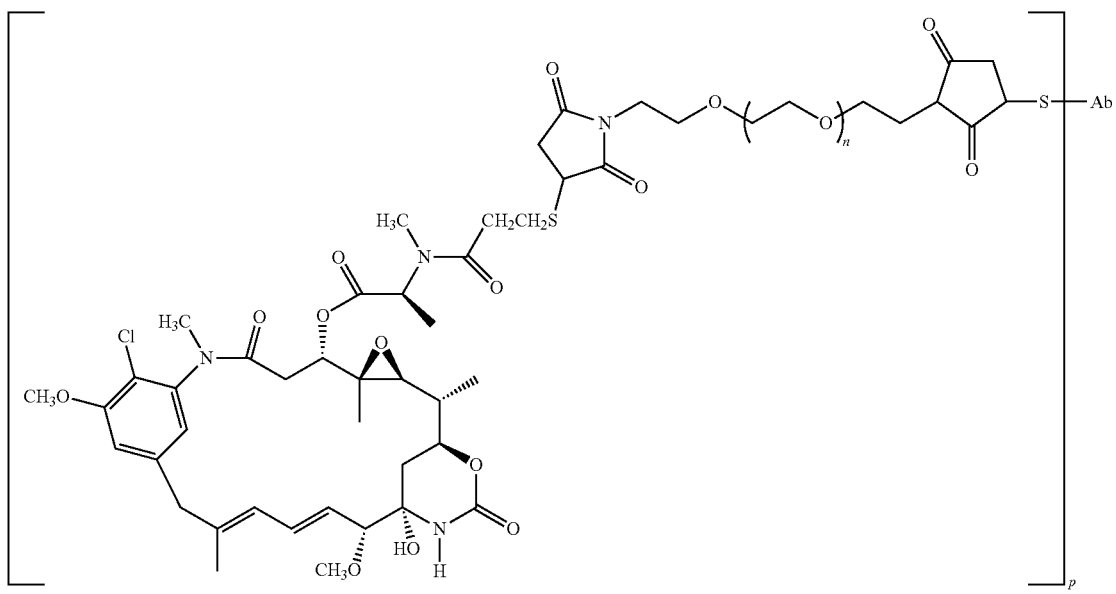

where Ab is antibody; n is 0, 1, or 2; and p is 1 to about 20. In some embodiments, p is 1 to 10, p is 1 to 7, p is 1 to 5, or p is 1 to 4.

Immunoconjugates containing maytansinoids, methods of making the same, and their therapeutic use are disclosed, for example, in U.S. Pat. Nos. 5,208,020 and 5,416,064; US 2005/0276812 A1; and European Patent EP 0 425 235 B1, the disclosures of which are hereby expressly incorporated by reference. See also Liu et al. *Proc. Natl. Acad. Sci. USA* 93:8618-8623 (1996); and Chari et al. *Cancer Research* 52:127-131 (1992).

In some embodiments, antibody-maytansinoid conjugates may be prepared by chemically linking an antibody to a maytansinoid molecule without significantly diminishing the biological activity of either the antibody or the maytansinoid molecule. See, e.g., U.S. Pat. No. 5,208,020 (the disclosure of which is hereby expressly incorporated by reference). In some embodiments, ADC with an average of 3-4 maytansinoid molecules conjugated per antibody molecule has shown efficacy in enhancing cytotoxicity of target cells without negatively affecting the function or solubility of the antibody. In some instances, even one molecule of toxin/antibody is expected to enhance cytotoxicity over the use of naked antibody.

Exemplary linking groups for making antibody-maytansinoid conjugates include, for example, those described herein and those disclosed in U.S. Pat. No. 5,208,020; EP Patent 0 425 235 B1; Chari et al. *Cancer Research* 52:127-131 (1992); US 2005/0276812 A1; and US 2005/016993 A1, the disclosures of which are hereby expressly incorporated by reference.

(2) Auristatins and Dolastatins

Drug moieties include dolastatins, auristatins, and analogs and derivatives thereof (U.S. Pat. Nos. 5,635,483; 5,780,58; 5,767,237; 6,124,431). Auristatins are derivatives of the marine mollusk compound dolastatin-10. While not intending to be bound by any particular theory, dolastatins and auristatins have been shown to interfere with microtubule dynamics, GTP hydrolysis, and nuclear and cellular division (Woyke et al (2001) *Antimicrob. Agents and Chemother.* 45(12):3580-3584) and have anticancer (U.S. Pat. No. 5,663,149) and antifungal activity (Pettit et al (1998) *Antimicrob. Agents Chemother.* 42:2961-2965). The dolastatin/auristatin drug moiety may be attached to the antibody through the N (amino) terminus or the C (carboxyl) terminus of the peptidic drug moiety (WO 02/088172; Doronina et al (2003) *Nature Biotechnology* 21(7):778-784; Francisco et al (2003) *Blood* 102(4): 1458-1465).

Exemplary auristatin embodiments include the N-terminus linked monomethylauristatin drug moieties $D_E$ and $D_F$, disclosed in U.S. Pat. Nos. 7,498,298 and 7,659,241, the disclosures of which are expressly incorporated by reference in their entirety:

$D_E$

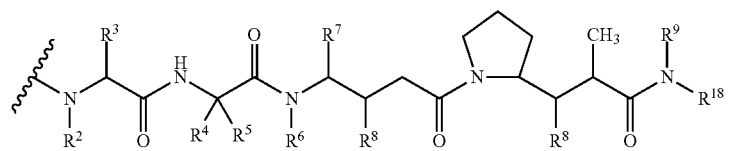

$D_F$

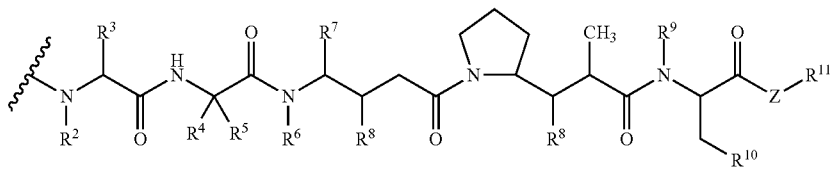

wherein the wavy line of $D_E$ and $D_F$ indicates the covalent attachment site to an antibody or antibody-linker component, and independently at each location:

$R^2$ is selected from H and $C_1$-$C_8$ alkyl;

$R^3$ is selected from H, $C_1$-$C_8$ alkyl, $C_3$-$C_8$ carbocycle, aryl, $C_1$-$C_8$ alkyl-aryl, $C_1$-$C_8$ alkyl-($C_3$-$C_8$ carbocycle), $C_3$-$C_8$ heterocycle and $C_1$-$C_8$ alkyl-($C_3$-$C_8$ heterocycle);

$R^4$ is selected from H, $C_1$-$C_8$ alkyl, $C_3$-$C_8$ carbocycle, aryl, $C_1$-$C_8$ alkyl-aryl, $C_1$-$C_8$ alkyl-($C_3$-$C_8$ carbocycle), $C_3$-$C_8$ heterocycle and $C_1$-$C_8$ alkyl-($C_3$-$C_8$ heterocycle);

$R^5$ is selected from H and methyl;

or $R^4$ and $R^5$ jointly form a carbocyclic ring and have the formula —$(CR^aR^b)_n$— wherein $R^a$ and $R^b$ are independently selected from H, $C_1$-$C_8$ alkyl and $C_3$-$C_8$ carbocycle and n is selected from 2, 3, 4, 5 and 6;

$R^6$ is selected from H and $C_1$-$C_8$ alkyl;

$R^7$ is selected from H, $C_1$-$C_8$ alkyl, $C_3$-$C_8$ carbocycle, aryl, $C_1$-$C_8$ alkyl-aryl, $C_1$-$C_8$ alkyl-($C_3$-$C_8$ carbocycle), $C_3$-$C_8$ heterocycle and $C_1$-$C_8$ alkyl-($C_3$-$C_8$ heterocycle);

each $R^8$ is independently selected from H, OH, $C_1$-$C_8$ alkyl, $C_3$-$C_8$ carbocycle and O—($C_1$-$C_8$ alkyl);

$R^9$ is selected from H and $C_1$-$C_8$ alkyl;

$R^{10}$ is selected from aryl or $C_3$-$C_8$ heterocycle;

Z is O, S, NH, or $NR^{12}$, wherein $R^{12}$ is $C_1$-$C_8$ alkyl;

$R^{11}$ is selected from H, $C_1$-$C_{20}$ alkyl, aryl, $C_3$-$C_8$ heterocycle, —$(R^{13}O)_m$—$R^{14}$, or —$(R^{13}O)_m$—$CH(R^{15})_2$;

m is an integer ranging from 1-1000;

$R^{13}$ is $C_2$-$C_8$ alkyl;

$R^{14}$ is H or $C_1$-$C_8$ alkyl;

each occurrence of $R^{15}$ is independently H, COOH, —$(CH_2)_n$—$N(R^{16})_2$, —$(CH_2)_n$—$SO_3H$, or —$(CH_2)_n$—$SO_3$—$C_1$-$C_8$ alkyl;

each occurrence of $R^{16}$ is independently H, $C_1$-$C_8$ alkyl, or —$(CH_2)_n$—COOH;

$R^{18}$ is selected from —$C(R^8)_2$—$C(R^8)_2$-aryl, —$C(R^8)_2$—$C(R^8)_2$—($C_3$-$C_8$ heterocycle), and —$C(R^8)_2$—$C(R^8)_2$—($C_3$-$C_8$ carbocycle); and n is an integer ranging from 0 to 6.

In one embodiment, $R^3$, $R^4$ and $R^7$ are independently isopropyl or sec-butyl and $R^5$ is —H or methyl. In an exemplary embodiment, $R^3$ and $R^4$ are each isopropyl, $R^5$ is —H, and $R^7$ is sec-butyl.

In yet another embodiment, $R^2$ and $R^6$ are each methyl, and $R^9$ is —H.

In still another embodiment, each occurrence of $R^8$ is —$OCH_3$.

In an exemplary embodiment, $R^3$ and $R^4$ are each isopropyl, $R^2$ and $R^6$ are each methyl, $R^5$ is —H, $R^7$ is sec-butyl, each occurrence of $R^8$ is —$OCH_3$, and $R^9$ is —H.

In one embodiment, Z is —O— or —NH—.

In one embodiment, $R^{10}$ is aryl.

In an exemplary embodiment, $R^{10}$ is -phenyl.

In an exemplary embodiment, when Z is —O—, $R^{11}$ is —H, methyl or t-butyl.

In one embodiment, when Z is —NH, $R^{11}$ is —$CH(R^{15})_2$, wherein $R^{15}$ is —$(CH_2)_n$—$N(R^{16})_2$, and $R^{16}$ is —$C_1$-$C_8$ alkyl or —$(CH_2)_n$—COOH.

In another embodiment, when Z is —NH, $R^{11}$ is —$CH(R^{15})_2$, wherein $R^{15}$ is —$(CH_2)_n$—$SO_3H$.

An exemplary auristatin embodiment of formula $D_E$ is MMAE, wherein the wavy line indicates the covalent attachment to a linker (L) of an antibody-drug conjugate:

MMAE

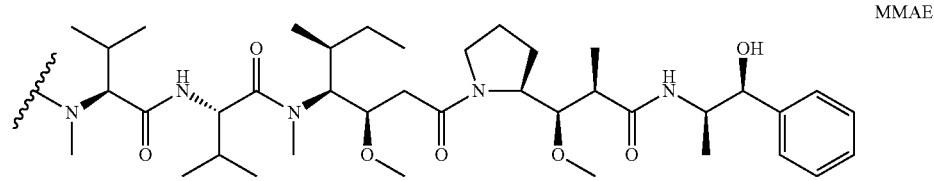 [SMILES: *N(C)[C@H](C(=O)N[C@H](C(=O)N(C)[C@@H]([C@@H](C)CC)[C@@H](CC(=O)N1CCC[C@H]1[C@H](OC)[C@@H](C)C(=O)N[C@H](C)[C@@H](O)c1ccccc1)OC)C(C)C)C(C)C]

An exemplary auristatin embodiment of formula $D_F$ is MMAF, wherein the wavy line indicates the covalent attachment to a linker (L) of an antibody-drug conjugate:

MMAF

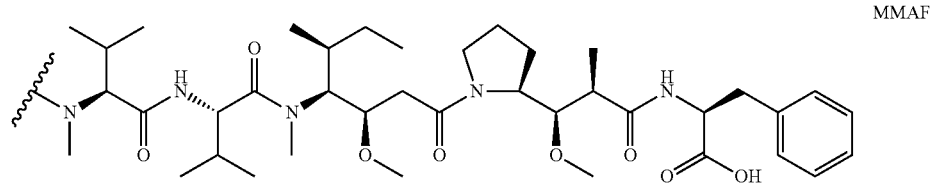 [SMILES: *N(C)[C@H](C(=O)N[C@H](C(=O)N(C)[C@@H]([C@@H](C)CC)[C@@H](CC(=O)N1CCC[C@H]1[C@H](OC)[C@@H](C)C(=O)N[C@@H](Cc1ccccc1)C(=O)O)OC)C(C)C)C(C)C]

Other exemplary embodiments include monomethylvaline compounds having phenylalanine carboxy modifications at the C-terminus of the pentapeptide auristatin drug moiety (WO 2007/008848) and monomethylvaline compounds having phenylalanine sidechain modifications at the C-terminus of the pentapeptide auristatin drug moiety (WO 2007/008603).

Nonlimiting exemplary embodiments of ADC of Formula I comprising MMAE or MMAF and various linker components have the following structures and abbreviations (wherein "Ab" is an antibody; p is 1 to about 8, "Val-Cit" is a valine-citrulline dipeptide; and "S" is a sulfur atom:

tides", volume 1, pp 76-136, 1965, Academic Press). Auristatin/dolastatin drug moieties may, in some embodiments, be prepared according to the methods of: U.S. Pat. No. 7,498,298; U.S. Pat. No. 5,635,483; U.S. Pat. No. 5,780,588; Pettit et al (1989) *J. Am. Chem. Soc.* 111:5463-5465; Pettit et al (1998) *Anti-Cancer Drug Design* 13:243-277; Pettit, G. R., et al. *Synthesis,* 1996, 719-725; Pettit et al (1996) *J. Chem. Soc. Perkin Trans.* 1 5:859-863; and Doronina (2003) *Nat. Biotechnol.* 21(7):778-784.

In some embodiments, auristatin/dolastatin drug moieties of formulas $D_E$ such as MMAE, and $D_F$, such as MMAF, and drug-linker intermediates and derivatives thereof, such as

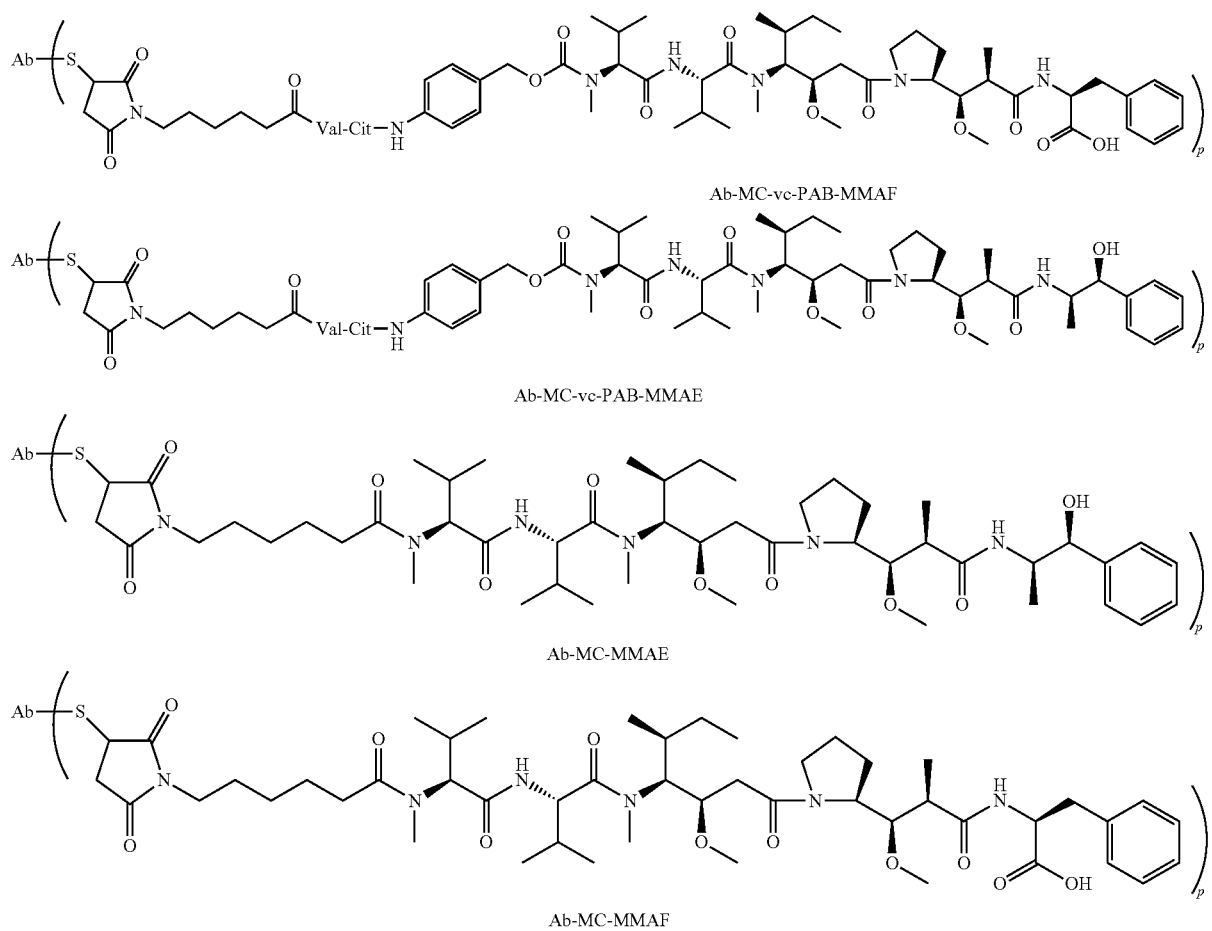

Nonlimiting exemplary embodiments of ADCs of Formula I comprising MMAF and various linker components further include Ab-MC-PAB-MMAF and Ab-PAB-MMAF. Immunoconjugates comprising MMAF attached to an antibody by a linker that is not proteolytically cleavable have been shown to possess activity comparable to immunoconjugates comprising MMAF attached to an antibody by a proteolytically cleavable linker (Doronina et al. (2006) *Bioconjugate Chem.* 17:114-124). In some such embodiments, drug release is believed to be effected by antibody degradation in the cell.

Typically, peptide-based drug moieties can be prepared by forming a peptide bond between two or more amino acids and/or peptide fragments. Such peptide bonds can be prepared, for example, according to a liquid phase synthesis method (see, e.g., E. Schröder and K. Lübke, "The Peptides", volume 1, pp 76-136, 1965, Academic Press).

MC-MMAF, MC-MMAE, MC-vc-PAB-MMAF, and MC-vc-PAB-MMAE, may be prepared using methods described in U.S. Pat. No. 7,498,298; Doronina et al. (2006) *Bioconjugate Chem.* 17:114-124; and Doronina et al. (2003) *Nat. Biotech.* 21:778-784 and then conjugated to an antibody of interest.

(3) Calicheamicin

In some embodiments, the immunoconjugate comprises an antibody conjugated to one or more calicheamicin molecules. The calicheamicin family of antibiotics, and analogues thereof, are capable of producing double-stranded DNA breaks at sub-picomolar concentrations (Hinman et al., (1993) *Cancer Research* 53:3336-3342; Lode et al., (1998) *Cancer Research* 58:2925-2928). Calicheamicin has intracellular sites of action but, in certain instances, does not readily cross the plasma membrane. Therefore, cellular uptake of these agents through antibody-mediated internalization may, in some embodiments, greatly enhances their cytotoxic effects. Nonlimiting exemplary methods of preparing antibody-drug conjugates with a calicheamicin drug moiety are described, for example, in U.S. Pat. Nos. 5,712,374; 5,714,586; 5,739,116; and 5,767,285.

In some embodiments, the calicheamicin drug moiety conjugated to the antibody is a compound having the formula:

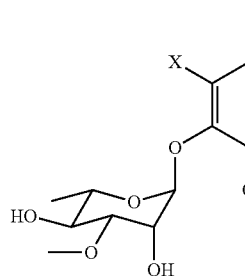
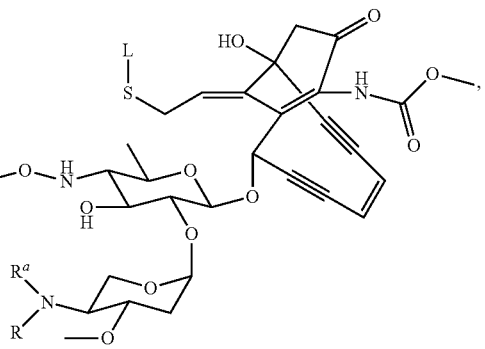

wherein X is Br or I; L is a linker; R is hydrogen, $C_{1-6}$alkyl, or —C(=O) $C_{1-6}$alkyl; and $R^a$ is hydrogen or $C_{1-6}$alkyl.

In some embodiments, X is Br, $R^a$ is hydrogen and R is isopropyl.

In other embodiments, X is Br, $R^a$ is hydrogen and R is ethyl.

In other embodiments, X is I, $R^a$ is hydrogen and R is isopropyl.

In other embodiments, X is I, $R^a$ is hydrogen and R is ethyl.

In some embodiments, X is Br, $R^a$ is hydrogen and R —C(=O)CH$_3$.

In other embodiments, X is I, $R^a$ is hydrogen and R is —C(=O)CH$_3$.

In other embodiments, X is I, $R^a$ is ethyl and R is —C(=O)CH$_3$.

In other embodiments, X is Br, $R^a$ is ethyl and R is —C(=O)CH$_3$.

(4) Pyrrolobenzodiazepines

In some embodiments, an ADC comprises a pyrrolobenzodiazepine (PBD). In some embodiments, PDB dimers recognize and bind to specific DNA sequences. The natural product anthramycin, a PBD, was first reported in 1965 (Leimgruber, et al., (1965) *J. Am. Chem. Soc.,* 87:5793-5795; Leimgruber, et al., (1965) *J. Am. Chem. Soc.,* 87:5791-5793). Since then, a number of PBDs, both naturally-occurring and analogues, have been reported (Thurston, et al., (1994) Chem. Rev. 1994, 433-465 including dimers of the tricyclic PBD scaffold (U.S. Pat. Nos. 6,884,799; 7,049,311; 7,067,511; 7,265,105; 7,511,032; 7,528,126; 7,557,099). Without intending to be bound by any particular theory, it is believed that the dimer structure imparts the appropriate three-dimensional shape for isohelicity with the minor groove of B-form DNA, leading to a snug fit at the binding site (Kohn, In Antibiotics III. Springer-Verlag, New York, pp. 3-11 (1975); Hurley and Needham-VanDevanter, (1986) *Acc. Chem. Res.,* 19:230-237). Dimeric PBD compounds bearing C2 aryl substituents have been shown to be useful as cytotoxic agents (Hartley et al (2010) *Cancer Res.* 70(17):6849-6858; Antonow (2010) *J. Med. Chem.* 53(7):2927-2941; Howard et al (2009) *Bioorganic and Med. Chem. Letters* 19(22):6463-6466).

In some embodiments, PBD compounds can be employed as prodrugs by protecting them at the N10 position with a nitrogen protecting group which is removable in vivo (WO 00/12507; WO 2005/023814).

PBD dimers have been conjugated to antibodies and the resulting ADC shown to have anticancer properties (US 2010/0203007). Nonlimiting exemplary linkage sites on the PBD dimer include the five-membered pyrrolo ring, the tether between the PBD units, and the N10-C11 imine group (WO 2009/016516; US 2009/304710; US 2010/047257; US 2009/036431; US 2011/0256157; WO 2011/130598).

Nonlimiting exemplary PBD dimer components of ADCs are of Formula A:

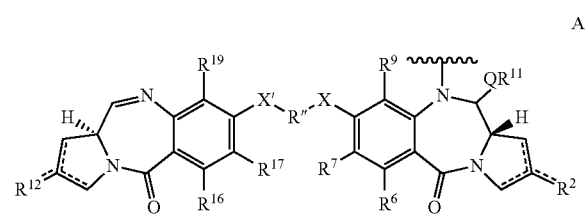

and salts and solvates thereof, wherein:
the wavy line indicates the covalent attachment site to the linker;
the dotted lines indicate the optional presence of a double bond between C1 and C2 or C2 and C3;
$R^2$ is independently selected from H, OH, =O, =CH$_2$, CN, R, OR, =CH—$R^D$, =C($R^D$)$_2$, O—SO$_2$—R, CO$_2$R and COR, and optionally further selected from halo or dihalo, wherein $R^D$ is independently selected from R, CO$_2$R, COR, CHO, CO$_2$H, and halo;
$R^6$ and $R^9$ are independently selected from H, R, OH, OR, SH, SR, NH$_2$, NHR, NRR', NO$_2$, Me$_3$Sn and halo;
$R^7$ is independently selected from H, R, OH, OR, SH, SR, NH$_2$, NHR, NRR', NO$_2$, Me$_3$Sn and halo;
Q is independently selected from O, S and NH;
$R^{11}$ is either H, or R or, where Q is O, SO$_3$M, where M is a metal cation;
R and R' are each independently selected from optionally substituted $C_{1-8}$ alkyl, $C_{1-12}$ alkyl, $C_{3-8}$ heterocyclyl, $C_{3-20}$ heterocycle, and $C_{5-20}$ aryl groups, and optionally in relation to the group NRR', R and R' together with the nitrogen atom to which they are attached form an optionally substituted 4-, 5-, 6- or 7-membered heterocyclic ring;

$R^{12}$, $R^{16}$, $R^{19}$ and $R^{17}$ are as defined for $R^2$, $R^6$, $R^9$ and $R^7$ respectively;

R" is a $C_{3-12}$ alkylene group, which chain may be interrupted by one or more heteroatoms, e.g. O, S, N(H), NMe and/or aromatic rings, e.g. benzene or pyridine, which rings are optionally substituted; and X and X' are independently selected from O, S and N(H).

In some embodiments, R and R' are each independently selected from optionally substituted $C_{1-12}$ alkyl, $C_{3-20}$ heterocycle, and $C_{5-20}$ aryl groups, and optionally in relation to the group NRR', R and R' together with the nitrogen atom to which they are attached form an optionally substituted 4-, 5-, 6- or 7-membered heterocyclic ring.

In some embodiments, $R^9$ and $R^{19}$ are H.

In some embodiments, $R^6$ and $R^{16}$ are H.

In some embodiments, $R^7$ are $R^{17}$ are both $OR^{7A}$, where $R^{7A}$ is optionally substituted $C_{1-4}$ alkyl.

In some embodiments, $R^{7A}$ is Me. In some embodiments, $R^{7A}$ is is $Ch_2Ph$, where Ph is a phenyl group.

In some embodiments, X is O.

In some embodiments, $R^{11}$ is H.

In some embodiments, there is a double bond between C2 and C3 in each monomer unit.

In some embodiments, $R^2$ and $R^{12}$ are independently selected from H and R. In some embodiments, $R^2$ and $R^{12}$ are independently R. In some embodiments, $R^2$ and $R^{12}$ are independently optionally substituted $C_{5-20}$ aryl or $C_{5-7}$ aryl or $C_{8-10}$ aryl. In some embodiments, $R^2$ and $R^{12}$ are independently optionally substituted phenyl, thienyl, napthyl, pyridyl, quinolinyl, or isoquinolinyl. In some embodiments, $R^2$ and $R^{12}$ are independently $=CH-R^D$.

In some embodiments, when $R^2$ and/or $R^{12}$ is $=CH-R^D$, each group may independently have either configuration shown below:

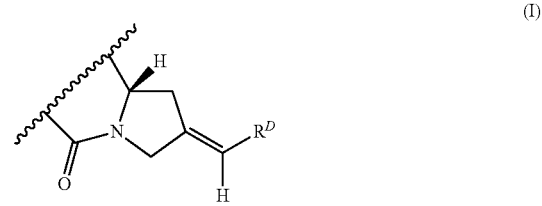

(I)

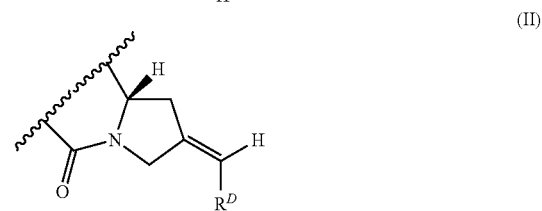

(II)

In some embodiments, a $=CH-R^D$ is in configuration (I).

In some embodiments, R" is a $C_3$ alkylene group or a $C_5$ alkylene group.

In some embodiments, an exemplary PBD dimer component of an ADC has the structure of Formula A(I):

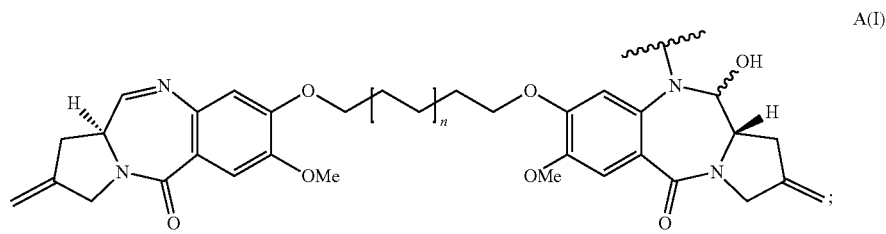

A(I)

wherein n is 0 or 1.

In some embodiments, an exemplary PBD dimer component of an ADC has the structure of Formula A(II):

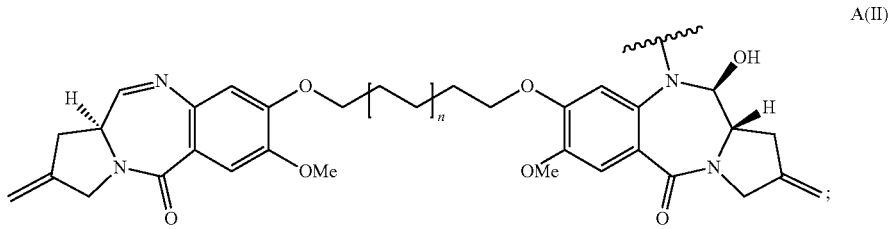

A(II)

$R^2$ and $R^{12}$ are independently selected from $=O$, $=CH_2$, $=CH-R^D$, and $=C(R^D)_2$. In some embodiments, $R^2$ and $R^{12}$ are each $=CH_2$. In some embodiments, $R^2$ and $R^{12}$ are each H. In some embodiments, $R^2$ and $R^{12}$ are each $=O$. In some embodiments, $R^2$ and $R^{12}$ are each $=CF_2$. In some embodiments, $R^2$ and/or $R^{12}$ are independently $=C(R^D)_2$. In wherein n is 0 or 1.

In some embodiments, an exemplary PBD dimer component of an ADC has the structure of Formula A III):

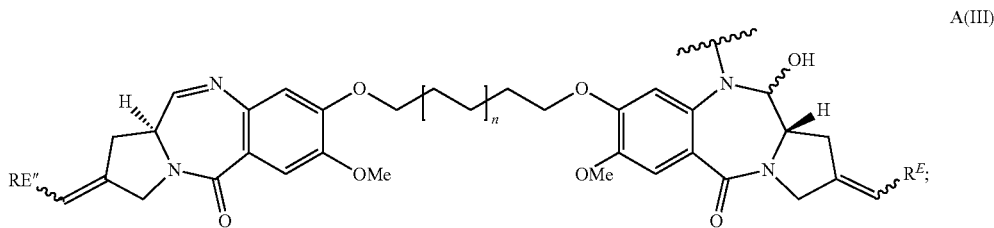

A(III)

wherein $R^E$ and $R^{E''}$ are each independently selected from H or $R^D$, wherein $R^D$ is defined as above; and wherein n is 0 or 1.

In some embodiments, n is 0. In some embodiments, n is 1. In some embodiments, $R^E$ and/or $R^{E''}$ is H. In some embodiments, $R^E$ and $R^{E''}$ are H. In some embodiments, $R^E$ and/or $R^{E''}$ is $R^D$, wherein $R^D$ is optionally substituted $C_{1-12}$ alkyl. In some embodiments, $R^E$ and/or $R^{E''}$ is $R^D$, wherein $R^D$ is methyl.

In some embodiments, an exemplary PBD dimer component of an ADC has the structure of Formula A(IV):

In some embodiments, $Ar^1$ and $Ar^2$ are each independently selected from optionally substituted phenyl, furanyl, thiophenyl and pyridyl. In some embodiments, $Ar^1$ and $Ar^2$ are each independently optionally substituted phenyl. In some embodiments, $Ar^1$ and $Ar^2$ are each independently optionally substituted thien-2-yl or thien-3-yl. In some embodiments, $Ar^1$ and $Ar^2$ are each independently optionally substituted quinolinyl or isoquinolinyl. The quinolinyl or isoquinolinyl group may be bound to the PBD core through any available ring position. For example, the quinolinyl may be quinolin-2-yl, quinolin-3-yl, quinolin-4yl, quinolin-5-yl,

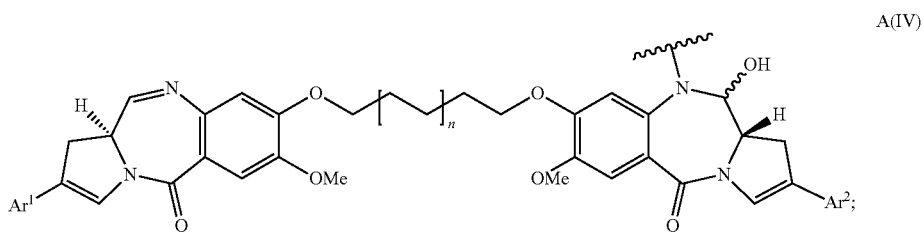

A(IV)

wherein $Ar^1$ and $Ar^2$ are each independently optionally substituted $C_{5-20}$ aryl; wherein $Ar^1$ and $Ar^2$ may be the same or different; and
wherein n is 0 or 1.

In some embodiments, an exemplary PBD dimer component of an ADC has the structure of Formula A(V):

quinolin-6-yl, quinolin-7-yl and quinolin-8-yl. In some embodiments, the quinolinyl is selected from quinolin-3-yl and quinolin-6-yl. The isoquinolinyl may be isoquinolin-1-yl, isoquinolin-3-yl, isoquinolin-4yl, isoquinolin-5-yl, isoquinolin-6-yl, isoquinolin-7-yl and isoquinolin-8-yl. In

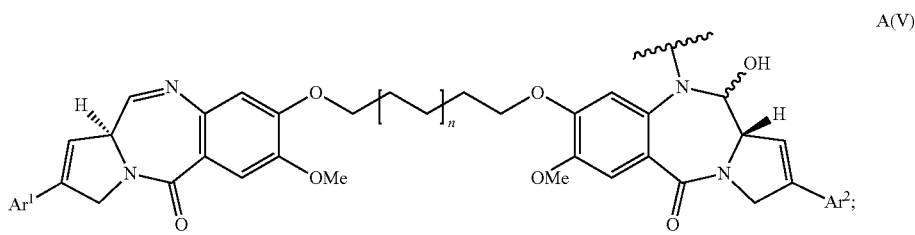

A(V)

wherein $Ar^1$ and $Ar^2$ are each independently optionally substituted $C_{5-20}$ aryl; wherein $Ar^1$ and $Ar^2$ may be the same or different; and
wherein n is 0 or 1.

some embodiments, the isoquinolinyl is selected from isoquinolin-3-yl and isoquinolin-6-yl.

Further nonlimiting exemplary PBD dimer components of ADCs are of Formula B:

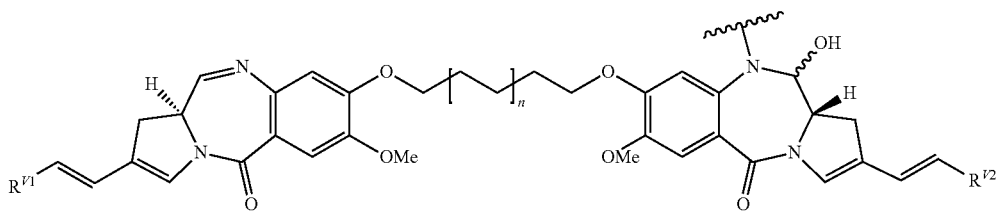

B and salts and solvates thereof, wherein:

the wavy line indicates the covalent attachment site to the linker;

the wavy line connected to the OH indicates the S or R configuration;

$R^{V1}$ and $R^{V2}$ are independently selected from H, methyl, ethyl and phenyl (which phenyl may be optionally substituted with fluoro, particularly in the 4 position) and $C_{5-6}$ heterocyclyl; wherein $R^{V1}$ and $R^{V2}$ may be the same or different; and n is 0 or 1.

In some embodiments, $R^{V1}$ and $R^{V2}$ are independently selected from H, phenyl, and 4-fluorophenyl.

In some embodiments, a linker may be attached at one of various sites of the PBD dimer drug moiety, including the N10 imine of the B ring, the C-2 endo/exo position of the C ring, or the tether unit linking the A rings (see structures C(I) and C(II) below).

Nonlimiting exemplary PBD dimer components of ADCs include Formulas C(I) and C(II):

wherein:

X is $CH_2$ (n=1 to 5), N, or O;

Z and Z' are independently selected from OR and $NR_2$, where R is a primary, secondary or tertiary alkyl chain containing 1 to 5 carbon atoms;

$R_1$, $R'_1$, $R_2$ and $R'_2$ are each independently selected from H, $C_1$-$C_8$ alkyl, $C_2$-$C_8$ alkenyl, $C_2$-$C_8$ alkynyl, $C_{5-20}$ aryl (including substituted aryls), $C_{5-20}$ heteroaryl groups, —$NH_2$, —NHMe, —OH, and —SH, where, in some embodiments, alkyl, alkenyl and alkynyl chains comprise up to 5 carbon atoms;

$R_3$ and $R'_3$ are independently selected from H, OR, NHR, and $NR_2$, where R is a primary, secondary or tertiary alkyl chain containing 1 to 5 carbon atoms;

$R_4$ and $R'_4$ are independently selected from H, Me, and OMe;

$R_5$ is selected from $C_1$-$C_8$ alkyl, $C_2$-$C_8$ alkenyl, $C_2$-$C_8$ alkynyl, $C_{5-20}$ aryl (including aryls substituted by halo, nitro, cyano, alkoxy, alkyl, heterocyclyl) and $C_{5-20}$ heteroaryl groups, where, in some embodiments, alkyl, alkenyl and alkynyl chains comprise up to 5 carbon atoms;

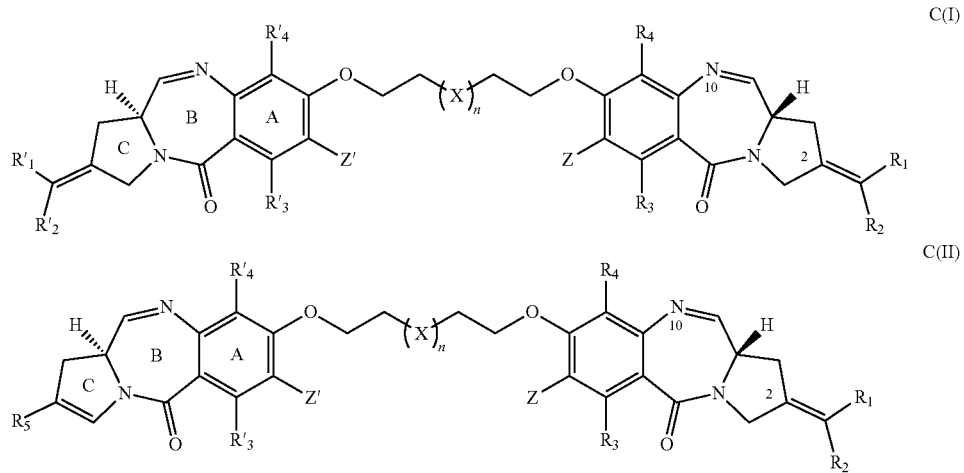

Formulas C(I) and C(II) are shown in their N10-C11 imine form. Exemplary PBD drug moieties also include the carbinolamine and protected carbinolamine forms as well, as shown in the table below:

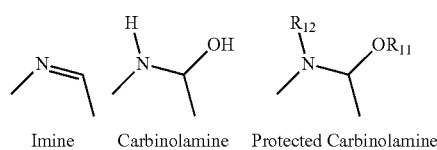

Imine   Carbinolamine   Protected Carbinolamine $R_{11}$ is H, $C_1$-$C_8$ alkyl, or a protecting group (such as acetyl, trifluoroacetyl, t-butoxycarbonyl (BOC), benzyloxycarbonyl (CBZ), 9-fluorenylmethylenoxycarbonyl (Fmoc), or a moiety comprising a self-immolating unit such as valine-citrulline-PAB);

$R_{12}$ is is H, $C_1$-$C_8$ alkyl, or a protecting group;

wherein a hydrogen of one of $R_1$, $R'_1$, $R_2$, $R'_2$, $R_5$, or $R_{12}$ or a hydrogen of the —$OCH_2CH_2(X)_nCH_2CH_2O$— spacer between the A rings is replaced with a bond connected to the linker of the ADC.

Exemplary PDB dimer portions of ADC include, but are not limited to (the wavy line indicates the site of covalent attachment to the linker):

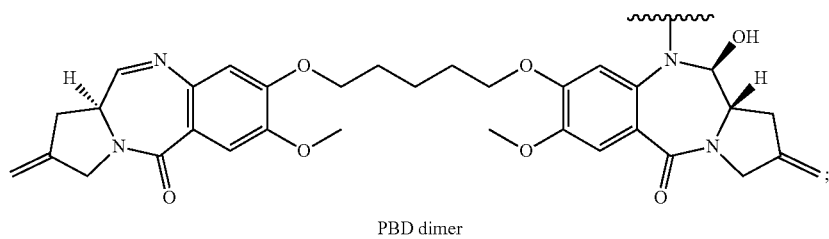
PBD dimer
Nonlimiting exemplary embodiments of ADCs comprising PBD dimers have the following structures:
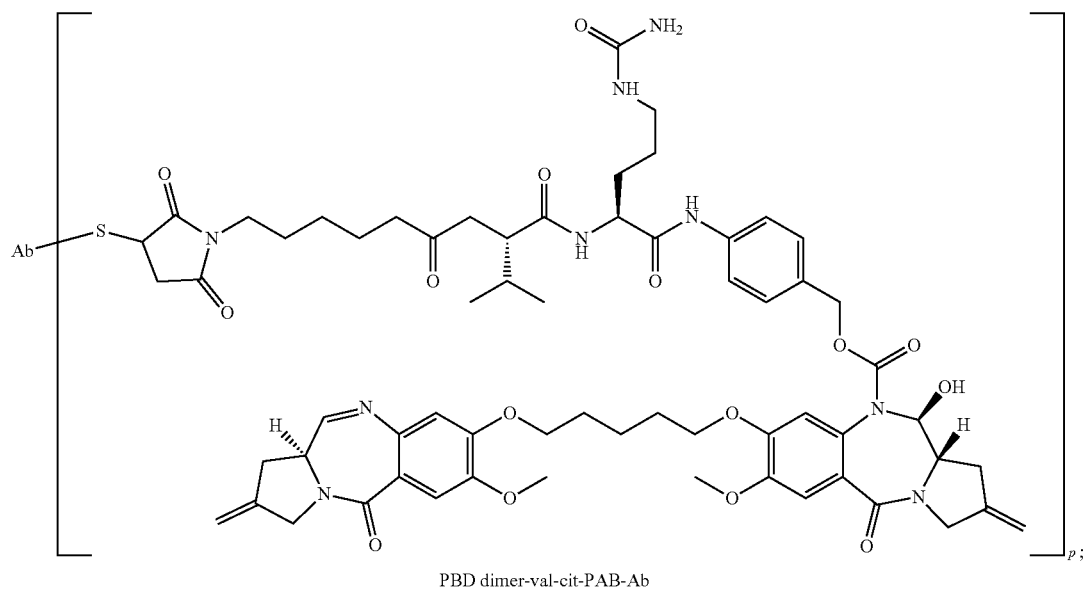
PBD dimer-val-cit-PAB-Ab
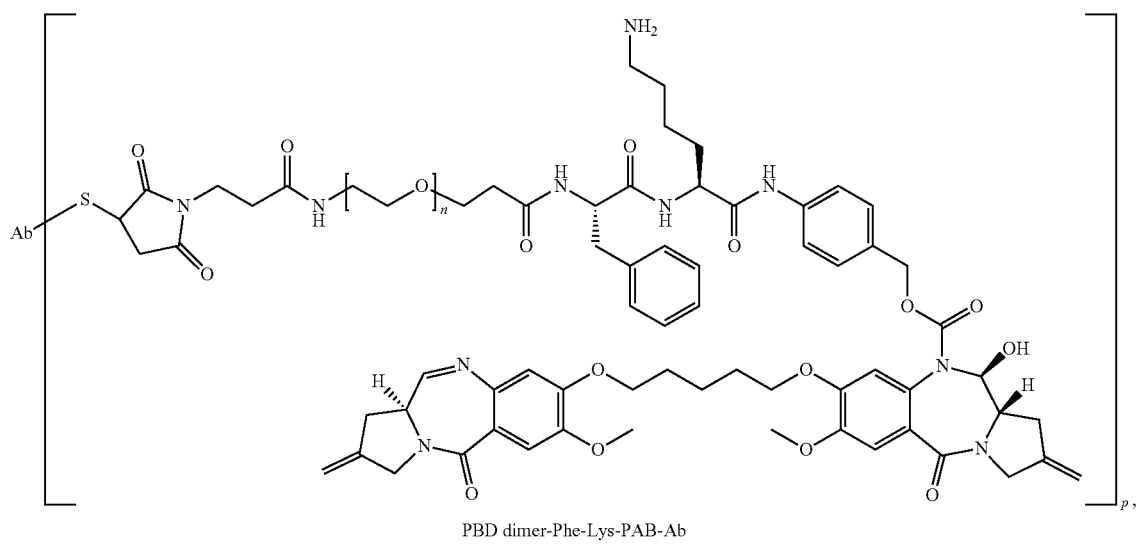
PBD dimer-Phe-Lys-PAB-Ab wherein:

n is 0 to 12. In some embodiments, n is 2 to 10. In some embodiments, n is 4 to 8. In some embodiments, n is selected from 4, 5, 6, 7, and 8.

In some embodiments, an ADC comprising a PBD dimer described herein may be made by conjugating a linker-drug intermediate including a pyridine leaving group via a sulfur atom with a cysteine thiol of an antibody to form a disulfide linkage. Further, in some embodiments, an ADC comprising a PBD dimer described herein may be made by conjugating a linker-drug intermediate including a thiopyridyl leaving group, wherein the pyridine ring is substituted with one or more nitro groups. In some embodiments, the pyridyl ring is monosubstituted with —$NO_2$. In some embodiments, the —$NO_2$ monosubstitution is para relative to the disulfide. In some embodiments, the PBD dimer is connected through the N10 position. For example, non-limiting exemplary ADC comprising a PBD dimer may be made by conjugating a monomethylethyl pyridyl disulfide, N10-linked PBD linker intermediate (shown below) to an antibody:

radicals which then react with cellular macromolecules to cause damage to the cells, and/or 3) interactions of the drug molecules with the cell membrane (see, e.g., C. Peterson et al., "Transport And Storage Of Anthracycline In Experimental Systems And Human Leukemia" in *Anthracycline Antibiotics In Cancer Therapy*; N. R. Bachur, "Free Radical Damage" id. at pp. 97-102). Because of their cytotoxic potential anthracyclines have been used in the treatment of numerous cancers such as leukemia, breast carcinoma, lung carcinoma, ovarian adenocarcinoma and sarcomas (see e.g., P. H-Wiernik, in *Anthracycline: Current Status And New Developments* p 11).

Nonlimiting exemplary anthracyclines include doxorubicin, epirubicin, idarubicin, daunomycin, nemorubicin, and derivatives thereof. Immunoconjugates and prodrugs of daunorubicin and doxorubicin have been prepared and studied (Kratz et al (2006) *Current Med. Chem.* 13:477-523; Jeffrey et al (2006) *Bioorganic & Med. Chem. Letters* 16:358-362; Torgov et al (2005) *Bioconj. Chem.* 16:717-721; Nagy et al (2000) *Proc. Natl. Acad. Sci. USA* 97:829-834; Dubowchik et al (2002) *Bioorg. & Med. Chem. Letters* 12:1529-1532; King et al (2002) *J. Med. Chem.* 45:4336-

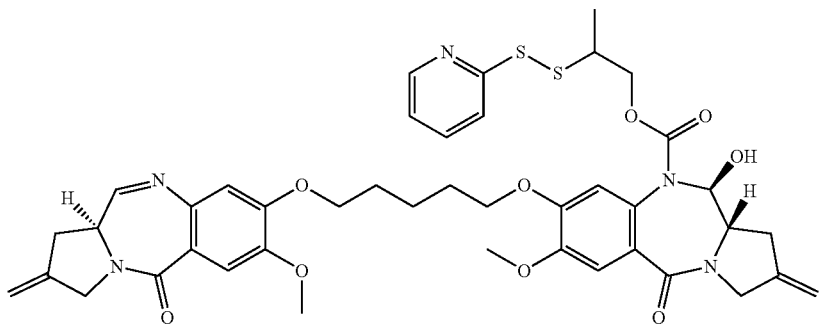

The linkers of PBD dimer-val-cit-PAB-Ab and the PBD dimer-Phe-Lys-PAB-Ab are protease cleavable, while the linker of PBD dimer-maleimide-acetal is acid-labile.

PBD dimers and ADCs comprising PBD dimers may be prepared according to methods known in the art. See, e.g., WO 2009/016516; US 2009/304710; US 2010/047257; US 2009/036431; US 2011/0256157; WO 2011/130598; WO 2013/055987.

(5) Anthracyclines

In some embodiments, an ADC comprising anthracycline. Anthracyclines are antibiotic compounds that exhibit cytotoxic activity. While not intending to be bound by any particular theory, studies have indicated that anthracyclines may operate to kill cells by a number of different mechanisms, including: 1) intercalation of the drug molecules into the DNA of the cell thereby inhibiting DNA-dependent nucleic acid synthesis; 2) production by the drug of free 4343; EP 0328147; U.S. Pat. No. 6,630,579). The antibody-drug conjugate BR96-doxorubicin reacts specifically with the tumor-associated antigen Lewis-Y and has been evaluated in phase I and II studies (Saleh et al (2000) *J. Clin. Oncology* 18:2282-2292; Ajani et al (2000) *Cancer Jour.* 6:78-81; Tolcher et al (1999) *J. Clin. Oncology* 17:478-484).

PNU-159682 is a potent metabolite (or derivative) of nemorubicin (Quintieri, et al. (2005) *Clinical Cancer Research* 11(4):1608-1617). Nemorubicin is a semisynthetic analog of doxorubicin with a 2-methoxymorpholino group on the glycoside amino of doxorubicin and has been under clinical evaluation (Grandi et al (1990) *Cancer Treat. Rev.* 17:133; Ripamonti et al (1992) *Brit. J. Cancer* 65:703;), including phase II/III trials for hepatocellular carcinoma (Sun et al (2003) *Proceedings of the American Society for Clinical Oncology* 22, Abs 1448; Quintieri (2003) *Proceedings of the American Association of Cancer Research*, 44:1st Ed, Abs 4649; Pacciarini et al (2006) *Jour. Clin. Oncology* 24:14116).

A nonlimiting exemplary ADC comprising nemorubicin or nemorubicin derivatives is shown in Formula Ia:

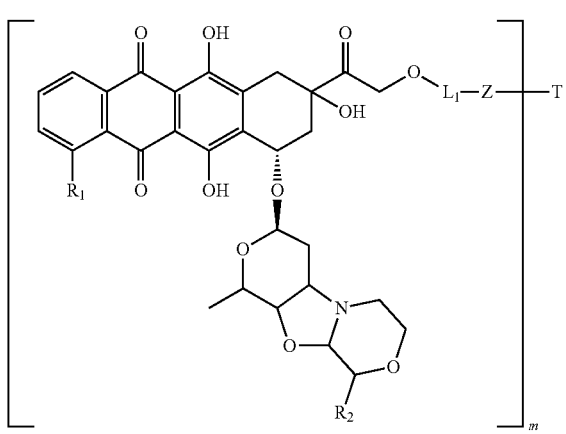

(Ia)

wherein $R_1$ is hydrogen atom, hydroxy or methoxy group and $R_2$ is a $C_1$-$C_5$ alkoxy group, or a pharmaceutically acceptable salt thereof;

$L_1$ and Z together are a linker (L) as described herein;

T is an antibody (Ab) as described herein; and m is 1 to about 20. In some embodiments, m is 1 to 10, 1 to 7, 1 to 5, or 1 to 4.

In some embodiments, $R_1$ and $R_2$ are both methoxy (—OMe).

A further nonlimiting exemplary ADC comprising nemorubicin or nemorubicin derivatives is shown in Formula Ib:

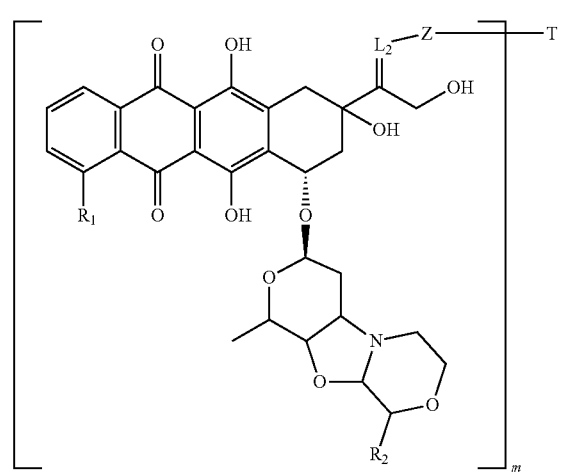

(Ib)

wherein $R_1$ is hydrogen atom, hydroxy or methoxy group and $R_2$ is a $C_1$-$C_5$ alkoxy group, or a pharmaceutically acceptable salt thereof;

$L_2$ and Z together are a linker (L) as described herein;

T is an antibody (Ab) as described herein; and m is 1 to about 20. In some embodiments, m is 1 to 10, 1 to 7, 1 to 5, or 1 to 4.

In some embodiments, $R_1$ and $R_2$ are both methoxy (—OMe).

In some embodiments, the nemorubicin component of a nemorubicin-containing ADC is PNU-159682. In some such embodiments, the drug portion of the ADC may have one of the following structures:

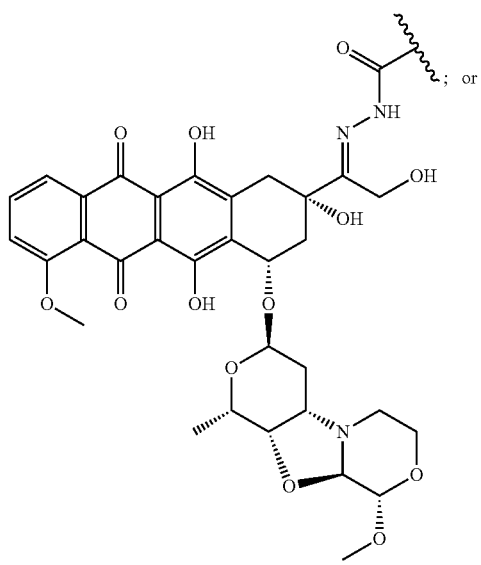

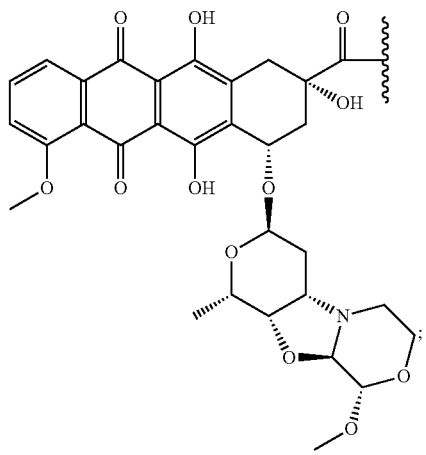

wherein the wavy line indicates the attachment to the linker (L).

Anthracyclines, including PNU-159682, may be conjugated to antibodies through several linkage sites and a variety of linkers (US 2011/0076287; WO2009/099741; US 2010/0034837; WO 2010/009124), including the linkers described herein.

Exemplary ADCs comprising a nemorubicin and linker include, but are not limited to:

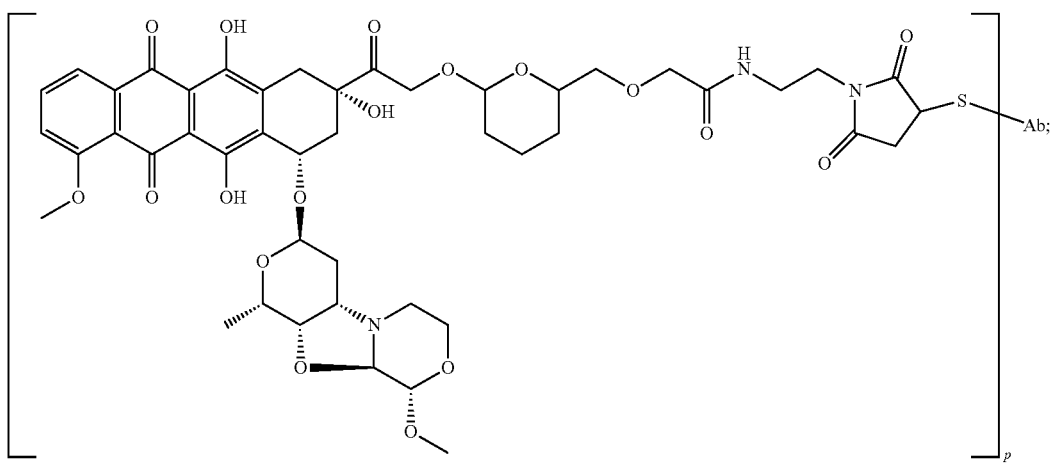
PNU-159682 maleimide acetal-Ab
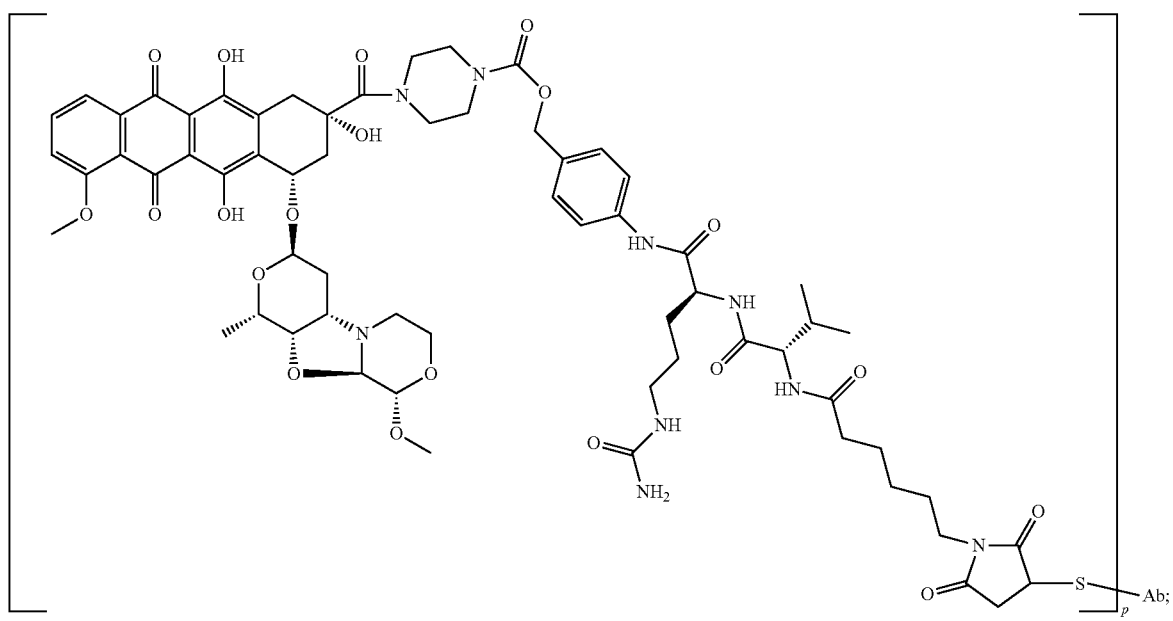
PNU-159682-val-cit-PAB-Ab
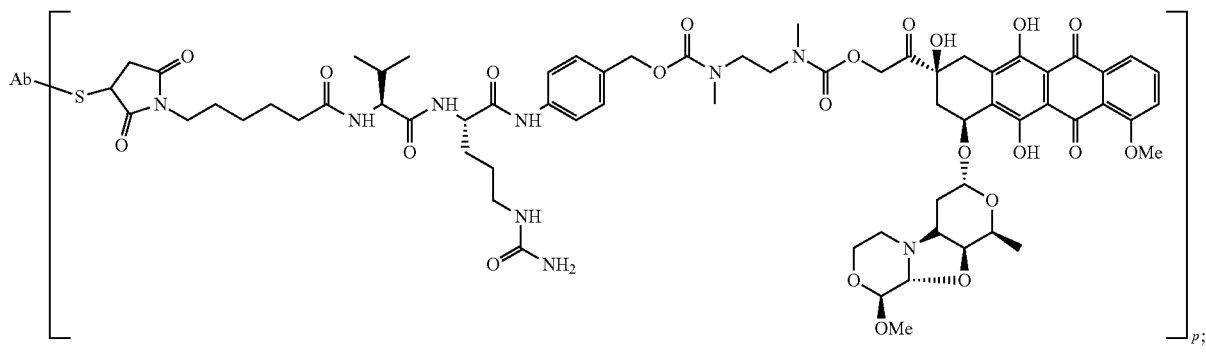
PNU-159682-val-cit-PAB-spacer-Ab

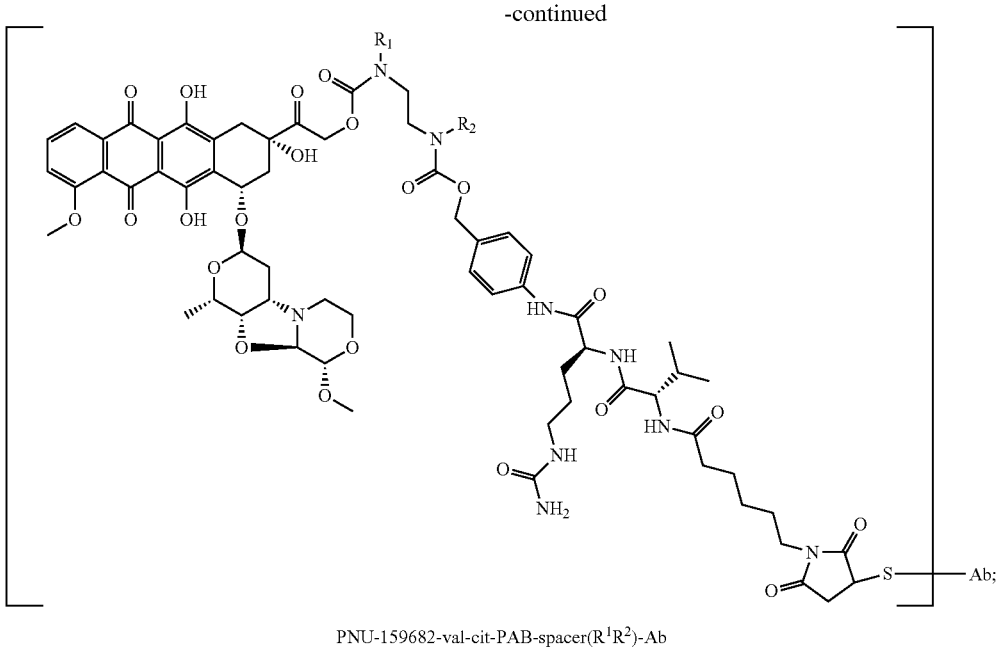

PNU-159682-val-cit-PAB-spacer($R^1R^2$)-Ab wherein:

$R_1$ and $R_2$ are independently selected from H and $C_1$-$C_6$ alkyl; and

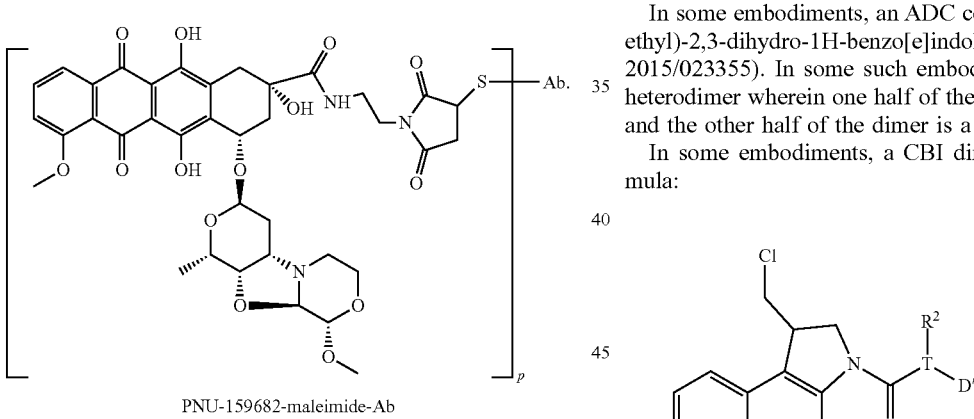

PNU-159682-maleimide-Ab

The linker of PNU-159682 maleimide acetal-Ab is acid-labile, while the linkers of PNU-159682-val-cit-PAB-Ab, PNU-159682-val-cit-PAB-spacer-Ab, and PNU-159682-val-cit-PAB-spacer($R_1R_2$)-Ab are protease cleavable.

(6) 1-(Chloromethyl)-2, 3-dihydro-1H-benzo[e]indole (CBI) Dimer Drug Moieties

In some embodiments, an ADC comprises 1-(chloromethyl)-2,3-dihydro-1H-benzo[e]indole (CBI). The 5-amino-1-(chloromethyl)-1,2-dihydro-3H-benz[e]indole (amino CBI) class of DNA minor groove alkylators are potent cytotoxins (Atwell, et al (1999) J. Med. Chem., 42:3400), and have been utilized as effector units in a number of classes of prodrugs designed for cancer therapy. These have included antibody conjugates, (Jeffrey, et al. (2005) J. Med. Chem., 48:1344), prodrugs for gene therapy based on nitrobenzyl carbamates (Hay, et al (2003) J. Med. Chem. 46:2456) and the corresponding nitro-CBI derivatives as hypoxia-activated prodrugs (Tercel, et al (2011) Angew. Chem., Int. Ed., 50:2606-2609). The CBI and pyrrolo[2,1-c][1,4]benzodiazepine (PBD) pharmacophores have been linked together by an alkyl chain (Tercel et al (2003) J. Med. Chem 46:2132-2151).

In some embodiments, an ADC comprises a 1-(chloromethyl)-2,3-dihydro-1H-benzo[e]indole (CBI) dimer (WO 2015/023355). In some such embodiments, the dimer is a heterodimer wherein one half of the dimer is a CBI moiety and the other half of the dimer is a PBD moiety.

In some embodiments, a CBI dimer comprises the formula:

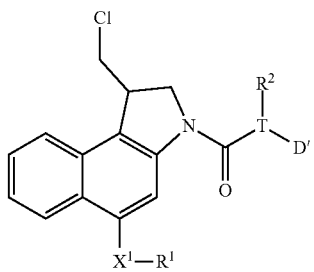

where $R^1$ is selected from H, $P(O)_3H_2$, $C(O)NR^aR^b$, or a bond to a linker (L);

$R^2$ is selected from H, $P(O)_3H_2$, $C(O)NR^aR^b$, or a bond to a linker (L);

$R^a$ and $R^b$ are independently selected from H and $C_1$-$C_6$ alkyl optionally substituted with one or more F, or $R^a$ and $R^b$ form a five or six membered heterocyclyl group;

T is a tether group selected from $C_3$-$C_{12}$ alkylene, Y, ($C_1$-$C_6$ alkylene)-Y—($C_1$-$C_6$ alkylene), ($C_1$-$C_6$ alkylene)-Y—($C_1$-$C_6$ alkylene)-Y—($C_1$-$C_6$ alkylene), ($C_2$-$C_6$ alkenylene)-Y—($C_2$-$C_6$ alkenylene), and ($C_2$-$C_6$ alkynylene)-Y—($C_2$-$C_6$ alkynylene);

where Y is independently selected from O, S, $NR^1$, aryl, and heteroaryl;

where alkylene, alkenylene, aryl, and heteroaryl are independently and optionally substituted with F, OH, O($C_1$-$C_6$ alkyl), $NH_2$, $NHCH_3$, $N(CH_3)_2$, $OP(O)_3H_2$, and $C_1$-$C_6$ alkyl, where alkyl is optionally substituted with one or more F;

or alkylene, alkenylene, aryl, and heteroaryl are independently and optionally substituted with a bond to L;

D' is a drug moiety selected from:

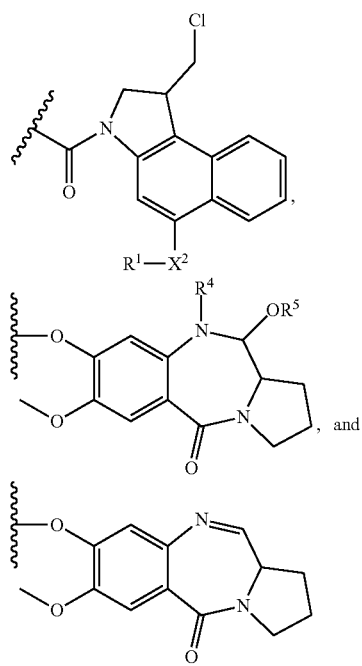

where the wavy line indicates the site of attachment to T;

$X^1$ and $X^2$ are independently selected from O and $NR^3$, where $R^3$ is selected from H and $C_1$-$C_6$ alkyl optionally substituted with one or more F;

$R^4$ is H, $CO_2R$, or a bond to a linker (L), where R is $C_1$-$C_6$ alkyl or benzyl; and $R^5$ is H or $C_1$-$C_6$ alkyl.

(6) Amatoxin

In some embodiments, the immunoconjugate comprises an antibody conjugated to one or more amatoxin molecules. Amatoxins are cyclic peptides composed of 8 amino acids. They can be isolated from *Amanita phalloides* mushrooms or prepared synthetically. Amatoxins specifically inhibit the DNA-dependent RNA polymerase II of mammalian cells, and thereby also the transcription and protein biosynthesis of the affected cells. Inhibition of transcription in a cell causes stop of growth and proliferation. See e.g., Moldenhauer et al. JNCI 104:1-13 (2012), WO2010115629, WO2012041504, WO2012119787, WO2014043403, WO2014135282, and WO2012119787, which are hereby incorporated by reference in its entirety. In some embodiments, the one or more amatoxin molecules are one or more α-amanitin molecules.

(7) Other Drug Moities

Drug moieties also include geldanamycin (Mandler et al (2000) *J. Nat. Cancer Inst.* 92(19):1573-1581; Mandler et al (2000) *Bioorganic & Med. Chem. Letters* 10:1025-1028; Mandler et al (2002) *Bioconjugate Chem.* 13:786-791); and enzymatically active toxins and fragments thereof, including, but not limited to, diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, *sapaonaria officinalis* inhibitor, gelonin, mitogellin, restrictocin, phenomycin, enomycin and the tricothecenes. See, e.g., WO 93/21232.

Drug moieties also include compounds with nucleolytic activity (e.g., a ribonuclease or a DNA endonuclease).

In certain embodiments, an immunoconjugate may comprise a highly radioactive atom. A variety of radioactive isotopes are available for the production of radioconjugated antibodies. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. In some embodiments, when an immunoconjugate is used for detection, it may comprise a radioactive atom for scintigraphic studies, for example $Tc^{99}$ or $I^{123}$, or a spin label for nuclear magnetic resonance (NMR) imaging (also known as magnetic resonance imaging, MRI), such as zirconium-89, iodine-123, iodine-131, indium-111, fluorine-19, carbon-13, nitrogen-15, oxygen-17, gadolinium, manganese or iron. Zirconium-89 may be complexed to various metal chelating agents and conjugated to antibodies, e.g., for PET imaging (WO 2011/056983).

The radio- or other labels may be incorporated in the immunoconjugate in known ways. For example, a peptide may be biosynthesized or chemically synthesized using suitable amino acid precursors comprising, for example, one or more fluorine-19 atoms in place of one or more hydrogens. In some embodiments, labels such as $Tc^{99}$, $I^{123}$, $Re^{186}$, $Re^{188}$ and $In^{111}$ can be attached via a cysteine residue in the antibody. In some embodiments, yttrium-90 can be attached via a lysine residue of the antibody. In some embodiments, the IODOGEN method (Fraker et al (1978) *Biochem. Biophys. Res. Commun.* 80: 49-57 can be used to incorporate iodine-123. "Monoclonal Antibodies in Immunoscintigraphy" (Chatal, CRC Press 1989) describes certain other methods.

In certain embodiments, an immunoconjugate may comprise an antibody conjugated to a prodrug-activating enzyme. In some such embodiments, a prodrug-activating enzyme converts a prodrug (e.g., a peptidyl chemotherapeutic agent, see WO 81/01145) to an active drug, such as an anticancer drug. Such immunoconjugates are useful, in some embodiments, in antibody-dependent enzyme-mediated prodrug therapy ("ADEPT"). Enzymes that may be conjugated to an antibody include, but are not limited to, alkaline phosphatases, which are useful for converting phosphate-containing prodrugs into free drugs; arylsulfatases, which are useful for converting sulfate-containing prodrugs into free drugs; cytosine deaminase, which is useful for converting non-toxic 5-fluorocytosine into the anticancer drug, 5-fluorouracil; proteases, such as *serratia* protease, thermolysin, subtilisin, carboxypeptidases and cathepsins (such as cathepsins B and L), which are useful for converting peptide-containing prodrugs into free drugs; D-alanylcarboxypeptidases, which are useful for converting prodrugs that contain D-amino acid substituents; carbohydrate-cleaving enzymes such as β-galactosidase and neuraminidase, which are useful for converting glycosylated prodrugs into free drugs; β-lactamase, which is useful for converting drugs derivatized with β-lactams into free drugs; and penicillin amidases, such as penicillin V amidase and penicillin G amidase, which are useful for converting drugs derivatized at their amine nitrogens with phenoxyacetyl or phenylacetyl groups, respectively, into free drugs. In some embodiments, enzymes may be covalently bound to antibodies by recombinant DNA techniques well known in the art. See, e.g., Neuberger et al., *Nature* 312:604-608 (1984).

c) Drug Loading

Drug loading is represented by p, the average number of drug moieties per antibody in a molecule of Formula I. Drug loading may range from 1 to 20 drug moieties (D) per antibody. ADCs of Formula I include collections of antibodies conjugated with a range of drug moieties, from 1 to 20. The average number of drug moieties per antibody in preparations of ADC from conjugation reactions may be characterized by conventional means such as mass spectroscopy, ELISA assay, and HPLC. The quantitative distribution of ADC in terms of p may also be determined. In some instances, separation, purification, and characterization of homogeneous ADC where p is a certain value from ADC with other drug loadings may be achieved by means such as reverse phase HPLC or electrophoresis.

For some antibody-drug conjugates, p may be limited by the number of attachment sites on the antibody. For example, where the attachment is a cysteine thiol, as in certain exemplary embodiments above, an antibody may have only one or several cysteine thiol groups, or may have only one or several sufficiently reactive thiol groups through which a linker may be attached. In certain embodiments, higher drug loading, e.g. p>5, may cause aggregation, insolubility, toxicity, or loss of cellular permeability of certain antibody-drug conjugates. In certain embodiments, the average drug loading for an ADC ranges from 1 to about 8; from about 2 to about 6; or from about 3 to about 5. Indeed, it has been shown that for certain ADCs, the optimal ratio of drug moieties per antibody may be less than 8, and may be about 2 to about 5 (U.S. Pat. No. 7,498,298).

In certain embodiments, fewer than the theoretical maximum of drug moieties are conjugated to an antibody during a conjugation reaction. An antibody may contain, for example, lysine residues that do not react with the drug-linker intermediate or linker reagent, as discussed below. Generally, antibodies do not contain many free and reactive cysteine thiol groups which may be linked to a drug moiety; indeed most cysteine thiol residues in antibodies exist as disulfide bridges. In certain embodiments, an antibody may be reduced with a reducing agent such as dithiothreitol (DTT) or tricarbonylethylphosphine (TCEP), under partial or total reducing conditions, to generate reactive cysteine thiol groups. In certain embodiments, an antibody is subjected to denaturing conditions to reveal reactive nucleophilic groups such as lysine or cysteine.

The loading (drug/antibody ratio) of an ADC may be controlled in different ways, and for example, by: (i) limiting the molar excess of drug-linker intermediate or linker reagent relative to antibody, (ii) limiting the conjugation reaction time or temperature, and (iii) partial or limiting reductive conditions for cysteine thiol modification.

It is to be understood that where more than one nucleophilic group reacts with a drug-linker intermediate or linker reagent, then the resulting product is a mixture of ADC compounds with a distribution of one or more drug moieties attached to an antibody. The average number of drugs per antibody may be calculated from the mixture by a dual ELISA antibody assay, which is specific for antibody and specific for the drug. Individual ADC molecules may be identified in the mixture by mass spectroscopy and separated by HPLC, e.g. hydrophobic interaction chromatography (see, e.g., McDonagh et al (2006) Prot. Engr. Design & Selection 19(7):299-307; Hamblett et al (2004) Clin. Cancer Res. 10:7063-7070; Hamblett, K. J., et al. "Effect of drug loading on the pharmacology, pharmacokinetics, and toxicity of an anti-CD30 antibody-drug conjugate," Abstract No. 624, American Association for Cancer Research, 2004 Annual Meeting, Mar. 27-31, 2004, Proceedings of the AACR, Volume 45, March 2004; Alley, S. C., et al. "Controlling the location of drug attachment in antibody-drug conjugates," Abstract No. 627, American Association for Cancer Research, 2004 Annual Meeting, Mar. 27-31, 2004, Proceedings of the AACR, Volume 45, March 2004). In certain embodiments, a homogeneous ADC with a single loading value may be isolated from the conjugation mixture by electrophoresis or chromatography.

Antibody drug conjugates 51-58 of Table A may be prepared by coupling a drug moiety with a linker reagent, and according to the procedures of WO 2013/055987; WO 2015/023355; WO 2010/009124; WO 2015/095227, and conjugated with any of the anti-CLL1 antibodies, including cysteine engineered antibodies, described herein. Specific antibody-drug conjugates are recited in Table B.

TABLE A

Antibody Drug Conjugates 51-58

| ADC No. | Structure |
|---|---|
| 51 | 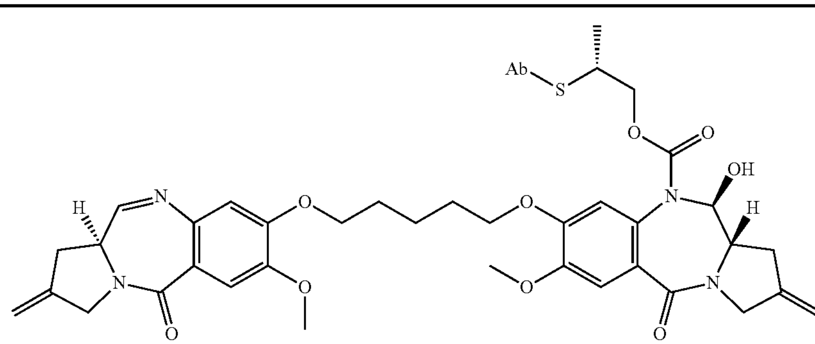 |

TABLE A-continued

Antibody Drug Conjugates 51-58

| ADC No. | Structure |
|---------|-----------|
| 52 | 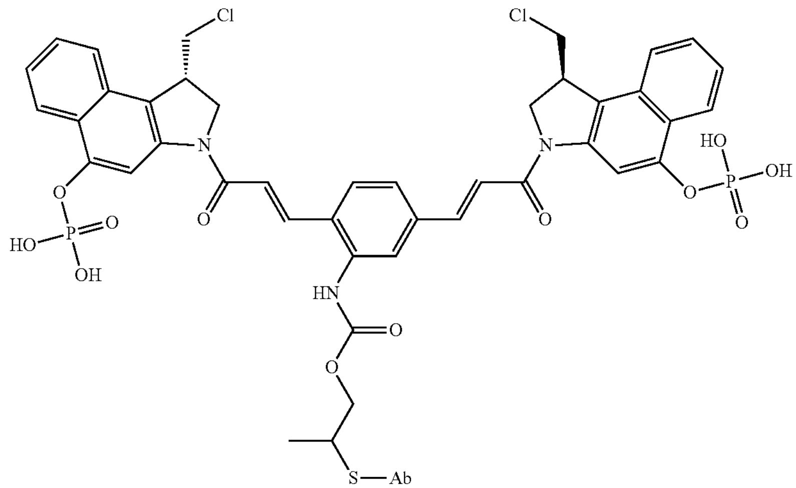 |
| 53 | 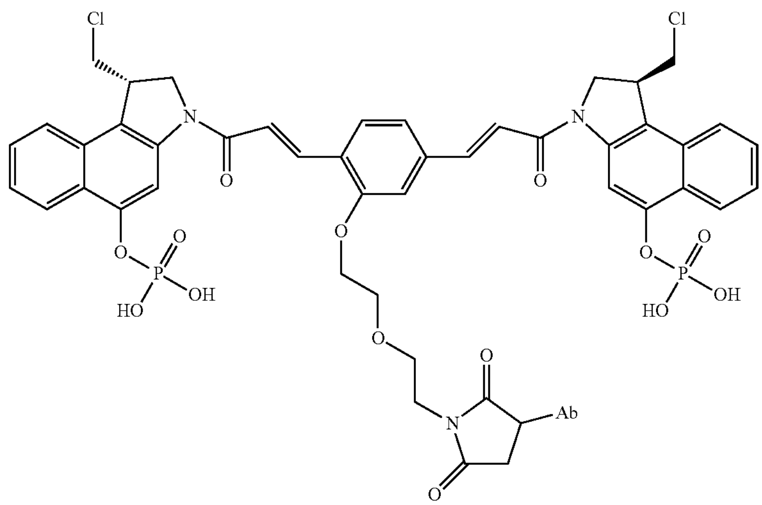 |
| 54 | 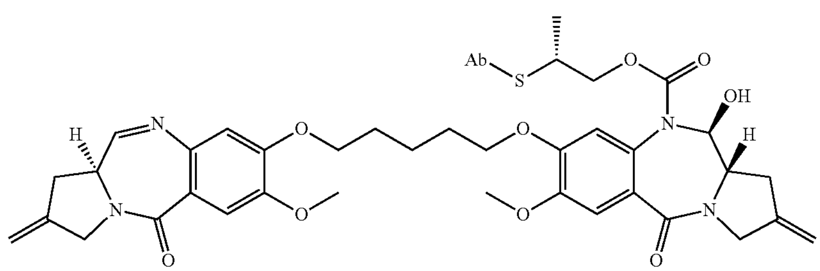 |
| 55 | 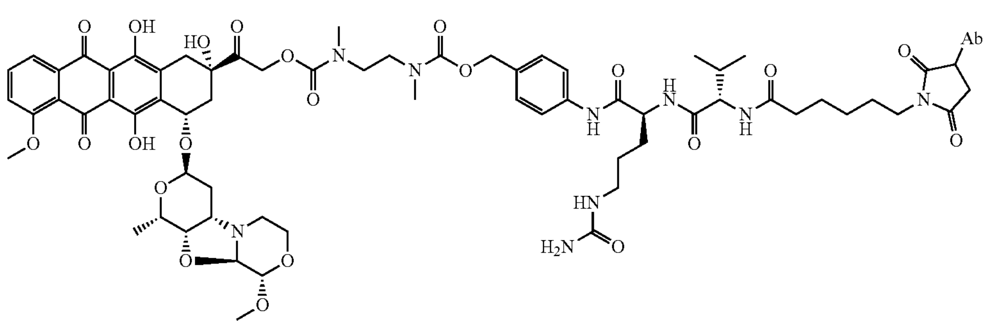 |

TABLE A-continued

Antibody Drug Conjugates 51-58

| ADC No. | Structure |
|---|---|
| 56 | 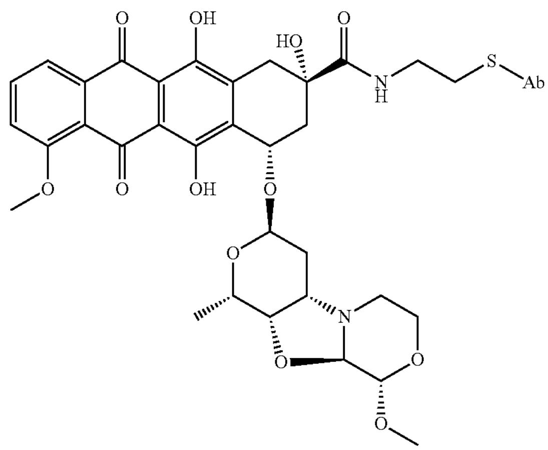 |
| 57 | 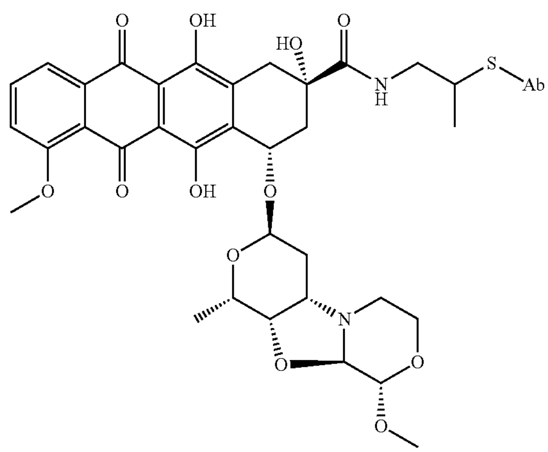 |
| 58 | 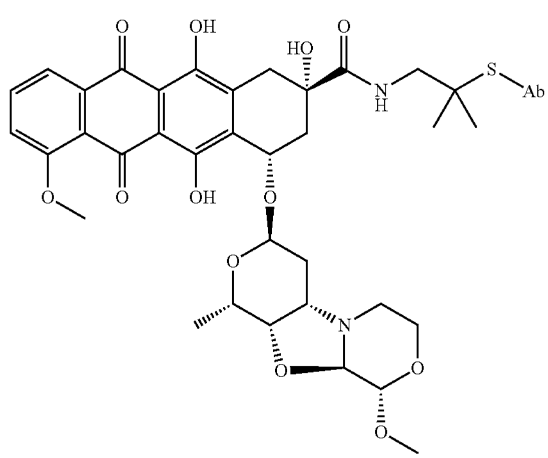 |

Additional exemplary antibody drug conjugates include:
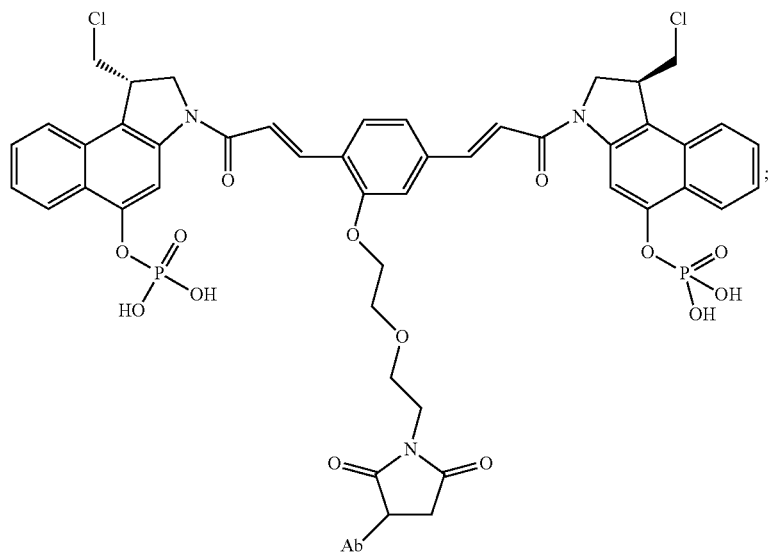
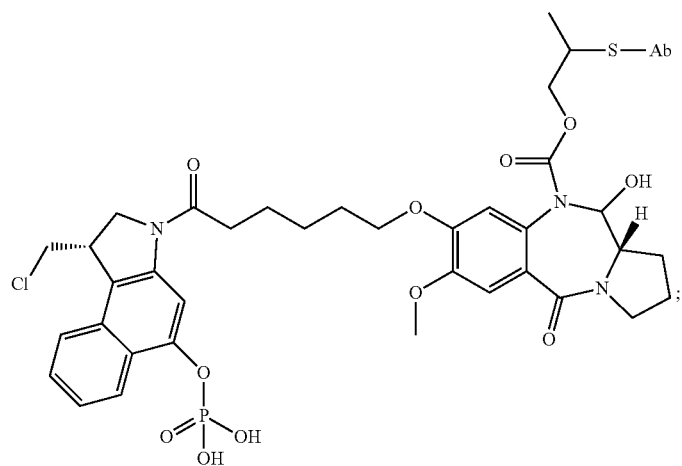
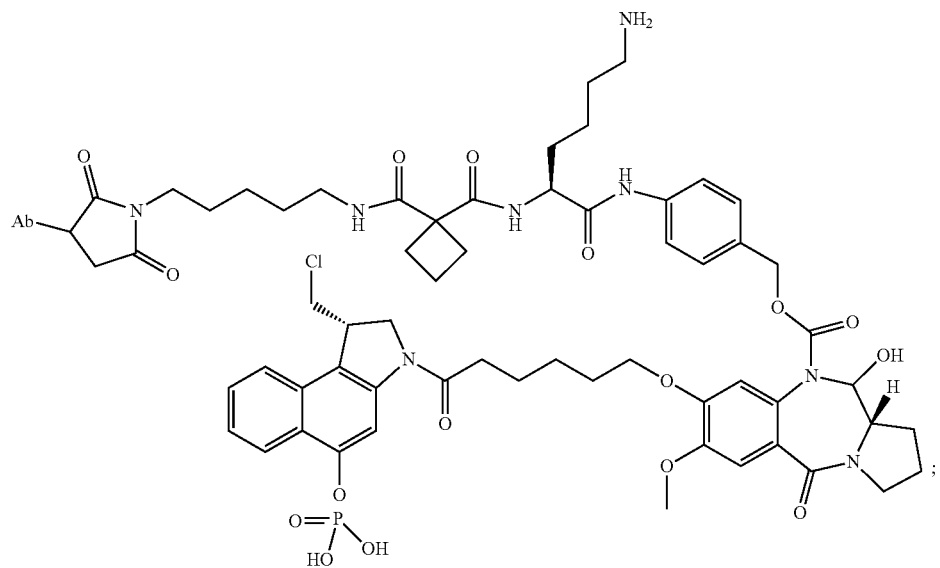

-continued

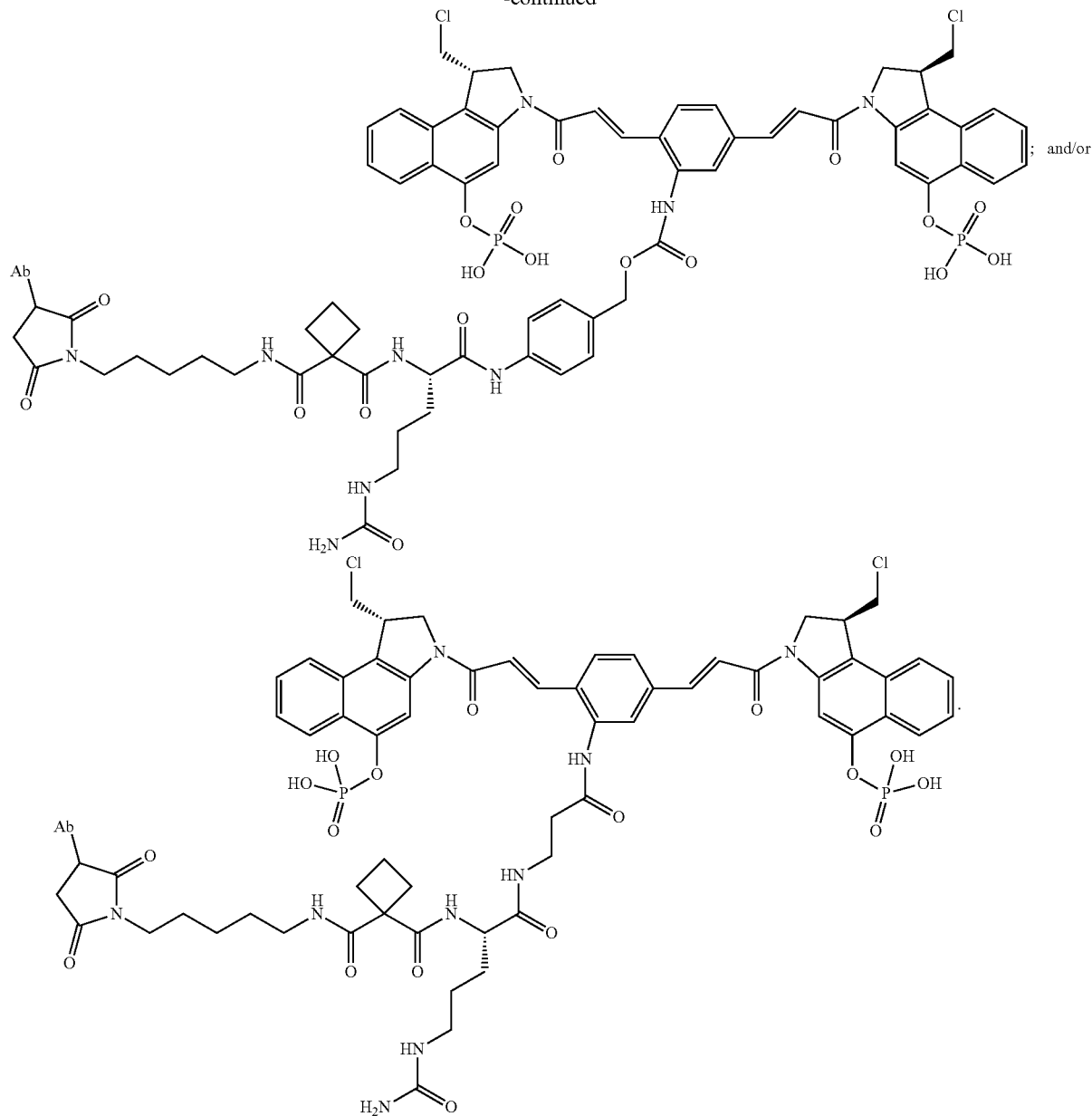

; and/or

It is noted that for simplicity the structures above and those of ADCs 51 to 58 only show one linker-drug group attached to an antibody. As mentioned above, more than one linker-drug group can be attached to an antibody.

TABLE B

Specific Antibody-drug conjugates (ADC)

| ADC No. | ADC formula | linker-drug LD No. (Table 1) | DAR* |
|---|---|---|---|
| ADC-101 | Thio Ch Anti-CLL-1 21C9 HC A118C-(LD-55) | 55 | 2.0 |
| ADC-102 | Thio Ch Anti-CLL-1 3H10 HC A118C-(LD-55) | 55 | 2.0 |
| ADC-103 | Thio Ch Anti-CLL-1 28H12 HC A118C-(LD-55) | 55 | 1.9 |
| ADC-104 | Thio Ch Anti-CLL-1 20B1 HC A118C-(LD-55) | 55 | 1.8 |
| ADC-105 | Thio Ch Anti-CLL-1 6E7 HC A118C-(LD-55) | 55 | 1.9 |
| ADC-106 | Thio Hu anti-CLL-1 6E7.H1eL4 HC A118C-(LD-54) | 54 | 1.95 |
| ADC-107 | Thio Hu anti-CLL-1 21C9.H3L2 HC A118C-(LD-54) | 54 | 1.96 |
| ADC-108 | Thio Hu anti-CLL-1 21C9.H3L2 LC K149C-(LD-54) | 51 | 1.9 |

TABLE B-continued

Specific Antibody-drug conjugates (ADC)

| ADC No. | ADC formula | linker-drug LD No. (Table 1) | DAR* |
|---|---|---|---|
| ADC-109 | Thio Hu anti-CLL-1 6E7.H1eL4 LC K149C-(LD-51) | 51 | 1.91 |
| ADC-110 | Thio Hu anti-CLL-1 6E7.N54A LC K149C-(LD-51) | 51 | 2.0 |
| ADC-111 | Thio Hu anti-CLL-1 6E7.H1eL4.N54A LC K149C-(LD-53) | 53 | 2.0 |
| ADC-112 | Thio Hu anti-CLL-1 6E7.H1eL4.N54A LC K149C-(LD-52) | 52 | 1.9 |
| ADC-113 | Thio Hu anti-CLL-1 6E7.N54A LC K149C-(LD-51) | 51 | 1.9 |
| ADC-114 | Thio Hu anti-CLL-1 6E7.N54A LC K149C-(LD-56) | 56 | 2.0 |
| ADC-115 | Thio Hu anti-CLL-1 6E7.N54A LC K149C-(LD-57) | 57 | 1.7 |
| ADC-116 | Thio Hu anti-CLL-1 6E7.N54A LC K149C-(LD-58) | 58 | 1.9 |

DAR = drug/antibody ratio average
A118C (EU numbering) = A121C (Sequential numbering) = A114C (Kabat numbering)
Wild-type ("WT"), cysteine engineered mutant antibody ("thio"), light chain ("LC"), heavy chain ("HC"), 6-maleimidocaproyl ("MC"), maleimidopropanoyl ("MP"), valine-citrulline ("val-cit" or "vc"), alanine-phenylalanine ("ala-phe"), p-aminobenzyl ("PAB"), and p-aminobenzyloxycarbonyl ("PABC")

d) Certain Methods of Preparing Immunoconjugates

An ADC of Formula I may be prepared by several routes employing organic chemistry reactions, conditions, and reagents known to those skilled in the art, including: (1) reaction of a nucleophilic group of an antibody with a bivalent linker reagent to form Ab-L via a covalent bond, followed by reaction with a drug moiety D; and (2) reaction of a nucleophilic group of a drug moiety with a bivalent linker reagent, to form D-L, via a covalent bond, followed by reaction with a nucleophilic group of an antibody. Exemplary methods for preparing an ADC of Formula I via the latter route are described in U.S. Pat. No. 7,498,298, which is expressly incorporated herein by reference.

Nucleophilic groups on antibodies include, but are not limited to: (i) N-terminal amine groups, (ii) side chain amine groups, e.g. lysine, (iii) side chain thiol groups, e.g. cysteine, and (iv) sugar hydroxyl or amino groups where the antibody is glycosylated. Amine, thiol, and hydroxyl groups are nucleophilic and capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; and (iii) aldehydes, ketones, carboxyl, and maleimide groups. Certain antibodies have reducible interchain disulfides, i.e. cysteine bridges. Antibodies may be made reactive for conjugation with linker reagents by treatment with a reducing agent such as DTT (dithiothreitol) or tricarbonylethylphosphine (TCEP), such that the antibody is fully or partially reduced. Each cysteine bridge will thus form, theoretically, two reactive thiol nucleophiles. Additional nucleophilic groups can be introduced into antibodies through modification of lysine residues, e.g., by reacting lysine residues with 2-iminothiolane (Traut's reagent), resulting in conversion of an amine into a thiol. Reactive thiol groups may also be introduced into an antibody by introducing one, two, three, four, or more cysteine residues (e.g., by preparing variant antibodies comprising one or more non-native cysteine amino acid residues).

Antibody-drug conjugates of the invention may also be produced by reaction between an electrophilic group on an antibody, such as an aldehyde or ketone carbonyl group, with a nucleophilic group on a linker reagent or drug. Useful nucleophilic groups on a linker reagent include, but are not limited to, hydrazide, oxime, amino, hydrazine, thiosemicarbazone, hydrazine carboxylate, and arylhydrazide. In one embodiment, an antibody is modified to introduce electrophilic moieties that are capable of reacting with nucleophilic substituents on the linker reagent or drug. In another embodiment, the sugars of glycosylated antibodies may be oxidized, e.g. with periodate oxidizing reagents, to form aldehyde or ketone groups which may react with the amine group of linker reagents or drug moieties. The resulting imine Schiff base groups may form a stable linkage, or may be reduced, e.g. by borohydride reagents to form stable amine linkages. In one embodiment, reaction of the carbohydrate portion of a glycosylated antibody with either galactose oxidase or sodium meta-periodate may yield carbonyl (aldehyde and ketone) groups in the antibody that can react with appropriate groups on the drug (Hermanson, Bioconjugate Techniques). In another embodiment, antibodies containing N-terminal serine or threonine residues can react with sodium meta-periodate, resulting in production of an aldehyde in place of the first amino acid (Geoghegan & Stroh, (1992) Bioconjugate Chem. 3:138-146; U.S. Pat. No. 5,362,852). Such an aldehyde can be reacted with a drug moiety or linker nucleophile.

Exemplary nucleophilic groups on a drug moiety include, but are not limited to: amine, thiol, hydroxyl, hydrazide, oxime, hydrazine, thiosemicarbazone, hydrazine carboxylate, and arylhydrazide groups capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; (iii) aldehydes, ketones, carboxyl, and maleimide groups.

Nonlimiting exemplary cross-linker reagents that may be used to prepare ADC are described herein in the section titled "Exemplary Linkers." Methods of using such cross-linker reagents to link two moieties, including a proteinaceous moiety and a chemical moiety, are known in the art. In some embodiments, a fusion protein comprising an antibody and a cytotoxic agent may be made, e.g., by recombinant techniques or peptide synthesis. A recombinant DNA molecule may comprise regions encoding the antibody and cytotoxic portions of the conjugate either adjacent to one another or separated by a region encoding a linker peptide which does not destroy the desired properties of the conjugate.

In yet another embodiment, an antibody may be conjugated to a "receptor" (such as streptavidin) for utilization in tumor pre-targeting wherein the antibody-receptor conjugate is administered to the patient, followed by removal of unbound conjugate from the circulation using a clearing agent and then administration of a "ligand" (e.g., avidin) which is conjugated to a cytotoxic agent (e.g., a drug or radionuclide).

E. Methods and Compositions for Diagnostics and Detection

In certain embodiments, any of the anti-CLL-1 antibodies provided herein is useful for detecting the presence of CLL-1 in a biological sample. The term "detecting" as used herein encompasses quantitative or qualitative detection. A "biological sample" comprises, e.g., a cell or tissue (e.g., biopsy material, including cancerous or potentially cancerous lymphoid tissue, such as lymphocytes, lymphoblasts, monocytes, myelomonocytes, and mixtures thereof).

In one embodiment, an anti-CLL-1 antibody for use in a method of diagnosis or detection is provided. In a further aspect, a method of detecting the presence of CLL-1 in a biological sample is provided. In certain embodiments, the method comprises contacting the biological sample with an anti-CLL-1 antibody as described herein under conditions permissive for binding of the anti-CLL-1 antibody to CLL-1, and detecting whether a complex is formed between the anti-CLL-1 antibody and CLL-1 in the biological sample. Such method may be an in vitro or in vivo method. In one embodiment, an anti-CLL-1 antibody is used to select subjects eligible for therapy with an anti-CLL-1 antibody, e.g. where CLL-1 is a biomarker for selection of patients. In a further embodiment, the biological sample is a cell or tissue.

In a further embodiment, an anti-CLL-1 antibody is used in vivo to detect, e.g., by in vivo imaging, a CLL-1-positive cancer in a subject, e.g., for the purposes of diagnosing, prognosing, or staging cancer, determining the appropriate course of therapy, or monitoring response of a cancer to therapy. One method known in the art for in vivo detection is immuno-positron emission tomography (immuno-PET), as described, e.g., in van Dongen et al., *The Oncologist* 12:1379-1389 (2007) and Verel et al., *J. Nucl. Med.* 44:1271-1281 (2003). In such embodiments, a method is provided for detecting a CLL-1-positive cancer in a subject, the method comprising administering a labeled anti-CLL-1 antibody to a subject having or suspected of having a CLL-1-positive cancer, and detecting the labeled anti-CLL-1 antibody in the subject, wherein detection of the labeled anti-CLL-1 antibody indicates a CLL-1-positive cancer in the subject. In certain of such embodiments, the labeled anti-CLL-1 antibody comprises an anti-CLL-1 antibody conjugated to a positron emitter, such as $^{68}$Ga, $^{18}$F, $^{64}$Cu, $^{86}$Y, $^{76}$Br, $^{89}$Zr, and $^{124}$I. In a particular embodiment, the positron emitter is $^{89}$Zr.

In further embodiments, a method of diagnosis or detection comprises contacting a first anti-CLL-1 antibody immobilized to a substrate with a biological sample to be tested for the presence of CLL-1, exposing the substrate to a second anti-CLL-1 antibody, and detecting whether the second anti-CLL-1 is bound to a complex between the first anti-CLL-1 antibody and CLL-1 in the biological sample. A substrate may be any supportive medium, e.g., glass, metal, ceramic, polymeric beads, slides, chips, and other substrates. In certain embodiments, a biological sample comprises a cell or tissue. In certain embodiments, the first or second anti-CLL-1 antibody is any of the antibodies described herein.

Exemplary disorders that may be diagnosed or detected according to any of the above embodiments include CLL-1-positive cancers, such as CLL-1-positive AML, CLL-1-positive CML, CLL-1-positive MDS, CLL-1-positive chronic myelomonocytic leukemia, CLL-1-positive APL, CLL-1-positive chronic myeloproliferative disorder, CLL-1-positive thrombocytic leukemia, CLL-1-positive pre-B-ALL, CLL-1-positive preT-ALL, CLL-1-positive multiple myeloma, CLL-1-positive mast cell disease, CLL-1-positive mast cell leukemia, CLL-1-positive mast cell sarcoma, CLL-1-positive myeloid sarcomas, CLL-1-positive lymphoid leukemia, and CLL-1-positive undifferentiated leukemia. In some embodiments, a CLL-1-positive cancer is a cancer that receives an anti-CLL-1 immunohistochemistry (IHC) or in situ hybridization (ISH) score greater than "0," which corresponds to very weak or no staining in >90% of tumor cells, under the conditions described herein in Example B. In another embodiment, a CLL-1-positive cancer expresses CLL-1 at a 1+, 2+ or 3+ level, as defined under the conditions described herein in Example B. In some embodiments, a CLL-1-positive cancer is a cancer that expresses CLL-1 according to a reverse-transcriptase PCR (RT-PCR) assay that detects CLL-1 mRNA. In some embodiments, the RT-PCR is quantitative RT-PCR.

In certain embodiments, labeled anti-CLL-1 antibodies are provided. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}$P, $^{14}$C, $^{125}$I, $^{3}$H, and $^{131}$I, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like. In another embodiment, a label is a positron emitter. Positron emitters include but are not limited to $^{68}$Ga, $^{18}$F, $^{64}$Cu, $^{86}$Y, $^{76}$Br, $^{89}$Zr, and $^{124}$I. In a particular embodiment, a positron emitter is $^{89}$Zr.

F. Pharmaceutical Formulations

Pharmaceutical formulations of an anti-CLL-1 antibody or immunoconjugate as described herein are prepared by mixing such antibody or immunoconjugate having the desired degree of purity with one or more optional pharmaceutically acceptable carriers (*Remington's Pharmaceutical Sciences* 16th edition, Osol, A. Ed. (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Exemplary pharmaceutically acceptable carriers herein further include insterstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases.

Exemplary lyophilized antibody or immunoconjugate formulations are described in U.S. Pat. No. 6,267,958. Aqueous antibody or immunoconjugate formulations include those described in U.S. Pat. No. 6,171,586 and WO2006/044908, the latter formulations including a histidine-acetate buffer.

The formulation herein may also contain more than one active ingredient as necessary for the particular indication being treated, preferably those with complementary activities that do not adversely affect each other.

Active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

Sustained-release preparations may be prepared. Suitable examples of sustained-release preparations include semipermeable matrices of solid hydrophobic polymers containing the antibody or immunoconjugate, which matrices are in the form of shaped articles, e.g. films, or microcapsules.

The formulations to be used for in vivo administration are generally sterile. Sterility may be readily accomplished, e.g., by filtration through sterile filtration membranes.

G. Therapeutic Methods and Compositions

Any of the anti-CLL-1 antibodies or immunoconjugates provided herein may be used in methods, e.g., therapeutic methods.

In one aspect, an anti-CLL-1 antibody or immunoconjugate provided herein is used in a method of inhibiting proliferation of a CLL-1-positive cell, the method comprising exposing the cell to the anti-CLL-1 antibody or immunoconjugate under conditions permissive for binding of the anti-CLL-1 antibody or immunoconjugate to CLL-1 on the surface of the cell, thereby inhibiting the proliferation of the cell. In certain embodiments, the method is an in vitro or an in vivo method. In further embodiments, the cell is a lymphocyte, lymphoblast, monocyte, or myelomonocyte cell. In further embodiments, the cell is a monocyte, granulocyte, and/or progenitors of the monocyte/granulocyte lineage. In some embodiments, the cell is positive for the presence of FLT3 internal tandem repeats. In some embodiments, the cell is positive for the presence of a MLL-AF9 fusion gene (e.g., MLL-AF9 translocation). In some embodiments, the cell is positive for the presence of a chromosome 11q23 translocation. In some embodiments, the cell is positive for positive for the presence of a translocation t(9;11)(p22;q23).

Inhibition of cell proliferation in vitro may be assayed using the CellTiter-Glo™ Luminescent Cell Viability Assay, which is commercially available from Promega (Madison, Wis.). That assay determines the number of viable cells in culture based on quantitation of ATP present, which is an indication of metabolically active cells. See Crouch et al. (1993) *J. Immunol. Meth.* 160:81-88, U.S. Pat. No. 6,602,677. The assay may be conducted in 96- or 384-well format, making it amenable to automated high-throughput screening (HTS). See Cree et al. (1995) *AntiCancer Drugs* 6:398-404. The assay procedure involves adding a single reagent (CellTiter-Glo® Reagent) directly to cultured cells. This results in cell lysis and generation of a luminescent signal produced by a luciferase reaction. The luminescent signal is proportional to the amount of ATP present, which is directly proportional to the number of viable cells present in culture. Data can be recorded by luminometer or CCD camera imaging device. The luminescence output is expressed as relative light units (RLU).

In another aspect, an anti-CLL-1 antibody or immunoconjugate for use as a medicament is provided. In further aspects, an anti-CLL-1 antibody or immunoconjugate for use in a method of treatment is provided. In certain embodiments, an anti-CLL-1 antibody or immunoconjugate for use in treating CLL-1-positive cancer is provided. In certain embodiments, the invention provides an anti-CLL-1 antibody or immunoconjugate for use in a method of treating an individual having a CLL-1-positive cancer, the method comprising administering to the individual an effective amount of the anti-CLL-1 antibody or immunoconjugate. In one such embodiment, the method further comprises administering to the individual an effective amount of at least one additional therapeutic agent, e.g., as described below.

In a further aspect, the invention provides for the use of an anti-CLL-1 antibody or immunoconjugate in the manufacture or preparation of a medicament. In one embodiment, the medicament is for treatment of CLL-1-positive cancer. In a further embodiment, the medicament is for use in a method of treating CLL-1-positive cancer, the method comprising administering to an individual having CLL-1-positive cancer an effective amount of the medicament. In one such embodiment, the method further comprises administering to the individual an effective amount of at least one additional therapeutic agent, e.g., as described below.

In a further aspect, the invention provides a method for treating CLL-1-positive cancer. In one embodiment, the method comprises administering to an individual having such CLL-1-positive cancer an effective amount of an anti-CLL-1 antibody or immunoconjugate. In some embodiments, the cancer is AML. In one such embodiment, the method further comprises administering to the individual an effective amount of at least one additional therapeutic agent, as described below.

A CLL-1-positive cancer according to any of the above embodiments may be, e.g., CLL-1-positive AML, CLL-1-positive CML, CLL-1-positive myelodysplastic syndrome (MDS), CLL-1-positive chronic myelomonocytic leukemia (CML), CLL-1-positive APL, CLL-1-positive chronic myeloproliferative disorder, CLL-1-positive thrombocytic leukemia, CLL-1-positive pre-B-ALL, CLL-1-positive preT-ALL, CLL-1-positive multiple myeloma, CLL-1-positive mast cell disease, CLL-1-positive mast cell leukemia, CLL-1-positive mast cell sarcoma, CLL-1-positive myeloid sarcomas, CLL-1-positive lymphoid leukemia, and CLL-1-positive undifferentiated leukemia. In some embodiments, a CLL-1-positive cancer is a cancer that receives an anti-CLL-1 immunohistochemistry (IHC) or in situ hybridization (ISH) score greater than "0," which corresponds to very weak or no staining in >90% of tumor cells, under the conditions described herein in Example B. In another embodiment, a CLL-1-positive cancer expresses CLL-1 at a 1+, 2+ or 3+ level, as defined under the conditions described herein in Example B. In some embodiments, a CLL-1-positive cancer is a cancer that expresses CLL-1 according to a reverse-transcriptase PCR (RT-PCR) assay that detects CLL-1 mRNA. In some embodiments, the RT-PCR is quantitative RT-PCR.

In some embodiments, cell proliferative disorder according to any of the above embodiments may be, e.g., AML, CML, and/or MDS. In some embodiments, CLL-1-positive cell proliferative disorder is a CLL-1-positive AML, CLL-1-positive CML, CLL-1-positive MDS. In some embodiments, the AML is one or more of AML subtype 1, AML subtype 2, AML subtype 3, AML subtype 4, AML subtype 5, AML subtype 6, and AML subtype 7. In some embodiments, the AML is AML subtype 3 (acute promyelocytic leukemia, APML). In some embodiments, the AML is one or more of AML subtype 1, AML subtype 2, AML subtype 4, AML subtype 5, AML subtype 6, and AML subtype 7, and not AML subtype 3.

In some embodiments, the cell proliferative disorder (e.g., CLL-1-positive cancer and/or AML) is positive for the presence of a mutation in FLT3, nucleophosmin (NPM1), CCAAT/enhancer binding protein alpha (C/EBPα) (CEBPA), and/or c-KIT. In some embodiments, the cell proliferative disorder (e.g., CLL-1-positive cancer and/or AML) is positive for the presence of FLT3 internal tandem repeats. In some embodiments, the cell proliferative disorder (e.g., CLL-1-positive cancer and/or AML) is positive for the presence of FLT3 tyrosine kinase domain point mutations. In some embodiments, the cell proliferative disorder (e.g., CLL-1-positive cancer and/or AML) is positive for the presence of a mutation in isocitrate dehydrogenase 1 and/or 2 (IDH1 and/or IDH2). In some embodiments, the cell proliferative disorder (e.g., CLL-1-positive cancer and/or AML) is positive for the presence of a mutation in DNA methyltransferase 3A (DNMT3A). In some embodiments, the cell proliferative disorder (e.g., CLL-1-positive cancer and/or AML) is NK-AML positive for the presence of (a) a mutation in NPM1 and FLT3, (b) wild-type NPM1 and mutated FLT3, and/or (c) wild-type NPM1 and FLT3.

In some embodiments, the cell proliferative disorder (e.g., CLL-1-positive cancer and/or AML) is positive cytogenetic abnormality such as one or more of t(15;17), t(8;21), inv (16), t(16;16), t(9;11)(p22;q23), t(6;9)(p23;q34), inv(3)(q21 q26.2), inv(3;3)(q21;q26.2), t(1;22)(p13;q13), t(8;21)(q22; q22), inv(16)(p13;1q22), t(16;16)(p13.1;q22), and/or t(15; 17)(q22;q12). In some embodiments, the cell proliferative disorder (e.g., CLL-1-positive cancer and/or AML) is positive for the presence of a MLL-AF9 fusion gene (e.g., MLL-AF9 translocation). In some embodiments, the cell proliferative disorder (e.g., CLL-1-positive cancer and/or AML) is positive for the presence of a chromosome 11q23 translocation. In some embodiments, the cell proliferative disorder (e.g., CLL-1-positive cancer) is a cell proliferative disorder (e.g., CLL-1-positive cancer and/or AML) positive for the presence of a translocation t(9;11)(p22;q23).

An "individual" according to any of the above embodiments may be a human.

In a further aspect, the invention provides pharmaceutical formulations comprising any of the anti-CLL-1 antibodies or immunoconjugate provided herein, e.g., for use in any of the above therapeutic methods. In one embodiment, a pharmaceutical formulation comprises any of the anti-CLL-1 antibodies or immunoconjugates provided herein and a pharmaceutically acceptable carrier. In another embodiment, a pharmaceutical formulation comprises any of the anti-CLL-1 antibodies or immunoconjugates provided herein and at least one additional therapeutic agent, e.g., as described below.

Antibodies or immunoconjugates of the invention can be used either alone or in combination with other agents in a therapy. For instance, an antibody or immunoconjugate of the invention may be co-administered with at least one additional therapeutic agent. In some embodiments, the additional therapeutic agent is an anthracycline. In some embodiments, the anthracycline is daunorubicin or idarubicin. In some embodiments, the additional therapeutic agent is cytarabine. In some embodiments, the additional therapeutic agent is cladribine. In some embodiments, the additional therapeutic agent is fludarabine or topotecan. In some embodiments, the additional therapeutic agent is 5-azacytidine or decitabine. In some embodiments, the additional therapeutic agent is ATRA (all-trans retinoic acid). In some embodiments, the additional therapeutic agent is arsenic trioxide. In some embodiments, the additional therapeutic agent is hydroxyurea. In some embodiments, the additional therapeutic agent is etoposide. In some embodiments, the additional therapeutic agent is mitoxantrone. In some embodiments, the additional therapeutic agent is clofarabine. In some embodiments, the additional therapeutic agent is hydroxyurea. In some embodiments, the additional therapeutic agent is FLT3 inhibitor such as quizartinib. In some embodiments, the additional therapeutic agent is an IDH2 inhibitor. In some embodiments, the additional therapeutic agent is CHK1 inhibitor. In some embodiments, the additional therapeutic agent is a Plk inhibitor such as volasertib.

In some embodiments of any of the methods, the additional therapeutic is a BCL2 inhibitor. In some embodiments, the BCL2 inhibitor is venatoclax.

In some embodiments of any of the methods, the additional therapeutic agent is an epigenetic modifier. In some embodiments, the epigenetic modifier is a histone deacetylase inhibitor. In some embodiments, the epigenetic modifier is DNA methyltransferases I inhibitor. In some embodiments, the epigenetic modifier is a histone methyltransferases inhibitor. In some embodiments, the epigenetic modifier is a BET inhibitor. In some embodiments, the BET inhibitor selectively targets the first bromodomain (BD1). In some embodiments, the BET inhibitor selectively targets the second bromodomain (BD2). In some embodiments, the BET inhibitor is one or more of GSK1210151A, GSK525762, OTX-01, TEN-010, CPI-203, and CPI-0610.

In some embodiments, the methods may further comprise an additional therapy. The additional therapy may be radiation therapy, surgery, chemotherapy, gene therapy, DNA therapy, viral therapy, RNA therapy, immunotherapy, bone marrow transplantation, nanotherapy, monoclonal antibody therapy, or a combination of the foregoing. The additional therapy may be in the form of adjuvant or neoadjuvant therapy. In some embodiments, the additional therapy is the administration of small molecule enzymatic inhibitor or anti-metastatic agent. In some embodiments, the additional therapy is the administration of side-effect limiting agents (e.g., agents intended to lessen the occurrence and/or severity of side effects of treatment, such as anti-nausea agents, etc.). In some embodiments, the additional therapy is radiation therapy. In some embodiments, the additional therapy is surgery. In some embodiments, the additional therapy is a combination of radiation therapy and surgery. In some embodiments, the additional therapy is gamma irradiation. In some embodiments, the additional therapy is stem cell transplant. In some embodiments, the additional therapy may be a separate administration of one or more of the therapeutic agents described above.

In some embodiments of any of the methods, the additional therapy comprises cancer immunotherapies. In some embodiments of any of the methods, the cancer immunotherapy comprises a PD-1 axis binding antagonist. In some embodiments of any of the methods, the cancer immunotherapy comprises a PD-1 binding antagonist. In some embodiments of any of the methods, the cancer immunotherapy comprises a PD-L1 binding antagonist. In some embodiments of any of the methods, the cancer immunotherapy therapy comprises a PD-L2 binding antagonist. In some embodiments of any of the methods, the cancer immunotherapy comprises CTLA-4 inhibition. In some embodiments of any of the methods, the cancer immunotherapy comprises immune agonists.

Such combination therapies noted above encompass combined administration (where two or more therapeutic agents are included in the same or separate formulations), and separate administration, in which case, administration of the antibody or immunoconjugate of the invention can occur prior to, simultaneously, and/or following, administration of the additional therapeutic agent and/or adjuvant. Antibodies or immunoconjugates of the invention can also be used in combination with radiation therapy.

An antibody or immunoconjugate of the invention (and any additional therapeutic agent) can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic. Various dosing schedules including but not limited to single or multiple administrations over various timepoints, bolus administration, and pulse infusion are contemplated herein.

Antibodies or immunoconjugates of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody or immunoconjugate need not be, but is optionally formulated with one or more agents currently used to prevent or treat the disorder in question. The effective amount of such other agents depends on the amount of antibody or immunoconjugate present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of an antibody or immunoconjugate of the invention (when used alone or in combination with one or more other additional therapeutic agents) will depend on the type of disease to be treated, the type of antibody or immunoconjugate, the severity and course of the disease, whether the antibody or immunoconjugate is administered for preventive or therapeutic purposes, previous therapy, the patient's clinical history and response to the antibody or immunoconjugate, and the discretion of the attending physician. The antibody or immunoconjugate is suitably administered to the patient at one time or over a series of treatments. Depending on the type and severity of the disease, about 1 µg/kg to 15 mg/kg (e.g. 0.1 mg/kg-10 mg/kg) of antibody or immunoconjugate can be an initial candidate dosage for administration to the patient, whether, for example, by one or more separate administrations, or by continuous infusion. One typical daily dosage might range from about 1 µg/kg to 100 mg/kg or more, depending on the factors mentioned above. For repeated administrations over several days or longer, depending on the condition, the treatment would generally be sustained until a desired suppression of disease symptoms occurs. One exemplary dosage of the antibody or immunoconjugate would be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g. every week or every three weeks (e.g. such that the patient receives from about two to about twenty, or e.g. about six doses of the antibody). An initial higher loading dose, followed by one or more lower doses may be administered. However, other dosage regimens may be useful. The progress of this therapy is easily monitored by conventional techniques and assays.

It is understood that any of the above formulations or therapeutic methods may be carried out using both an immunoconjugate of the invention and an anti-CLL-1 antibody.

H. Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the disorder and may have a sterile access port (for example the container may be an intravenous solution bag or a vial having a stopper pierceable by a hypodermic injection needle). At least one active agent in the composition is an antibody or immunoconjugate of the invention. The label or package insert indicates that the composition is used for treating the condition of choice. Moreover, the article of manufacture may comprise (a) a first container with a composition contained therein, wherein the composition comprises an antibody or immunoconjugate of the invention; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution or dextrose solution. It may further include other materials desirable from a commercial and user standpoint, including other buffers, diluents, filters, needles, and syringes.

III. EXAMPLES

The following are examples of methods and compositions of the invention. It is understood that various other embodiments may be practiced, given the general description provided above.

Example 1

A. Monoclonal Antibody Generation

Monoclonal antibodies against human (hu) and cynomolgus (cyno) CLL-1 were generated using the following procedures by immunizing animals with recombinant hu and cyno CLL-1 extracellular domain (ECD, amino acids of 65-265 huCLL-1 and 65-265 cynoCLL-1) fused to a N-terminal Flag (DYKDDDDK) expressed in a mammalian expression system. The huCLL1 ECD protein (amino acids 65-265) comprised a SNP, AAA(Lys, K) 244->CAA (GLN, Q), which has a minor allele frequency (MAF) of 29%.

Positive clones were expanded and re-screened for binding to huCLL-1 and cynoCLL-1 by ELISA and FACS. Five clones were identified: m3H10, m6E7, m20B1, m21C9, and m28H12 that reacted strongly by fluorescent activated cell sorting (FACS) with stable cell lines expressing recombinant hu and cyno CLL-1, and with tumor-derived CLL-1 expressed on Acute Myeloid Leukemia tumor cell lines. Alignment of the amino acid sequences of the murine heavy and light variable domains are shown in FIGS. 1A and B. m3H10 and m21C9 share the same heavy and light chain CDRs, only the amino acid sequences of m21C9 heavy and light chain variable region is shown in FIG. 1.

B. Species Cross-Reactivity and Binding Affinity

Monoclonal antibodies were tested to determine if they cross-react with cynoCLL-1 extracellular domain (ECD) (which is 85.07% identical and 87.35% similar to the huCLL-1 protein ECD). The chimeric anti-CLL-1 human IgG were captured by mouse anti-human IgG coated on the CM5 sensor chip. For kinetics measurements, three-fold serial dilutions of human or cyno CLL-1 (4.1 nM to 1000 nM) were injected in HBS-EP buffer. Association rates (kon) and dissociation rates (koff) were calculated using a simple one-to-one *Langmuir* binding model. The equilibrium dissociation constant (KD) was calculated as the ratio koff/kon. Table 2 below shows that the chimeric version of the five antibodies (m3H10, m6E7, m20B1, m21C9, and m28H12) recognized both recombinant hu and cynoCLL-1 and provides details regarding the kinetics of the interaction with hu and cyno-CLL-1. Further confirmation of cross-reactivity to cyno CLL-1 was done by FACS analyses of blood from cynomolgus (Mauritian origin) (data not shown).

TABLE 2

Biacore of Anti-CLL-1 Antibodies

| Ligand | Analyte | Ka (M$^{-1}$s$^{-1}$) | Kd (s$^{-1}$) | KD (M) |
|---|---|---|---|---|
| ch3H10 | huCLL-1-Flag | $2.7 \times 10^5$ | $2.4 \times 10^{-3}$ | 8.7 nM |
|  | CynoCLL-1 Flag | $1.7 \times 10^5$ | $7.7 \times 10^{-4}$ | 4.3 nM |
| ch6E7 | huCLL-1-Flag | $4.6 \times 10^5$ | $4.4 \times 10^{-4}$ | 0.9 nM |
|  | CynoCLL-1 Flag | $4.0 \times 10^5$ | $4.6 \times 10^{-4}$ | 1.1 nM |
| ch20B1 | huCLL-1-Flag | $2.2 \times 10^5$ | $1.0 \times 10^{-3}$ | 4.5 nM |
|  | CynoCLL-1 Flag | $1.9 \times 10^5$ | $1.2 \times 10^{-3}$ | 6.1 nM |
| ch21C9 | huCLL-1-Flag | $2.5 \times 10^5$ | $2.4 \times 10^{-3}$ | 9.7 nM |
|  | CynoCLL-1 Flag | $1.6 \times 10^5$ | $1.2 \times 10^{-3}$ | 7.1 nM |
| ch28H12 | huCLL-1-Flag | $5.0 \times 10^5$ | $9.5 \times 10^{-3}$ | 18 nM |
|  | CynoCLL-1 Flag | $6.7 \times 10^5$ | $2.3 \times 10^{-4}$ | 0.3 nM |

Scatchard analysis was performed following standard procedures (Holmes et al., *Science* 256:1205-1210 (1992)) to determine the relative binding affinities of the antibodies including ch6E7 and ch21C9.

Anti-CLL-1 antibodies were [I$^{125}$] labeled using the indirect Iodogen method. The [I$^{125}$] labeled anti-CLL-1 antibodies were purified from free $^{125}$I—Na by gel filtration using a NAP-5 column (GE Healthcare); the purified iodinated anti-CLL-1 antibodies had a range of specific activities of 8-10 µCi/µg. Competition assay mixtures of 50 µL volume containing a fixed concentration of [I$^{125}$] labeled antibody and decreasing concentrations of serially diluted, unlabeled antibody were placed into 96-well plates. HEK293AD cells stably expressing recombinant hu or cyno-CLL-1 or HL-60 tumor cells expressing endogenous CLL-1 were cultured in growth media at 37° C. in 5% $CO_2$. Cells were detached from the flask using Sigma Cell Dissociation Solution and were washed with binding buffer, which consisted of Dulbecco's Modified Eagle Medium (DMEM) with 1% bovine serum albumin (BSA), 300 mM human IgG and 0.1% sodium azide. The washed cells were added to the 96 well plates at a density of 100,000 cells in 0.2 mL of binding buffer. The final concentration of the [I$^{125}$] labeled antibody in each well was ~250 pM. The final concentration of the unlabeled antibody in the competition assay ranged from 1000 nM through ten 2-fold dilution steps to a 0 nM buffer-only assay. Competition assays were carried out in triplicate. Competition assays were incubated for 2 hours at room temperature. After the 2-hour incubation, the competition assays were transferred to a Millipore Multiscreen filter plate (Billerica, Mass.) and washed 4 times with binding buffer to separate the free from bound [I$^{125}$] labeled antibody. The filters were counted on a Wallac Wizard 1470 gamma counter (PerkinElmer Life and Analytical Sciences Inc.; Wellesley, Mass.). The binding data was evaluated using NewLigand software (Genentech), which uses the fitting algorithm of Munson and Robard to determine the binding affinity of the antibody (Munson and Robard 1980).

Table 3 shows the affinity (kD range of 0.45-1.2 nM) to recombinant hu and cynoCLL-1 expressed by HEK293AD CLL-1 stable cells and to HL-60 cells.

TABLE 3

Antibody Affinity [kD = nM] to CLL-1 (Scatchard Analysis).

| Cells |  | ch6E7 | ch21C9 |
|---|---|---|---|
| HL-60 | $K_D$ (nM) | 0.65 | 0.45 |
| EOL-1 | $K_D$ (nM) |  |  |
| 293AD/huCLL-1 | $K_D$ (nM) | 0.80 | 0.59 |
| 293AD/cynoCLL-1 | $K_D$ (nM) | 1.0 | 1.2 |

C. Monoclonal Antibody Epitope Grouping

Epitope grouping was also determined using a cell-based competition binding FACS assay. HL-60 cells were pre-incubated with or without 50-100 fold excess of unlabeled competing antibodies, then stained with directly labeled detection antibodies, a reduction of the signal from detecting antibody indicating that the unlabeled competing antibody binds to the same or similar region on CLL-1 as the detecting antibody—this should occur when the same antibody is used as both detector and competitor. When there is no blocking of detector signal by a different unlabeled antibody, the unlabeled antibody is binding to a different region in CLL-1.

TABLE 4

Anti-CLL-1 Competition Experiments

| Detecting antibodies | Competing antibodies | | | | |
|---|---|---|---|---|---|
| | ch6E7 | ch20B1 | ch21C9 | ch28H12 | R&D |
| R&D Systems-PE (Clone 687317) | ✓ | ✗ | ✓ | ✗ | ✓ |
| ch6E7-DyLight650 | ✓ | ✗ | n/a | ✗ | n/a |
| ch28H12-DyLight650 | n/a | ✗ | n/a | ✓ | n/a |
| ch21C9-DyLight650 | ✓ | ✗ | ✓ | ✗ | ✓ |
| eBioscience HB3-PE | ✗ | ✗ | ✗ | ✗ | ✓ |
| BD Biosciences 50C1-PE | ✗ | ✗ | ✗ | ✗ | ✗ |

Table 4 shows epitope grouping of the antibodies to CLL-1. ch6E7 and ch21C9, but not ch20B1 and ch28H12, bin with R&D Systems-PE (Clone 687317). R&D Systems also blocked eBioscience clone HB3, but ch6E7 and ch21C9 were unable to block eBioscience clone HB3 binding. ch20B1 and ch28H12 failed to compete with any other antibody suggesting each antibody binds a distinct epitope. All antibodies failed to compete with BD Biosciences clone 50C1 also suggesting that it binds a distinct epitope.

D. Humanization of Anti-CLL-1 Antibodies

Monoclonal antibody 6E7 and 21C9 was humanized as described below. Residue numbers are according to Kabat et al., Sequences of proteins of immunological interest, 5th Ed., Public Health Service, National Institutes of Health, Bethesda, Md. (1991).

Variants constructed during the humanization of 6E7 and 21C9 were assessed in the form of an IgG. The VL and VH domains from murine 6E7 and 21C9 were aligned with the human VL kappa I (VLKI) and human VH subgroup I (VHI) consensus sequences. Hypervariable regions from the murine antibodies were engineered into VLKI and VHI acceptor frameworks. Specifically, from the mu6E7 and mu21C9 VL domain, positions 24-34 (L1), 50-56 (L2) and 89-97 (L3) were grafted into VLKI and from the mu6E7 and mu21C9 VH domain, positions 26-35 (H1), 50-65 (H2) and 93-102 (H3) were grafted into VHI.

The binding affinity of the antibodies in this section was determined by BIAcore™ T200 Format. Briefly, BIAcore™ research grade CM5 chips were activated with 1-ethyl-3-(3-dimethylaminopropyl) carbodiimide (EDC) and N-hydroxysuccinimide (NHS) reagents according to the supplier's instructions. Goat anti-human Fc IgGs were coupled to the chips to achieve approximately 10,000 response units (RU) in each flow cell. Unreacted coupling groups were blocked with 1M ethanolamine. For kinetics measurements, antibodies were captured to achieve approximately 300 RU. Three-fold serial dilutions of human CLL-1 was injected in HBS-P buffer (0.01M HEPES pH7.4, 0.15M NaCl, 0.005% surfactant P20) at 25° C. with a flow rate of 30 µl/min. Association rates (kon) and dissociation rates (koff) were calculated using a 1:1 Langmuir binding model (BIAcore™ T200 Evaluation Software version 2.0). The equilibrium dissociation constant (Kd) was calculated as the ratio koff/kon.

The binding affinity of the CDR graft humanized 6E7 antibody was compared to chimeric 6E7. Additional variants of the CDR graft humanized 6E7 antibody were made to evaluate the contribution of other vernier positions to binding to CLL-1. For 6E7, initially four additional light chains (L1: CDRs graft+(L4, L48, and K49), L2: CDRs graft+L4, L3: CDRs graft+K49, and L4: CDRs graft+K49) and five additional heavy chains (H1: CDRs graft+(A67, L69, V71, K73), H2: CDRs graft+A67, H3: CDRs graft+L69, H4:CDRs graft+V71, and H5: CDRs graft+K73). K49 on the light chain was the key mouse vernier residue, and L69 and V71 on the heavy chain were determined to be the key mouse vernier residues based on mutational analysis (data not shown). Chimeric 6E7 bound with a KD of 9.59E-10 M, while CDRs graft+K49(LC)+(A67, L69, V71, K73 (HC)), CDRs graft+K49(LC)+(L69, V71 (HC)) bound with a KD of 1.40E-9M, and 1.37E-9M, respectively.

The binding affinity of the CDR graft humanized 21C9 antibody was compared to chimeric 21C9 antibody. Additional variants of the CDR graft humanized 21C9 antibody were made to evaluate the contribution of other vernier positions to binding to CLL-1. For 21C9, initially three additional light chains (L1: CDRs graft+(F36 and S43), L2: CDRs graft+F36, L3: CDRs graft+S43) and five additional heavy chains (HI: CDRs graft+(A67, L69, V71, K73), H2: CDRs graft+A67, H3: CDRs graft+L69, H4:CDRs graft+V71, and H5: CDRs graft+K73). F36 on the light chain was the key mouse vernier residue. Chimeric 21C9 bound with a KD of 8.615E-9 M, while CDRs graft+(F36 and S43 (LC))+L69 (HC) and CDRs graft+F36 (LC)+L69 (HC), bound with a KD of 1.053E-8M and 9.785-9M, respectively. L69 on the heavy chain were determined to be the key mouse vernier residues.

The humanized 6E7.L4H1e and 21C9.L2H3 were tested for their ability to bind human and cyno CLL-1 as described above except that cynoCLL-1 replaced huCLL-1 in the cyno binding assay. Binding properties for the humanized antibodies are shown below in Table 5. The binding affinity of the humanized 6E7.L4H1e was 0.34, 0.29, 0.22, and 0.35 Kd (nM) as determined by Scatchard using HL-60, EOL-1, 293AD/cynoCLL1, and 293AD/huCLL-1 cells, respectively. The binding affinity of humanized 21C9.L2H3 was 1.3, 0.74, 2.4, and 3.6 Kd (nM) as determined by Scatchard using HL-60, EOL-1, 293AD/cynoCLL1, and 293AD/huCLL-1 cells, respectively.

TABLE 5

| Antibody | huKD (M) | huka (1/Ms) | hukd (1/s) | cynoKD (M) | cynoka (1/Ms) | cynokd (1/s) |
|---|---|---|---|---|---|---|
| 6E7.L4H1e | 6.218E−10 | 8.236E+5 | 5.121E−4 | 3.170E−10 | 7.391E+5 | 2.343E−4 |
| 21C9.L2H3 | 1.171E−8 | 2.244E+5 | 2.628E−3 | 9.472E−9 | 1.683E+5 | 1.594E−3 |

The humanized antibodies 6E7.L4H1e and 21C9.L2H3 were tested under thermal stress (40° C., pH 5.5, 2 weeks) and 2,2'-azobis (2-amidinopropane) hydrochloride (AAPH) Analysis. Samples were thermally stressed to mimic stability over the shelf life of the product. Samples were buffer exchanged into 20 mM His Acetate, 240 mM sucrose, pH 5.5 and diluted to a concentration of 1 mg/mL. One mL of sample was stressed at 40C for 2 weeks and a second was stored at ~70C as a control. Both samples were then digested using trypsin to create peptides that could be analysed using liquid chromatography (LC)-mass spectrometry (MS) analysis. For each peptide in the sample retention time, from the LC as well as high resolution accurate mass and peptide ion fragmentation information (amino acid sequence information) were acquired in the MS. Extracted ion chromatograms (XIC) were taken for peptides of interest (native and modified peptide ions) from the data sets at a window of +−10 ppm and peaks were integrated to determine area. Relative percentages of modification were calculated for each sample by taking the (area of the modified peptide) divided by (area of the modified peptide plus the area of the native peptide) multiplied by 100.

Both 6E7.L4H1e and h21C9.L2H3 have $N^{54}G^{55}$ in DR-H2, which is susceptible to deamination (t0=13.2% and t2wk 14.5% for 6E7.L4H1e and r0=11% and t2wk=11.9%). N54 variants of both antibodies were tested to determine if potential deamination could be reduced without affecting binding to hu and cynoCLL-1. See Table 6.

TABLE 6

| Antibody | huKD (M) | huka (1/Ms) | hukd (1/s) | cynoKD (M) | cynoka (1/Ms) | cynokd (1/s) |
|---|---|---|---|---|---|---|
| 6E7.L4H1eN54 | 1.082E−9 | 9.096E+5 | 9.837E−4 | 2.256E−9 | 8.044E+5 | 1.815E−3 |
| 6E7.L4H1eA54 | 3.082E−9 | 7.103E+5 | 2.189E−3 | 3.143E−9 | 6.087E+5 | 1.913E−3 |
| 6E7.L4H1eE54 | 5.090E−9 | 4.882E+5 | 2.485E−3 | 4.256E−9 | 6.641E+5 | 2.827E−3 |
| 6E7.L4H1eS54 | 1.413E−8 | 5.098E+5 | 7.205E−3 | 6.371E−9 | 5.133E+5 | 3.270E−3 |
| 6E7.L4H1eD54 | 1.132E−7 | 3.044E+5 | 3.444E−2 | 4.870E−8 | 1.785E+5 | 8.694E−3 |
| 21C9.L2H3N54 | 1.510E−8 | 1.889E+5 | 2.853E−3 | 9.302E−9 | 2.358E+5 | 2.194E−3 |
| 21C9.L2H3S54 | 2.859E−7 | 1.416E+5 | 4.047E−2 | 5.669E−6 | 3656 | 2.072E−2 |
| 21C9.L2H3A54 | 6.215E−7 | 1.113E+5 | 6.915E−2 | 4.818E−5 | 445.3 | 2.146E−2 |
| 21C9.L2H3E54 | 8.625E−7 | 1.022E+5 | 8.816E−2 | 4.961E−5 | 747.5 | 3.709E−2 |
| 21C9.L2H3D54 | 8.017E−7 | 2.858E+5 | 2.291E−2 | 2.172E−7 | 4.072E+4 | 8.846E−3 |

For the humanized 6E7.L4H1e CDR-H2 N54 antibody variants, A54 had acceptable binding characteristics which were most similar to N54. For the humanized 21C9.L2H3 CDR-H2 N54 antibody variants, all the variants showed a drop in affinity to huCLL-1 in off-rate (10-30 fold) and cynoCLL-1 in on rate (60-500 fold). The binding affinity of the humanized 6E7.L4H1e was 0.67, 0.68, 0.6, and 0.25 Kd (nM) as determined by Scatchard using 293AD/cynoCLL1, 293AD/huCLL-1, HL-60, and EOL-1 cells, respectively. The binding affinity of humanized 6E7.L4H1eN54A was 0.9, 0.89, 0.64, and 0.32 Kd (nM) as determined by Scatchard using 293AD/cynoCLL1, 293AD/huCLL-1, HL-60, and EOL-1 cells, respectively. Alignment of the heavy and light variable domain amino acid sequences of humanized 6E7 and 21C9 antibodies are shown in FIG. 2A-B and FIG. 3A-B, respectively.

E. Epitope Mapping

To determine the binding epitope of the CLL-1, examination of (a) free antigen CLL-1 and (b) three different antigen-mAb complexes using hydroxyl radical footprinting (HRF) techniques was performed. The samples were exposed to hydroxyl radicals for intervals of 0, 10, 15, and 20 milliseconds (ms) using the X28c Beam line at the Brookhaven National Laboratory. The labeled samples were subjected to deglycosylation using PNGase F. A pilot experiment was first carried out on the deglycosylated samples for optimizing the experimental protocol. The pilot investigation using MS revealed that the samples contained significant amount of polymer contamination, requiring additional clean up. In order to remove the polymer contamination, the samples were precipitated using Trichloroacetic acid in acetone, and subjected to LC-MS analysis. The precipitation step was successful, and the polymer contamination signal in the MS was significantly attenuated. The cleaned samples were subjected to reduction and alkylation, digestion using Trypsin, followed by liquid chromatography coupled with high-resolution mass spectrometry (LC-MS). The MS data was analyzed using ProtMapMS, resulting in dose response plots for each peptide. Results from the free antigen were compared against each of the complex forms. A homology-based model of the antigen was generated using Swiss-Model software, and the solvent protected regions were mapped for each of the three complexes.

The overall sequence coverage obtained using Trypsin mapping was 90.05%. The missing regions were comprised primarily of tryptic peptides that were shorter than 4 residues in length, which can be inherently difficult to detect due to their weak retention properties on the LC column. The HRF process introduces stable side chain oxidative modifications resulting in specific mass shifts, which were identified from the tandem mass spectrometry data. The selected ion chromatograms (SIC) were extracted and integrated for the unoxidized and all oxidized forms of peptide ion (with particular m/z). These peak area values were used to characterize reaction kinetics in the form of dose response (DR) plots, which measure the loss of intact peptide as a function of the hydroxyl radical exposure. The solvent protected regions in the complex experience gradual oxidation reaction as opposed to the free antigen. Differences in the rate of oxidation (called rate constant, RC) serve to highlight the location of the epitope.

ProtMapMS was used to process the MS data, resulting in RC values for each peptide. Final results are shown in Table 1. Peptide location and the corresponding sequence are shown in columns 1 and 2. The third column shows the protection ratio, PR (=RCAntigen/RCComplex) for complex 1 (6E7.L4H1eA54 antibody and CLL-1 antigen). Similarly, fourth and fifth columns show the corresponding protection ratios for complex 2 (21C9.L2H3 antibody engineered with a light chain comprising a cysteine residue at K149 according to Kabat numbering (K149C) and CLL-1 antigen) and complex 3 (R&D Systems monoclonal anti-CLL1 antibody (Clone 687317) and CLL-1 antigen). If the PR value for a given peptide for a particular is less than 1, the corresponding region experienced gain in solvent accessibility due to structural changes introduced during complex formation. A PR value close to 1 indicates that the solvent accessibility of the region remains unchanged, while a PR>1 suggests that the corresponding region exhibits protection from the solvent as a function of the complex formation. The PR values for most of the peptides for each complex are close to 1, indicating minimal change in solvent accessibility for the corresponding regions. Peptide 142-158 consistently shows the highest PR value for all three antibodies, implying significant protection for the region. In addition to protection of the peptide 142-158, the R&D Systems monoclonal anti-CLL1 antibody (Clone 687317, unlike 6E7.L4H1eAG and 21C9.L2H3, also showed significant protection of the region 103-116 as evidenced by the overlapping peptides 103-116 and 105-116.

| Pep locn of SEQ ID NO: 1 | Sequence | SEQ ID NO: | RCA/ RC1 | RCA/ RC2 | RCA/ RC3 |
|---|---|---|---|---|---|
| 65-69 | DYKDDDDKLEHVTLK | 52 | 1.4 | 1.0 | 1.0 |
| 68-69 | DDDDKLEHVTLK | 53 | 1.1 | 0.9 | 0.8 |
| 75-87 | MNKLQNISEELQR | 54 | 1.4 | 1.1 | 0.90 |
| 78-87 | LQNISEELQR | 55 | 1.3 | 1.0 | 0.8 |
| 88-102 | NISLQLMSNMNISNK | 56 | 1.1 | 0.5 | 0.5 |
| 103-116 | IRNLSTTLQTIATK | 50 | 1.1 | 0.8 | 2.1 |
| 105-116 | NLSTTLQTIATK | 51 | 1.2 | 1.0 | 2.2 |
| 105-119* | NLSTTLQTIATKLCR | 57 | NA | NA | NA |
| 120-124* | ELYSK | 58 | NA | NA | NA |
| 137-141 | WIWHK | 59 | 1.0 | 0.6 | 1.3 |
| 142-158 | DSCYFLSDDVQTWQESK | 49 | 3.1 | 2.0 | 3.1 |
| 159-160 | MACAAQNASLLK | 60 | 1.0 | 1.2 | 0.8 |
| 171-181 | INNKNALEFIK | 61 | 1.7 | 1.3 | 1.1 |
| 175-181 | NALEFIK | 62 | 1.3 | 1.0 | 1.3 |
| 175-185* | NALEFIKSQSR | 63 | NA | NA | NA |
| 186-201 | SYDYWLGLSPEEDSTR | 64 | 1.0 | 1.0 | 1.0 |
| 186-204* | SYDYWLGLSPEEDSTRGMR | 65 | NA | NA | NA |
| 205-117 | VDNIINSSAWVIR | 66 | 1.2 | 1.0 | 1.0 |
| 218-232 | NAPDLNNMYCGYINR | 67 | 1.2 | 1.0 | 0.9 |
| 233-243 | LYVQYYHCTYK | 68 | 1.0 | 1.1 | 1.0 |
| 246-250* | MICEK | 69 | NA | NA | NA |
| 251-263 | MANPVQLGSTYFR | 70 | 0.99 | 1.1 | 1.0 |

F. Internalization of Anti-CLL-1 Antibody

One desirable attribute of an ADC target is the ability to internalize the antibody into a degradative compartment in the cell. To determine whether anti-CLL-1 antibody gets internalized upon binding, HL-60 or HL-60 cells were pre-incubated for 2 hours at 37° C. with 0.3 mg/ml hIgG in RPMI medium to reduce non-specific binding to FcR before seeding in cell culture treated 4-well chamber slides (Nalge Nunc International). Antibody directly conjugated to Dylight 488 at a final concentration of 1 µg/mL was incubated with hIgG-blocked cells on ice for 30 minutes in the dark. The cells were immediately imaged to show membrane staining (T0) and followed with time-lapsed photography over a 10 hour period at 37° C. with a Leica SP5 confocal microscope. A representative example, ch21C9, is rapidly internalized within 30 minutes by HL-60 cells (data not shown). Localization of ch21C9 to the lysosome was confirmed using an in vitro cell-based assay measuring the ability of an antibody drug conjugate to kill target cells.

G. Production of Anti-CLL-1 Antibody Drug Conjugates

For larger scale antibody production, antibodies were produced in CHO cells. Vectors coding for VL and VH were transfected into CHO cells and IgG was purified from cell culture media by protein A affinity chromatography.

Anti-CLL-1 antibody-drug conjugates (ADCs) were produced by conjugating antibodies ch21C9, ch3H10, ch28H12, ch20B1, ch6E7, 6E7.L4H1e, 6E7.L4H1eA54, 21C9.L2H3 via linkers to PBD and PNU derivatives.

As initially isolated, the engineered cysteine residues in antibodies exist as mixed disulfides with cellular thiols (e.g., glutathione) and are thus unavailable for conjugation. Partial reduction of these antibodies (e.g., with DTT), purification, and reoxidation with dehydroascorbic acid (DHAA) gives antibodies with free cysteine sulfhydryl groups available for conjugation, as previously described, e.g., in Junutula et al. (2008) Nat. Biotechnol. 26:925-932 and US 2011/0301334. Briefly, the antibodies were combined with the drug-linker moiety to allow conjugation of the drug-linker moiety to the free cysteine residues of the antibody. After several hours, the ADCs were purified.

H. Efficacy of Anti-CLL-1 Antibody Drug Conjugates in HL-60 and EOL-1 Human Acute Myeloid Leukemia Cell Line Xenograft Models The efficacy of the anti-CLL-1 ADCs was investigated using human Acute Myeloid Leukemia xenograft models, HL-60 (AML subtype M2) and EOL-1 (AML subtype M4a). Both are associated with intermediate to poor prognosis as a result of their genetics and molecular aberrations. Female C.B-17 SCID mice (Charles River Laboratories; Hollister, Calif.) were each inoculated subcutaneously in the flank area with five million cells of HL-60 or EOL-1. When the xenograft tumors reached an average tumor volume of 100-300 mm$^3$ (referred to as Day 0), animals were randomized into groups of 7-10 mice each and received a single intravenous injection of the ADCs. Approximately 4 hours prior to administration of ADCs, animals were dosed intraperitoneally with excess amount (30 mg/kg) of anti-gD control antibody to block possible nonspecific antibody binding sites on the tumor cells. Tumors and body weights of mice were measured 1-2 times a week throughout the study. Mice were promptly euthanized when body weight loss was >20% of their starting weight. All animals were euthanized before tumors reached 3000 mm3 or showed signs of impending ulceration. The presence of the antibodies was confirmed by PK bleeds at 1, 7 and 14 days post injection.

Figure 4:
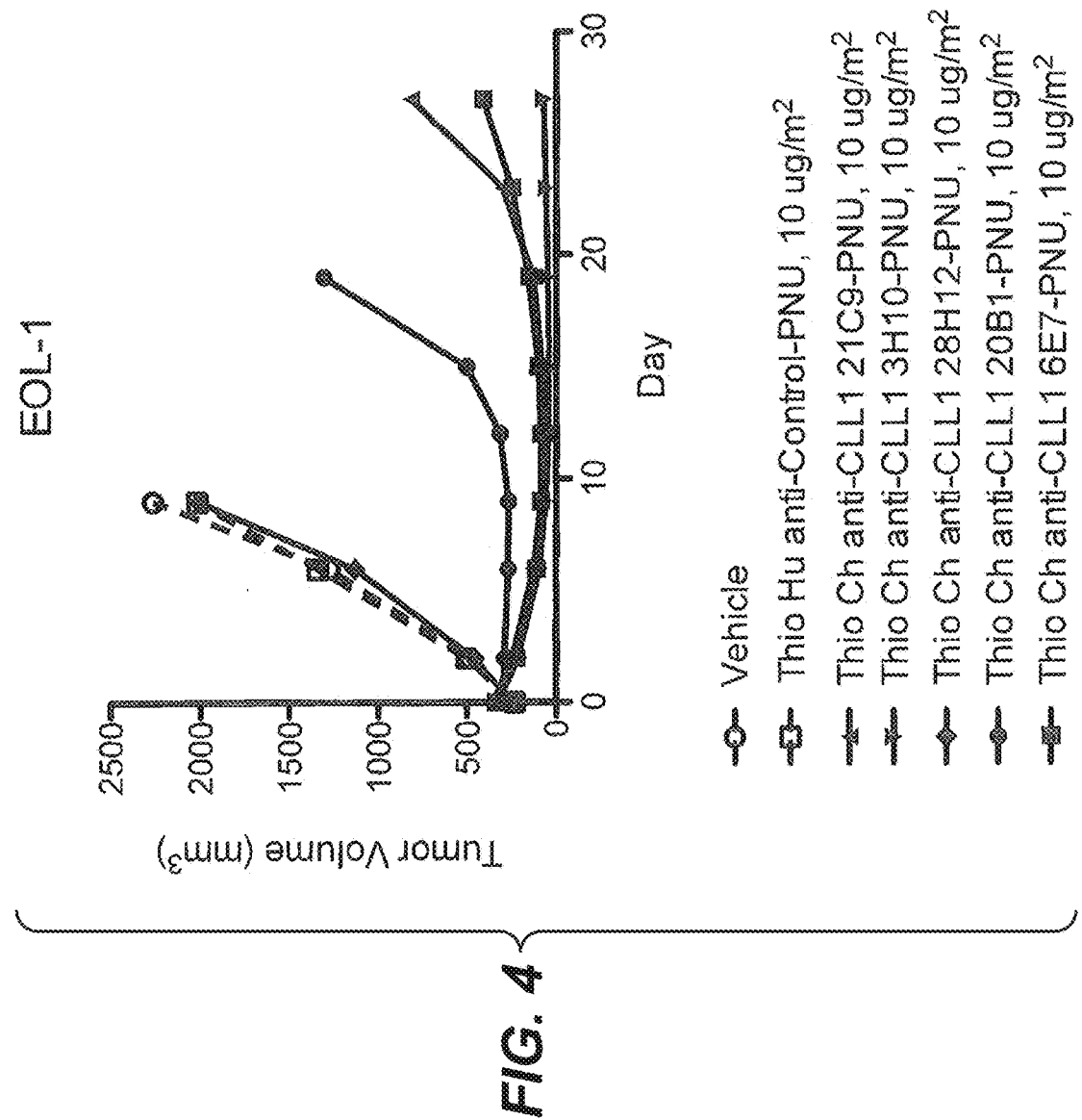
FIG. 4 shows change in tumor volume ($mm^3$) over time upon treatment with ch21C9, ch3H10, ch28H12, ch20B1, and ch6E7 conjugated to PNU via a cysteine engineered heavy chain at amino acid residue 118 according to EU numbering (A118C) at 10 $\mu g/m^2$ in the EOL-1 xenograft model.
Figure 5:
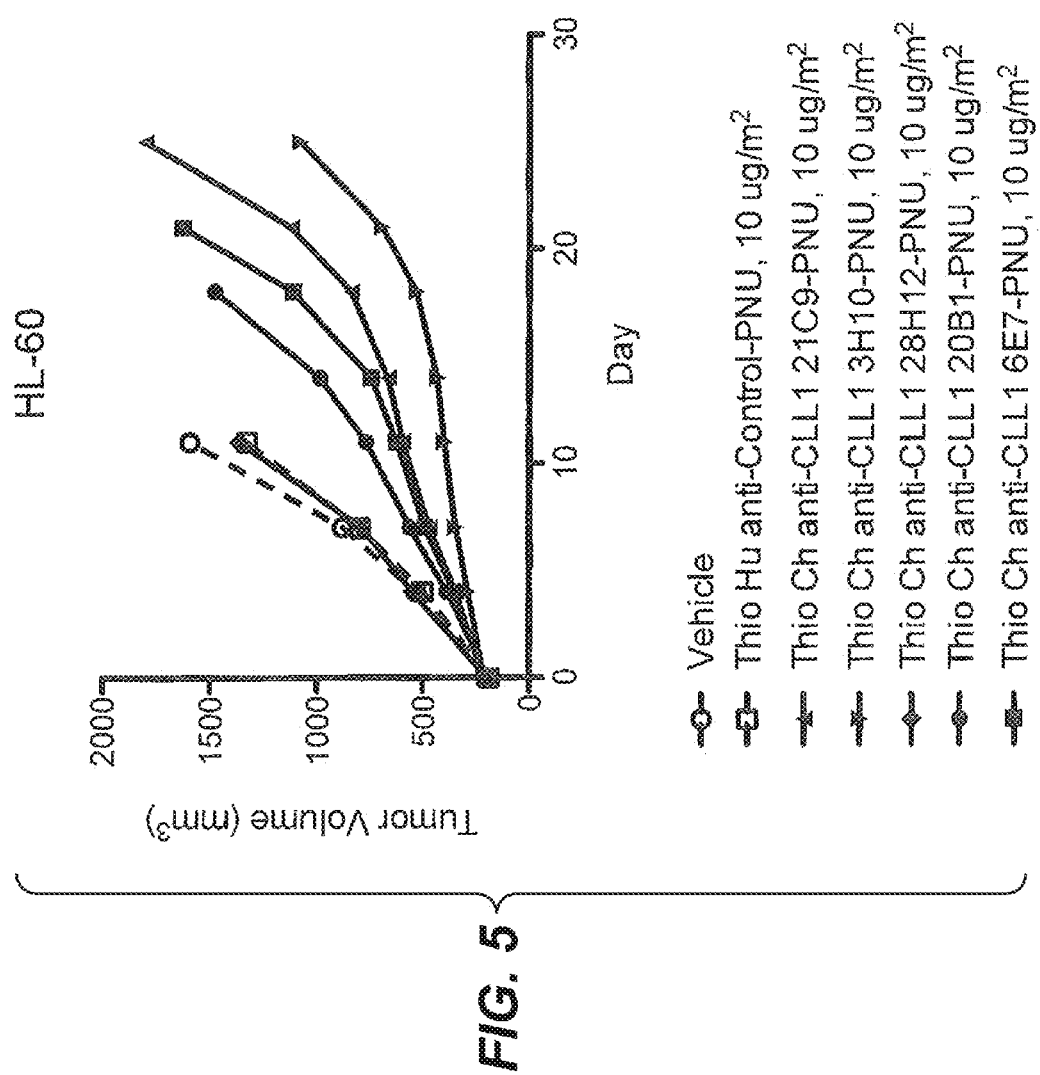
FIG. 5 shows change in tumor volume ($mm^3$) over time upon treatment with ch21C9, ch3H10, ch28H12, ch20B1, and ch6E7 conjugated to PNU via a cysteine engineered heavy chain at amino acid residue 118 according to EU numbering (A118C) at 10 $\mu g/m^2$ in the HL-60 xenograft model.

As shown in FIG. 4, the ch21C9, ch28H12, ch20B1, ch6E7, and ch3H10 conjugated to the PNU drug moiety:

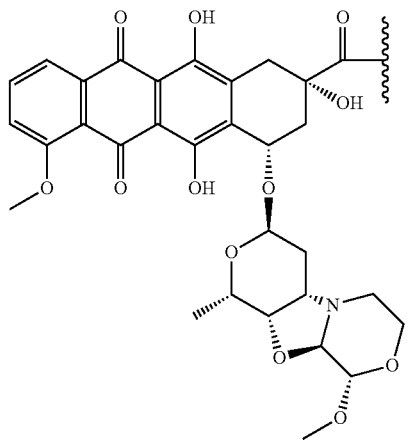 [SMILES: *C(=O)[C@]1(O)Cc2c(O)c3c(c(O)c2[C@@H](O[C@H]2C[C@H]4[C@H](O[C@@H]5[C@@H](OC)OCCN54)[C@H](C)O2)C1)C(=O)c1c(OC)cccc1C3=O]

via a free cysteine at heavy chain amino acid 118 according to EU numbering (A1118C) significantly reduced EOL-1 tumor volume while ch20B1 moderately reduced tumor volume and ch28H12 had little effect. Similar results were seen using HL-60 as shown in FIG. 5.

The humanized antibodies, 6E7.L4H1e and 21C9.L2H3, were conjugated to PBD derivatives (SG34) via different cysteine engineered conjugation sites at various dosages (10 and 20 μg/m²). The antibodies comprised an engineered free cysteine at heavy chain amino acid 118 according to EU numbering (A1118C) or light chain amino acid 149 according to Kabat numbering (K149C). The structures of the antibody-drug conjugates is shown below:

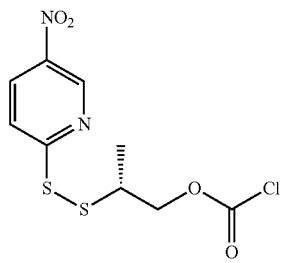

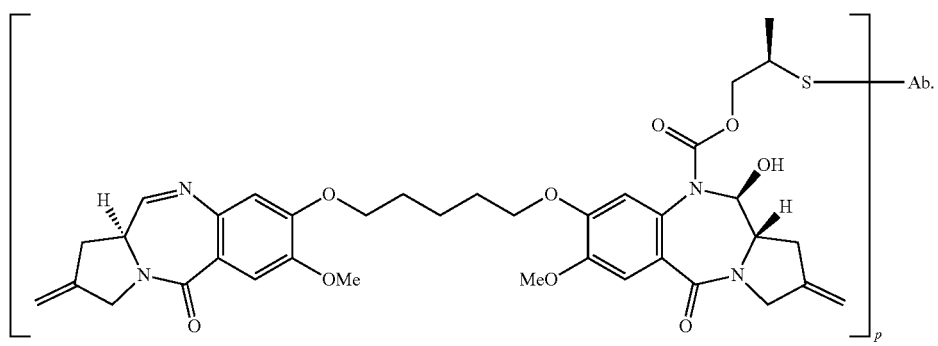

Figure 6:
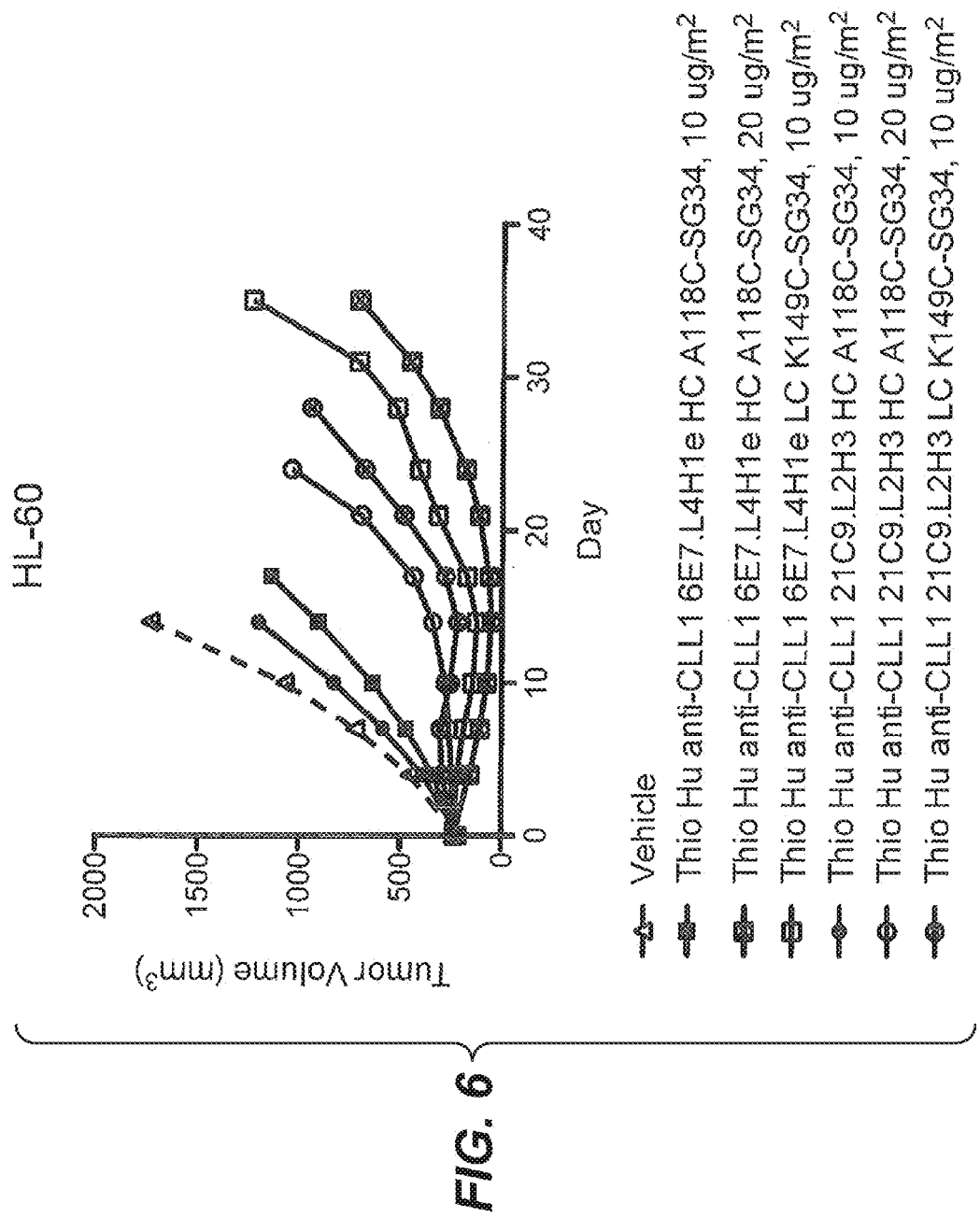
FIG. 6 shows change in tumor volume ($mm^3$) over time upon treatment with the humanized antibody 6E7.L4H1e or 21C9.L2H3 with a cysteine engineered heavy chain at amino acid residue 118 according to EU numbering (A118C) or cysteine engineered light chain at amino acid residue number 149 according to Kabat numbering (K149C) conjugated to PBD (SG34) at 10 $\mu g/m^2$ or 20 $\mu g/m^2$ in HL-60 xenograft model. A structure of the antibody conjugated to SG34 is shown below.

As shown in FIG. 6 in the HL-60 xenograft model, the light chain K149C cysteine engineered immunoconjugate comprising either 6E7L4H1e or 21C9.L2H3 showed greater reduction in tumor volume than the heavy chain A1118C cysteine engineered immunoconjugate comprising either 6E7.L4H1e or 21C9.L2H3.

The ability to reduce tumor volume was also compared between 6E7.L4H1e and the engineered variant to remove the potential deamination site 6E7.L4H1eA54 to determine if activity as well as binding of the antibody was retained. As shown in FIG. 7, both 6E7L4H1e and 6E7 significantly reduced tumor volume in the HL-60 xenograft model.

Example 2

Synthesis of Linker-Drug (LD) Intermediates Used to Make the Antibody Drug Conjugates Exemplified in (Table A)

Linker-drug intermediate of ADC-51: (R)-2-((5-nitropyridin-2-yl)disulfanyl)propyl (11S,11aS)-11-hydroxy-7-methoxy-8-((5-(((S)-7-methoxy-2-methylene-5-oxo-2,3,5,11a-tetrahydro-1H-benzo[e]pyrrolo[1,2-a][1,4]diazepin-8-yl)oxy)pentyl)oxy)-2-methylene-5-oxo-2,3,11,11a-tetrahydro-1H-benzo[e]pyrrolo[1,2-a][1,4]diazepine-10(5H)-carboxylate (MS (ESI): 875 [M+H]⁺) was prepared by the procedures of WO2013/055987.

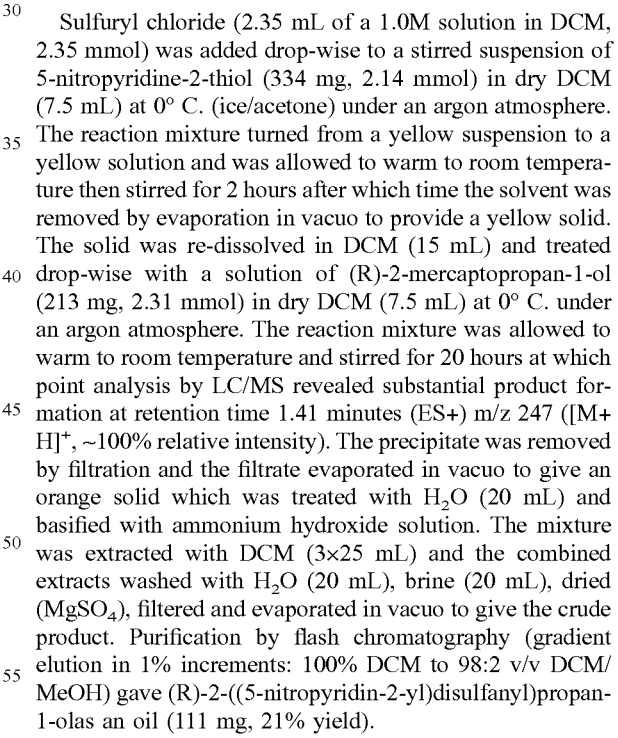

Sulfuryl chloride (2.35 mL of a 1.0M solution in DCM, 2.35 mmol) was added drop-wise to a stirred suspension of 5-nitropyridine-2-thiol (334 mg, 2.14 mmol) in dry DCM (7.5 mL) at 0° C. (ice/acetone) under an argon atmosphere. The reaction mixture turned from a yellow suspension to a yellow solution and was allowed to warm to room temperature then stirred for 2 hours after which time the solvent was removed by evaporation in vacuo to provide a yellow solid. The solid was re-dissolved in DCM (15 mL) and treated drop-wise with a solution of (R)-2-mercaptopropan-1-ol (213 mg, 2.31 mmol) in dry DCM (7.5 mL) at 0° C. under an argon atmosphere. The reaction mixture was allowed to warm to room temperature and stirred for 20 hours at which point analysis by LC/MS revealed substantial product formation at retention time 1.41 minutes (ES+) m/z 247 ([M+H]⁺, ~100% relative intensity). The precipitate was removed by filtration and the filtrate evaporated in vacuo to give an orange solid which was treated with H₂O (20 mL) and basified with ammonium hydroxide solution. The mixture was extracted with DCM (3×25 mL) and the combined extracts washed with H₂O (20 mL), brine (20 mL), dried (MgSO₄), filtered and evaporated in vacuo to give the crude product. Purification by flash chromatography (gradient elution in 1% increments: 100% DCM to 98:2 v/v DCM/MeOH) gave (R)-2-((5-nitropyridin-2-yl)disulfanyl)propan-1-ol as an oil (111 mg, 21% yield).

Triphosgene (48 mg, 0.16 mmol) was added to a stirred solution of (R)-2-((5-nitropyridin-2-yl)disulfanyl)propan-1-ol (111 mg, 0.45 mmol) and pyridine (34 μL, 33.5 mg, 0.42 mmol) in dry DCM (5 mL). The reaction mixture was allowed to stir under an argon atmosphere for 45 minutes after which time the solvent was removed by evaporation in vacuo to provide (R)-2-((5-nitropyridin-2-yl)disulfanyl)propyl carbonochloridate as a yellow film. The product was carried through to the next step without purification or analysis.

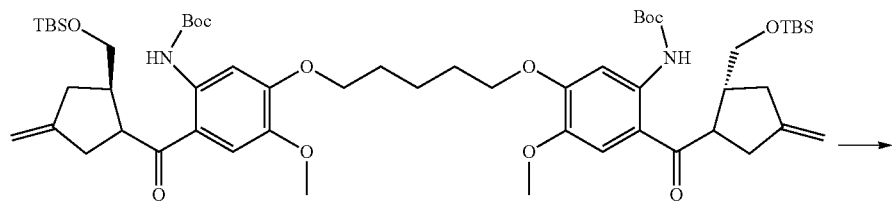

51a

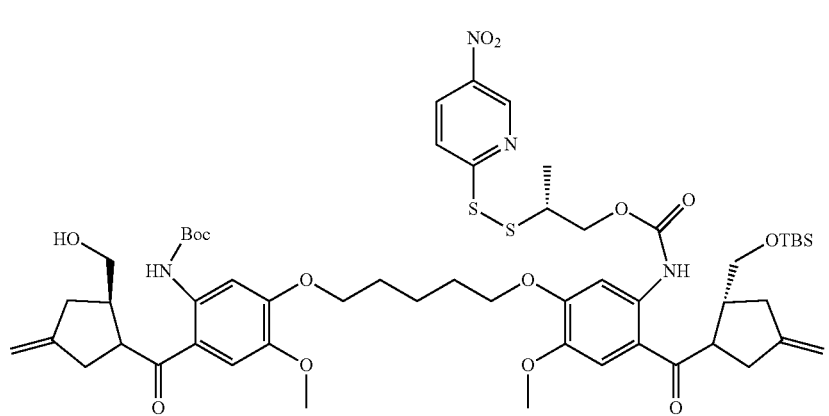

51b

A solution of (R)-2-((5-nitropyridin-2-yl)disulfanyl)propyl carbonochloridate (~139 mg, 0.45 mmol) in dry DCM (5 mL) was added drop-wise to a stirred solution of di-tert-butyl ((pentane-1,5-diylbis(oxy))bis(6-((2R)-2-(((tert-butyldimethylsilyl)oxy)methyl)-4-methylenecyclopentane-1-carbonyl)-4-methoxy-3,1-phenylene))dicarbamate 51a, made by the procedures of Example 1 in WO 2013/055987, (430 mg, ~0.45 mmol) and pyridine (40 µL, 39 mg, 0.49 mmol) in dry DCM (12 mL) at room temperature. The reaction mixture was allowed to stir under an argon atmosphere for 2.5 hours at which point analysis by LC/MS revealed substantial product formation at retention time 2.42 minutes (ES+) m/z 1226 ([M+H]$^+$, ~20% relative intensity), 1248 ([M+Na]$^+$, ~60% relative intensity). The mixture was diluted with DCM (20 mL) and treated with $SiO_2$ and the solvent removed by evaporation in vacuo. The resulting residue was subjected to purification by flash chromatography (gradient elution in 10% increments: 80:20 v/v hexane/EtOAc to 70:30 v/v hexane/EtOAc) to give tert-Butyl (2-((S)-2-(((tert-butyldimethylsilyl)oxy)methyl)-4-methylenepyrrolidine-1-carbonyl)-5-((5-(4-((S)-2-(((tert-butyldimethylsilyl)oxy)methyl)-4-methylenepyrrolidine-1-carbonyl)-2-methoxy-5-((((R)-2-((5-nitropyridin-2-yl)disulfanyl)propoxy)carbonyl)amino)phenoxy)pentyl)oxy)-4-methoxyphenyl)carbamate 51b as a yellow foam (419 mg, 76% yield). (MS (ESI): 1224 [M+H]$^+$)

51c

Glacial acetic acid (24 mL) was added to a stirred solution of the TBS-protected 51b (419 mg, 0.34 mmol) in THF (8 mL) and $H_2O$ (8 mL). The reaction mixture was allowed to stir for 16 hours at which point analysis by LC/MS revealed reaction completion with desired product observed at retention time 1.82 minutes (ES+) m/z 997 ([M+H]$^+$, ~100% relative intensity), 1019 ([M+Na]$^+$, ~45% relative intensity). The reaction mixture was added drop-wise to a chilled (0-5° C.) saturated solution of $NaHCO_3$ (400 mL). The neutral solution was allowed to warm to room temperature and extracted with EtOAc (4×100 mL), the combined organic layers were washed with H$_2$O (80 mL), brine (100 mL), dried (MgSO$_4$), filtered and evaporated in vacuo to give the crude product. Purification by flash chromatography (gradient elution in 1% increments: 100% DCM to 98:2 v/v DCM/MeOH) gave tert-Butyl (2-((S)-2-(hydroxymethyl)-4-methylenepyrrolidine-1-carbonyl)-5-((5-(4-((S)-2-(hydroxymethyl)-4-methylenepyrrolidine-1-carbonyl)-2-methoxy-5-((((R)-2-((5-nitropyridin-2-yl)disulfanyl)propoxy)carbonyl)amino)phenoxy)pentyl)oxy)-4-methoxyphenyl)carbamate 51c as a yellowish foam (341 mg, 100% yield). (MS (ESI): 995 [M+H]$^+$).

evaporated in vacuo to provide the crude product. Purification by flash chromatography (gradient elution in 0.4% increments: 100% CHCl$_3$ to 98.4:1.6 v/v CHCl$_3$/MeOH) gave LD-51 as a yellow foam (127 mg, 66% yield): LC/MS (15-minute run), retention time 6.18 minutes (ES+) m/z 875 ([M+H]$^+$; ~100% relative intensity); $^1$H NMR (400 MHz, CDCl$_3$) δ 9.21 (s, 1H), 8.30 (d, 1H, J=8.8 Hz), 7.69 (d, 1H, J=4.5 Hz), 7.62 (d, 1H, J=8.9 Hz), 7.49 (s, 1H), 7.25 (s, 1H), 6.79 (s, 1H), 6.74 (s, 1H), 5.58 (dd, 1H, J=4.4, 9.8 Hz), 5.22-5.10 (m, 4H), 4.43 (d, 1H, J=3.7 Hz), 4.33-4.25 (m, 4H), 4.15-3.98 (m, 5H), 3.95-3.80 (m, 7H), 3.68-3.59 (m,

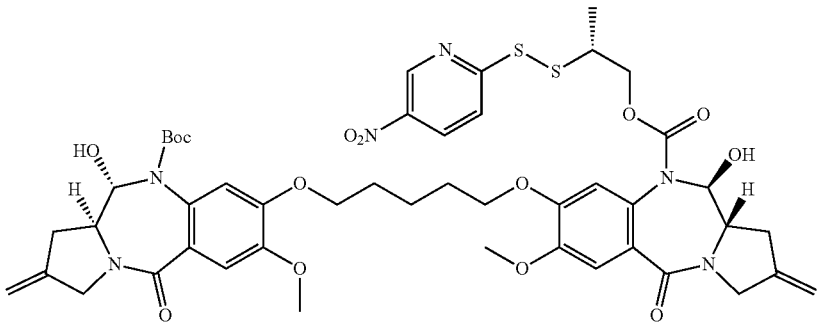

51d

1H), 3.20-3.07 (m, 2H), 2.99-2.87 (m, 2H), 2.76-2.68 (m, 2H), 1.99-1.83 (m, 4H), 1.72-1.57 (m, 2H), 1.19 (d, 3H, J=6.6 Hz).

A solution of anhydrous DMSO (107 μL, 188 mg, 1.50 mmol) in dry DCM (7.5 mL) was added drop-wise to a stirred solution of oxalyl chloride (410 μL of a 2.0M solution in DCM, 0.82 mmol) in dry DCM (7.5 mL) at −45° C. (dry ice/CH$_3$CN) under an argon atmosphere. After 15 minutes stirring at −45° C., the reaction mixture was treated drop-wise with a solution of 51c (341 mg, 0.34 mmol) in dry DCM (15 mL). After stirring at −45° C. for a further 1 hour, the reaction mixture was treated drop-wise with a solution of TEA (476 μL, 342 mg, 3.42 mmol) in dry DCM (7.5 mL). The reaction mixture was allowed to warm to room temperature over a period of 1.5 hours and diluted with DCM (50 mL) then washed with saturated NH$_4$Cl (15 mL), saturated NaHCO$_3$ (15 mL), brine (15 mL), dried (MgSO$_4$), filtered and evaporated in vacuo to give the crude product. Purification by flash chromatography (gradient elution in 0.4% increments: 100% DCM to 98.4:1.6 v/v DCM/MeOH) gave tert-butyl (11S,11aS)-11-hydroxy-8-((5-(((11S,11aS)-11-hydroxy-7-methoxy-2-methylene-10-(((R)-2-((5-nitropyridin-2-yl)disulfanyl)propoxy)carbonyl)-5-oxo-2,3,5,10,11,11a-hexahydro-1H-benzo[e]pyrrolo[1,2-a][1,4]diazepin-8-yl)oxy)pentyl)oxy)-7-methoxy-2-methylene-5-oxo-2,3,11,11a-tetrahydro-1H-benzo[e]pyrrolo[1,2-a][1,4]diazepine-10(5H)-carboxylate 51d as a yellowish foam (227 mg, 67% yield): LC/MS retention time 1.69 minutes (ES+) m/z 993 ([M+H]$^+$; ~80% relative intensity), 1015 ([M+Na]$^+$·, ~20% relative intensity).

A solution of 95:5 v/v TFA/H$_2$O (4 mL) was added to a crude sample of 51d (216 mg, 0.22 mmol) at 0° C. (ice/acetone). After stirring at 0° C. for 30 minutes the reaction was deemed complete as judged by LC/MS, desired product peak at retention time 1.60 minutes (ES+) m/z 875 ([M+H]$^+$; ~100% relative intensity). The reaction mixture was kept cold and added drop-wise to a chilled saturated aqueous solution of NaHCO$_3$ (100 mL). The mixture was extracted with DCM (3×30 mL) and the combined organic layers washed with brine (50 mL), dried (MgSO$_4$), filtered and Linker-drug intermediate of ADC-52: 2-((5-nitropyridin-2-yl)disulfanyl)propyl (2,5-bis((E)-3-((S)-1-(chloromethyl)-5-(phosphonooxy)-1,2-dihydro-3H-benzo[e]indol-3-yl)-3-oxoprop-1-en-1-yl)phenyl)carbamate (MS (ESI): 1098 [M+H]$^+$) was prepared by the procedures of WO 2015/023355LD-53: (S)-1-(chloromethyl)-3-((E)-3-(4-((E)-3-((S)-1-(chloromethyl)-5-(phosphonooxy)-1,2-dihydro-3H-benzo[e]indol-3-yl)-3-oxoprop-1-en-1-yl)-2-(2-(2-(2,5-dioxo-2,5-dihydro-H-pyrrol-1-yl)ethoxy)ethoxy)phenyl)acryloyl)-2,3-dihydro-1H-benzo[e]indol-5-yl dihydrogen phosphate (MS (ESI): 994 [M+H]$^+$) was prepared by the procedures of WO 2015/023355

Linker-drug intermediate of ADC-54: (R)-2-((3-nitropyridin-2-yl)disulfanyl)propyl (11S,11aS)-11-hydroxy-7-methoxy-8-((5-(((S)-7-methoxy-2-methylene-5-oxo-2,3,5,11a-tetrahydro-1H-benzo[e]pyrrolo[1,2-a][1,4]diazepin-8-yl)oxy)pentyl)oxy)-2-methylene-5-oxo-2,3,11,11a-tetrahydro-1H-benzo[e]pyrrolo[1,2-a][1,4]diazepine-10 (5H)-carboxylate (MS (ESI): 876 [M+H]$^+$) was prepared by the procedures of WO 2013/055987.

Linker-drug intermediate of ADC-55: 4-((S)-2-((S)-2-(6-(2,5-dioxo-2,5-dihydro-1H-pyrrol-1-yl)hexanamido)-3-methylbutanamido)-5-ureidopentanamido)benzyl (2-oxo-2-((2S,4S)-2,5,12-trihydroxy-7-methoxy-4-(((1S,3R,4aS,9S,9aR,10aS)-9-methoxy-1-methyloctahydro-1H-pyrano[4',3':4,5]oxazolo[2,3-c][1,4]oxazin-3-yl)oxy)-6,11-dioxo-1,2,3,4,6,11-hexahydrotetracen-2-yl)ethyl) ethane-1,2-diylbis (methylcarbamate).

Following Example 3 of U.S. Pat. No. 8,389,697, to a solution of PNU-159682 (15.3 mg, 0.02038 mmol), prepared as reported in WO 1998/02446 and Example 1 of U.S. Pat. No. 8,470,984, in 3 ml of methanol and 2 ml of H$_2$O, a solution of NaIO$_4$ (5.1 mg, 0.0238 mmol) in 1 ml of H$_2$O was added. The reaction mixture was stirred at room temperature for 3 hours, until no starting material was detectable (TLC and HPLC analysis). The solvents were removed under reduced pressure and the crude red solid (2S,4S)-2,5,12-trihydroxy-7-methoxy-4-{[(1S,3R,4aS,9S,9aR,10aS)-9-methoxy-1-methyloctahydro-1H-pyrano[4',3':4,5][1,3]oxazolo[2,3-c][1,4]oxazin-3-yl]oxy}-6,11-dioxo-1,2,3,4,6,11-hexahydrotetracene-2-carboxylic acid 55a (MS (ESI): 628 [M+H]$^+$) which was converted to LD-55 (MS (ESI): 1355 [M+H]$^+$) by the procedures of WO 2010/009124.

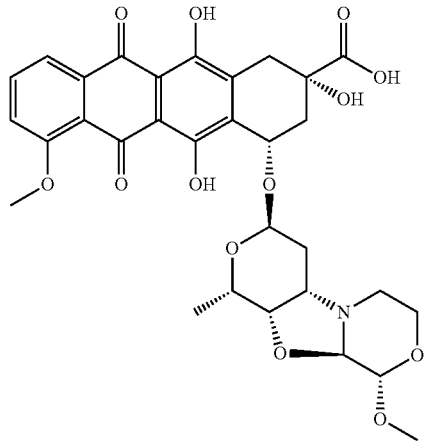

55a

Linker-drug intermediate of ADC-56: (2S,4S)-2,5,12-trihydroxy-7-methoxy-4-(((1S,3R,4aS,9S,9aR,10aS)-9-methoxy-1-methyloctahydro-1H-pyrano[4',3':4,5]oxazolo[2,3-c][1,4]oxazin-3-yl)oxy)-N-(2-((5-nitropyridin-2-yl)disulfanyl)ethyl)-6,11-dioxo-1,2,3,4,6,11-hexahydrotetracene-2-carboxamide (MS (ESI): 842 [M+H]$^+$) was prepared by the procedures of WO 2013/055987.

Linker-drug intermediate of ADC-57: (2S,4S)-2,5,12-trihydroxy-7-methoxy-4-(((1S,3R,4aS,9S,9aR,10aS)-9-methoxy-1-methyloctahydro-1H-pyrano[4',3':4,5]oxazolo[2,3-c][1,4]oxazin-3-yl)oxy)-N-(2-((5-nitropyridin-2-yl)disulfanyl)propyl)-6,11-dioxo-1,2,3,4,6,11-hexahydrotetracene-2-carboxamide (MS (ESI): 856 [M+H]$^+$) was prepared by the procedures of U.S. Pat. No. 8,389,697.

Linker-drug intermediate of ADC-58: (2S,4S)-2,5,12-trihydroxy-7-methoxy-4-(((1S,3R,4aS,9S,9aR,10aS)-9-methoxy-1-methyloctahydro-1H-pyrano[4',3':4,5]oxazolo[2,3-c][1,4]oxazin-3-yl)oxy)-N-(2-methyl-2-((5-nitropyridin-2-yl)disulfanyl)propyl)-6,11-dioxo-1,2,3,4,6,11-hexahydrotetracene-2-carboxamide (MS ((ESI): 870 [M+H]+) was prepared by the procedures of U.S. Pat. No. 8,389,697.

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

TABLE OF SEQUENCES

| NAME | SEQUENCE | SEQ ID NO |
|---|---|---|
| Human CLL-1 (UniProt No. Q5QGZ9; NCBI Ref. NP_612210.4) | MSEEVTYADL QFQNSSEMEK IPEIGKFGEK APPAPSHVWR PAALFLTLLC LLLLIGLGVL ASMFHVTLKI EMKKMNKLQN ISEELQRNIS LQLMSNMNIS NKIRNLSTTL QTIATKLCRE LYSKEQEHKC KPCPRRWIWH KDSCYFLSDD VQTWQESKMA CAAQNASLLK INNKNALEFI KSQSRSYDYW LGLSPEEDST RGMRVDNIIN SSAWVIRNAP DLNNMYCGYI NRLYVQYYHC TYKKRMICEK MANPVQLGST YFREA | 1 |
| Human CLL-1 ECD (aa 65-265 of SEQ ID NO: 1) | HVTLKIEMKKMNKLQNISEELQRNISLQLMSNMNISNKIRNL STTLQTIATKLCRELYSKEQEHKCKPCPRRWIWHKDSCYFL SDDVQTWQESKMACAAQNASLLKINNKNALEFIKSQSRSY DYWLGLSPEEDSTRGMRVDNIINSSAWVIRNAPDLNNMYC GYINRLYVQYYHCTYKKRMICEKMANPVQLGSTYFREA | 2 |
| Human CLL-1 C-type lectin-like domain (CTLD) (aa 133-250 of SEQ ID NO: 1 | CPRRWIWHKDSCYFLSDDVQTWQESKMACAAQNASLLKIN NKNALEFIKSQSRSYDYWLGLSPEEDSTRGMRVDNIINSSA WVIRNAPDLNNMYCGYINRLYVQYYHCTYKKRMICEK | 3 |
| Cyno CLL-1 | MSEEVTYADLKFQNSSETEKIQEIAKFGGKAPPAPSCVWRP AALFLTVLCLLMLIGLGVLGSMFHITLKTAMKKMNKLQNIN EELQRNVSLQLMSNMNSS NKIRNLSTTLQTIATRLCRELYSKEQEHKCKPCPRRWIWHK DSCYFLSDDVRTWQESRMACAAQNASLLKINNKNALEFIKS QSTSYPYWLGLSPEKDYS YGTSVDDIINSSAWVTRNASDLNNMFCGYINRIYVHYDYCI YRKKMICEKMANPVQLGFIHFREA | 4 |
| m6E7-HVR L1 6E7L4H1 e-HVR L1 6E7L4H1 eA54-HVR L1 | RASQSVSTSSYNYMH | 5 |

TABLE OF SEQUENCES

| NAME | SEQUENCE | SEQ ID NO |
|---|---|---|
| m6E7-HVR L2<br>6E7L4H1e-HVR L2<br>6E7L4H1 eA54-HVR L2 | YASNLES | 6 |
| m6E7-HVR L3<br>6E7L4H1e-HVR L3<br>6E7L4H1 eA54-HVR L3 | QHSWEIPLT | 7 |
| m6E7-HVR H1<br>6E7L4H1e-HVR H1<br>6E7L4H1 eA54-HVR H1 | DYYMEI | 8 |
| m6E7-HVR H2<br>6E7L4H1e-HVR H2 | RINPYNGAAFYSQNFKD | 9 |
| m6E7-HVR H3<br>6E7L4H1e-HVR H3<br>6E7L4H1eA54-HVR H3 | ERGADLEGYAMDY | 10 |
| 6E7L4H1eA54-HVR H2 | RINPYAGAAFYSQNFKD | 11 |
| m20B1-HVR L1 | SASSSISYMY | 12 |
| m20B1-HVR L2 | DTSKLAS | 13 |
| m20B1-HVR L3 | HQRSSWT | 14 |
| m20B1-HVR H1 | SYDIN | 15 |
| m20B1-HVR H2 | WIYPGDGTTEYNERFKG | 16 |
| m20B1-HVR H3 | SYDYDYAMDY | 17 |
| m21C9-HVR L1<br>21C9.L2H-HVR L1 | KASQDVSTAVA | 18 |
| m21C9-HVR L2<br>21C9.L2H-HVR L2 | SPSYRYT | 19 |
| m21C9-HVR L3<br>21C9.L2H-HVR L3 | QQLYSTPYT | 20 |
| m21C9-HVR H1<br>21C9.L2H-HVR H1 | DYYLD | 21 |
| m21C9-HVR H2<br>21C9.L2H-HVR H2 | RVNPYNGGTIYNQKFKG | 22 |
| m21C9-HVR H3<br>21C9.L2H-HVR H3 | DHYRYDPLLDY | 23 |
| m28H12-HVR L1 | RASQSVSSSSYSYMH | 24 |
| m28H12-HVR L2 | YASNLES | 25 |
| m28H12-HVR L3 | QHSWEIPYT | 26 |
| m28H12-HVR H1 | DTYMH | 27 |
| m28H12-HVR H2 | RIDPANGDTDYDPKFQG | 28 |
| m28H12-HVR H3 | SGPPYYVMDY | 29 |
| m6E7 $V_L$ | DIVLTQSPSSLIVSLGQRATISCRASQSVSTSSYNYMHWYQQKPGQPPKLLLKYASNLESGVPARFSGSGSGTDFTLNIHPVEEEDTATYYCQHSWEIPLTFGAGTKLEIK | 30 |

TABLE OF SEQUENCES

| NAME | SEQUENCE | SEQ ID NO |
|---|---|---|
| m6E7 $V_H$ | QVQLQQSGPELVKPGASVKISCKASGYSFTDYYMHWVKQS HIKSLEWIGRINPYNGAAFYSQNFKDKASLTVDKSSTAYM ELHSLTSEDSAVYYCAIERGADLEGYAMDYWGQGTSVTVS S | 31 |
| 6E7L4H1e $V_L$ | DIQMTQSPSSLSASVGDRVTITCRASQSVSTSSYNYMHWYQ QKPGKPPKLLIKYASNLESGVPSRFSGSGSGTDFTLTISSLQP EDFATYYCQHSWEIPLTFGQGTKVEIK | 32 |
| 6E7L4H1e $V_H$ | EVQLVQSGAEVKKPGASVKVSCKASGYSFTDYYMHWVRQ APGQGLEWIGRINPYNGAAFYSQNFKDRVTLTVDTSTSTAY LELSSLRSEDTAVYYCAIERGADLEGYAMDYWGQGTLVTV SS | 33 |
| 6E7L4H1eAG $V_H$ | EVQLVQSGAEVKKPGASVKVSCKASGYSFTDYYMHWVRQ APGQGLEWIGRINPYAGAAFYSQNFKDRVTLTVDTSTSTAY LELSSLRSEDTAVYYCAIERGADLEGYAMDYWGQGTLVTV SS | 34 |
| m20B1 $V_L$ | DIVLTQSPAIMSASPGEKVTMTCSASSSISYMYWYQQKPGTS PKRWIYDTSKLASGVPARFSGSGSGTSYSLTISSMEAEDAAT YYCHQRSSWTFGGGTKLEIK | 35 |
| m20B1 $V_H$ | EVQLQQSGPELVKPGALVKISCKASGYTFTSYDINWLKQRP GQGLEWIGWIYPGDGTTEYNERFKGKATLTADKSSSTAYLQ LSSLTSENSAVYFCARSYDYDYAMDYWGQGTSVTVSS | 36 |
| m21C9 $V_L$ | DIQMTQSHKFMSTSVGDRVSITCKASQDVSTAVAWFQQKP GQSPKLLIYSPSYRYTGVPDRFTGSGSGTDFTFTISSVQAEDL AVYYCQQLYSTPYTFGGGTKLEIK | 37 |
| m21C9 $V_H$ | EVQLQQSGPELVKPGASVKMSCKASGYTFTDYYLDWVKQS HGESFEWIGRVNPYNGGTIYNQKFKGKATLTVDKSSSTAY MDLNSLTSEDSAVYYCARDHYRYDPLLDYWGQGTTLTVSS | 38 |
| 21C9.L2H3 $V_L$ | DIQMTQSPSSLSASVGDRVTITCKASQDVSTAVAWFQQKPG KAPKLLIYSPSYRYTGVPSRFSGSGSGTDFTLTISSLQPEDFA TYYCQQLYSTPYTFGQGTKVEIK | 39 |
| 21C9.L2H3 $V_H$ | EVQLVQSGAEVKKPGASVKVSCKASGYTFTDYYLDWVRQ APGQGLEWIGRVNPYNGGTIYNQKFKGRVTLTRDTSTSTAY LELSSLRSEDTAVYYCARDHYRYDPLLDYWGQGTLVTVSS | 40 |
| m28H12 $V_L$ | DIQMTQSPASLAVSLGQRATISCRASQSVSSSSYSYMHWYQ QKPGQPPKLLIKYASNLESGVPARFSGRGSGTDFTLNIHPVE EEDTATYYCQHSWEIPYTFGGGTRLEIK | 41 |
| m28H12 $V_H$ | QVQLQQSGAELVKPGASVKLSCTASGFNIKDTYMHWVKQR PEQGLEWIGRIDPANGDTDYDPKFQGKATVTADTSSNTAYL QLSSLTSEDTAVYYCTISGPPYYVMDYWGQGTSVTVSS | 42 |
| 6E7L4H1eE54-HVR H2 | RINPYEGAAFYSQNFKD | 43 |
| 6E7L4H1eS54-HVR H2 | RINPYSGAAFYSQNFKD | 44 |
| 6E7L4H1eConsensus-HVR H2 | RINPYX$_1$GAAFYSQNFKD, wherein X$_1$ is A, E, S, or N | 45 |
| 6E7L4H1eConcensus-HVR VH | EVQLVQSGAEVKKPGASVKVSCKASGYSFTDYYMHWVRQ APGQGLEWIGRINPY X$_1$GAAFYSQNFKDRVTLTVDTSTSTAYLELSSLRSEDTAVYY CAIERGADLEGYAMDYWGQGTLVTVSS, wherein X$_1$ is A, E, S or N | 46 |
| 6E7L4H1eConcensus2-HVR H2 | RINPYX$_2$GAAFYSQNFKD, wherein X$_2$ is A, E, or S | 47 |
| 6E7L4H1eConcensus2-HVR VH | EVQLVQSGAEVKKPGASVKVSCKASGYSFTDYYMHWVRQ APGQGLEWIGRINPY X$_2$GAAFYSQNFKDRVTLTVDTSTSTAYLELSSLRSEDTAVYY | 48 |

| NAME | SEQUENCE | SEQ ID NO |
|---|---|---|
| | CAIERGADLEGYAMDYWGQGTLVTVSS, wherein X₂ is A, E, or S | |

What is claimed is:

1. An isolated nucleic acid encoding an anti-CLL-1 antibody, wherein the antibody comprises
   (a) HVR-H1 comprising the amino acid sequence of SEQ ID NO:8;
   (b) HVR-H2 comprising the amino acid sequence of SEQ ID NO: 11;
   (c) HVR-H3 comprising the amino acid sequence of SEQ ID NO: 10;
   (d) HVR-L1 comprising the amino acid sequence of SEQ ID NO:5;
   (e) HVR-L2 comprising the amino acid sequence of SEQ ID NO:6; and
   (f) HVR-L3 comprising the amino acid sequence of SEQ ID NO:7.

2. The isolated nucleic acid of claim 1, wherein the antibody comprises one or more engineered free cysteine amino acid residues.

3. The isolated nucleic acid of claim 2, wherein the one or more engineered free cysteine amino acid residues is located in the light chain.

4. The isolated nucleic acid of claim 3, wherein the one or more engineered free cysteine amino acid residues in the light chain comprises K149C according to Kabat numbering.

5. The isolated nucleic acid of claim 1, wherein the antibody is a humanized antibody.

6. The isolated nucleic acid of claim 1, wherein the antibody is an antibody fragment that binds CLL-1.

7. The isolated nucleic acid of claim 1, wherein the antibody is an IgG1, IgG2a, or IgG2b antibody.

8. The isolated nucleic acid of claim 1, wherein the antibody is an IgG1 antibody.

9. The isolated nucleic acid of claim 4, wherein the antibody is an IgG1 antibody.

10. An isolated nucleic acid encoding an anti-CLL-1 antibody, wherein the antibody comprises (a) a heavy chain variable region comprising the amino acid sequence of SEQ ID NO:34 and (b) a light chain variable region comprising the amino acid sequence of SEQ ID NO:32.

11. The isolated nucleic acid of claim 10, wherein the antibody comprises one or more engineered free cysteine amino acid residues.

12. The isolated nucleic acid of claim 11, wherein the one or more engineered free cysteine amino acid residues is located in the light chain.

13. The isolated nucleic acid of claim 12, wherein the one or more engineered free cysteine amino acid residues in the light chain comprises K149C according to Kabat numbering.

14. The isolated nucleic acid of claim 10, wherein the antibody is a humanized antibody.

15. The isolated nucleic acid of claim 10, wherein the antibody is an antibody fragment that binds CLL-1.

16. The isolated nucleic acid of claim 10, wherein the antibody is an IgG1, IgG2a, or IgG2b antibody.

17. The isolated nucleic acid of claim 10, wherein the antibody is an IgG1 antibody.

18. The isolated nucleic acid of claim 13, wherein the antibody is an IgG1 antibody.

19. An expression vector comprising the isolated nucleic acid of claim 1.

20. An expression vector comprising the isolated nucleic acid of claim 10.

21. An isolated host cell comprising the expression vector of claim 19.

22. An isolated host cell comprising the expression vector of claim 20.

23. An isolated host cell comprising a first nucleic acid sequence and a second nucleic acid sequence, wherein the first nucleic acid sequence encodes a heavy chain variable region of an anti-CLL-1 antibody, wherein the heavy chain variable region comprises:
  (a) HVR-H1 comprising the amino acid sequence of SEQ ID NO:8;
  (b) HVR-H2 comprising the amino acid sequence of SEQ ID NO: 11;
  (c) HVR-H3 comprising the amino acid sequence of SEQ ID NO: 10;
and the second nucleic acid sequence encodes a light chain variable region of the anti-CLL-1 antibody, wherein the light chain variable region comprises:
  (a) HVR-L1 comprising the amino acid sequence of SEQ ID NO:5;
  (b) HVR-L2 comprising the amino acid sequence of SEQ ID NO:6; and
  (c) HVR-L3 comprising the amino acid sequence of SEQ ID NO:7.

24. The isolated host cell of claim 23, wherein the anti-CLL-1 antibody comprises one or more engineered free cysteine amino acid residues.

25. The isolated host cell of claim 24, wherein the one or more engineered free cysteine amino acid residues is located in the light chain.

26. The isolated host cell of claim 25, wherein the one or more engineered free cysteine amino acid residues in the light chain comprises K149C according to Kabat numbering.

27. The isolated host cell of claim 23, wherein the anti-CLL-1 antibody is a humanized antibody.

28. The isolated host cell of claim 23, wherein the anti-CLL-1 antibody is an antibody fragment that binds CLL-1.

29. The isolated host cell of claim 23, wherein the anti-CLL-1 antibody is an IgG1, IgG2a, or IgG2b antibody.

30. The isolated host cell of claim 23, wherein the anti-CLL-1 antibody is an IgG1 antibody.

31. The isolated host cell of claim 26, wherein the anti-CLL-1 antibody is an IgG1 antibody.

32. An isolated host cell comprising a first nucleic acid sequence and a second nucleic acid sequence, wherein the first nucleic acid sequence encodes a heavy chain variable region of an anti-CLL-1 antibody, wherein the heavy chain variable region comprises the amino acid sequence of SEQ ID NO:34, and the second nucleic acid sequence encodes a light chain variable region of the anti-CLL-1 antibody, wherein the light chain variable region comprises the amino acid sequence of SEQ ID NO:32.

33. The isolated host cell of claim 32, wherein the anti-CLL-1 antibody comprises one or more engineered free cysteine amino acid residues.

34. The isolated host cell of claim 33, wherein the one or more engineered free cysteine amino acid residues is located in the light chain.

35. The isolated host cell of claim 14, wherein the one or more engineered free cysteine amino acid residues in the light chain comprises K149C according to Kabat numbering.

36. The isolated host cell of claim 32, wherein the anti-CLL-1 antibody is a humanized antibody.

37. The isolated host cell of claim 32, wherein the anti-CLL-1 antibody is an antibody fragment that binds CLL-1.

38. The isolated host cell of claim 32, wherein the anti-CLL-1 antibody is an IgG1, IgG2a, or IgG2b antibody.

39. The isolated host cell of claim 32, wherein the anti-CLL-1 antibody is an IgG1 antibody.

40. The isolated host cell of claim 35, wherein the anti-CLL-1 antibody is an IgG1 antibody.

41. An isolated host cell that produces an anti-CLL-1 antibody, wherein the antibody comprises
  (a) HVR-H1 comprising the amino acid sequence of SEQ ID NO:8;
  (b) HVR-H2 comprising the amino acid sequence of SEQ ID NO: 11;
  (c) HVR-H3 comprising the amino acid sequence of SEQ ID NO: 10;
  (d) HVR-L1 comprising the amino acid sequence of SEQ ID NO:5;
  (e) HVR-L2 comprising the amino acid sequence of SEQ ID NO:6; and
  (f) HVR-L3 comprising the amino acid sequence of SEQ ID NO:7.

42. The isolated host cell of claim 41, wherein the anti-CLL-1 antibody comprises one or more engineered free cysteine amino acid residues.

43. The isolated host cell of claim 42, wherein the one or more engineered free cysteine amino acid residues is located in the light chain.

44. The isolated host cell of claim 43, wherein the one or more engineered free cysteine amino acid residues in the light chain comprises K149C according to Kabat numbering.

45. The isolated host cell of claim 41, wherein the anti-CLL-1 antibody is a humanized antibody.

46. The isolated host cell of claim 41, wherein the anti-CLL-1 antibody is an antibody fragment that binds CLL-1.

47. The isolated host cell of claim 41, wherein the anti-CLL-1 antibody is an IgG1, IgG2a, or IgG2b antibody.

48. The isolated host cell of claim 41, wherein the anti-CLL-1 antibody is an IgG1 antibody.

49. The isolated host cell of claim 44, wherein the anti-CLL-1 antibody is an IgG1 antibody.

50. An isolated host cell that produces an anti-CLL-1 antibody, wherein the antibody comprises a heavy chain variable region comprising the amino acid sequence of SEQ ID NO:34 and a light chain variable region comprising the amino acid sequence of SEQ ID NO:32.

51. The isolated host cell of claim 50, wherein the anti-CLL-1 antibody comprises one or more engineered free cysteine amino acid residues.

52. The isolated host cell of claim 51, wherein the one or more engineered free cysteine amino acid residues is located in the light chain.

53. The isolated host cell of claim 52, wherein the one or more engineered free cysteine amino acid residues in the light chain comprises K149C according to Kabat numbering.

54. The isolated host cell of claim 50, wherein the anti-CLL-1 antibody is a humanized antibody.

55. The isolated host cell of claim 50, wherein the anti-CLL-1 antibody is an antibody fragment that binds CLL-1.

56. The isolated host cell of claim 50, wherein the anti-CLL-1 antibody is an IgG1, IgG2a, or IgG2b antibody.

57. The isolated host cell of claim 50, wherein the anti-CLL-1 antibody is an IgG1 antibody.

58. The isolated host cell of claim 50, wherein the anti-CLL-1 antibody is an IgG1 antibody.

59. The isolated host cell of claim 23, which is a prokaryotic host cell.

60. The isolated host cell of claim 23, which is a eukaryotic host cell.

61. The isolated host cell of claim 60, which is a Chinese hamster ovary (CHO) cell.

62. The isolated host cell of claim 32, which is a prokaryotic host cell.

63. The isolated host cell of claim 32, which is a eukaryotic host cell.

64. The isolated host cell of claim 63, which is a Chinese hamster ovary (CHO) cell.

65. The isolated host cell of claim 41, which is a prokaryotic host cell.

66. The isolated host cell of claim 41, which is a eukaryotic host cell.

67. The isolated host cell of claim 66, which is a Chinese hamster ovary (CHO) cell.

68. The isolated host cell of claim 50, which is a prokaryotic host cell.

69. The isolated host cell of claim 50, which is a eukaryotic host cell.

70. The isolated host cell of claim 69, which is a Chinese hamster ovary (CHO) cell.

71. A method of producing an anti-CLL-1 antibody comprising culturing the host cell of claim 21, so that the antibody is produced, and isolating the antibody from the culture.

72. A method of producing an anti-CLL-1 antibody comprising culturing the host cell of claim 22, so that the antibody is produced, and isolating the antibody from the culture.

73. A method of producing an anti-CLL-1 antibody comprising culturing the host cell of claim 23, so that the antibody is produced, and isolating the antibody from the culture.

74. A method of producing an anti-CLL-1 antibody comprising culturing the host cell of claim 32, so that the antibody is produced, and isolating the antibody from the culture.

75. A method of producing an anti-CLL-1 antibody comprising culturing the host cell of claim 41, so that the antibody is produced, and isolating the antibody from the culture.

76. A method of producing an anti-CLL-1 antibody comprising culturing the host cell of claim 50, so that the antibody is produced, and isolating the antibody from the culture.

77. A method of producing an anti-CLL-1 antibody comprising culturing the host cell of claim 61, so that the antibody is produced, and isolating the antibody from the culture.

78. A method of producing an anti-CLL-1 antibody comprising culturing the host cell of claim 64, so that the antibody is produced, and isolating the antibody from the culture.

79. A method of producing an anti-CLL-1 antibody comprising culturing the host cell of claim 67, so that the antibody is produced, and isolating the antibody from the culture.

80. A method of producing an anti-CLL-1 antibody comprising culturing the host cell of claim 70, so that the antibody is produced, and isolating the antibody from the culture.

\* \* \* \* \*

SEQUENCE LISTING

<160> NUMBER OF SEQ ID NOS: 73

<210> SEQ ID NO 1
<211> LENGTH: 265
<212> TYPE: PRT
<213> ORGANISM: Homo sapiens

<400> SEQUENCE: 1

```
Met Ser Glu Glu Val Thr Tyr Ala Asp Leu Gln Phe Gln Asn Ser Ser
1               5                   10                  15

Glu Met Glu Lys Ile Pro Glu Ile Gly Lys Phe Gly Glu Lys Ala Pro
            20                  25                  30

Pro Ala Pro Ser His Val Trp Arg Pro Ala Ala Leu Phe Leu Thr Leu
        35                  40                  45

Leu Cys Leu Leu Leu Leu Ile Gly Leu Gly Val Leu Ala Ser Met Phe
    50                  55                  60

His Val Thr Leu Lys Ile Glu Met Lys Lys Met Asn Lys Leu Gln Asn
65                  70                  75                  80

Ile Ser Glu Glu Leu Gln Arg Asn Ile Ser Leu Gln Leu Met Ser Asn
                85                  90                  95

Met Asn Ile Ser Asn Lys Ile Arg Asn Leu Ser Thr Thr Leu Gln Thr
            100                 105                 110

Ile Ala Thr Lys Leu Cys Arg Glu Leu Tyr Ser Lys Glu Gln Glu His
        115                 120                 125

Lys Cys Lys Pro Cys Pro Arg Arg Trp Ile Trp His Lys Asp Ser Cys
    130                 135                 140

Tyr Phe Leu Ser Asp Asp Val Gln Thr Trp Gln Glu Ser Lys Met Ala
145                 150                 155                 160

Cys Ala Ala Gln Asn Ala Ser Leu Leu Lys Ile Asn Asn Lys Asn Ala
                165                 170                 175

Leu Glu Phe Ile Lys Ser Gln Ser Arg Ser Tyr Asp Tyr Trp Leu Gly
            180                 185                 190

Leu Ser Pro Glu Glu Asp Ser Thr Arg Gly Met Arg Val Asp Asn Ile
        195                 200                 205

Ile Asn Ser Ser Ala Trp Val Ile Arg Asn Ala Pro Asp Leu Asn Asn
    210                 215                 220

Met Tyr Cys Gly Tyr Ile Asn Arg Leu Tyr Val Gln Tyr Tyr His Cys
225                 230                 235                 240

Thr Tyr Lys Lys Arg Met Ile Cys Glu Lys Met Ala Asn Pro Val Gln
                245                 250                 255

Leu Gly Ser Thr Tyr Phe Arg Glu Ala
            260                 265
```

<210> SEQ ID NO 2
<211> LENGTH: 201
<212> TYPE: PRT

<213> ORGANISM: Homo sapiens

<400> SEQUENCE: 2

```
His Val Thr Leu Lys Ile Glu Met Lys Lys Met Asn Lys Leu Gln Asn
1               5                   10                  15
Ile Ser Glu Glu Leu Gln Arg Asn Ile Ser Leu Gln Leu Met Ser Asn
            20                  25                  30
Met Asn Ile Ser Asn Lys Ile Arg Asn Leu Ser Thr Thr Leu Gln Thr
        35                  40                  45
Ile Ala Thr Lys Leu Cys Arg Glu Leu Tyr Ser Lys Glu Gln Glu His
    50                  55                  60
Lys Cys Lys Pro Cys Pro Arg Arg Trp Ile Trp His Lys Asp Ser Cys
65                  70                  75                  80
Tyr Phe Leu Ser Asp Asp Val Gln Thr Trp Gln Glu Ser Lys Met Ala
                85                  90                  95
Cys Ala Ala Gln Asn Ala Ser Leu Leu Lys Ile Asn Asn Lys Asn Ala
            100                 105                 110
Leu Glu Phe Ile Lys Ser Gln Ser Arg Ser Tyr Asp Tyr Trp Leu Gly
        115                 120                 125
Leu Ser Pro Glu Glu Asp Ser Thr Arg Gly Met Arg Val Asp Asn Ile
    130                 135                 140
Ile Asn Ser Ser Ala Trp Val Ile Arg Asn Ala Pro Asp Leu Asn Asn
145                 150                 155                 160
Met Tyr Cys Gly Tyr Ile Asn Arg Leu Tyr Val Gln Tyr Tyr His Cys
                165                 170                 175
Thr Tyr Lys Lys Arg Met Ile Cys Glu Lys Met Ala Asn Pro Val Gln
            180                 185                 190
Leu Gly Ser Thr Tyr Phe Arg Glu Ala
        195                 200
```

<210> SEQ ID NO 3
<211> LENGTH: 118
<212> TYPE: PRT
<213> ORGANISM: Homo sapiens

<400> SEQUENCE: 3

```
Cys Pro Arg Arg Trp Ile Trp His Lys Asp Ser Cys Tyr Phe Leu Ser
1               5                   10                  15
Asp Asp Val Gln Thr Trp Gln Glu Ser Lys Met Ala Cys Ala Ala Gln
            20                  25                  30
Asn Ala Ser Leu Leu Lys Ile Asn Asn Lys Asn Ala Leu Glu Phe Ile
        35                  40                  45
Lys Ser Gln Ser Arg Ser Tyr Asp Tyr Trp Leu Gly Leu Ser Pro Glu
    50                  55                  60
Glu Asp Ser Thr Arg Gly Met Arg Val Asp Asn Ile Ile Asn Ser Ser
65                  70                  75                  80
Ala Trp Val Ile Arg Asn Ala Pro Asp Leu Asn Asn Met Tyr Cys Gly
                85                  90                  95
Tyr Ile Asn Arg Leu Tyr Val Gln Tyr Tyr His Cys Thr Tyr Lys Lys
            100                 105                 110
Arg Met Ile Cys Glu Lys
        115
```

<210> SEQ ID NO 4
<211> LENGTH: 265
<212> TYPE: PRT

<213> ORGANISM: Artificial Sequence
<220> FEATURE:
<223> OTHER INFORMATION: Description of Artificial Sequence: Synthetic
      polypeptide

<400> SEQUENCE: 4

Met Ser Glu Glu Val Thr Tyr Ala Asp Leu Lys Phe Gln Asn Ser Ser
1               5                   10                  15

Glu Thr Glu Lys Ile Gln Glu Ile Ala Lys Phe Gly Gly Lys Ala Pro
            20                  25                  30

Pro Ala Pro Ser Cys Val Trp Arg Pro Ala Ala Leu Phe Leu Thr Val
        35                  40                  45

Leu Cys Leu Leu Met Leu Ile Gly Leu Gly Val Leu Gly Ser Met Phe
    50                  55                  60

His Ile Thr Leu Lys Thr Ala Met Lys Met Asn Lys Leu Gln Asn
65                  70                  75                  80

Ile Asn Glu Glu Leu Gln Arg Asn Val Ser Leu Gln Leu Met Ser Asn
                85                  90                  95

Met Asn Ser Ser Asn Lys Ile Arg Asn Leu Ser Thr Thr Leu Gln Thr
            100                 105                 110

Ile Ala Thr Arg Leu Cys Arg Glu Leu Tyr Ser Lys Glu Gln Glu His
        115                 120                 125

Lys Cys Lys Pro Cys Pro Arg Arg Trp Ile Trp His Lys Asp Ser Cys
130                 135                 140

Tyr Phe Leu Ser Asp Asp Val Arg Thr Trp Gln Glu Ser Arg Met Ala
145                 150                 155                 160

Cys Ala Ala Gln Asn Ala Ser Leu Leu Lys Ile Asn Asn Lys Asn Ala
                165                 170                 175

Leu Glu Phe Ile Lys Ser Gln Ser Thr Ser Tyr Pro Tyr Trp Leu Gly
            180                 185                 190

Leu Ser Pro Glu Lys Asp Tyr Ser Tyr Gly Thr Ser Val Asp Asp Ile
        195                 200                 205

Ile Asn Ser Ser Ala Trp Val Thr Arg Asn Ala Ser Asp Leu Asn Asn
210                 215                 220

Met Phe Cys Gly Tyr Ile Asn Arg Ile Tyr Val His Tyr Asp Tyr Cys
225                 230                 235                 240

Ile Tyr Arg Lys Lys Met Ile Cys Glu Lys Met Ala Asn Pro Val Gln
                245                 250                 255

Leu Gly Phe Ile His Phe Arg Glu Ala
            260                 265

<210> SEQ ID NO 5
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Arg Ala Ser Gln Ser Val Ser Thr Ser Ser Tyr Asn Tyr Met His
1               5                   10                  15

<210> SEQ ID NO 6
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 6

Tyr Ala Ser Asn Leu Glu Ser
1               5

<210> SEQ ID NO 7
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Gln His Ser Trp Glu Ile Pro Leu Thr
1               5

<210> SEQ ID NO 8
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Asp Tyr Tyr Met His
1               5

<210> SEQ ID NO 9
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Arg Ile Asn Pro Tyr Asn Gly Ala Ala Phe Tyr Ser Gln Asn Phe Lys
1               5                   10                  15

Asp

<210> SEQ ID NO 10
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Glu Arg Gly Ala Asp Leu Glu Gly Tyr Ala Met Asp Tyr
1               5                   10

<210> SEQ ID NO 11
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Arg Ile Asn Pro Tyr Ala Gly Ala Ala Phe Tyr Ser Gln Asn Phe Lys
1               5                   10                  15

Asp

<210> SEQ ID NO 12
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Ser Ala Ser Ser Ser Ile Ser Tyr Met Tyr
1               5                   10

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Asp Thr Ser Lys Leu Ala Ser
1               5

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

His Gln Arg Ser Ser Trp Thr
1               5

<210> SEQ ID NO 15
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Ser Tyr Asp Ile Asn
1               5

<210> SEQ ID NO 16
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Trp Ile Tyr Pro Gly Asp Gly Thr Thr Glu Tyr Asn Glu Arg Phe Lys
1               5                   10                  15

Gly

<210> SEQ ID NO 17
<211> LENGTH: 10
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 17

Ser Tyr Asp Tyr Asp Tyr Ala Met Asp Tyr
1               5                   10

<210> SEQ ID NO 18
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Lys Ala Ser Gln Asp Val Ser Thr Ala Val Ala
1               5                   10

<210> SEQ ID NO 19
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Ser Pro Ser Tyr Arg Tyr Thr
1               5

<210> SEQ ID NO 20
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Gln Gln Leu Tyr Ser Thr Pro Tyr Thr
1               5

<210> SEQ ID NO 21
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Asp Tyr Tyr Leu Asp
1               5

<210> SEQ ID NO 22
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Arg Val Asn Pro Tyr Asn Gly Gly Thr Ile Tyr Asn Gln Lys Phe Lys
1               5                   10                  15
```

Gly

```
<210> SEQ ID NO 23
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Asp His Tyr Arg Tyr Asp Pro Leu Leu Asp Tyr
1               5                   10

<210> SEQ ID NO 24
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Arg Ala Ser Gln Ser Val Ser Ser Ser Tyr Ser Tyr Met His
1               5                   10                  15

<210> SEQ ID NO 25
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Tyr Ala Ser Asn Leu Glu Ser
1               5

<210> SEQ ID NO 26
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Gln His Ser Trp Glu Ile Pro Tyr Thr
1               5

<210> SEQ ID NO 27
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Asp Thr Tyr Met His
1               5

<210> SEQ ID NO 28
<211> LENGTH: 17
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 28

Arg Ile Asp Pro Ala Asn Gly Asp Thr Asp Tyr Asp Pro Lys Phe Gln
1               5                   10                  15

Gly

<210> SEQ ID NO 29
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Ser Gly Pro Pro Tyr Tyr Val Met Asp Tyr
1               5                   10

<210> SEQ ID NO 30
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Asp Ile Val Leu Thr Gln Ser Pro Ser Ser Leu Ile Val Ser Leu Gly
1               5                   10                  15

Gln Arg Ala Thr Ile Ser Cys Arg Ala Ser Gln Ser Val Ser Thr Ser
            20                  25                  30

Ser Tyr Asn Tyr Met His Trp Tyr Gln Gln Lys Pro Gly Gln Pro Pro
        35                  40                  45

Lys Leu Leu Leu Lys Tyr Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Thr Ala Thr Tyr Tyr Cys Gln His Ser Trp
                85                  90                  95

Glu Ile Pro Leu Thr Phe Gly Ala Gly Thr Lys Leu Glu Ile Lys
            100                 105                 110

<210> SEQ ID NO 31
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Gln Val Gln Leu Gln Gln Ser Gly Pro Glu Leu Val Lys Pro Gly Ala
1               5                   10                  15

Ser Val Lys Ile Ser Cys Lys Ala Ser Gly Tyr Ser Phe Thr Asp Tyr
            20                  25                  30

Tyr Met His Trp Val Lys Gln Ser His Ile Lys Ser Leu Glu Trp Ile
        35                  40                  45

Gly Arg Ile Asn Pro Tyr Asn Gly Ala Ala Phe Tyr Ser Gln Asn Phe
    50                  55                  60

Lys Asp Lys Ala Ser Leu Thr Val Asp Lys Ser Ser Ser Thr Ala Tyr

```
                    65                  70                  75                  80

Met Glu Leu His Ser Leu Thr Ser Glu Asp Ser Ala Val Tyr Tyr Cys
                85                  90                  95

Ala Ile Glu Arg Gly Ala Asp Leu Glu Gly Tyr Ala Met Asp Tyr Trp
            100                 105                 110

Gly Gln Gly Thr Ser Val Thr Val Ser Ser
        115                 120

<210> SEQ ID NO 32
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Thr Ser
            20                  25                  30

Ser Tyr Asn Tyr Met His Trp Tyr Gln Gln Lys Pro Gly Lys Pro Pro
        35                  40                  45

Lys Leu Leu Ile Lys Tyr Ala Ser Asn Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln His Ser Trp
                85                  90                  95

Glu Ile Pro Leu Thr Phe Gly Gln Gly Thr Lys Val Glu Ile Lys
            100                 105                 110

<210> SEQ ID NO 33
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Asp Tyr
            20                  25                  30

Tyr Met His Trp Val Arg Gln Ala Pro Gly Gln Gly Leu Glu Trp Ile
        35                  40                  45

Gly Arg Ile Asn Pro Tyr Asn Gly Ala Ala Phe Tyr Ser Gln Asn Phe
    50                  55                  60

Lys Asp Arg Val Thr Leu Thr Val Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Ile Glu Arg Gly Ala Asp Leu Glu Gly Tyr Ala Met Asp Tyr Trp
            100                 105                 110

Gly Gln Gly Thr Leu Val Thr Val Ser Ser
        115                 120
```

```
<210> SEQ ID NO 34
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Asp Tyr
                20                  25                  30

Tyr Met His Trp Val Arg Gln Ala Pro Gly Gln Gly Leu Glu Trp Ile
            35                  40                  45

Gly Arg Ile Asn Pro Tyr Ala Gly Ala Ala Phe Tyr Ser Gln Asn Phe
        50                  55                  60

Lys Asp Arg Val Thr Leu Thr Val Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Ile Glu Arg Gly Ala Asp Leu Glu Gly Tyr Ala Met Asp Tyr Trp
            100                 105                 110

Gly Gln Gly Thr Leu Val Thr Val Ser Ser
        115                 120

<210> SEQ ID NO 35
<211> LENGTH: 104
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Asp Ile Val Leu Thr Gln Ser Pro Ala Ile Met Ser Ala Ser Pro Gly
1               5                   10                  15

Glu Lys Val Thr Met Thr Cys Ser Ala Ser Ser Ser Ile Ser Tyr Met
                20                  25                  30

Tyr Trp Tyr Gln Gln Lys Pro Gly Thr Ser Pro Lys Arg Trp Ile Tyr
            35                  40                  45

Asp Thr Ser Lys Leu Ala Ser Gly Val Pro Ala Arg Phe Ser Gly Ser
        50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys His Gln Arg Ser Ser Trp Thr Phe Gly
                85                  90                  95

Gly Gly Thr Lys Leu Glu Ile Lys
            100

<210> SEQ ID NO 36
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Glu Val Gln Leu Gln Gln Ser Gly Pro Glu Leu Val Lys Pro Gly Ala
1               5                   10                  15
```

```
Leu Val Lys Ile Ser Cys Lys Ala Ser Gly Tyr Thr Phe Thr Ser Tyr
            20                  25                  30

Asp Ile Asn Trp Leu Lys Gln Arg Pro Gly Gln Gly Leu Glu Trp Ile
        35                  40                  45

Gly Trp Ile Tyr Pro Gly Asp Gly Thr Thr Glu Tyr Asn Glu Arg Phe
    50                  55                  60

Lys Gly Lys Ala Thr Leu Thr Ala Asp Lys Ser Ser Ser Thr Ala Tyr
65                  70                  75                  80

Leu Gln Leu Ser Ser Leu Thr Ser Glu Asn Ser Ala Val Tyr Phe Cys
                85                  90                  95

Ala Arg Ser Tyr Asp Tyr Asp Tyr Ala Met Asp Tyr Trp Gly Gln Gly
            100                 105                 110

Thr Ser Val Thr Val Ser Ser
            115
```

<210> SEQ ID NO 37
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

```
Asp Ile Gln Met Thr Gln Ser His Lys Phe Met Ser Thr Ser Val Gly
1               5                   10                  15

Asp Arg Val Ser Ile Thr Cys Lys Ala Ser Gln Asp Val Ser Thr Ala
            20                  25                  30

Val Ala Trp Phe Gln Gln Lys Pro Gly Gln Ser Pro Lys Leu Leu Ile
        35                  40                  45

Tyr Ser Pro Ser Tyr Arg Tyr Thr Gly Val Pro Asp Arg Phe Thr Gly
    50                  55                  60

Ser Gly Ser Gly Thr Asp Phe Thr Phe Thr Ile Ser Ser Val Gln Ala
65                  70                  75                  80

Glu Asp Leu Ala Val Tyr Tyr Cys Gln Gln Leu Tyr Ser Thr Pro Tyr
                85                  90                  95

Thr Phe Gly Gly Gly Thr Lys Leu Glu Ile Lys
            100                 105
```

<210> SEQ ID NO 38
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

```
Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asp Tyr
            20                  25                  30

Tyr Leu Asp Trp Val Lys Gln Ser His Gly Glu Ser Phe Glu Trp Ile
        35                  40                  45

Gly Arg Val Asn Pro Tyr Asn Gly Gly Thr Ile Tyr Asn Gln Lys Phe
    50                  55                  60

Lys Gly Lys Ala Thr Leu Thr Val Asp Lys Ser Ser Ser Thr Ala Tyr
65                  70                  75                  80
```

```
Met Asp Leu Asn Ser Leu Thr Ser Glu Asp Ser Ala Val Tyr Tyr Cys
                85                  90                  95

Ala Arg Asp His Tyr Arg Tyr Asp Pro Leu Leu Asp Tyr Trp Gly Gln
            100                 105                 110

Gly Thr Thr Leu Thr Val Ser Ser
        115                 120

<210> SEQ ID NO 39
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Thr Ala
            20                  25                  30

Val Ala Trp Phe Gln Gln Lys Pro Gly Lys Ala Pro Lys Leu Leu Ile
        35                  40                  45

Tyr Ser Pro Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Leu Tyr Ser Thr Pro Tyr
                85                  90                  95

Thr Phe Gly Gln Gly Thr Lys Val Glu Ile Lys
            100                 105

<210> SEQ ID NO 40
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Leu Asp Trp Val Arg Gln Ala Pro Gly Gln Gly Leu Glu Trp Ile
        35                  40                  45

Gly Arg Val Asn Pro Tyr Asn Gly Gly Thr Ile Tyr Asn Gln Lys Phe
    50                  55                  60

Lys Gly Arg Val Thr Leu Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Asp His Tyr Arg Tyr Asp Pro Leu Leu Asp Tyr Trp Gly Gln
            100                 105                 110

Gly Thr Leu Val Thr Val Ser Ser
        115                 120

<210> SEQ ID NO 41
```

-continued

<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Asp Ile Gln Met Thr Gln Ser Pro Ala Ser Leu Ala Val Ser Leu Gly
1               5                   10                  15

Gln Arg Ala Thr Ile Ser Cys Arg Ala Ser Gln Ser Val Ser Ser Ser
            20                  25                  30

Ser Tyr Ser Tyr Met His Trp Tyr Gln Gln Lys Pro Gly Gln Pro Pro
        35                  40                  45

Lys Leu Leu Ile Lys Tyr Ala Ser Asn Leu Glu Ser Gly Val Pro Ala
    50                  55                  60

Arg Phe Ser Gly Arg Gly Ser Gly Thr Asp Phe Thr Leu Asn Ile His
65                  70                  75                  80

Pro Val Glu Glu Glu Asp Thr Ala Thr Tyr Tyr Cys Gln His Ser Trp
                85                  90                  95

Glu Ile Pro Tyr Thr Phe Gly Gly Gly Thr Arg Leu Glu Ile Lys
            100                 105                 110

<210> SEQ ID NO 42
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Gln Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Thr
            20                  25                  30

Tyr Met His Trp Val Lys Gln Arg Pro Glu Gln Gly Leu Glu Trp Ile
        35                  40                  45

Gly Arg Ile Asp Pro Ala Asn Gly Asp Thr Asp Tyr Asp Pro Lys Phe
    50                  55                  60

Gln Gly Lys Ala Thr Val Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Thr Ile Ser Gly Pro Pro Tyr Tyr Val Met Asp Tyr Trp Gly Gln Gly
            100                 105                 110

Thr Ser Val Thr Val Ser Ser
        115

<210> SEQ ID NO 43
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Arg Ile Asn Pro Tyr Glu Gly Ala Ala Phe Tyr Ser Gln Asn Phe Lys
1               5                   10                  15

-continued

Asp

<210> SEQ ID NO 44
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Arg Ile Asn Pro Tyr Ser Gly Ala Ala Phe Tyr Ser Gln Asn Phe Lys
1               5                   10                  15

Asp

<210> SEQ ID NO 45
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Ala, Glu, Ser or Asn

<400> SEQUENCE: 45

Arg Ile Asn Pro Tyr Xaa Gly Ala Ala Phe Tyr Ser Gln Asn Phe Lys
1               5                   10                  15

Asp

<210> SEQ ID NO 46
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (55)..(55)
<223> OTHER INFORMATION: Ala, Glu, Ser or Asn

<400> SEQUENCE: 46

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Asp Tyr
                20                  25                  30

Tyr Met His Trp Val Arg Gln Ala Pro Gly Gln Gly Leu Glu Trp Ile
            35                  40                  45

Gly Arg Ile Asn Pro Tyr Xaa Gly Ala Ala Phe Tyr Ser Gln Asn Phe
        50                  55                  60

Lys Asp Arg Val Thr Leu Thr Val Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Ile Glu Arg Gly Ala Asp Leu Glu Gly Tyr Ala Met Asp Tyr Trp
            100                 105                 110

Gly Gln Gly Thr Leu Val Thr Val Ser Ser
        115                 120

<210> SEQ ID NO 47

```
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Ala, Glu or Ser

<400> SEQUENCE: 47

Arg Ile Asn Pro Tyr Xaa Gly Ala Ala Phe Tyr Ser Gln Asn Phe Lys
1               5                   10                  15

Asp

<210> SEQ ID NO 48
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (55)..(55)
<223> OTHER INFORMATION: Ala, Glu or Ser

<400> SEQUENCE: 48

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Asp Tyr
            20                  25                  30

Tyr Met His Trp Val Arg Gln Ala Pro Gly Gln Gly Leu Glu Trp Ile
        35                  40                  45

Gly Arg Ile Asn Pro Tyr Xaa Gly Ala Ala Phe Tyr Ser Gln Asn Phe
    50                  55                  60

Lys Asp Arg Val Thr Leu Thr Val Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Ile Glu Arg Gly Ala Asp Leu Glu Gly Tyr Ala Met Asp Tyr Trp
            100                 105                 110

Gly Gln Gly Thr Leu Val Thr Val Ser Ser
        115                 120

<210> SEQ ID NO 49
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Asp Ser Cys Tyr Phe Leu Ser Asp Asp Val Gln Thr Trp Gln Glu Ser
1               5                   10                  15

Lys

<210> SEQ ID NO 50
<211> LENGTH: 14
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 50

Ile Arg Asn Leu Ser Thr Thr Leu Gln Thr Ile Ala Thr Lys
1               5                   10

<210> SEQ ID NO 51
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Asn Leu Ser Thr Thr Leu Gln Thr Ile Ala Thr Lys
1               5                   10

<210> SEQ ID NO 52
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Asp Tyr Lys Asp Asp Asp Asp Lys Leu Glu His Val Thr Leu Lys
1               5                   10                  15

<210> SEQ ID NO 53
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Asp Asp Asp Asp Lys Leu Glu His Val Thr Leu Lys
1               5                   10

<210> SEQ ID NO 54
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Met Asn Lys Leu Gln Asn Ile Ser Glu Glu Leu Gln Arg
1               5                   10

<210> SEQ ID NO 55
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Leu Gln Asn Ile Ser Glu Glu Leu Gln Arg
1               5                   10
```

```
<210> SEQ ID NO 56
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Asn Ile Ser Leu Gln Leu Met Ser Asn Met Asn Ile Ser Asn Lys
1               5                   10                  15

<210> SEQ ID NO 57
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Asn Leu Ser Thr Thr Leu Gln Thr Ile Ala Thr Lys Leu Cys Arg
1               5                   10                  15

<210> SEQ ID NO 58
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Glu Leu Tyr Ser Lys
1               5

<210> SEQ ID NO 59
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Trp Ile Trp His Lys
1               5

<210> SEQ ID NO 60
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Met Ala Cys Ala Ala Gln Asn Ala Ser Leu Leu Lys
1               5                   10

<210> SEQ ID NO 61
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61
```

```
Ile Asn Asn Lys Asn Ala Leu Glu Phe Ile Lys
1               5                   10
```

<210> SEQ ID NO 62
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

```
Asn Ala Leu Glu Phe Ile Lys
1               5
```

<210> SEQ ID NO 63
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

```
Asn Ala Leu Glu Phe Ile Lys Ser Gln Ser Arg
1               5                   10
```

<210> SEQ ID NO 64
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

```
Ser Tyr Asp Tyr Trp Leu Gly Leu Ser Pro Glu Glu Asp Ser Thr Arg
1               5                   10                  15
```

<210> SEQ ID NO 65
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

```
Ser Tyr Asp Tyr Trp Leu Gly Leu Ser Pro Glu Glu Asp Ser Thr Arg
1               5                   10                  15

Gly Met Arg
```

<210> SEQ ID NO 66
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

```
Val Asp Asn Ile Ile Asn Ser Ser Ala Trp Val Ile Arg
1               5                   10
```

<210> SEQ ID NO 67
<211> LENGTH: 15

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Asn Ala Pro Asp Leu Asn Asn Met Tyr Cys Gly Tyr Ile Asn Arg
1               5                   10                  15

<210> SEQ ID NO 68
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Leu Tyr Val Gln Tyr Tyr His Cys Thr Tyr Lys
1               5                   10

<210> SEQ ID NO 69
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Met Ile Cys Glu Lys
1               5

<210> SEQ ID NO 70
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Met Ala Asn Pro Val Gln Leu Gly Ser Thr Tyr Phe Arg
1               5                   10

<210> SEQ ID NO 71
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Asp Tyr Lys Asp Asp Asp Asp Lys
1               5

<210> SEQ ID NO 72
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Asp Ile Gln Met Thr Gln Ser Pro Ser Ser Leu Ser Ala Ser Val Gly
```

```
1               5                   10                  15
Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ser Tyr Pro Phe
                85                  90                  95

Thr Phe Gly Gln Gly Thr Lys Val Glu Ile Lys
                100                 105

<210> SEQ ID NO 73
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Ile His Trp Val Arg Gln Ala Pro Gly Gln Gly Leu Glu Trp Ile
        35                  40                  45

Gly Trp Ile Asn Pro Gly Ser Gly Asn Thr Asn Tyr Ala Gln Lys Phe
    50                  55                  60

Gln Gly Arg Val Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Phe Asp Tyr Trp Gly Gln Gly Thr Leu Val Thr Val Ser Ser
                100                 105                 110
```